(12) United States Patent
Horwitz et al.

(10) Patent No.: US 7,300,660 B2
(45) Date of Patent: *Nov. 27, 2007

(54) ABUNDANT EXTRACELLULAR PRODUCTS AND METHODS FOR THEIR PRODUCTION AND USE

(75) Inventors: Marcus A. Horwitz, Los Angeles, CA (US); Günter Harth, Los Angeles, CA (US); Bai-Yu Lee, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 751 days.

This patent is subject to a terminal disclaimer.

(21) Appl. No.: 10/695,155

(22) Filed: Oct. 27, 2003

(65) Prior Publication Data

US 2004/0228873 A1 Nov. 18, 2004

Related U.S. Application Data

(63) Continuation-in-part of application No. 08/786,533, filed on Jan. 21, 1997, now abandoned, which is a continuation-in-part of application No. 08/652,842, filed on May 23, 1996, now abandoned, which is a continuation-in-part of application No. 08/568,357, filed on Dec. 6, 1996, now abandoned, which is a continuation-in-part of application No. 08/551,149, filed on Oct. 31, 1995, now abandoned, which is a continuation-in-part of application No. 08/447,398, filed on May 23, 1995, now Pat. No. 6,761,894, which is a continuation-in-part of application No. 08/289,667, filed on Aug. 12, 1994, now abandoned, which is a continuation-in-part of application No. 08/156,358, filed on Nov. 23, 1993, now Pat. No. 6,752,993, application No. 10/695,155, which is a continuation-in-part of application No. 08/545,926, filed on Oct. 20, 1995, now abandoned, which is a continuation-in-part of application No. 08/447,398, filed on May 23, 1995, now Pat. No. 6,761,894.

(51) Int. Cl.
*A61K 39/04* (2006.01)
*A61K 49/00* (2006.01)
*A61K 39/38* (2006.01)
*A61K 39/00* (2006.01)

(52) U.S. Cl. ............... 424/248.1; 424/9.1; 424/9.2; 424/184.1; 424/185.1; 424/192.1; 424/200.1; 424/234.1; 435/320.1; 530/300; 530/350; 536/23.7

(58) Field of Classification Search ............ 424/9.1, 424/9.2, 184.1, 185.1, 192.1, 200.1, 234.1, 424/248.1; 435/320.1; 530/300, 350; 536/23.7
See application file for complete search history.

(56) References Cited

U.S. PATENT DOCUMENTS

| | | | |
|---|---|---|---|
| 3,888,837 A | 6/1975 | Tsumita et al. |
| 3,943,119 A | 3/1976 | Tsumita et al. |
| 4,123,427 A | 10/1978 | Dniel |
| 4,285,931 A | 8/1981 | Limjuco et al. |
| 4,460,503 A | 7/1984 | Savrda et al. |
| 4,724,144 A | 2/1988 | Rook et al. |
| 4,777,130 A | 10/1988 | Maes |
| 4,889,800 A | 12/1989 | Shinnick et al. |
| 4,906,742 A | 3/1990 | Young et al. |
| 4,952,395 A | 8/1990 | Shinnick et al. |
| 4,965,192 A | 10/1990 | Maes |
| 4,976,958 A | 12/1990 | Shinnick et al. |
| 5,108,745 A | 4/1992 | Horwitz |
| 5,154,923 A | 10/1992 | Van Eden et al. |
| 5,169,940 A | 12/1992 | Patarroyo |

(Continued)

FOREIGN PATENT DOCUMENTS

EP 0499003 A1 8/1992

(Continued)

OTHER PUBLICATIONS

C. Abou-Zeid et al., "The Secreted Antigens of *Mycobacterium tuberculosis* . . . Available Antibodies," 1988, 134:531-538, J. Gen. Micro.

(Continued)

*Primary Examiner*—Rodney P Swartz
(74) *Attorney, Agent, or Firm*—Louis C. Cullman; Michelle S. Glasky; Kirkpatrick & Lockhart Preston Gates Ellis LLP

(57) ABSTRACT

Vaccines based on one or more combinations of majorly abundant extracellular products of pathogens and methods for their use and production are presented. The most prevalent or majorly abundant extracellular products of a target pathogen are selected irrespective of their absolute molecular immunogenicity and used as vaccines to stimulate a protective immune response in mammalian hosts against subsequent infection by the target pathogen. The majorly abundant extracellular products may be characterized and distinguished by their respective N-terminal amino acid, amino acid, or DNA sequences. As the vaccines may comprise different combinations of the extracellular products, subunits thereof, or encoding nucleic acids, a broad range of effective immunotherapeutic compositions are provided by the present invention. In addition to other infectious agents, the vaccines so produced can be used to stimulate an effective immune response against intracellular pathogens and in particular *Mycobacterium tuberculosis*.

28 Claims, 25 Drawing Sheets

U.S. PATENT DOCUMENTS

| | | | |
|---|---|---|---|
| 5,171,839 A | 12/1992 | Patarroyo | |
| 5,225,324 A | 7/1993 | McFadden et al. | |
| 5,254,459 A | 10/1993 | Patarroyo | |
| 5,268,170 A | 12/1993 | Van Eden et al. | |
| 6,471,967 B1 * | 10/2002 | Horwitz et al. | 424/248.1 |
| 6,752,993 B1 * | 6/2004 | Horwitz | 424/248.1 |

FOREIGN PATENT DOCUMENTS

| | | |
|---|---|---|
| GB | 2239246 | 6/1991 |
| WO | WO 85/03639 | 8/1985 |
| WO | WO 88/02027 | 3/1988 |
| WO | WO 88/05823 | 8/1988 |
| WO | WO 88/06626 | 9/1988 |
| WO | WO 89/05825 | 6/1989 |
| WO | WO 89/12455 | 12/1989 |
| WO | WO 90/00594 | 1/1990 |
| WO | WO 90/02564 | 3/1990 |
| WO | WO 90/10449 | 9/1990 |
| WO | WO 90/15873 | 12/1990 |
| WO | WO 91/04272 | 4/1991 |
| WO | WO 91/14448 | 10/1991 |
| WO | WO 92/01783 | 2/1992 |
| WO | WO 92/01796 | 2/1992 |
| WO | WO 92/04462 | 3/1992 |
| WO | WO 92/16628 | 10/1992 |
| WO | WO 92/21376 | 12/1992 |
| WO | WO 92/21697 | 12/1992 |
| WO | WO 92/22326 | 12/1992 |
| WO | WO 93/07897 | 4/1993 |
| WO | WO 93/14118 | 7/1993 |
| WO | WO 93/14789 | 8/1993 |
| WO | WO 94/02508 | 2/1994 |
| WO | WO 95/01440 | 1/1995 |
| WO | WO 95/01441 | 1/1995 |
| WO | WO 95/14713 | 6/1995 |

OTHER PUBLICATIONS

C. Abou-zeid et al., "Characterization of Fibronectin . . . *Mycobacterium bovis* BCG," Dec. 1988, 56(12):3046-3051, Infection and Immunity.

C. Abou-zeid et al., "Genetic and Immunological Analysis . . . Fibronectin-Binding Proteins," Aug. 1991, 59(8):2712-2718, Infection and Immunity.

E. Adams et al., "T cell reactivity . . . household contacts," 1990, 80:206-212, Clin. Exp. Immunol.

Allison, A.C. and N.E. Byars, "An adjuvant formulation that selectively elicits the formation of antibodies of protective isotypes and of cell-mediated immunity," J. Immunol. Meth. 95:157-68, 1986.

Andersen, P., and I Heron. "Specificity of a Protective Memory Immune Response against *Mycobacterium tuberculosis*." Infection and Immunology 61 (1993) 844-51.

Belisle, J. T., et al. "Indentification of a Mycolyltransferase from *Mycobacterium tuberculosis* and the Coincident Definition of the Physiological Function of Antigen 85B." In the program from the Thirtieth U.S.-Japan Tuberculosis Research Conference, Leprosy Research Conference and Tuberculosis/Leprosy Symposium. U.S.-Japan Cooperative Medical Science Program. Ft. Collins, Colorado (Jul. 19-21, 1995) 212-6.

Berdal, Bjorn P., et al. "Demonstration of Extracellular Chymotrypsin-Like Activity from Various Legionella Species." Journal of Clinical Microbiology 16 (Sep. 1982) 452-7.

V. Bhardwaj & M.J. Colston, "The processiong and presentation of mycobacterial . . . monocytes," 1988, 18:691-696, Eur. J. Immunol.

S.J. Blander & M.A. Horwitz, "Vaccination with the Major Secretory Protein . . . Legionnaires' Disease," Mar. 1989, 169:691-705, J. Exp. Med.

Blander, Steven J., et al. "A Live Avirulent Mutant *Legionella pneumophila* Vaccine Induces Protective Immunity against Lethal Aerosol Challenge." J. Clin. Invest. 83 (Mar. 1989) 810-5.

Blander, Steven J., et al. "An Immunoprotective Molecule, the Major Secretory Protein of *Legionella pneumophila*, Is Not a Virulence Factor in a Guinea Pig Model of Legionnaires' Disease." Journal of Clinical Investigation 86 (Sep. 1990) 817-24.

Blander, Steven J., and Marcus A. Horwitz. "Vaccination with *Legionella pneumophila* Membranes Induces Cell-mediated and Protective Immunity in a Guinea Pig Model of Legionnaries' Disease." Journal of Clinical Investigation 87 (Mar. 1991 1054-9.

Blander, Steven J., and Marcus A. Horwitz. "Vaccination with the Major Secretory Protein of Legionella Induces Humoral and Cell-mediated Immune Responses and Protective Immunity across Different Serogroups of *Legionella pneumophila* and Different Species of Legionella." Journal of Immunology 147 (Jul. 1991) 285-91.

Blander, Steven J., and Marcus A. Hortwitz. "Major Cytoplasmic Membrane Protein of *Legionella pneumophila*, a Genus Common Antigen and Member of the hsp 60 Family of Heat Shock Proteins, Induces Protective Immunity in a Guinea Pig Model of Legionnaries' Disease." Journal of Clinical Investigation 91 (Feb. 1993) 717-23.

Bloch, Hubert, and William Segal. "Viability and Multiplication of Vaccines in Immunization Against Tuberculosis." American Review of Tuberculosis 7(1955) 228-48.

B.R. Bloom et al., "Genes for the protein antigens of the tuberculosis and leprosy bacilli," 1985, 5:839-845, Science Reports.

Bloom, Barry R. "New Approaches to Vaccine Development." Reviews of Infectious Disease, 1989, 11(2): S460-6.

Borremans et al., "Cloning, sequence determination, and expression of 32-kilodalton-protein gene of *Mycobacterium tuberculosis*," Infect. Immun. 57(10):3123-30, 1989.

Brennan, Patrick J. "Structural of Mycobacteria: Recent Developments in Defining Cell Wall Carbohydrates and Proteins." Reviews of Infectious Disease, 1989, 11(2): S420-30.

R.F. Breiman & M.A. Horwitz, "Guinea Pigs Sublethally Infected . . . Challenge," Mar. 1987, 164:799-811, J. Exp. Med.

W.J. Britton et al., "Immunoreactivity of a 70 kD Protein . . . Chromatography," Sep. 1986, 691-708, J.Ex.Medicine.

K.M. Citron, "Control and prevention of tuberculosis in Britain," 1988, 44(3):704-716, Br. Med. Bull.

Chen, E. Y., and P. H. Seeburg. "Supercoli Sequencing: A Fast and Simple Method for Sequencing Plasmid DNA." DNA 4 (1985) 165-70.

Collins, et al., "Biological activity of protein antigens isolated from *Mycobacterium tuberculosis* culture filtrate," Infect. Immun. 1988, vol. 56(5), 1260-1266.

Clemens, D. L., and M. A. Horwitz. "Characterization of the *Mycobacterium tuberculosis* Phagosome and Evidence That Phagosmal Is Inhibited." Journal of Experimental Medicine 181 (1995) 257-70.

G.W. Comstock, "Identification of an Effective Vaccine Against Tuberculosis," 1988, 138:479-480, Am. Rev. Respir. Dis.

J. Content et al., "The Genes Coding for the Antigen 85 Complexes . . . *M. tuberculosis*," Sep. 1991, 59(9):3205-3212, Infection and Immunity.

A.J. Crowle, "Immunization against Tuberculosis: What Kind of Vaccine?" Nov. 1988, 56(11):2769-2773, Infection and Immunity.

Daniel, Thomas M. "Rapid Diagnosis of Tuberculosis: Laboratory Techniques Applicable in Developing Countries," Reviews of Infectious Disease, 1989, 11(2):S471-8.

Dannenberg, Arthur M., Jr. "Immune Mechanisms in the Pathogenesis of Pulmonary Tuberculosis." Review of Infectious Disease, 1989 11(2):S369-78.

De Vries, Rene R.P. "Regulation of T Cell Responsiveness Against Mycobacterial Antigens by HLA Class 2 Immune Response Genes." Reviews of Infectious Disease, 1989, 11(2):S400-3.

A. Drowart et al., "Isoelectrophoretic Characterization of Protein Antigens . . . Antigen 85 Complex," 1992, 36:697-702, Scand. J. Immunol.

Dubos, Rene J., et al. "Antituberculosis Immunity Induced in Mice by Vaccination with Living Cultures of Attenuated Tubercle Bacilli." Journal of Experimental Medicine 97 (1953) 207-20.

H.D. Eberhard, "Leser-Zuchriften—Tuberkulose-Schutzimpfung," 1982, 1821-1822, Dtsch. med. Wschr.

Ellner, Jerrold J. and Robert S. Wallis. "Immunologic Aspects of Mycobacterial Infections," Reviews of Infectious Disease, 1989, 11(2): S455-9.

F. Emmrich et al., "A Recombinant 64 Kilodalton Protein . . . Mycobacterial Antigens," Apr. 1986, 163:1024-1029, J. Exp. Med.

Feller, D. C., and V. F. de la Cruz. "Identifying Antigenic T-Cell Sites." Nature 349 (1991) 720-1.

P.E.M. Fine et al., "The relationship between delayed type hypersensitivity . . . mycobacterial vaccines in man," 1986, 57:275-283, Lepr.Rev., Suppl. 2.

P.E.M. Fine, "BCG vaccination against Tuberculosis and leprosy," 1988, 44:691-703, Br. Med. Bull.

Fine, Paul E.M. "The BCG Story: Lessons from the Past and Implications for the Future." Reviews of Infectious Disease, 1989, 11(2): S353-9.

E. Freerksen, "Kommentare Tuberkulose-Schutzimpfung," 1982, 1564-1569, Dtsch. med. Wschr.

R.J. Garsia et al., "Homology of the 70-Kilodalton Antigens . . . Eucaryotes," Jan. 1989, 57(1):204-212, Infection and Immunity.

H.P. Godfrey et al., "Modulation of Expression . . . Fibronectin-Binding Proteins," Jun. 1992, 60(6):2522-2528, Infection and Immunity.

J.M. Grange, "Molecular Biology: New Hopes and Challenges," 1988, 69:1-4, Tubercle.

Grossett, Jacques H. "Present Status of Chemotherapy for Tuberculosis." Reviews of Infectious Disease, 1989, 11(2): S347-52.

Grunstein, M., and D. S. Hogness. "Colony Hybridization: A Method for the Isolation of Cloned DNAs That Contain a Specific Gene." Proc. Natl. Acad. Sci. USA 72 (1975) 3961-6.

H. Hahn, "Antibacterial Defence Mechanisms," 1983, S112-S121, Infection II (1983) Suppl. 2.

Harth, Gunter, et al. "Glutamine Synthetase of *Mycobacterium tuberculosis*: Extracellular Release and Characterization of Its Enzymatic Activity." Proc. Natl. Acad. Sci. USA 91 (1994) 9342-6.

Hatfull, G. F., and G. J. Sarkis. "DNA Sequence, Structure and Gene Expression of Mycobacteriophage L5: A Phage system for Mycobacterial Genetics." Mol. Micro. 7 (1993) 395-405.

D.V. Havlir et al., "Human Immune Response to *Mycobacterium tuberculosis* Antigens," Feb. 1991, 59(2):665-670, Infection and Immunity.

Heym et al., "Characterization of the katG gene encoding a catalase-peroxidase required for the isoniazid susceptibility of *Mycobacterium tuberculosis*," J. Bacteriol. 1993, vol. 175(13), 4255-4259.

Horwitz, Marcus A., and Samuel C. Silverstein. "Legionnaires' Disease Bacterium (*Legionella pneumophila*) Multiples Intracellularly in Human Monocytes." Journal of Clinical Investigation 66 (Sep. 1980) 441-50.

Horwitz, Marcus A. "Cell-mediated Immunity in Legionnaires' Disease." Journal of Clinical Investigation 71 (Jun. 1983) 1686-97.

Horwitz, Marcus A. "Characterization of Avirulent Mutant *Legionella pneumophila* that Survive but do not Multiply with Human Monocytes." J. Exp. Med. 166 (Nov. 1987) 1310-28.

M.A.Horwitz, "Intracellular parasitism," 1988, 1:41-46, Current Opinion in Immunology.

M.A. Horwitz, "The Immunobiology of *Legionella pneumophila*," Chapter 11, 1989, 141-156, Intracellular Parasitism.

Horwitz, Marcus A., et al. "Progress in the Development of a Subunit Vaccine Against Tuberculosis." From the Twenty-Ninth U.S.-Japan Leprosy Research Conference, Tuberculosis Research Conference, and Leprosy/Tuberculosis Symposium (Aug. 19-22, 1994).

Horwitz, Marcus A., et al. "Protective Immunity Against Tuberculosis Induced by Vaccination with Major Extracellular Proteins of *Mycobacterium tuberculosis*." Proc. Natl. Acad. Sci. USA 92 (1995) 1530-34.

Horwitz, Marcus A., et al., "Progress in the Development of a Subunit Vaccine against Tuberculosis and a New Nonhuman Primate Model of Pulmonary Tuberculosis," Journal of Cellular Biochemistry, Supplement O (19B), Feb. 1995, p. 60, Abstract No. B3-014.

Huygen, Kris, et al. "Specific Lymphoproliferation, Gamma Interferon Production, and Serum Immnoglobulin G Directed against a Purified 32 kDa Mycobacterial Protein Antigen (P32) in Patients with Active Tuberculosis." Scandinavian Journal of Immunology 27 (1988) 187-94.

Huygen, Kris, et al. "Immunogenicity of a Tuberculosis DNA Vaccine Containing Genes Encoding the Components of the Secreted Antigen 85 Complex." Journal of Cellular Biochemistry—Molecular Mechanisms in Tuberculosis from the Keystone Symposia on Molecular & Cellular Biology, Supplement 19B, 1995 (Feb.5-Mar. 15, 1995) Abstract No. B3-408.

Jacobs, William R., Jr., et al. "Myobacteriophage Vector Systems." Reviews of Infectious Disease, 1989, 11(2): S404-10.

W.S. Jordan, Jr., "Impediments to the Development of Additional Vaccines . . . Next Decade," May-Jun. 1989, II(Supp.3):S603-612, Rev. Infec. Diseases.

S.H.E. Kaufmann, "T Cell Clones and their Products: . . . Infections," 1985, S177-S182, Infection 13 Suppl.2.

S.H.E. Kaufmann & D.B. Young, "Vaccination against Tuberculosis and Leprosy," 1992, 184:208-229, Immunobiol.

Kaufman, Stefan H.E. "In Vitro Analysis of the Cellular Mechanism Involved in Immunity to Tuberculosis." Reviews of Infectious Disease, 1989, 11(2): S448-54.

Kingston et al., "Immunological activity of a 14-kilodalton recombinant protein of *Mycobacterium tuberculosis* H37Rv," Infect. Immun. 1987, vol. 55(12), 3149-3154.

Kitaura, H., et al. "Cloning, Sequencing and Expresssion of the Gene for Alpha Antigen from Mycobacterium intracellulare and Use of PCR for the Rapid Identification of Mycobacterium intracellulare." Biochemical and Biophysical Research Communications 196 (1993) 1466-73.

Kiyotani, K., et al., "Mycobacterial Lipase Inhibitor: A New Lipase Inhibitor Isolated from Culture Filtrate of *Mycobacterium tuberculosis*," Chemical Abstracts, vol. 100, No. 23, Jun. 4, 1984, p. 252, col. 1, Abstracts No. 187918d.

E. Krambovitis, "Detection of antibodies to *Mycobacterium tuberculosis* plasma . . . assay," 1986, 21:257-264, Med. Microbiol.

Kremer, L., et al. "Analysis of the *Mycobacterium tuberculosis* 85A Antigen Promoter Region." Journal of Bacteriology 177 (1995) 642-53.

Kubica, George P., and Lawrence G. Wayne, eds. The Mycobacteria: A Sourcebook. 2 parts. New York: Marcel Dekker, Inc. 33-57.

Kyte, J., R. F. Doolittle. "Simple Method for Displaying the Hydropathic Character of a Protein." Journal of Molecular Biology 157 (1982) 105-32.

F.M. LaForce, "Immunization, Immunoprophylaxis . . . Infections," May 8, 1987, 257(18):2464-2470, JAMA.

P.H. Lagrange et al., "Immunological Mechanism Controlling Mycobacterial Infectiosn," 1983, 163-172, Bull. Europ. Physiopath. Resp.

Lamb, Jonathan R., et al. Identification of Mycobacterial Antigens Recognized by T Lymphocytes. Reviews of Infectious Disease, 1989, 11(2):S443-7.

P. Launois et al., "T cell response . . . in leprosy patients," 1991. 86:286-290, Clin. Exp. Immunol.

P. Launois et al., "IL-6 Production in Response to Purified Mycobacterial Heat-Shock Protein . . . Leprosy," 1993, 148:283-290, Cellular Immunology.

Launois, P., et al. "T-Cell-Epitope Mapping of the Major Secreted Mycobacterial Antigen Ag85A in Tuberculosis and Leprosy." Infection and Immunity 62 (1994) 3679-87.

Lee, Bai-Yu, et al., "Characterization of the Major Membrane Protein of Virulent *Mycobacterium tuberculosis*," Infection and Immunity, vol. 60, No. 5, May 1992, pp. 2066-2074.

Lee, Byong-Wha Esther, et al. "Cell-Mediated Immune Responses to the Native 71kD Protein of *Mycobacterium tuberculosis* in Guinea Pigs and Humans." From the Twenty-Seventh U.S.-Japan Leprosy Research Conference, Tuberculosis Research Conference, And Leprosy/Tuberculosis Symposium (Aug. 4-7, 1992).

Lee, B.-Y., and M. A. Horwitz. "Identification of Macrophage and Stress-Induced Protein of *Mycobacterium tuberculosis*." Journal of Clinical Investigation 96 (1995) 245-9.

Lee, T. D., and S. Vemuri. "MacProMass: A Computer Program to Correlate Mass Spectral Data to Peptide and Protein Structures." Biomed. Environmental Mass Spectroscopy 19 (1990) 639-45.

B.J. Luft et al., "Immunologic and Structural Characterization . . . Borrelia burgdorferi," Apr. 15, 1991, 146(8):2776-2782, Journal of Immunology.

K. Matsuo et al., "Cloning and Expression of the *Mycobacterium bovis* . . . Antigen," Sep. 1988, 170(9):3847-3854, Journal of Bacteriology.

Maugh, Thomas H., 2d. "Promising Tests Reported for New TB Vaccine." Los Angeles Times, Feb. 28, 1995, p. 1, col. 3.
K.R. McKenzie et al., "Sequence and Immunogenicity . . . *Mycobacterium leprae*," Jul. 1, 1991, 147(1):312-319, Journal of Immunology.
L. de Mendonca Lima, "Nucleotide sequence of the gene coding . . . *Mycobacterium leprae*," 1991, 19(20):5789, Nucleic Acids Research.
A.Mehlert & D.B.Young, "Biochemical and antigenic . . . heat-shock protein family," 1989, 3(2):125-130, Molecular Microbiology.
Meyer, Sven Nissen. "Animal Studies on Effects of BCG, H37Ra and *Mycobacterium phlei* in Tuberculosis Immunization." Tubercle 37(Jan.-Feb. 1956) 11-12.
Muller, Hans E. "Proteolytic Action of *Legionella pneumophila* on Human Serum Proteins." Infection and Immunity 27 (Jan. 1980) 51-3.
Munk, et al., "T cell responses of normal individuals towards recombinant protein antigens of *Mycobacterium tuberculosis*," Eur. J. Immunol. 1988, vol. 18, 1835-1838.
A.S. Mustafa et al. "Characterisitcs of human T-cell clones . . . patients," 1986, 57:123-130, Symposium on the Immunology of Lerposy, Lepr. Rev. Suppl. 2.
Myung, Seok J., et al., "Affinity Purification of Beta Antigen of *Mycobacterium tuberculosis* by Using Specific Monoclonal Antibody and Its Application for the Diagnosis of Tuberculosis Meningitis by Elisa," Chemical Abstracts, vol. 112, No. 19, May 7, 1990, p. 534, col. 2, Abstract No. 176521r.
Nagai, Sadamu, et al., "Isolation and Partial Characterization of Major Protein Antigens in the Culture Fluid of *Mycobacterium tuberculosis*," Infect. Immun., vol. 59, No. 10, Oct. 1991, pp. 372-382.
Oettinger, Thomas, et al., "Cloning and B-Cell-Epitope Mapping of MPT64 from *Mycobacterium tuberculosis* H37Rv," Infection and Immunity, vol. 62, No. 5, May 1994, pp. 2058-2064.
Ohara, Naoya, et al., "Cloning and Sequencing of the Gene for Alpha Antigene from *Mycobacterium avium* and Mapping of B-Cell Epitopes," Infect. Immun., vol. 61, No. 4, Apr. 1993, pp. 1173-1179.
I.M. Orme & F.M. Collins, "Infection with *Mycobacterium kansasii* and efficacy of vaccination against tuberculosis," 1983, 581-586, Immunology.
Ian M. Orme, "The Kinetics of Emergence and Loss . . . *Mycobacterium tuberculosis*," Jan. 1, 1987, 138:293-298, J. Immunol.
I.M. Orme, "Characterisitics and Specificity of Acquired Immunologic Memory to *M. tuberculosis* Infection," May 15, 1988, 140 (10):3589-93, J. Immunology.
I.M. Orme, "Induction of Nonspecific Acquired Resistance . . . Vaccines," Dec. 1988, 56(12):3310-3312, Infection and Immunity.
Orme, Ian M., et al. "T. Lymphocytes Mediating Protection and Cellular Cytolysis During the Course of *Mycobacterium tuberculosis* Infection." The Journal of Immunology 148 (Jan. 1992) 189-96.
P.G. Pal & M.A. Horwitz, "Immunization with Extracellular Proteins . . . Pulmonary Tuberculosis," Nov. 1992, 60(11):4781-4792, Infection and Immunity.
Pal, Primepares G., et al, "Immunization with Extracellular Proteins of *Mycobacterium tuberculosis* Induces Cell-Mediated and Protective Immunity in a Guinea Pig Model of Pulmonary Tuberculosis," Clinical Research, vol. 39, No. 2, 1991, p. 174A.
Palmer, C., et al., "Experimental Studies of Vaccination, Allergy, and Immunity in Tuberculosis." Bulletin of the World Health Organization 12 (1955) 47-62.
Patel, Rubina J., et al. A Cloned DNA Fragment for Identification of *Mycobacterium tuberculosis*. Reviews of Infectious Disease, 1989, 11(2): S411-9.
P. Peake et al., "Mechanism of Interaction of the 85B Secreted Protein . . . Fibronectin," Nov. 1993, 61(11):4828-4834, Infection and Immunity.
M.C.V. Pessolani & P.J. Brennan, "*Mycobacterium leprae* Produces . . . Antigen 85 Complex," Nov. 1991, 60(11):4452-4459, Infection and Immunity.
Piessens, Willy F. "Introduction to the Immunology of Tuberculosis," Reviews of Infectious Disease, 1989, 11(2):S436-42.
Pio, Antonio, "Impact of Present Control Methods on the Problem of Tuberculosis." Reviews of Infectious Disease, 1989, 11(2):S360-5.
Parenti, Francesco, "New Experimental Drugs for the Treatment of Tuberculosis." Reviews of Infectious Disease, 1989, 11(2):S479-83.
Pribnow, D. "Nucleotide Sequence of an RNA Polymerase Binding Site at an Early T7 Promoter." Proceedings of the National Academy of Science USA 72 (1975) 784-8.
Quinn, Thomas C. "Interactions of the Human Immunodeficiency Virus and Tuberculosis and the Implications for BCG Vaccination," Reviews of Infectious Disease, 1989, 11(2): S379-84.
A.J. Radford et al., "Cloning of a Species-Specific Antigen of *Mycobacterium bovis*," Apr. 1988, 56(4):921-925, Infection and Immunity.
A. Rambukkana et al., "Identification and Characterization of Epitopes . . . *Mycobacterium leprae*," Nov. 1992, 60(11):4517-4527, Infection and Immunity.
A. Rambukkana et al., "Heterogeneity of Monoclonal Antibody-React. Epitopes . . . Cell Wall Surface," Dec. 1992, 60(12):5172-5181, Infection and Immunity.
A. Rambukkana et al., "The Mycobacterial Secreted Antigen 85 . . . Armadillo Tissues," May 1993, 61(5):1835-1845, Infection and Immunity.
A. Rees et al., "Specificity of proliferative response . . . mycobacterial antigens," 1988, 18:1881-1887, Eur. J. Immunol.
E. Ribi et al., "Induction of Resistance to Tuberculosis in Mice . . . Unrelated Materials," 1982, 345-356, Zbl.Bakt.Hyg., I.
T.F. Rinke de Wit, "The *Mycobacterium leprae* Antigen 85 . . . MPT51 Proteins," Sep. 1993, 61(9):3642-3647, Infection and Immunity.
Roche, Paul W., et al. "T-Cell Determinants and Antibody Binding Sites on the Major Mycobacterial Secretory Protein MPB59 of *Mycobacterium bovis*." Infection and Immunity 62 (Dec. 1994) 5319-26.
H.S.Rumschlag et al., "Serological Responses . . . *Mycobacterium tuberculosis*," Oct. 1988, 26(10):2200-2202, J. Clin. Microbio.
Salata et al., "Purification and characterization of the 30,000 dalton native antigen of *Mycobacterium tuberculosis* and characterization of six monoclonal antibodies reactive with a major epitope of this antigen," J. Lab. Clin., Med. 1991, vol. 118. 589-598.
Sanger, F., et al. "DNA Sequencing with Chain-Terminating Inhibitors." Proceedings of the National Academy of Science USA 74 (1977) 5463-7.
Sensi, Piero. "Approaches to the Development of New Antituberculosis Drugs." Reviews of Infectious Disease, 1989, 11(2): S467-70.
Shine, J., and L. Dalgamo. "The 3'-Terminal Sequence of *Escherichia coli* 16S Ribosomal RNA: Complementarily to Nonsense Triplets and Ribosome Binding Sites." Proc. Natl. Acad. Sci. USA 71 (1974) 1342-6.
Shinnick, T. M. "The 65-Kilodalton Antigen of *Mycobacterium tuberculosis*." J. Bacteriol. 169 (1987) 1080-8.
Silver, Richard F., "T-Cell Epitopes of the 39kD Alpha Antigen of *Mycobacterium tuberculosis* BCG: Potential for Use in Vaccines and Diagnosis." Journal of Cellular Biochemistry—Molecular Mechanisms in Tuberculosis from the Keystone Symposia on Molecular & Cellular Biology, Supplement 19B, 1995 (Feb. 5-Mar. 15, 1995) Abstract No. B3-336:94.
Skamene, Emil. "Genetic Control of Susceptibility to Mycobacterial Infections." Reviews of Infectious Disease, 1989, 11(2): S394-9.

Smith, Donald W., and Ernst H. Wiegeshaus. "What Animal Models Can TeachUs about the Pathogenesis of Tuberculosis in Humans." Reviews of Infectious Disease, 1989, 11(2):S358-93.

Stead, William W. "Pathogensis of Tuberculosis: Clinical and Epidemiologic Perspective." Reviews of Infectious Disease, 1989, 11(2): S369-78.

Styblo, Karel, "Overview and Epidemiologic Assessment of the Current Global Tuberculosis Situation with an Emphasis on Control in Developing Countries," Reviews of Infectious Disease, 1989, 11(2): S339-46.

J.E.R. Thole et al., "Molecular and immunological analysis . . . *Mycobacterium leprae*," 1992, 6(2):153-163, Molecular Microbiology.

M. Turneer et al., "Humoral Immune Response in Human Tuberculosis . . . *Bacillus calmette-guerin*," Sep. 1988, 26:1714-1719, J. Clin. Microbio.

Verbon et al., "Development of a serological test for tuberculosis", Nederlands Tijdscrift voor Geneekunde, vol. 135, No. 4, pp. 134-138, Jan. 26, 1991.

Verbon, Annelies, et al., "The 14,000-Molecular-Weight Antigen of *Mycobacterium tuberculosis* is Related to the Alpha-Crystallin Family of Low-Molecular-Weight Heat Shock Proteins," Journal of Bacteriology, vol. 174, No. 4, Feb. 1992, pp. 1352-1359.

Verbon, A., et al., "Characterization of B Cell Epitopes on the 16K antigen of *Mycobacterium tuberculosis*," Clin. Exp. Immunol., vol. 89, No. 3, 1992, pp. 395-401.

Von Heijne, G. "A New Method for Predicting Signal Sequence Cleavage Sites." Nucleic Acids Research 14 (1986) 4683-90.

Wallis, et al., "Identification by two-dimensional gel electrophoresis of a 58-kilodalton tumor necrosis factor-inducing protein of *Mycobacterium tuberculosis*," Infect. Immun. 1993, vol. 61(2), 627-632.

Weiss, David W., "Vaccination Against Tuberculosis with Nonliving Vaccines", Jan. 15, 1959, pp. 340-358.

Weiss, David W., and A.Q. Wells, "Immunization with Dead Tubercle Bacilli." Tubercle 37 (Apr. 1956) 137-40.

Wiegeshaus, E.H., et al., "Evaluation of the protective potency of new tuberculosis vaccines", Reviews of Infectious Diseases, vol. II, Suppl. 2, pp. S484-S490, Mar. 1, 1989.

H.G. Wiker et al., "Evidence for Three Separate Genes . . . Antigen 85 Complex," Jan. 1990, 58(1):272-274, Infection and Immunity.

H.G. Wiker et al., "Localization index for distinction . . . *Mycobacterium tuberculosis*," 1991, 137:875-884, Journal of General Microbiology.

H.G. Wiker & M. Harboe, "The Antigen 85 Complex: a Major Secretion Product of *M. tuberculosis*," Dec. 1992, 56(4):648-661, Microbiology Reviews.

Wilson, G.S., and A.A. Miles, "Tuberculosis." Chap. 59 in Topley and Wilson's Principles of Bacteriology and Immunity. 4th ed. 2 vols. London: Edward Arnold (Publishers Ltd. (1955).

L. De Wit, et al., "Nucleotide sequence . . . *Mycobacterium bovis* BCG," 1990, 18(13):3995, Nucleic Acids Research.

De Wit, Luk, et al., "Nucleotide Sequence of the 85B-Protein Gene of *Mycobacterium bovis* BCG and *Mycobacterium tuberculosis*," DNA Sequence, vol. 4, No. 4, 1994, pp. 267-270.

A. Worsaae et al., "Allergenic and Blastogenic Reactivity . . . Guinea Pigs," Dec. 1987, 55(12):2922-2927, Infection and Immunity.

Yamaguchi, Ryuji, et al., "Cloning and Characterization of the Immunogenic Protein MPB64 of *Mycobacterium bovis* BCG," Infection and Immunity, vol. 57, No. 1, Jan. 1989, pp. 283-288.

Yanisch-Perron, C., et al. "Improved M13 Phage Cloning Vectors and Host Strains: Nucleotide Sequences of the M13mp18 and pUC19 Vectors." Gene 33 (1985) 103-19.

Youmans, G.P. "Acquired Immunity in Tuberculosis." Chap. 8 in Tuberculosis. Edited by G.P. Youmans Philadelphia: The W.B. Saunders Co. (1979).

R.A. Young et al., "Dissection of *Mycobacterium tuberculosis* antigens using recombinant DNA," May 1985, 82:2583-2587, Proc. Natl. Acad. Sci. USA.

D. Young et al., "Immunological Activity . . . *Mycobacterium tuberculosis*," Oct. 1986, 177-183, Infection and Immunity, vol. 54, No. 1.

D. Young et al., "Stress proteins are immune targets in leprosy and tuberculosis," Jun. 1988, 85:4267-4270, Proc. Natl. Acad. Sci.

Young, D.B., et al. "Mycobacterial Protein Antigens: A Compilation." Mol. Micro. 6 (2):133-45. (1992).

Young, Douglas B., and Angela Mehlert. "Serology of Mycobacteria: Characterization of Antigens Recognized by Monoclonal Antibodies." Reviews of Infectious Disease, 1989, 11(2): S431-5.

Zhang, Y. et al., "Genetic analysis of superoxide dismutase, the 23 kilodalton antigen of *Mycobacterium tuberculosis*," Mol. Microbiol. 1991, vol. 5(2), 381-391.

"Use of BCG Vaccines . . . : A Joint Statement by the ACIP and the Adv'y Comm. for Elim. of Tuberculosis," Nov. 4, 1988, 37(43):663-675, MMWR.

* cited by examiner

Fig. 2.

| PURIFIED EXTRACELLULAR PROTEINS STUDIED | |
|---|---|
| APPARENT MW BY SDS-PAGE (KD) | N TERMINAL 5 AMINO ACIDS |
| 110 | NSKSV |
| 80 | TDRVS |
| *71 | ARAVG |
| 58 | TEKTP |
| 45 | DPEPA |
| *32A | FSRPG |
| 32B | FSRPG |
| *30 | FSRPG |
| 24 | APYEN |
| 23.5 | APKTY |
| *23 | AETYL |
| *16 | AYPIT |
| 14 | ADPRL |
| 12 | FDTRL |

Fig. 3.

| EXTENDED N-TERMINAL SEQUENCE OF 30/32 KD COMPLEX OF M. TUBERCULOSIS EXTRACELLULAR PROTEINS | | | | | | | | | | | | | | | | | | | | |
|---|---|---|---|---|---|---|---|---|---|---|---|---|---|---|---|---|---|---|---|---|
| | 1 | | | | | | | | | 10 | | | | | | | | | | 20 |
| 30 | F | S | R | P | G | L | P | V | E | Y | L | Q | V | P | S | P | S | M | G | R |
| 32A | – | – | – | – | – | – | – | – | – | – | – | – | – | – | – | – | – | – | – | – |
| 32B | – | – | – | – | – | – | – | – | – | – | – | – | – | A | – | – | – | – | – | – |
| | 21 | | | | | | | | | 30 | | | | | | | | | | 40 |
| 30 | D | I | K | V | Q | F | Q | S | G | G | N | N | S | P | A | V | Y | L | L | D |
| 32A | – | – | – | – | – | – | – | – | – | A | – | – | – | – | L | – | – | – | – | – |
| 32B | – | – | | | | | | | | | | | | | | | | | | |

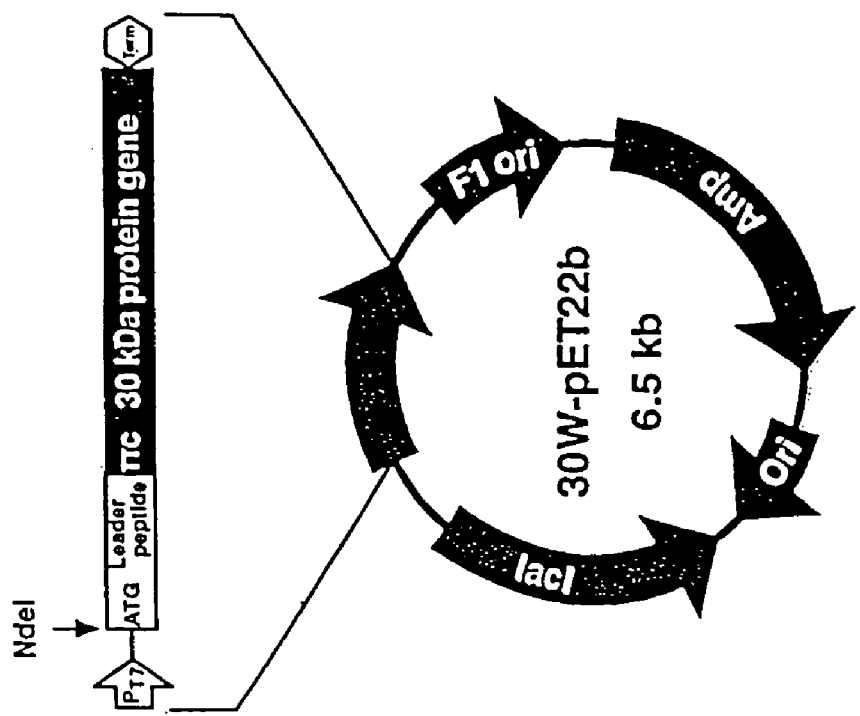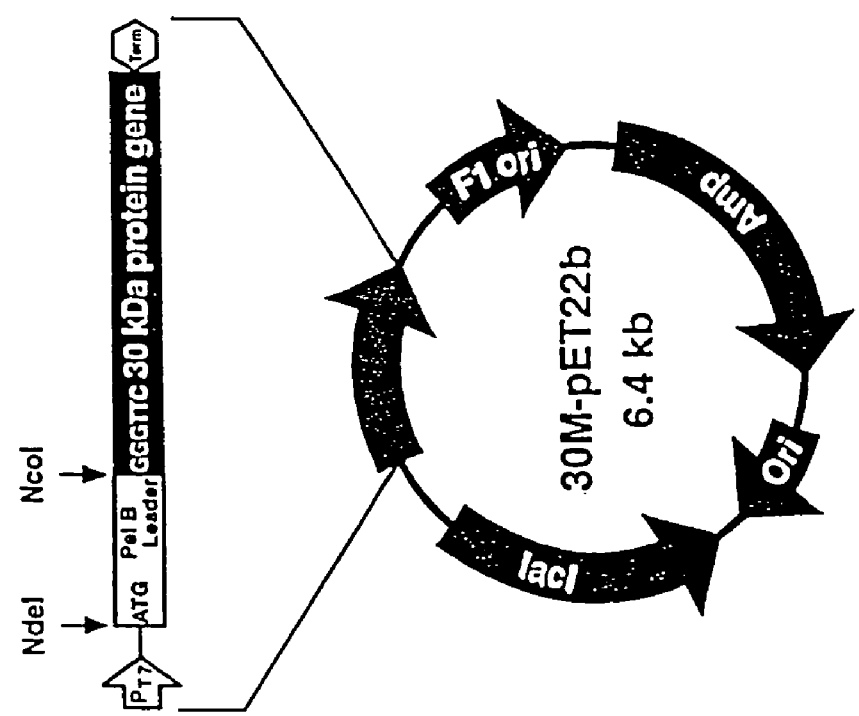
FIG. 14

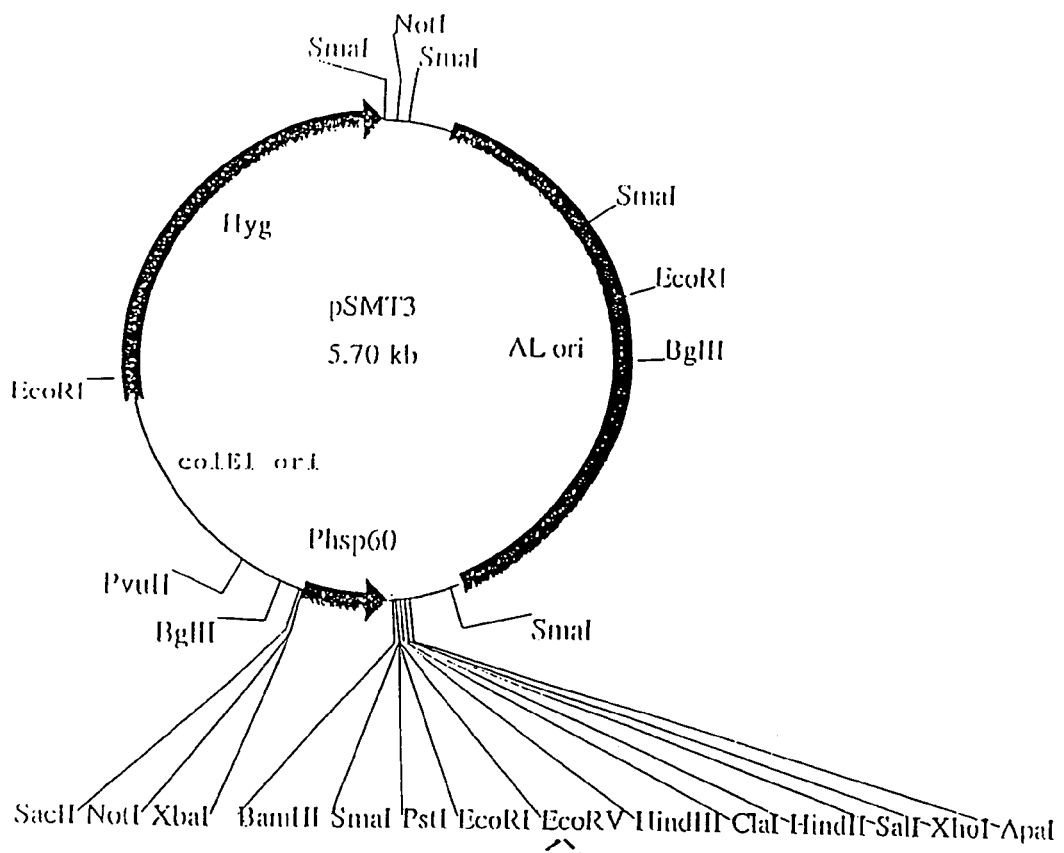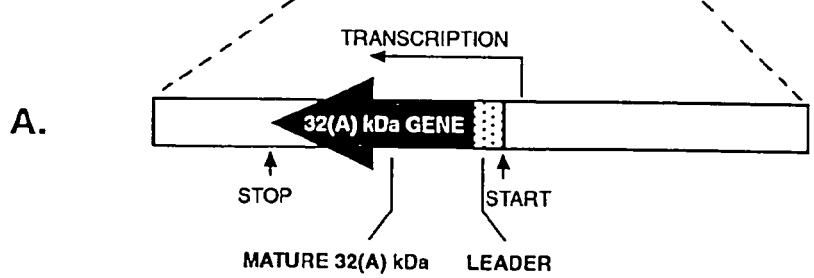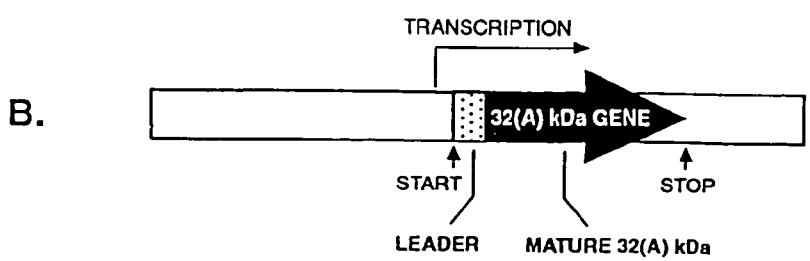
FIG. 19

ABUNDANT EXTRACELLULAR PRODUCTS AND METHODS FOR THEIR PRODUCTION AND USE

CROSS-REFERENCE TO RELATED APPLICATIONS

This application is a continuation-in-part of U.S. patent application Ser. No. 08/786,533 filed on Jan. 21, 1997, now abandoned, which is a continuation-in-part of U.S. patent application Ser. No. 08/652,842, filed on May 23, 1996, now abandoned, which is a continuation-in-part of U.S. patent application Ser. No. 08/568,357 filed on Dec. 6, 1996, now abandoned, which is a continuation-in-part of U.S. patent application Ser. No. 08/551,149 filed on Oct. 31, 1995, now abandoned, which is a continuation-in-part of U.S. patent application Ser. No. 08/447,398 filed on May 23, 1995, now U.S. Pat. No. 6,761,894, which is a continuation-in-part of U.S. patent application Ser. No. 08/289,667 filed on Aug. 12, 1994, now abandoned, which is a continuation-in-part of U.S. patent application Ser. No. 08/156,358 filed on Nov. 23, 1993, now U.S. Pat. No. 6,752,993, all incorporated herein by reference.

This application is also a continuation-in-part of U.S. patent application Ser. No. 08/545,926, filed on Oct. 20, 1995, now abandoned, which is a continuation-in-part of U.S. patent application Ser. No. 08/447,398 filed on May 23, 1995, now U.S. Pat. No. 6,761,894, which is a continuation-in-part of U.S. patent application Ser. No. 08/289,667 filed on Aug. 12, 1994, now abandoned, which is a continuation-in-part of U.S. patent application Ser. No. 08/156,358 filed on Nov. 23, 1993, now U.S. Pat. No. 6,752,993, all incorporated herein by reference.

REFERENCE TO GOVERNMENT

This invention was made with Government support under Grant No. AI-31338 awarded by the Department of Health and Human Services. The Government has certain rights in this invention.

FIELD OF THE INVENTION

The present invention generally relates to immunotherapeutic agents and vaccines against pathogenic organisms such as bacteria, protozoa, viruses and fungus. More specifically, unlike prior art vaccines and immunotherapeutic agents based upon pathogenic subunits or products which exhibit the greatest or most specific molecular immunogenicity, the present invention uses the most prevalent or majorly abundant immunogenic determinants released by a selected pathogen such as *Mycobacterium tuberculosis* to stimulate an effective immune response in mammalian hosts. Accordingly, the acquired immunity and immunotherapeutic activity produced through the present invention is directed to those antigenic markers which are displayed most often on infected host cells during the course of a pathogenic infection without particular regard to the relative or absolute immunogenicity of the administered compound.

BACKGROUND OF THE INVENTION

It has long been recognized that parasitic microorganisms possess the ability to infect animals thereby causing disease and often the death of the host. Pathogenic agents have been a leading cause of death through-out history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic vectors is evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium* and the genus *Legionella*, complete all or part of their life cycle within the cells of the infected host organism rather than extracellularly. Around the world, intracellular bacteria are responsible for millions of deaths each year and untold suffering. Tuberculosis, caused by *Mycobacterium tuberculosis*, is the leading cause of death from infectious disease worldwide, with 10 million new cases and 2.9 million deaths every year. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, and Legionellosis including Legionnaires3 disease. At this time, relatively little can be done to prevent debilitating infections in susceptible individuals exposed to these organisms.

Due to this inability to effectively protect populations from tuberculosis and the inherent human morbidity and mortality caused by tuberculosis, this is one of the most important diseases confronting mankind. More specifically, human pulmonary tuberculosis primarily caused by *M. tuberculosis* is a major cause of death in developing countries. Capable of surviving inside macrophages and monocytes, *M. tuberculosis* may produce a chronic intracellular infection. By concealing itself within the cells primarily responsible for the detection of foreign elements and subsequent activation of the immune system, *M. tuberculosis* is relatively successful in evading the normal defenses of the host organism. These same pathogenic characteristics have heretofore prevented the development of an effective immunotherapeutic agent or vaccine against tubercular infections. At the same time tubercle bacilli are relatively easy to culture and observe under laboratory conditions. Accordingly, *M. tuberculosis* is particularly well suited for demonstrating the principles and advantages of the present invention.

Those skilled in the art will appreciate that the following exemplary discussion of *M. tuberculosis* is in no way intended to limit the scope of the present invention to the treatment of *M. tuberculosis*. Similarly, the teachings herein are not limited in any way to the treatment of tubercular infections. On the contrary, this invention may be used to advantageously provide safe and effective vaccines and immunotherapeutic agents against the immunogenic determinants of any pathogenic agent expressing extracellular products and thereby inhibit the infectious transmission of those organisms.

Currently it is believed that approximately half of the world's population is infected by *M. tuberculosis* resulting in millions of cases of pulmonary tuberculosis annually. While this disease is a particularly acute health problem in the developing countries of Latin America, Africa, and Asia, it is also becoming more prevalent in the first world. In the United States specific populations are at increased risk, especially urban poor, immunocompromised individuals and immigrants from areas of high disease prevalence. Largely due to the AIDS epidemic the incidence of tuberculosis is presently increasing in developed countries, often in the form of multi-drug resistant *M. tuberculosis.*

Recently, tuberculosis resistance to one or more drugs was reported in 36 of the 50 United States. In New York City, one-third of all cases tested in 1991 were resistant to one or more major drugs. Though nonresistant tuberculosis can be cured with a long course of antibiotics, the outlook regarding drug resistant strains is bleak. Patients infected with strains resistant to two or more major antibiotics have a fatality rate of around 50%. Accordingly, a safe and effective vaccine against such varieties of *M. tuberculosis* is sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of the bones, spleen, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic but possibly contagious.

When *M. tuberculosis* is not controlled by the infected subject, it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation.

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic vector of the genus *Mycobacterium* is *M. leprae* which causes millions of cases of the ancient disease leprosy. Other species of this genus which cause disease in animals and man include *M. kansasii, M. avium intracellulare, M. fortuitum, M. marinum, M. chelonei, M. africanum, M. ulcerans, M. microti* and *M. scrofulaceum.* The pathogenic mycobacterial species frequently exhibit a high degree of homology in their respective DNA and corresponding protein sequences and some species, such as *M. tuberculosis* and *M. bovis* are highly related.

For obvious practical and moral reasons, initial work in humans to determine the efficacy of experimental compositions with regard to such afflictions is infeasible. Accordingly, in the early development of any drug or vaccine it is standard procedure to employ appropriate animal models for reasons of safety and expense. The success of implementing laboratory animal models is predicated on the understanding that immunodominant epitopes are frequently active in different host species. Thus, an immunogenic determinant in one species, for example a rodent or guinea pig, will generally be immunoreactive in a different species such as in humans. Only after the appropriate animal models are sufficiently developed will clinical trials in humans be carried out to further demonstrate the safety and efficacy of a vaccine in man.

With regard to alveolar or pulmonary infections by *M. tuberculosis,* the guinea pig model closely resembles the human pathology of the disease in many respects. Accordingly, it is well understood by those skilled in the art that it is appropriate to extrapolate the guinea pig model of this disease to humans and other mammals. As with humans, guinea pigs are susceptible to tubercular infection with low doses of the aerosolized human pathogen *M. tuberculosis.* Unlike humans where the initial infection is usually controlled, guinea pigs consistently develop disseminated disease upon exposure to the aerosolized pathogen, facilitating subsequent analysis. Further, both guinea pigs and humans display cutaneous delayed-type hypersensitivity reactions characterized by the development of a dense mononuclear cell induration or rigid area at the skin test site. Finally, the characteristic tubercular lesions of humans and guinea pigs exhibit similar morphology including the presence of Langhans giant cells. As guinea pigs are more susceptible to initial infection and progression of the disease than humans, any protection conferred in experiments using this animal model provides a strong indication that the same protective immunity may be generated in man or other less susceptible mammals. Accordingly, for purposes of explanation only and not for purposes of limitation, the present invention will be primarily demonstrated in the exemplary context of guinea pigs as the mammalian host. Those skilled in the art will appreciate that the present invention may be practiced with other mammalian hosts including humans and domesticated animals.

Any animal or human infected with a pathogenic vector and, in particular, an intracellular organism presents a difficult challenge to the host immune system. While many infectious agents may be effectively controlled by the humoral response and corresponding production of protective antibodies, these mechanisms are primarily effective only against those pathogens located in the body's extracellular fluid. In particular, opsonizing antibodies bind to extracellular foreign agents thereby rendering them susceptible to phagocytosis and subsequent intracellular killing. Yet this is not the case for other pathogens. For example, previous studies have indicated that the humoral immune response does not appear to play a significant protective role against infections by intracellular bacteria such as *M. tuberculosis*. However, the present invention may generate a beneficial humoral response to the target pathogen and, as such, its effectiveness is not limited to any specific component of the stimulated immune response.

More specifically, antibody mediated defenses seemingly do not prevent the initial infection of intracellular pathogens and are ineffectual once the bacteria are sequestered within the cells of the host. As water soluble proteins, antibodies can permeate the extracellular fluid and blood, but have difficulty migrating across the lipid membranes of cells. Further, the production of opsonizing antibodies against bacterial surface structures may actually assist intracellular pathogens in entering the host cell. Accordingly, any effective prophylactic measure against intracellular agents, such as *Mycobacterium*, should incorporate an aggressive cell-mediated immune response component leading to the rapid proliferation of antigen specific lymphocytes which activate the compromised phagocytes or cytotoxically eliminate them. However, as will be discussed in detail below, inducing a cell-mediated immune response does not equal the induction of protective immunity. Though cell-mediated immunity may be a prerequisite to protective immunity, the production of vaccines in accordance with the teachings of the present invention requires animal based challenge studies.

This cell-mediated immune response generally involves two steps. The initial step, signaling that the cell is infected, is accomplished by special molecules (major histocompatibility or MHC molecules) which deliver pieces of the pathogen to the surface of the cell. These MHC molecules bind to small fragments of bacterial proteins which have been degraded within the infected cell and present them at the surface of the cell. Their presentation to T-cells stimulates the immune system of the host to eliminate the infected host cell or induces the host cell to eradicate any bacteria residing within.

Unlike most infectious bacteria *Mycobacterium*, including *M. tuberculosis*, tend to proliferate in vacuoles which are substantially sealed off from the rest of the cell by a membrane. Phagocytes naturally form these protective vacuoles making them particularly susceptible to infection by this class of pathogen. In such vacuoles the bacteria are effectively protected from degradation, making it difficult for the immune system to present integral bacterial components on the surface of infected cells. However, the infected cell's MHC molecules will move to the vacuole and collect any free (released) bacterial products or move to other sites in the host cell to which the foreign extracellular bacterial products have been transported for normal presentation of the products at the cell surface. As previously indicated, the presentation of the foreign bacterial products will provoke the proper response by the host immune system.

The problems intracellular pathogens pose for the immune system also constitute a special challenge to vaccine development. Thus far, the production of an effective vaccine against *Mycobacterium* infections and, in particular, against *M. tuberculosis* has eluded most researchers. At the present time the only widely available vaccine against intracellular pathogens is the live attenuated vaccine BCG, an avirulent strain of *M. bovis*, which is used as a prophylactic measure against the tubercle bacillus. Yet in 1988, extensive World Health Organization studies from India determined that the efficacy of the best BCG vaccines was so slight as to be unmeasurable. Despite this questionable efficacy, BCG vaccine has been extensively employed in high incidence areas of tuberculosis throughout the world. Complicating the matter even further individuals who have been vaccinated with BCG will often develop sensitivity to tuberculin which negates the usefulness of the most common skin test for tuberculosis screening and control.

Another serious problem involving the use of a live, attenuated vaccine such as BCG is the possibility of initiating a life-threatening disease in immunocompromised patients. These vaccines pose a particular risk for persons with depressed cell-mediated immunity because of their diminished capacity to fight a rapidly proliferating induced infection. Such individuals include those weakened by malnourishment and inferior living conditions, organ transplant recipients, and persons infected with HIV. In the case of BCG vaccine, high risk individuals also include those suffering from lung disorders such as emphysema, chronic bronchitis, pneumoconiosis, silicosis or previous tuberculosis. Accordingly, the use of attenuated vaccines is limited in the very population where they have the greatest potential benefit.

The use of live attenuated vaccines may also produce other undesirable side effects. Because live vaccines reproduce in the recipient, they provoke a broader range of antibodies and a less directed cell-mediated immune response than noninfectious vaccines. Often this shotgun approach tends to occlude the immune response directed at the molecular structures most involved in cellular prophylaxis. Moreover, the use of live vaccines with an intact membrane may induce opsonizing antibodies which prepare a foreign body for effective phagocytosis. Thus, upon host exposure to virulent strains of the target organism, the presence of such antibodies could actually enhance the uptake of nonattenuated pathogens into host cells where they can survive and multiply. Further, an attenuated vaccine contains thousands of different molecular species and consequently is more likely to contain a molecular species that is toxic or able to provoke an adverse immune response in the patient. Other problems with live vaccines include virulence reversion, natural spread to contacts, contaminating viruses and viral interference, and difficulty with standardization.

Similarly, noninfectious vaccines, such as killed organisms or conventional second generation subunit vaccines directed at strongly antigenic membrane bound structures, are limited with respect to the inhibition of intracellular bacteria. Like attenuated vaccines, killed bacteria provoke an indiscriminate response which may inhibit the most effective prophylactic determinants. Further, killed vaccines still present large numbers of potentially antigenic structures to the immune system thereby increasing the likelihood of toxic reactions or opsonization by the immune system. Traditional subunit vaccines incorporating membrane bound structures, whether synthesized or purified, can also induce a strong opsonic effect facilitating the entry of the intracellular pathogen into phagocytes in which they multiply. By increasing the rate of bacterial inclusion, killed vaccines directed to intracellular surface antigens may increase the relative virulence of the pathogenic agent. Thus, conventional attenuated or killed vaccines directed against strongly antigenic bacterial surface components may be contraindicated in the case of intracellular pathogens.

In order to circumvent the problems associated with the use of traditional vaccines, developments have been made using extracellular proteins or their immunogenic analogs to stimulate protective immunity against specific intracellular pathogens. For example, this inventor's U.S. Pat. No. 5,108,745, issued Apr. 28, 1992 discloses vaccines and methods of producing protective immunity against *Legionella pneumophila* and *M. tuberculosis* as well as other intracellular pathogens. These prior art vaccines are broadly based on extracellular products originally derived from proteinaceous compounds released extracellularly by the pathogenic bacteria into broth culture in vitro and released extracellularly by bacteria within infected host cells in vivo. As disclosed therein, these vaccines are selectively based on the identification of extracellular products or their analogs which stimulate a strong immune response against the target pathogen in a mammalian host.

More specifically, these prior art candidate extracellular proteins were screened by determining their ability to provoke either a strong lymphocyte proliferative response or a cutaneous delayed-type hypersensitivity response in mammals which were immune to the pathogen of interest. Though this disclosed method and associated vaccines avoid many of the drawbacks inherent in the use of traditional vaccines, conflicting immunoresponsive results due to cross-reactivity and host variation may complicate the selection of effective immunizing agents. Thus, while molecular immunogenicity is one indication of an effective vaccine, other factors may complicate its use in eliciting an effective immune response in vivo.

More importantly, it surprisingly was discovered that, particularly with respect to *M. tuberculosis*, conventional prior art methods for identifying effective protective immunity inducing vaccines were cumbersome and potentially ineffective. For example, SDS-PAGE analysis of bulk *M. tuberculosis* extracellular protein followed by conventional Western blot techniques aimed at identifying the most immunogenic of these extracellular components produced inconsistent results. Repeated testing failed to identify which extracellular product would produce the strongest immunogenic response and, consistent with prior art thinking, thereby function as the most effective vaccine. Many of the extracellular products of *M. tuberculosis* are well known in the art, having been identified and, in some cases, sequenced. Further, like any foreign protein, it can be shown that these known compounds induce an immune response. However, nothing in the art directly indicates that any of these known compounds will induce protective immunity as traditionally identified.

Accordingly, it is a principal object of the present invention to provide vaccines or immunotherapeutic agents and methods for their production and use in mounting an effective immune response against infectious bacterial pathogens which do not rely upon traditional vaccine considerations and selection techniques based upon highly specific, strongly immunogenic operability.

It is another object of the present invention to provide vaccines or immunotherapeutic agents and methods for their use to impart acquired immunity in a mammalian host against intracellular pathogens including *M. tuberculosis, M. bovis, M. kansasii, M. avium-intracellulare, M. fortuitum, M. chelonei, M. marinum, M. scrofulaceum, M. leprae, M. africanum, M. ulcerans* and *M. microti*.

It is an additional object of the present invention to provide easily produced vaccines and immunotherapeutic agents exhibiting reduced toxicity relative to killed or attenuated vaccines.

SUMMARY OF THE INVENTION

The present invention accomplishes the above-described and other objects by providing compounds for use as vaccines and/or immunotherapeutic agents and methods for their production and use to generate protective or therapeutic immune responses in mammalian hosts against infection by pathogens. In a broad aspect, the invention provides the means to induce a protective or therapeutic immune response against infectious vectors producing extracellular compounds. While the compounds of the present invention are particularly effective against pathogenic bacteria, they may be used to generate a protective or therapeutic immune response to any pathogen. producing majorly abundant extracellular products.

For purposes of the present invention, the term "majorly abundant" should be understood as a relative term identifying those extracellular products released in the greatest quantity by the pathogen of interest. For example, with respect to *M. tuberculosis* grown under various conditions of culture to an optical density of approximately 0.5, one skilled in the art should expect to obtain on the order of 10 mg/L or more of a majorly abundant extracellular product. Thus, out of the total exemplary 4 mg/L total output of extracellular product for *M tuberculosis* grown under normal or heat shock conditions, approximately fifteen to twenty (alone or in combination) of the one hundred or so known extracellular products will constitute approximately ninety percent of the total quantity. These are the majorly abundant extracellular products contemplated as being within the scope of the present invention and are readily identifiable as the broad bands appearing in SDS/PAGE gels. In addition, the extracellular products of interest may further be characterized and differentiated by amino acid sequencing. The remaining extracellular products are minor. Those skilled in the art will also appreciate that the relative quantitative abundance of specific major extracellular products may vary depending upon conditions of culture. However, in most cases, the identification of an individual majorly abundant extracellular product will not change.

Accordingly, the present invention may be used to protect a mammalian host against infection by viral, bacterial, fungal or protozoan pathogens. It should be noted that in some cases, such as in viral infections, the majorly abundant extracellular products may be generated by the infected host cell. While active against all microorganisms releasing majorly abundant extracellular products, the vaccines and methods of the present invention are particularly effective in generating protective immunity against intracellular pathogens, including various species and serogroups of the genus *Mycobacterium*. The vaccines of the present invention are also effective as immunotherapeutic agents for the treatment of existing disease conditions.

Surprisingly, it has been found by this inventor that immunization with the most or majorly abundant products released extracellularly by bacterial pathogens or their immunogenic analogs can provoke an effective immune response irrespective of the absolute immunogenicity of the administered compound. Due to their release from the organism and hence their availability to host molecules involved in antigen processing and presentation and due to their naturally high concentration in tissue during infection, the majorly abundant extracellular products of a pathogenic agent are processed and presented to the host immune system more often than other bacterial components. In the case of intracellular pathogens, the majorly abundant extracellular products are the principal immunogenic determinants presented on the surface of the infected host cells and therefore exhibit a greater presence in the surrounding environment. Accordingly, acquired immunity against the majorly abundant extracellular products of a pathogenic organism allows the host defense system to swiftly detect pathogens sequestered inside host cells and effectively inhibit them.

More particularly, the principal or majorly abundant products released by pathogenic bacteria appear to be processed by phagocytes and other host immune system mechanisms at a greater rate than less prevalent or membrane bound pathogenic components regardless of their respective immunogenic activity or specificity. This immunoprocessing disparity is particularly significant when the pathogenic agent is an intracellular bacteria sequestered from normal immune activity. By virtue of their profuse and continual presentation to the infected host's immune system, the most prevalent bacterial extracellular products or their immunogenic analogs provoke a vigorous immune response largely irrespective of their individual molecular immunogenic characteristics.

Majorly abundant extracellular products are the principal constituents of proteins and other molecular entities which are released by the target pathogen into the surrounding environment. Current research indicates that in some instances a single majorly abundant extracellular product may comprise up to 40% by weight of the products released by a microorganism. More often, individual majorly abundant extracellular products account for between from about 0.5% to about 25% of the total products released by the infectious pathogen. Moreover, the top five or six majorly abundant extracellular products may be found to comprise between 60% to 70% of the total mass released by a microorganism. Of course those skilled in the art will appreciate that the relative levels of extracellular products may fluctuate over time as can the absolute or relative quantity of products released. For example, pH, oxidants, osmolality, heat and other conditions of stress on the organism, stage of life cycle, reproducetion status and the composition of the surrounding environment may alter the composition and quantity of products released. Further, the absolute and relative levels of extracellular products may differ greatly from species to species and even between strains within a species.

In the case of intracellular pathogens extracellular products appear to expand the population of specifically immune lymphocytes capable of detecting and exerting an antimicrobial effect against macrophages containing live bacteria. Further, by virtue of their repeated display on the surface of infected cells, the majorly abundant or principal extracellular products function as effective antigenic markers. Accordingly, pursuant to the teachings of the present invention, vaccination and the inducement of protective immunity directed to the majorly abundant extracelluar products of a pathogenic bacteria or their immunogenically equivalent determinants, prompts the host immune system to mount a rapid and efficient immune response with a strong cell-mediated component when subsequently infected by the target pathogen.

In direct contrast to prior art immunization activeities which have primarily been focused on the production of vaccines and the stimulation of immune responses based upon the highly specific molecular antigenicity of individuall screened pathogen components, the present invention advantageously exploits the relative abundance of bacterial extracellular products or their immunogenic analogs (rather than their immunogenic specificities) to establish or induce protective immunity with compounds which may actually exhibit lower immunogenic specificity than less prevalent extracellular products. For the purposes of this disclosure an immunogenic analog is any molecule or compound sufficiently analogous to at least one majorly abundant extracellular product expressed by the target pathogen, or any fraction thereof, to have the capacity to stimulate a protective immune response in a vaccinated mammalian host upon subsequent infection by the target pathogen. In short, the vaccines of the present invention are identified or produced by selecting the majorly abundant product or products released extracellularly by a specific pathogen (or molecular analogs capable of stimulating a substantially equivalent immune response) and isolating them in a relatively pure form or subsequently sequencing the DNA or RNA responsible for their production to enable their synthetic or endogenous production. The desired prophylactic immune response to the target pathogen may then be elicited by formulating one or more of the isolated immunoreactive products or the encoding genetic material using techniques well known in the art and immunizing a mammalian host prior to infection by the target pathogen.

It is anticipated that the present invention will consist of at least one, two or, possibly even several well defined immunogenic determinants. As a result, the present invention produces consistent, standardized vaccines which may be developed, tested and administered with relative ease and speed. Further, the use of a few well defined molecules corresponding to the majorly abundant secretory or extracellular products greatly reduces the risk of adverse side effects associated with conventional vaccines and eliminates the possible occlusion of effective immunogenic markers. Similarly, because the present invention is not an attenuated or a killed vaccine the risk of infection during production, purification or upon administration is effectively eliminated. As such, the vaccines of the present invention may be administered safely to immunocompromised individuals, including asymptomatic tuberculosis patients and those infected with HIV. Moreover, as the humoral immune response is directed exclusively to products released by the target pathogen, there is little chance of generating a detrimental opsonic immune component. Accordingly, the present invention allows the stimulated humoral response to assist in the elimination of the target pathogen from antibody susceptible areas.

Another beneficial aspect of the present invention is the ease by which the vaccines may be harvested or produced and subsequently purified and sequenced. For example, the predominantly abundant extracellular products may be obtained from cultures of the target pathogen, including *M. tuberculosis* or *M. bovis*, with little effort. As the desired compounds are released into the media during growth, they can readily be separated from the intrabacterial and membrane-bound components of the target pathogen utilizing conventional techniques. More preferably, the desired immunoreactive constituents of the vaccines of the present invention may be produced and purified from genetically engineered organisms into which the genes expressing the specific extracellular products of *M. tuberculosis, M. bovis, M. leprae* or any other pathogen of interest have been cloned. As known in the art, such engineered organisms can be modified to produce higher levels of the selected extracellular products or modified immunogenic analogs. Alternatively, the immunoprotective products, portions thereof or analogs thereof, can be chemically synthesized using techniques well known in the art or directly expressed in host cells injected with naked genes encoding therefor. Whatever production source is employed, the immunogenic components of the predominant or majorly abundant extracellular products may be separated and subsequently formulated into deliverable vaccines using common biochemical procedures such as fractionation, chromatography or other purification methodology and conventional formulation techniques or directly expressed in host cells containing directly introduced genetic constructs encoding therefor.

For example, in an exemplary embodiment of the present invention the target pathogen is *M. tuberculosis* and the majorly abundant products released extracellularly by *M. tuberculosis* into broth culture are separated from other bacterial components and used to elicit an immune response in mammalian hosts. Individual proteins or groups of proteins are then utilized in animal based challenge experiments to identify those which induce protective immunity making them suitable for use as vaccines in accordance with the teachings of the present invention. More specifically, following the growth and harvesting of the bacteria, by virtue of their physical abundance the principal extracellular products are separated from intrabacterial and other components through centrifugation and filtration. If desired, the resultant bulk filtrate is then subjected to fractionation using ammonium sulfate precipitation with subsequent dialysis to give a mixture of extracellular products, commonly termed EP. Solubilized extracellular products in the dialyzed fractions are then purified to substantial homogeneity using suitable chromatographic techniques as known in the art and as described more fully below.

These exemplary procedures result in the production of fourteen individual proteinaceous major extracellular products of *M. tuberculosis* having molecular weights ranging from 110 kilo Daltons (KD) to 12 KD. Following purification each individual majorly abundant extracellular product exhibits one band corresponding to its respective molecular weight when subjected to polyacrylamide gel electrophoresis thereby allowing individual products or groups of products corresponding to the majorly abundant extracellular products to be identified and prepared for use as vaccines in accordance with the teachings of the present invention. The purified majorly abundant extracellular products may further be characterized and distinguished by determining all or part of their respective amino acid sequences using techniques common in the art. sequencing may also provide information regarding possible structural relationships between the majorly abundant extracellular products.

Subsequently, immunization and the stimulation of acquired immunity in a mammalian host system may be accomplished through the teachings of the present invention utilizing a series of subcutaneous or intradermal injections of these purified extracellular products over a course of time. For example, injection with a purified majorly abundant bacterial extracellular product or products in incomplete Freund's adjuvant followed by a second injection in the same adjuvant approximately three weeks later can be used to elicit a protective response upon subsequent challenge with the virulent pathogen. Other exemplary immunization protocols within the scope and teachings of the present invention may include a series of three or four injections of purified extracellular product or products or their analogs in Syntex Adjuvant Formulation (SAF) over a period of time. While a series of injections may generally prove more efficacious, the single administration of a selected majorly abundant extracellular product or its immunogenic subunits or analogs can impart the desired immune response and is contemplated as being within the scope of the present invention as well.

Such exemplary protocols can be demonstrated using art accepted laboratory models such as guinea pigs. For example, as will be discussed in detail, immunization of several guinea pigs with a combination of five majorly abundant extracellular products (purified from *M. tuberculosis* as previously discussed) was accomplished with an immunization series of three injections of the bacterial products in SAF adjuvant with corresponding sham-immunization of control animals. Exemplary dosages of each protein ranged from 100 µg to 2 µg. Following the last vaccination all of the animals were simultaneously exposed to an infectious and potentially lethal dose of aerosolized *M. tuberculosis* and monitored for an extended period of time. The control animals showed a significant loss in weight when compared with the animals immunized with the combination of the majorly abundant extracellular products of *M. tuberculosis*. Moreover, half of the control animals died during the observation period while none of the immunized animals succumbed to *tuberculosis*. Autopsies conducted after this experiment revealed that the nonimmunized control animals had significantly more colony forming units (CFU) and corresponding damage in their lungs and spleens than the protected animals. Seventeen additional combinations of purified majorly abundant extracellular products provided immunoprophylaxis when tested, thereby demonstrating the scope of the present invention and broad range of vaccines which may be formulated in accordance with the teachings thereof.

However, it should be emphasized that the present invention is not restricted to combinations of secretory or extracellular products. For example, several alternative experimental protocols demonstrate the capacity of a single abundant extracellular product to induce mammalian protective immunity in accordance with the teachings of the present invention. In each experiment guinea pigs were immunized with a single majorly abundant extracellular product purified from *M. tuberculosis* EP using the chromatography protocols detailed herein. In one example the animals were vaccinated in multiple experiments with an adjuvant composition containing a purified abundant secretory product having a molecular weight corresponding to 30 KD. In another example of the present invention, different guinea pigs were vaccinated with an adjuvant composition containing an abundant extracellular product isolated from *M. tuberculosis* having a molecular weight corresponding to 71 KD. Following their respective immunizations both sets of animals and the appropriate controls were exposed to lethal doses of aerosolized *M. tuberculosis* to determine vaccine effectiveness.

More particularly, in one experiment six guinea pigs were immunized with 100 µg of 30 KD protein in SAF on three occasions spread over a period of six weeks. Control animals were simultaneously vaccinated with corresponding amounts of a bulk preparation of extracellular proteins (EP) or buffer. Three weeks after the final vaccination, the animals were challenged with an aerosolized lethal dose of *M. tuberculosis* and monitored for a period of 14 weeks. The 30 KD immunized guinea pigs and those immunized with the bulk extracellular preparation had survival rates of 67% and 50% respectively (illustrating the unexpectedly superior performance of the majorly abundant extracellular product versus EP), while the shamimmunized animals had a survival rate of only 17%. Upon termination of the experiment the animals were sacrificed and examined for viable tubercle bacilli. Not surprisingly, the nonimmunized animal showed markedly higher concentrations of *M. tuberculosis* in the lungs and spleen.

Similar experiments were performed on those animals vaccinated with 71 KD protein. In one experiment six guinea pigs were vaccinated with an SAF adjuvant composition containing 100 µg purified 71 KD protein two times over a period of three weeks. Other animals were similarly immunized with a bulk preparation of unpurified extracellular proteins or EP for use as a positive control and with buffer for use as a negative control. Following exposure to lethal doses of aerosolized tubercle bacilli the weight of the guinea pigs was monitored for a period of 6 months. Once again the animals immunized with the purified form of the abundant extracellular product developed protective immunity with respect to the virulent *M. tuberculosis*. By the end of that period the buffer immunized animals showed a significant loss in weight when compared with the immunized animals. Further, while the positive controls and 71 KD immunized animals had survival rates of 63% and 50% respectively, the nonimmunized animals all died before the end of the observation period.

It is important to note that the formulation of the vaccine is not critical to the present invention and may be optimized to facilitate administration. Solutions of the purified immunogenic determinants derived from the majorly abundant pathogenic extracellular products may be administered alone or in combination in any manner designed to generate a protective immune response. The purified protein solutions may be delivered alone, or formulated with an adjuvant before being administered.

Alternatively, genetic material encoding the genes for one or more of the immunogenic determinants derived from the majorly abundant pathogenic extracellular products may be coupled with eucaryotic promoter and/or secretion sequences and injected directly into a mammalian host to induce endogenous expression of the immunogenic determinants and subsequent protective immunity.

Other objects, features and advantages of the present invention will be apparent to those skilled in the art from a consideration of the following detailed description of preferred exemplary embodiments thereof taken in conjunction with the figures which will first be described briefly.

BRIEF DESCRIPTION OF THE DRAWINGS

FIG. 2 is a tabular representation identifying the five N-terminal amino acids of fourteen exemplary majorly abundant extracellular products of M. tuberculosis (Sequence ID Nos. 1-14) and the apparent molecular weight for such products.

FIG. 3 is a tabular representation of the extended N-terminal amino acid sequence of three exemplary majorly abundant secretory products of M tuberculosis (Sequence ID Nos. 15-17) which were not distinguished by the five N-terminal amino acids shown in FIG. 2.

FIG. 8a is a graph of the values measured at 2 days after incubation of lymphocytes with this antigen while

FIG. 12a illustrates the percentage of 24 guinea pigs immunized with the 30 KD protein responding to overlapping peptides (15-mer) covering the entire 30 KD protein sequence.

FIG. 14 provides a diagrammatic representation of the constructs used for the expression of recombinant 30 KD protein. the diagram depicts the pET22b vectors used for the expression of recombinant 30 KD protein. The vectors express the mature 30 KD protein fused to its own leader (30W-pET22b) or the plasmid encoded pel B leader (30M-pET22b). Abbreviations used: Ori, ColE1 type origin of replication; F1 ori, phage F1 origin of replication; Amp, ampicillin resistance gene; 30 W/M, full length (30 W) or mature (30M) 30 KD protein; lacI, lac repressor gene; $P_{T7}$, phage T7 RNA polymerase specific promoter; NdeI and NcoI restriction enzyme sites at vector/insert junctions.

FIG. 19 provides a diagrammatic representation of the constructs used for the expression of recombinant 32A KD protein. The diagram depicts the pSMT3 vector used for the expression of recombinant 32A KD protein. In (A) the DNA fragment carrying the gene for the 32A KD protein is arranged in the opposite direction from the hsp 60 promoter. In (B) the DNA fragment carrying the gene for the 32A KD protein is arranged in the same direction as the hsp 60 promoter.

FIG. 25 depicts the survival of animals immunized with proteins in the presence of adjuvant only and in the presence of adjuvant and IL-12.

DETAILED DESCRIPTION

Figure 1D:
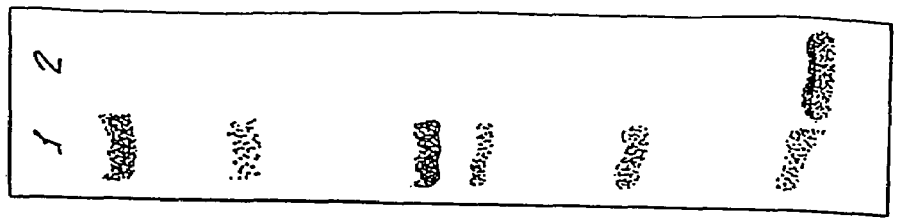
FIG. 1 is a representation of 4 coomassie blue stained gels, labeled 1a to 1d, illustrating the purification of exemplary majorly abundant extracellular products of M. tuberculosis as identified by sodium deodecyl sulfate polyacrylamide gel electrophoresis (SDS-PAGE).

The present invention is directed to compounds and methods for their production and use against pathogenic organisms as vaccines and immunotherapeutic agents. More specifically, the present invention is directed to the production and use of majorly abundant extracellular products released by pathogenic organisms, their immunogenic analogs or the associated genetic material encoding therefor as vaccines or immunotherapeutic agents and to associated methods for generating protective immunity in mammalian hosts against infection. These compounds will be referred to as vaccines throughout this application for purposes of simplicity.

In exemplary embodiments, illustrative of the teachings of the present invention, the majorly abundant extracellular products of *M. tuberculosis* were distinguished and subsequently purified. Guinea pigs were immunized with purified forms of these majorly prevalent extracellular products with no determination of the individual product's specific molecular immunogenicity. Further, the exemplary immunizations were carried out using the purified extracellular products alone or in combination and with various dosages and routes of administration. Those skilled in the art will recognize that the foregoing strategy can be utilized with any pathogenic organism or bacteria to practice the method of the present invention and, accordingly, the present invention is not specifically limited to vaccines and methods directed against *M. tuberculosis*.

In these exemplary embodiments, the majorly abundant extracellular products of *M. tuberculosis* were separated and purified using column chromatography. Determination of the relative abundance and purification of the extracellular products was accomplished using polyacrylamide gel electrophoresis. Following purification of the vaccine components, guinea pigs were vaccinated with the majorly abundant extracellular products alone or in combination and subsequently challenged with *M. tuberculosis*. As will be discussed in detail, in addition to developing the expected measurable responses to these extracellular products following immunization, the vaccines of the present invention unexpectedly conferred an effective immunity in these laboratory animals against subsequent lethal doses of aerosolized *M. tuberculosis*.

While these exemplary embodiments used purified forms of the extracellular products, those skilled in the art will appreciate that the present invention may easily be practiced using immunogenic analogs which are produced through recombinant means or other forms of chemical synthesis using techniques well known in the art. Further, immunogenic analogs, homologs or selected segments of the majorly abundant extracellular products may be employed in lieu of the naturally occurring products within the scope and teaching of the present invention.

A further understanding of the present invention will be provided to those skilled in the art from the following nonlimiting examples which illustrate exemplary protocols for the identification, isolation, production and use of majorly abundant extracellular products (alone and in combination) as vaccines.

EXAMPLE 1

Isolation and Production of Bulk Extracellular Proteins (EP) from *Mycobacterium tuberculosis*

*M. tuberculosis* Erdman strain (ATCC 35801) was obtained from the American Tissue Culture Collection (Rockville, Md.). The lyophilized bacteria were reconstituted in Middlebrook 7H9 culture medium (Difco Laboratories, Detroit, Mich.) and maintained on Middlebrook 7H11 agar. 7H11 agar was prepared using Bacto Middlebrook 7H10 agar (Difco), OADC Enrichment Medium (Difco), 0.1% casein enzymatic hydrolysate (Sigma), and glycerol as previously described by Cohn (Cohn, M.1., *Am. Rev. Respir. Dis.* 98:295-296) and incorporated herein by reference. Following sterilization by autoclaving, the agar was dispensed into bacteriologic petri dishes (100 by 15 mm) and allowed to cool.

*M. tuberculosis* was then plated using sterile techniques and grown at 37° C. in 5% $CO_2$-95% air, 100% humidity. After culture on 7H11 for 7 days, the colonies were scraped from the plates, suspended in 7H9 broth to $10^8$ CFU/ml and aliquoted into 1.8-ml Nunc cryotubes (Roskilde, Denmark). Each liter of the broth was prepared by rehydrating 4.7 g of Bacto Middlebrook 7H9 powder with 998 ml of distilled water, and 2 ml of glycerol (Sigma Chemical Co., St. Louis, Mo.) before adjusting the mixture to a pH value of 6.75 and autoclaving the broth for 15 min at 121° C. The aliquoted cells were then slowly frozen and stored at −70° C. Cells stored under these conditions remained viable indefinitely and were used as needed.

Figure 1C:
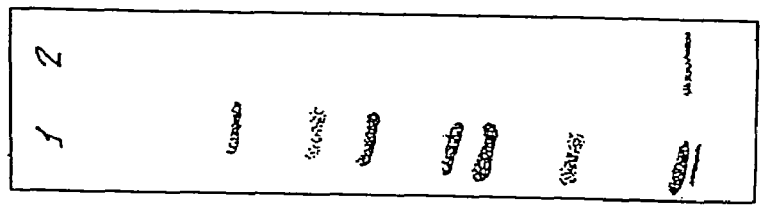

Bulk extracellular protein (EP) preparations were obtained from cultures of *M. tuberculosis* grown in the Middlebrook 7H9 broth made as above. Following reconstitution, 150 ml aliquots of the broth were autoclaved for 15 min at 121° C. and dispensed into vented Co-star 225 cm² tissue culture flasks. *M. tuberculosis* cells stored at −70° C. as described in the previous paragraph were thawed and used to inoculate 7H11 agar plates. After culture for 7 days, the colonies were scraped from the plates, suspended in a few ml of 7H9 broth, and sonicated in a water bath to form a single cell suspension. The *M. tuberculosis* cells were suspended in the sterile 150 ml aliquots at an initial optical density of 0.05, as determined by a Perkin-Elmer Junior model 35 spectrophotometer (Norwalk, Conn.). The cells were then incubated at 37° C. in 5% $CO_2$-95% air for 3 weeks until the suspension showed an optical density of 0.4 to 0.5. These cultures were used as stock bottles for subsequent cultures also in 7H9 broth. The stock bottles were sonicated in a water bath to form a single cell suspension. The *M. tuberculosis* cells were then diluted in 7H9 broth to an initial optical density of 0.05 and incubated at 37° C. in 5% $CO^2$-95% air for 2½ to 3 weeks until the suspension showed an optical density of 0.4 to 0.5. Culture supernatant was then decanted and filter sterilized sequentially through 0.8 μm and 0.2 μm low-protein-binding filters (Gelman Sciences Inc., Ann Arbor, Mich.). The filtrate was then concentrated approximately 35 fold in a Filtron Minisette with an Omega membrane having a 10 KD cutoff and stored at 4° C. Analysis of the bulk extracellular protein preparation by sodium deodecyl sulfate-polyacrylamide gel electrophoresis (SDS-PAGE) revealed a protein composition with multiple bands. Bulk extracellular protein mixture (EP) was prepared by obtaining a 40-95% ammonium sulfate cut of the culture filtrate.

EXAMPLE 2

Purification of Principal Majorly Abundant Extracellular Products of *Mycobacterium tuberculosis*

Ammonium sulfate (grade I, Sigma) was added to the sterile culture filtrate of Example 1 in concentrations ranging from 10% to 95% at 0° C. and gently stirred to fractionate the proteins. The suspension was then transferred to plastic bottles and centrifuged in a swinging bucket rotor at 3,000 rpm on a RC3B Sorvall Centrifuge to pellet the resulting precipitate. The supernatant fluid was decanted and, depending on the product of interest, the supernatant fluid or pellet was subjected to further purification. When the product of interest was contained in the supernatant fluid a second ammonium sulfate cut was executed by increasing the salt concentration above that of the first cut. After a period of gentle stirring the solution was then centrifuged as previously described to precipitate the desired product and the second supernatant fluid was subjected to further purification.

Following centrifugation, the precipitated proteins were resolubilized in the appropriate cold buffer and dialyzed extensively in a Spectrapor dialysis membrane (Spectrum Medical Industries, Los Angeles, Calif.) with a 6,000 to 8,000 molecular weight cut-off to remove the salt. Extracellular protein concentration was determined by a bicinchoninic acid protein assay (Pierce Chemical Co., Rockford, Ill.) and fraction components were determined using SDS-PAGE. The fractions were then applied to chromatography columns for further purification.

Using the general scheme outlined immediately above fourteen extracellular products were purified from the bulk extracellular protein filtrate obtained by the process detailed in Example 1. The exact ammonium sulfate precipitation procedure and chromatography protocol is detailed below for each extracellular product isolated.

A. 110 KD Extracellular Product

1. A 50-100% ammonium sulfate precipitate was obtained as discussed above.
2. The resolubilized precipitate was dialyzed and applied to a DEAE Sepharose CL-6B or QAE Sepharose ion exchange column in column buffer consisting of 10% sorbitol, 10 mM potassium phosphate, pH 7, 5 mM 2-mercaptoethanol, and 0.2 mM EDTA and eluted with a sodium chloride gradient. Fractions containing 110 KD protein elute at approximately 550 mM salt and were collected.
3. Collected fractions were applied to S200 Sepharose size fractionation column in PBS (phosphate buffered saline) buffer. The protein eluted as a homogeneous 110 KD protein.

B. 80 KD Extracellular Product

1. The 0-25% ammonium sulfate cut (1 hour at 0° C.) was discarded and the 25-60% ammonium sulfate cut (overnight at 0° C.) was retained as discussed above.
2. A DEAE CL-6B column (Pharmacia) was charged with 25 mM Tris, pH 8.7 containing 1M NaCl and equilibrated with 25 mM Tris, pH 8.7, 10 mM NaCl and the protein sample was dialyzed against 25mM Tris, pH 8.7, 10 mM NaCl and applied to the column.

The column was washed overnight with the same buffer. A first salt gradient of 10 mM to 200 mM NaCl in 25 mM Tris, pH 8.7 was run through the column to elute other proteins. A second salt gradient (200 to 300 mM NaCl) was run through the column and the 80 KD protein eluted at approximately 275 mM NaCl.

3. A Q-Sepharose HP column was charged with 25 mM Tris, pH 8.7, 1M NaCl and re-equilibrated to 25 mM Tris, pH 8.7, 10 mM NaCl. The protein sample was dialyzed against 25 mM Tris, ph 8.7, 10 mM NaCl and applied to the column. The column was washed in the same buffer and then eluted with 200-300 mM NaCl in 25 mM Tris, pH 8.7. 4. Fractions containing the 80 KD protein were collected and dialyzed against 25 mM Tris, pH 8.7, 10 mM NaCl, and then concentrated in a Speed-Vac concentrator to 1-2 ml. The protein sample was applied to a Superdex 75 column and eluted with 25 mM Tris, pH 8.7, 150 mM NaCl. The 80 KD protein eluted as a homogenous protein.

C. 71 KD Extracellular Product

1. A 40-95% ammonium sulfate precipitate was obtained as discussed above with the exception that the 71 KD product was cultured in 7H9 broth at pH 7.4 and at 0% $CO_2$ and heat-shocked at 42° C. for 3 h once per week. The precipitate was dialyzed against Initial Buffer (20 mM Hepes, 2 mM MgAc, 25 mM KCl, 10 mM $(NH4)_2SO_4$, 0.8 mM DL-Dithiothreitol, pH 7.0).
2. The resolubilized precipitate was applied to an ATP Agarose column equilibrated with Initial Buffer. Effluent was collected and reapplied to the ATP Agarose column. The 71 KD protein bound to the column.
3. Subsequently the ATP Agarose column was washed, first with Initial Buffer, then 1 M KCl, then Initial Buffer.
4. Homogeneous 71 KD protein was eluted from the column with 10 mM ATP and dialyzed against phosphate buffer.

D. 58 KD Extracellular Product

1. A 25-50% ammonium sulfate precipitate was obtained as discussed above.

2. The resolubilized precipitate was dialyzed and applied to a DEAE-Sepharose CL-6B or QAE-Sepharose column and eluted with NaCl. Collected fractions containing the 58 KD Protein eluted at approximately 400 mM NaCl.
3. Collected fractions were then applied to a Sepharose CL-6B size fractionation column. The protein eluted at approximately 670-700,000 Daltons.
4. The eluted protein was applied to a thiopropylsepharose column. The homogeneous 58 KD protein eluted at approximately 250-350 mM 2-mercaptoethanol. The eluted protein was monitored using SDS-PAGE and exhibited the single band shown in FIG. 1a, col. 2.

E. 45 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 2.5 mM Tris, pH 8.7 containing 1 M NaCl and equilibrated with 25 mM Tris, 10 mM NaCl, pH 8.7.
   b. The protein sample was dialyzed against 25 mM Tris, 10 mM NaCl, pH 8.7 and applied to column. The column was then washed overnight with the same buffer.
   c. The column was eluted with a salt gradient (10 mM to 200 mM) in 25 mM Tris, pH 8.7 buffer. The 45 KD protein eluted at approximately 40 mM NaCl.
3. a. A Q-Sepharose HP (Pharmacia) column was charged with 25 mM Tris, pH 8.7 containing 1 M NaCl and re-equilibrated with 25 mM Tris, 10 mM NaCl, pH 8.7.
   b. The protein sample was dialyzed against 25 mM Tris, 10 mM NaCl, pH 8.7 and applied to column with subsequent washing using the same buffer.
   c. The column was eluted with 10-150 mM NaCl in 25 mM Tris, pH 8.7.
4. a. Fractions containing the 45 KD product were collected, pooled and dialyzed against 25 mM Tris, 10 mM NaCl, pH 8.7, before concentration to 1 ml in a Speed Vac concentrator.
   b. Concentrate was Applied to Superdex 75 column equilibrated with 25 mM Tris 150 mM NaCl, pH 8.7. The product eluted as a homogeneous protein. The eluted protein was monitored using SDS-PAGE and resulted in the single band shown in FIG. 1B, col. 2.

F. 32 KD Extracellular Product (A)
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 mM Tris, 10 mM NaCl, pH 8.7.
   b. The protein sample was dialyzed against 25 mM Tris, 10 mM NaCl, pH 8.7 and applied to the column with subsequent washing overnight with same buffer.
   c. The column was eluted with a salt gradient (10 mM to 200 mM) in 25 mM Tris, pH 8.7 buffer. The 32 KD protein eluted at approximately 70 mM NaCl.
3. a. Fractions containing the 32 KD product were collected, pooled and dialyzed against 25 mM Tris, 10 mM NaCl, pH 8.7, before concentrating the protein sample to 1 ml in a Speed-Vac Concentrator.
   b. The concentrate was then Applied to a Superdex 75 column equilibrated with 25 mM Tris, 150 mM NaCl, pH 8.7 and eluted with this buffer. The 32 KD product eluted as homogeneous protein.
4. a. A Q-Sepharose HP column (Pharmacia) was charged with 25 mM Tris, pH 8.7 containing 1 M NaCl, and re-equilibrated with 25 mM Tris, 10 mM NaCl, pH 8.7.
   b. The protein sample was dialyzed against 25 mM Tris, 10 mM NaCl, pH 8.7 and applied to the column with subsequent washing in the same buffer.
   c. The column was eluted with a 100-300 mM NaCl gradient. Labeled 32A, the homogeneous protein elutes at approximately 120 mM NaCl and is shown as a single band in FIG. 1B, col. 4.

G. 32 KD Extracellular Product (B)
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 MM Tris, 10 mM NaCl, pH 8.7.
   b. The protein sample was dialyzed against 25 mM Tris, 10 mM NaCl, pH 8.7 and applied to the column with subsequent washing overnight with same buffer.
   c. A preliminary salt gradient of 10 mM to 200 mM NaCl in 25 mM Tris, pH 8.7 was run, eluting various proteins. Following column equilibration, a second salt gradient (200 to 300 mM NaCl) was run. The 32 KD protein eluted at approximately 225 mM NaCl.
3. a. A Q-Sepharose HP column (Pharmacia) was charged with 25 mM Tris, pH 8.7 containing 1 M NaCl, and re-equilibrated with 25 mM Tris, 10 mM NaCl, pH 8.7.
   b. The protein sample was dialyzed against 25 mM Tris, 10 mM NaCl, pH 8.7 and applied to the column with subsequent washing in the same buffer.
   c. The column was eluted with a 200-300 mM NaCl gradient in the same buffer.
4. a. Fractions containing the 32 KD product were collected, pooled and dialyzed against 25 mM Tris, 10 mM NaCl, pH 8.7, before concentrating the protein sample to 1 ml in a Speed-Vac Concentrator.
   b. The concentrate was then applied to a Superdex 75 column equilibrated with 25 mM Tris, 150 mM NaCl, pH 8.7 and eluted with the same buffer. The 32 KD product, labeled 32B to distinguish it from the protein of 32 KD separated using protocol H, eluted as homogeneous protein and is shown as a single band on FIG. 1B, col. 3.

H. 30 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 mM Tris, 10 mM NaCl, pH 8.7.
   b. The protein sample was dialyzed against 25 mM Tris, 10 mM NaCl, pH 8.7 and applied to the column with subsequent washing overnight with same buffer.
   c. The column was eluted with a salt gradient (10 mM to 200 mM) in 25 mM Tris, pH 8.7 buffer. The 30 KD protein eluted at approximately 140 mM NaCl.
3. a. Fractions containing the 30 KD product were collected, pooled and dialyzed against 25 mM Tris, 10 mM NaCl, pH 8.7, before concentrating the protein sample to 1 ml in a Speed-Vac Concentrator.

b. The concentrate was then Applied to a Superdex 75 column equilibrated with 25 mM Tris, 150 mM NaCl, pH 8.7 and eluted with this buffer. The 30 KD product eluted as homogeneous protein and is shown as a single band on FIG. 1B, col. 5.

I. 24 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 mM Tris, 10 mM NaCl, pH 8.7.
   b. The protein sample was dialyzed against 25 mM Tris, 10 mM NaCl, pH 8.7 and applied to the column with subsequent washing overnight with same buffer.
   c. A preliminary salt gradient of 10 mM to 200 mM NaCl in 25 mM Tris, pH 8.7 was run, eluting various proteins. Following column equilibration a second salt gradient (200 to 300 mM NaCl) was run. The 24 KD elutes at approximately 250 mM NaCl.
3. a. A Q-Sepharose HP column (Pharmacia) was charged with 25 mM Tris, pH 8.7 containing 1 M NaCl, and re-equilibrated with 25 mM Tris, 10 mM NaCl, pH 8.7.
   b. The protein sample was dialyzed against 25 mM Tris, 10 mM NaCl, pH 8.7 and applied to the column with subsequent washing in the same buffer.
   c. The column was eluted with a 200-300 mM NaCl gradient in the same buffer.
4. a. Fractions containing the 24 KD product were collected, pooled and dialyzed against 25 mM Tris, 10 mM NaCl, pH 8.7, before concentrating the protein sample to 1 ml in a Speed-Vac Concentrator.
   b. The concentrate was then applied to a Superdex 75 column equilibrated with 25 mM Tris, 150 mM NaCl, pH 8.7 and eluted with the same buffer. The 24 KD product eluted as homogeneous protein and is shown as a single band on FIG. 1B, col 7.

J. 23.5 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 mM Tris, 10 mM NaCl, pH 8.7.
   b. The protein sample was dialyzed against 25 mM Tris, 10 mM NaCl, pH 8.7 and applied to the column prior to subsequent washing overnight with same buffer.
   c. The column was eluted with a salt gradient (10 mM to 200 mM) in 25 mM Tris, pH 8.7 buffer. The 23.5 KD protein eluted at approximately 80 mM NaCl.
3. a. A Q-Sepharose HP column was charged with 25 mM Tris, pH 8.7 containing 1 M NaCl, and re-equilibrated with 25 mM Tris, 10 mM NaCl, pH 8.7.
   b. The protein sample was dialyzed against 25 mM Tris, 10 mM NaCl, pH 8.7 and applied to the column with subsequent washing in the same buffer.
   c. The column was eluted with 100-300 mM NaCl in 25 mM Tris, pH 8.7.
   d. Steps 3a to 3c were repeated.
4. a. Fractions containing 23.5 KD product were collected, pooled and dialyzed against 25 mM Tris, 10 mM NaCl, pH 8.7, before concentrating the protein sample to 1 ml in a Speed-Vac Concentrator.
   b. The concentrate was then applied to a Superdex 75 column equilibrated with 25 mM Tris, 150 mM NaCl, pH 8.7 and eluted with the same buffer. The 23.5 KD product eluted as homogeneous protein. The eluted protein was monitored using SDS-PAGE and resulted in the single band shown in FIG. 1B, col 6.

Figure 1B:
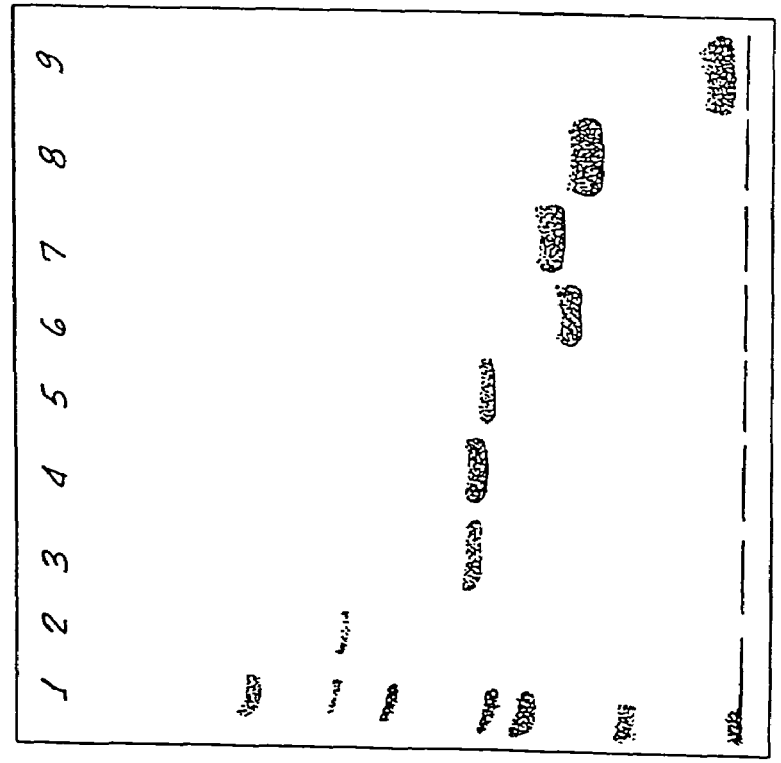
Figure 1A:
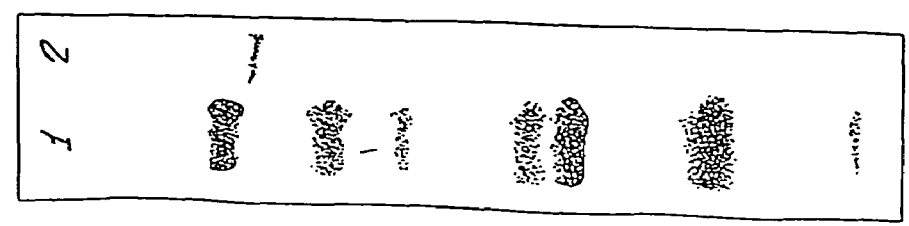
Figure 4:
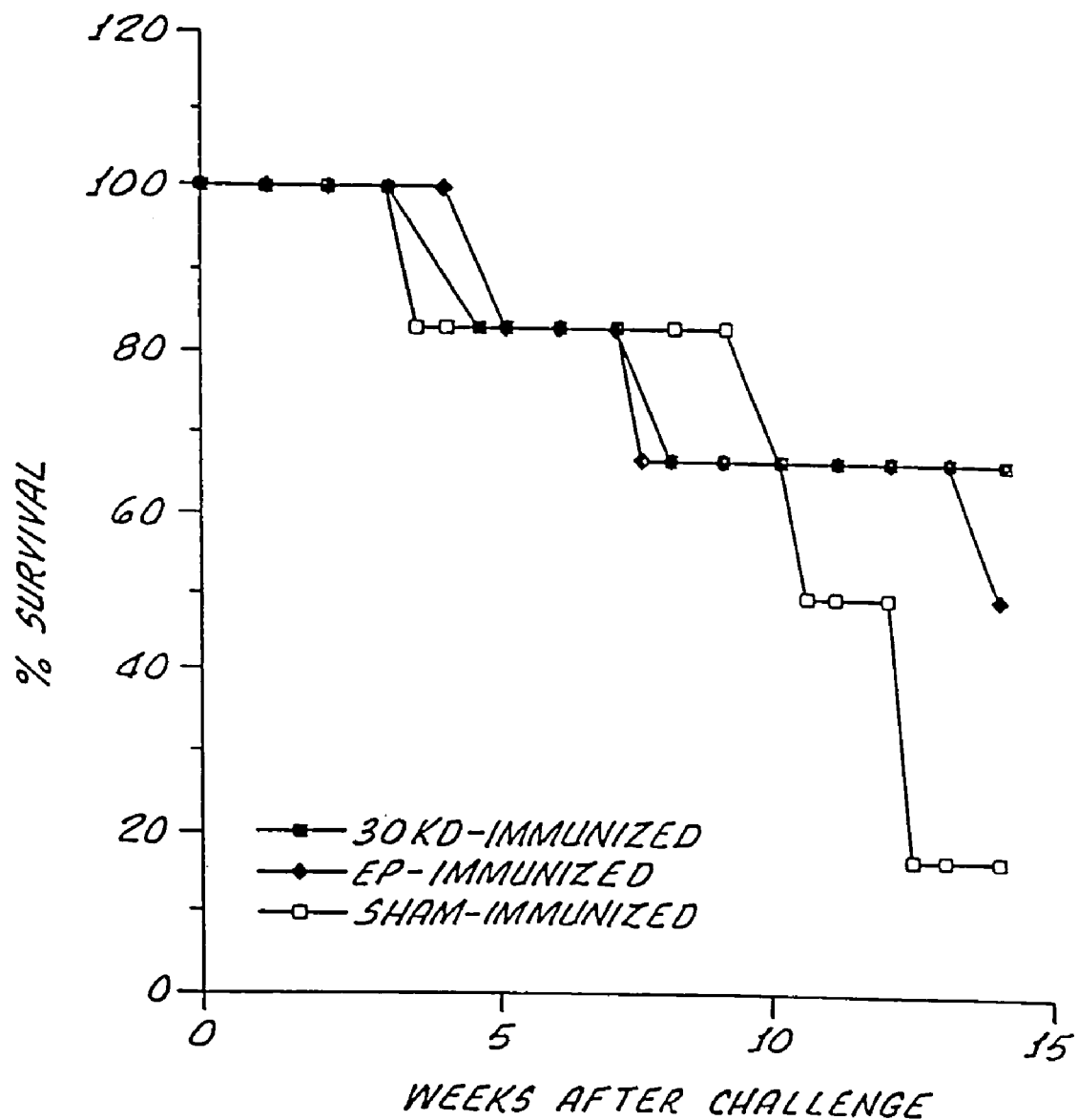
FIG. 4 is a graphical comparison of the survival rate of guinea pigs immunized with exemplary purified majorly abundant 30 KD secretory product of M. tuberculosis versus positive controls immunized with a prior art bulk preparation of extracellular proteins and nonimmunized negative controls following exposure to an aerosolized lethal dose of M. tuberculosis.

K. 23 KD Extracellular Product
1. a. Ammonium sulfate cuts of 0-25% (1 h at 0° C.) and 25-60% (overnight at 0° C.) were discarded.
   b. A 60-95% ammonium sulfate cut was retained.
2. a. A DEAE CL-6B column (Pharmacia) was charged with 50 mM Bis-Tris pH 7.0 containing 1 M NaCl and equilibrated with 50 mM Bis-Tris, 100 mM NaCl, pH 7.0.
   b. The protein sample was dialyzed against 50 mM Bis-Tris, pH 7.0, 100 mM NaCl buffer and applied to the column before washing the column overnight with the same buffer.
   c. The column was eluted with a 100 to 300 mM NaCl linear gradient in 50 mM Bis-Tris pH 7.0.
   d. Fractions were collected containing the 23 KD protein which eluted at approximately 100-150 mM NaCl.
3. a. The protein fractions were dialyzed against 25 mM Tris, pH 8.7, 10 mM NaCl and concentrated to 1-2 ml on a Savant Speed Vac Concentrator.
   b. The concentrate was applied to a Superdex 75 column equilibrated with 25 mM Tris, 150 mM NaCl, pH 8.7. The product elutes as a homogeneous protein as is shown in FIG. 1B col. 8.

1. 16 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 2.5 mM Tris, pH 8.7 containing 1 M NaCl and then equilibrated with 25 mM Tris, 10 mM NaCl, pH 8.7.
   b. The protein sample was dialyzed against 25 mM Tris, 10 mM NaCl, pH 8.7 and applied to the column with subsequent washing overnight in the same buffer.
   c. The column was eluted with a salt gradient (10 mM to 200 mM) in 25 mM Tris, pH 8.7 buffer. The 16 KD protein eluted at approximately 50 mM NaCl.
3. a. Fractions containing 16 KD product were collected, pooled and dialyzed against 25 mM Tris, 10 mM NaCl, pH 8.7, before concentrating the protein sample to 1 ml in a Speed-Vac Concentrator.
   b. The concentrate was then applied to a Superdex 75 column equilibrated with 25 mM Tris, 150 mM NaCl, pH 8.7 and eluted with the same buffer. A 16 KD product eluted as homogeneous protein. The eluted protein was monitored using SDS-PAGE and resulted in the single band shown in FIG. 1B, col. 9.

M. 14 KD Extracellular Product
1. a. A 0-25% ammonium sulfate cut (1 hour at 0° C.) was discarded.
   b. The 25-60% ammonium sulfate cut (overnight at 0° C.) was retained.
2. a. A DEAE CL-6B column (Pharmacia) was charged with 25 mM Tris, pH 8.7 containing 1 M NaCl and then equilibrated with 25 MM Tris, 10 mM NaCl, pH 8.7.

b. The protein sample was dialyzed against 25 mM Tris, 10 mM NaCl, pH 8.7 and applied to the column with subsequent washing overnight in the same buffer.

c. The column was eluted with a salt gradient (10 mM to 200 mM) in 25 mM Tris, pH 8.7 buffer. The 14 KD protein eluted at approximately 60 mM NaCl.

3. a. A Q-Sepharose HP column was charged with 25 mM Tris, pH 8.7 containing 1 M NaCl, and re-equilibrated with 25 mM NaCl, pH 8.7.

b. The protein sample was dialyzed against 25 mM Tris, 10 mM NaCl, pH 8.7 and applied to the column with subsequent washing in the same buffer.

c. The column was eluted with 10-150 mM NaCl in 25 mM Tris, pH 8.7.

d. Steps 3a through 3c were repeated.

4. a. Fractions containing 14 KD product were collected, pooled and dialyzed against 25 mM Tris, 10 mM NaCl, pH 8.7, before concentrating the protein sample to 1 ml in a Speed-Vac Concentrator.

b. The concentrate was then applied to a Superdex 75 column equilibrated with 25 mM Tris, 150 mM NaCl, pH 8.7 and eluted with this buffer. The 14 KD product eluted as homogeneous protein. The eluted protein was monitored using SDS-PAGE and resulted in the single band shown in FIG. 1C, col 2.

N. 12 KD Extracellular Products

1. A 0-10% ammonium sulfate precipitate was obtained (overnight at 4° C.).

2. The resolubilized precipitate was applied to a S200 Sephacryl size fractionation column eluting the protein as a 12 KD molecule.

3. The protein fractions were applied to a DEAE-Sepharose CL-6B or QAE-Sepharose ion exchange column and eluted with an NaCl gradient as previously described. Fractions containing two homogeneous proteins having molecular weights of approximately 12 KD eluted at approximately 300-350 mM NaCl and were collected. The proteins were labeled 12A and 12B and purified as a doublet shown in FIG. 1D, col. 2.

As illustrated in the SDS-PAGE profile of FIG. 1, the principal or majorly abundant extracellular proteins of *M. tuberculosis* were purified to homogeneity through the use of the protocols detailed in Examples 2A-2N above. More particularly. FIG. 1 illustrates four exemplary 12.5% acrylamide gels developed using SDS-PAGE and labeled 1a, 1b, 1c, and 1d. The standard in lane 1 of gels 1a-1c has proteins with molecular weights of 66, 45, 36. 29, 24, 20, and 14 KD. In gel 1d the standard in lane 1 contains proteins with molecular weights of 68, 45, 31, 29, 20, and 14 KD. The lanes containing the respective purified extracellular products show essentially one band at the reported molecular weight of the individual protein. It should be noted that in gel 1d the 12 KD protein runs as a doublet visible in lane 2. Sequence analysis shows that the lower 12 KD (or 12B KD band) is equivalent to the upper 12 KD (or 12A KD) band except that it lacks the first 3 N-terminal amino acids.

Further analysis of these individual exemplary majorly abundant extracellular products is provided in FIG. 2. More particularly FIG. 2 is a tabular compilation of N-terminal sequence data obtained from these purified extracellular products showing that the majority of the isolated products are indeed distinct (Sequence ID Nos. 1-14). Proteins 32A, 32B and 30 all had the same 5 N-terminal amino acids therefore further sequencing was necessary to fully characterize and differentiate them. FIG. 3 shows the extended N-terminal amino acid sequences for these three purified secretory products (Sequence ID Nos. 15-17). Different amino acids at positions 16 (Sequence ID No. 17), 31 (Sequence ID No. 16) and 36 (Sequence ID No. 16) demonstrate that these isolated proteins are distinct from one another despite their similarity in molecular weight.

In addition to proteins 30, 32A and 32B, extended N-terminal amino acid sequences of other majorly abundant extracellular products were determined to provide primary structural data and to uncover possible relationships between the proteins. Sequencing was performed on the extracellular products purified according to Example 2 using techniques well known in the art. Varying lengths of the N-terminal amino acid sequence, determined for each individual extracellular product, are shown below identified by the apparent molecular weight of the intact protein, and represented using standard one letter abbreviations for the naturally occurring amino acids. In keeping with established rules of notation, the N-terminal sequences are written left to right in the direction of the amino terminus to the carboxy terminus. Those positions where the identity of the determined amino acid is less than certain are underlined. Where the amino acid at a particular position is unknown or ambiguous, the position in the sequence is represented by a dash. Finally, where two amino acids are separated by a slash, the correct constituent has not been explicitly identified and either one may occupy the position in that sequence.

```
PROTEIN  N-TERMINAL AMINO ACID SEQUENCE 5      10     15    20     25    30    35
12 KD    FDTRL MRLED EMKEG RYEVR AELPG VDPDK DVDIM   (Sequence ID No. 18)

40     45
         VRDGQ LTIKA ERT 5      10     15    20     25     30
14 KD    ADPRL QFTAT TLSGA PFDGA S/NLQGK PAVLW      (Sequence ID Nos. 19 and 20)

5      10     15    20     25     30
16 KD    AYPIT GKLGS ELTMT DTVGQ VVLGW KVSDL        (Sequence ID Nos. 21 and 22)

35     40    45
         F/YKSTA VIPGY TV-EQ QI 5      10     15     20
```

-continued

| PROTEIN | N-TERMINAL AMINO ACID SEQUENCE | |
|---|---|---|
| 23 KD | AETYL PDLDW DYGAL EPHIS GQ | (Sequence ID No. 23) |
| 23.5 KD |       5      10<br>APKTY -EELK GTD | (Sequence ID No. 24) |
| 24 KD |       5     10    15    20    25    30    35<br>APYEN LMVPS PSMGR DIPVA FLAGG PHAVY LLDAF<br>     40    45    50    55    60<br>NAGPD VSNWV TAGNA MMTLA -KGIC/S | (Sequence ID Nos. 25 and 26) |
| 30 KD |       5     10    15    20    25    30    35<br>FSRPG LPVEY LQVPS PSMGR DIKVQ FQSGG NNSPA<br>     40<br>VYLLD | (Sequence ID No. 27) |
| 32A KD |       5     10    15    20    25    30    35<br>FSRPG LPVEY LQVPS PSMGR DIKVQ FQSGG ANSPA<br>     40<br>LYLLD | (Sequence ID No. 28) |
| 32B KD |       5     10    15    20<br>FSRPG LPVEY LQVPS A-MGR DI | (Sequence ID No. 29) |
| 45 KD |       5     10    15    20    25    30<br>DPEPA PPVPD DAASP PDDAA APPAP ADPP- | (Sequence ID No. 30) |
| 58 KD |       5     10    15    20<br>TEKTP DDVFK LAKDE KVLYL | (Sequence ID No. 31) |
| 71 KD |       5<br>ARAVG I | (Sequence ID No. 32) |
| 80 KD |       5<br>TDRVS VGN | (Sequence ID No. 33) |
| 110 KD |       5     10    15    20<br>NSKSV NSFGA HDTLK V-ERK RQ | (Sequence ID No. 34) |

DNA sequencing was performed on the 30, 32A, 16, 58, 23.5, and 24 KD proteins using techniques well known in the art. These DNA sequences, and the corresponding aminoacids, including upstream and downstream sequences, are shown below identified by the apparent molecular weight of the intact protein and represented using standard abbreviations and rules of notation.

```
                          30 KD DNA SEQUENCE
        (Nucleotide sequence and encoded protein are SEQ ID NOS 35 and 161, respectively)

1/1                              31/11
ATG ACA GAC GTG AGC CGA AAG ATT CGA GCT TGG GGA CGC CGA          (Sequence ID No. 35)
met thr asp val ser arg lys ile arg ala trp gly arg arg 61/21
TTG ATG ATC GGC ACG GCA GCG GCT GTA GTC CTT CCG GGC CTG
leu met ile gly thr ala ala ala val val leu pro gly leu 91/31
GTG GGG CTT GCC GGC GGA GCG GCA ACC GCG GGC GCG
val gly leu ala gly gly ala ala thr ala gly ala 121/41            151/51
TTC TCC CGG CCG GGG CTG CCG GTC GAG TAC CTG CAG GTG CCG
phe ser arg pro gly leu pro val glu tyr leu gln val pro 181/61
TCG CCG TCG ATG GGC CGC GAC ATC AAG GTT CAG TTC CAG AGC
ser pro ser met gly arg asp ile lys val gln phe gln ser 211/71                          241/81
GGT GGG AAC AAC TCA CCT GCG GTT TAT CTG CTC GAC GGC CTG
```

-continued

```
gly gly asn asn ser pro ala val tyr leu leu asp gly leu
                      271/91
CGC GCC CAA GAC GAC TAC AAC GGC TGG GAT ATC AAC ACC CCG
arg ala gln asp asp tyr asn gly trp asp ile asn thr pro
              301/101
GCG TTC GAG TGG TAC TAC CAG TCG GGA CTG TCG ATA GTC ATG
ala phe glu trp tyr tyr gln ser gly leu ser ile val met
331/111                               361/121
CCG GTC GGC GGG CAG TCC AGC TTC TAC AGC GAC TGG TAC AGC
pro val gly gly gln ser ser phe tyr ser asp trp tyr ser
                      391/131
CCG GCC TGC GGT AAG GCT GGC TGC CAG ACT TAC AAG TGG GAA
pro ala cys gly lys ala gly cys gln thr tyr lys trp glu
              421/141                         451/151
ACC TTC CTG ACC AGC GAG CTG CCG CAA TGG TTG TCC GCC AAC
thr phe leu thr ser gLu leu pro gln trp leu ser ala asn
                              481/161
AGG GCC GTG AAG CCC ACC GGC AGC GCT GCA ATC GGC TTG TCG
arg ala val lys pro thr gly ser ala ala ile gly leu ser
                      511/171
ATG GCC GGC TCG TCG GCA ATG ATC TTG GCC GCC TAC CAC CCC
met ala gly ser ser ala met ile leu ala ala tyr his pro
541/181                             571/191
CAG CAG TTC ATC TAC GCC GGC TCG CTG TCG GCC CTG CTG GAC
gln gln phe ile tyr ala gly ser leu ser ala leu leu asp
                      601/201
CCC TCT CAG GGG ATG GGG CCT AGC CTG ATC GGC CTC GCG ATG
pro ser gln gly met gly pro ser leu ile gly leu ala met
              631/211                           661/221
GGT GAC GCC GGC GGT TAC AAG GCC GCA GAC ATG TGG GGT CCC
gly asp ala gly gly tyr lys ala ala asp met trp gly pro
                      691/231
TCG AGT GAC CCG GCA TGG GAG CGC AAC GAC CCT ACG CAG CAG
ser ser asp pro ala trp glu arg asn asp pro thr gln gln
              721/241
ATC CCC AAG CTG GTC GCA AAC AAC ACC CGG CTA TGG GTT TAT
ile pro lys leu val ala asn asn thr arg leu trp val tyr
751/251                             781/261
TGC GGG AAC GGC ACC CCG AAC GAG TTG GGC GGT GCC AAC ATA
cys gly asn gly thr pro asn glu leu gly gly ala asn ile
                      811/271
CCC GCC GAG TTC TTG GAG AAC TTC GTT CGT AGC AGC AAC CTG
pro ala glu phe leu glu asn phe val arg ser ser asn leu
              841/281                         871/291
AAG TTC CAG GAT GCG TAC AAC GCC GCG GGC GGG CAC AAC GCC
lys phe gln asp ala tyr asn ala ala gly gly his asn ala
                              901/301
GTG TTC AAC TTC CCG CCC AAC GGC ACG CAC AGC TGG GAG TAC
val phe asn phe pro pro asn gly thr his ser trp glu tyr
              931/311
TGG GGC GCT CAG CTC AAC GCC ATG AAG GGT GAC CTG CAG AGT
trp gly ala gin leu asn ala met lys gly asp leu gln ser
961/321
TCG TTA GGC GCC GGC TGA
ser leu gly ala gly OPA
```

32 KD DNA SEQUENCE
      (Nucleotide sequence and encoded protein are SEQ ID NOS 36 and 162, respectively)

```
1/1                               31/11
ATG CAG CTT GTT GAC AGG GTT CGT GGC GCC GTC ACG GGT ATG                    (Sequence ID No. 36)
```

```
                                          -continued
met gln leu val asp arg val arg gly ala val thr gly met
                              61/21
TCG CGT CGA CTC GTG GTC GGG GCC GTC GGC GCG GCC CTA GTG
ser arg arg leu val val gly ala val gly ala ala leu val
           91/31                             121/41
TCG GGT CTG GTC GGC GCC GTC GGT GGC ACG GCG ACC GCG GGG
ser gly leu val gly ala val gly gly thr ala thr ala gly
                         151/51
GCA TTT TCC CGG CCG GGC TTG CCG GTG GAG TAC CTG CAG GTG
ala phe ser arg pro gly leu pro val glu tyr leu gln val
                 181/61
CCG TCG CCG TCG ATG GGC CGT GAC ATC AAG GTC GAA TTC CAA
pro ser pro ser met gly arg asp ile lys val glu phe gln
211/71                                 241/81
AGT GGT GGT GCC AAC TCG CCC GCC CTG TAC CTG CTC GAC GGC
ser gly gly ala asn ser pro ala leu tyr leu leu asp gly
                         271/91
CTG CGC GCG CAG GAC GAC TTC AGC GGC TGG GAC ATC AAC ACC
leu arg ala gln asp asp phe ser gly trp asp ile asn thr
           301/101                             331/111
CCG GCG TTC GAG TCC TAC GAC CAG TCG GGC CTG TCG GTG GTC
pro ala phe glu trp tyr asp gln ser gly leu ser val val
                             361/121
ATG CCG GTG GGT GGC CAG TCA AGC TTC TAC TCC GAC TGG TAC
met pro val gly gly gln ser ser phe tyr ser asp trp tyr
                 391/131
CAG CCC GCC TGC CGC AAG GCC GGT TGC CAG ACT TAC AAG TGG
gln pro ala cys gly lys ala gly cys gln thr tyr lys trp
421/141                                     451/151
GAG ACC TTC CTG ACC AGC GAG CTG CCG GGG TGG CTG CAG GCC
glu thr phe leu thr ser glu leu pro gly trp leu gln ala
                         481/161
AAC AGG CAC GTC AAG CCC ACC GGA AGC GCC GTC TGC GGT CTT
asn arg his val lys pro thr gly ser ala val val gly leu
             511/171                             541/181
TCG ATG GCT GCT TCT TCG GCG CTG ACG CTG GCG ATC TAT CAC
ser met ala ala ser ser ala leu thr leu ala ile tyr his
                                     571/191
CCC CAG CAG TTC GTC TAC GCG GGA GCG ATG TCG GGC CTG TTG
pro gln gln phe val tyr ala gly ala met ser gly leu leu
             601/201
GAC CCC TCC CAG GCG ATG GGT CCC ACC CTG ATC GGC CTG GCG
asp pro ser gln ala met gly pro thr leu ile gly leu ala
631/211                                 661/221
ATG GGT GAC GCT GGC GGC TAC AAG GCC TCC GAC ATG TGG GGC
met gly asp ala gly gly tyr lys ala ser asp met trp gly
                             691/231
CCG AAG GAG GAC CCG GCG TGG CAG CGC AAC GAC CCG CTG TTG
pro lys glu asp pro ala trp gln arg asn asp pro leu leu
             721/241                             751/251
AAC GTC GGG AAG CTG ATC GCC AAC AAC ACC CGC GTC TGG GTG
asn val gly lys leu ile ala asn asn thr arg val trp val
                             781/261
TAC TGC GGC AAC GGC AAG CCG TCG GAT CTG GGT GGC AAC AAC
tyr cys gly asn gly lys pro ser asp leu gly gly asn asn
                 811/271
CTG CCG GCC AAG TTC CTC GAG GGC TTC GTG CGG ACC AGC AAC
leu pro ala lys phe leu glu gly phe val arg thr ser asn
841/281                                 871/291
```

```
ATC AAG TTC CAA GAC GCC TAC AAC GCC GGT GGC GGC CAC AAC
ile lys phe gln asp ala tyr asn ala gly gly gly his asn 901/301
GGC GTG TTC GAC TTC CCG GAC AGC GGT ACG CAC AGC TGG GAG
gly val phe asp phe pro asp ser gly thr his ser trp glu 931/311                         961/321
TAC TGG GGC GCG CAG CTC AAC GCT ATG AAG CCC GAC CTG CAA
tyr trp gly ala gln leu asn ala met lys pro asp leu gln 991/331
CGG GCA CTG GGT GCC ACG CCC AAC ACC GGG CCC GCG CCC CAG
arg ala leu gly ala thr pro asn thr gly pro ala pro gln GGC GCC TAG
gly ala AMB
```

16 KD DNA SEQUENCE
(Nucleotide and encoded protein are SEQ ID NOS 92 and 163, respectively)

```
1/1                                 31/11
atg AAG CTC ACC ACA ATG ATC AAG ACG GCA GTA GCG GTC GTG GCC atg GCG GCC ATC GCG     (Sequence ID No. 92)
Met lye leu thr thr met ile lys thr ala val ala val val ala met ala ala ile ala 61/21                               91/31
ACC TTT GCG GCA CCG GTC GCG TTG GCT GCC TAT CCC ATC ACC GGA AAA CTT GGC AGT GAG
thr phe ala ala pro val ala leu ala ala tyr pro ile thr gly lye leu gly ser glu 121/41                              151/51
CTA ACG ATG ACC GAC ACC GTT GGC CAA GTC GTG CTC GGC TGG AAG GTC AGT GAT CTC AAA
leu thr met thr asp thr val gly gln val val leu gly trp lys val ser asp leu lys 181/61                              211/71
TCC AGC ACG GCA GTC ATC CCC GGC TAT CCG GTG GCC GGC CAG GTC TGG GAG GCC ACT GCC
ser ser thr ala val ile pro gly tyr pro val ala gly gln val trp glu ala thr ala 241/81                              271/91
ACG GTC AAT GCG ATT CGC GGC AGC GTC ACG CCC GCG GTC TCG CAG TTC AAT GCC CGC ACC
thr val asn ala ile arg gly ser val thr pro ala val ser gln phe asn ala arg thr 301/101                             331/111
GCC GAC GGC ATC AAC TAC CGG GTG CTG TGG CAA GCC GCG GGC CCC GAC ACC ATT AGC GGA
ala asp gly ile asn tyr arg val leu trp gln ala ala gly pro asp thr ile ser gly 361/121                             391/131
GCC ACT ATC CCC CAA GGC GAA CAA TCG ACC GGC AAA ATC TAC TTC GAT GTC ACC GGC CCA
ala thr ile pro gln gly glu gln ser thr gly lye ile tyr phe asp val thr gly pro 421/141                             451/151
TCG CCA ACC ATC GTC GCG ATG AAC AAC GGC ATG GAG GAT CTG CTG ATT TGG GAG CCG TAG
ser pro thr ile val ala met asn asn gly met glu asp leu leu ile trp glu pro AMB
```

58 KD DNA SEQUENCE
(Nucleotide and encoded protein are SEQ ID NOS 93 and 164, respectively)

```
1/1                                 31/11
gtg ACG GAA AAG ACG CCC GAC GAC GTC TTC AAA CTT GCC AAG GAC GAG AAG GTC GAA TAT     (Sequence ID No. 93)
val thr glu lys thr pro asp asp val phe lys leu ala lys asp glu lys val glu tyr 61/21                               91/31
GTC GAC GTC CGG TTC TGT GAC CTG CCT GGC ATC ATG CAG CAC TTC ACG ATT CCG GCT TCG
val asp val arg phe cys asp leu pro gly ile met gln his phe thr ile pro ala ser 121/41                              151/51
GCC TTT GAC AAG AGC GTG TTT GAC GAC GGC TTG GCC TTT GAC GGC TCG TCG ATT CGC GGG
ala phe asp lys ser val phe asp asp gly leu ala phe asp gly ser ser ile arg gly 181/61                              211/71
TTC CAG TCG ATC CAC GAA TCC GAC ATG TTG CTT CTT CCC GAT CCC GAG ACG GCG CGC ATC
phe gln ser ile his glu ser asp met leu leu leu pro asp pro glu thr ala arg ile 241/81                              271/91
GAC CCG TTC CGC GCG GCC AAG ACG CTG AAT ATC AAC TTC TTT GTG CAC GAC CCG TTC ACC
asp pro phe arg ala ala lys thr leu asn ile asn phe phe val his asp pro phe thr 301/101                             331/111
CTG GAG CCG TAC TCC CGC GAC CCG CGC AAC ATC GCC CGC AAG GCC GAG AAC TAC CTG ATC
leu glu pro tyr ser arg asp pro arg asn ile ala arg lys ala glu asn tyr leu ile
```

-continued

```
361/121                              391/131
AGC ACT GGC ATC GCC GAC ACC GCA TAC TTC GGC GCC GAG GCC GAG TTC TAC ATT TTC GAT
ser thr gly ile ala asp thr ala tyr phe gly ala glu ala glu phe tyr ile phe asp 421/141                              451/151
TCG GTG AGC TTC GAC TCG CGC GCC AAC GGC TCC TTC TAC GAG GTG GAC GCC ATC TCG GGG
ser val ser phe asp ser arg ala asn gly ser phe tyr glu val asp ala ile ser gly 481/161                              511/171
TGG TGG AAC ACC GGC GCG GCG ACC GAG GCC GAC GGC ACT CCC AAC CGG GGC TAC AAG GTC
trp trp asn thr gly ala ala thr glu ala asp gly ser pro asn arg gly tyr lys val 541/181                              571/191
CGC CAC AAG GGC GGG TAT TTC CCA GTG GCC CCC AAC GAC CAA TAC GTC GAC CTG CGC GAC
arg his lys gly gly tyr phe pro val ala pro asn asp gln tyr val asp leu arg asp 601/201                              631/211
AAG ATG CTG ACC AAC CTG ATC AAC TCC GGC TTC ATC CTG GAG AAG GGC CAC CAC GAG GTG
lys met leu thr asn leu ile asn ser gly phe ile leu glu lys gly his his glu val 661/221                              691/231
GGC AGC GGC GGA CAG GCC GAG ATC AAC TAC CAG TTC AAT TCG CTG CTG CAC GCC GCC GAC
gly ser gly gly gln ala glu ile asn tyr gln phe asn ser leu leu his ala ala asp 721/241                              751/251
GAC ATG CAG TTG TAC AAG TAC ATC ATC AAG AAC ACC GCC TGG CAG AAC GGC AAA ACG GTC
asp met gln leu tyr lys tyr ile ile lys asn thr ala trp gln asn gly lys thr val 781/261                              811/271
ACG TTC ATG CCC AAG CCG CTG TTC GGC GAC AAC GGG TCC GGC ATG CAC TGT CAT CAG TCG
thr phe met pro lys pro leu phe gly asp asn gly ser gly met his cys his gln ser 841/281                              871/291
CTG TGG AAG GAC GGG GCC CCG CTG ATG TAC GAC GAG ACG GGT TAT GCC GGT CTG TCG GAC
leu trp lys asp gly ala pro leu met tyr asp glu thr gly tyr ala gly leu ser asp 901/301                              931/311
ACG GCC CGT CAT TAC ATC GGC GGC CTG TTA CAC CAC GCG CCG TCG CTG CTG GCC TTC ACC
thr ala arg his tyr ile gly gly leu leu his his ala pro ser leu leu ala phe thr 961/321                              991/331
AAC CCG ACG GTG AAC TCC TAC AAG CGG CTG GTT CCC GGT TAC GAG GCC CCG ATC AAC CTG
asn pro thr val asn ser tyr lys arg leu val pro gly tyr glu ala pro ile asn leu 1021/341                             1051/351
GTC TAT AGC CAG CGC AAC CGG TCG GCA TGC GTG CGC ATC CCG ATC ACC GGC AGC AAC CCG
val tyr ser gln arg asn arg ser ala cys val arg ile pro ile thr gly ser asn pro 1081/361                             1111/371
AAG GCC AAG CGG CTG GAG TTC CGA AGC CCC GAC TCG TCG GGC AAC CCG TAT CTG GCG TTC
lys ala lys arg leu glu phe arg ser pro asp ser ser gly asn pro tyr leu ala phe 1141/381                             1171/391
TCG GCC ATG CTG ATG GCA GGC CTG GAC GGT ATC AAG AAC AAG ATC GAG CCG CAG GCG CCC
ser ala met leu met ala gly leu asp gly ile lys asn lys ile glu pro gln ala pro 1201/401                             1231/411
GTC GAC AAG GAT CTC TAC GAG CTG CCG CCG GAA GAG GCC GCG AGT ATC CCG CAG ACT CCG
val asp lys asp leu tyr glu leu pro pro glu glu ala ala ser ile pro gln thr pro 1261/921                             1291/431
ACC CAG CTG TCA GAT GTG ATC GAC CGT CTC GAG GCC GAC CAC GAA TAC CTC ACC GAA GGA
thr gln leu ser asp val ile asp arg leu glu ala asp his glu tyr leu thr glu gly 1321/441                             1351/451
GGG GTG TTC ACA AAC GAC CTG ATC GAG ACG TGG ATC AGT TTC AAG CGC GAA AAC GAG ATC
gly val phe thr asn asp leu ile gLu thr trp ile ser phe lys arg glu asn glu ile 1381/461                             1411/471
GAG CCG GTC AAC ATC CGG CCG CAT CCC TAC GAA TTC GCG CTG TAC TAC GAC GTT taa
glu pro val asn ile arg pro his pro tyr glu phe ala leu tyr tyr asp val OCH
```

23.5 KD DNA SEQUENCE
(Nucleotide and encoded protein are SEQ ID NOS 94 and 165, respectively)

```
1/1                                  31/11
GTG CGC ATC AAG ATC TTC ATG CTG GTC ACG GCT GTC GTT TTG CTC TGT TGT TCG GGT GTG    (Sequence ID No. 94)
val arg ile lys ile phe met leu val thr ala val val leu leu cys cys ser gly val
```

-continued

```
61/21                              91/31
GCC ACG GCC GCG CCC AAG ACC TAC TGC GAG GAG TTG AAA GGC ACC GAT ACC GGC CAG GCG
ala thr ala ala pro lys thr tyr cys glu glu leu lys gly thr asp thr gly gln ala 121/41                             151/51
TGC CAG ATT CAA ATG TCC GAC CCG GCC TAC AAC ATC AAC ATC AGC CTG CCC AGT TAC TAC
cys gln ile gln met ser asp pro ala tyr asn ile asn ile ser leu pro ser tyr tyr 181/61                             211/71
CCC GAC CAG AAG TCG CTG GAA AAT TAC ATC GCC CAG ACG CGC GAC AAG TTC CTC AGC GCG
pro asp gln lys ser leu glu asn tyr ile ala gln thr arg asp lys phe leu ser ala 241/81                             271/91
GCC ACA TCG TCC ACT CCA CGC GAA GCC CCC TAC GAA TTG AAT ATC ACC TCG GCC ACA TAC
ala thr ser ser thr pro arg glu ala pro tyr glu leu asn ile thr ser ala thr tyr 301/101                            331/111
CAG TCC GCG ATA CCG CCG CGT GGT ACG CAG GCC GTG GTG CTC AAG GTC TAC CAG AAC GCC
gln ser ala ile pro pro arg gly thr gln ala val val leu lys val tyr gln asn ala 361/121                            391/131
GGC GGA ACG CAC CCA ACG ACC ACG TAC AAG GCC TTC GAT TGG GAC CAG GCC TAT CGC AAG
gly gly thr his pro thr thr thr tyr lys ala phe asp trp asp gln ala tyr arg lys 421/141                            451/151
CCA ATC ACC TAT GAC ACG CTG TCG CAG GCT GAC ACC GAT CCG CTG CCA GTC GTC TTC CCC
pro ile thr tyr asp thr leu ser gln ala asp thr asp pro leu pro val val phe pro 481/161                            511/171
ATT GTG CAA GGT GAA CTG AGC AAG CAG ACC GGA CAA CAG GTA TCG ATA GCG CCG AAT GCC
ile val gln gly glu leu ser lys gln thr gly gln gln val ser ile ala pro asn ala 541/181                            571/191
GGC TTG GAC CCG GTG AAT TAT CAG AAC TTC GCA GTC ACG AAC GAC GGG GTG ATT TTC TTC
gly leu asp pro val asn tyr gln asn phe ala val thr asn asp gly val ile phe phe 601/201                            631/211
TTC AAC CCG GGG GAG TTG CTG CCC GAA GCA GCC GGC CCA ACC CAG GTA TTG GTC CCA CGT
phe asn pro gly glu leu leu pro glu ala ala gly pro thr gln val leu val pro arg 661/221
TCC GCG ATC GAC TCG ATG CTG GCC TAG
ser ala ile asp ser met leu ala AMB
```

24 KD DNA SEQUENCE
(Nucleotide and encoded protein are SEQ ID NOS 94 and 165, respectively)

```
1/1                                31/11
ATG AAG GGT CGG TCG GCG CTG CTG CGG GCG CTC TGG ATT GCC GCA CTG TCA TTC GGG TTG    (Sequence ID No. 95)
Met lys gly arg ser ala leu leu arg ala leu trp ile ala ala leu ser phe gly leu 61/21                              91/31
GGC GGT GTC GCG GTA GCC GCG GAA CCC ACC GCC AAG GCC GCC CCA TAC GAG AAC CTG ATG
gly gly val ala val ala ala glu pro thr ala lys ala ala pro tyr glu asn leu met 121/41                             151/51
GTG CCG TCG CCC TCG ATG GGC CGG GAC ATC CCG GTG GCC TTC CTA GCC GGT GGG CCG CAC
val pro ser pro ser met gly arg asp ile pro val ala phe leu ala gly gly pro his 181/61                             211/71
GCG GTG TAT CTG CTG GAC GCC TTC AAC GCC GGC CCG GAT GTC AGT AAC TGG GTC ACC GCG
ala val tyr leu leu asp ala phe asn ala gly pro asp val ser asn trp val thr ala 241/81                             271/91
GGT AAC GCG ATG AAC ACG TTG GCG GGC AAG GGG ATT TCG GTG GTG GCA CCG GCC GGT GGT
gly asn ala met asn thr leu ala gly lys gly ile ser val val ala pro ala gly gly 301/101                            331/111
GCG TAC AGC ATG TAC ACC AAC TGG GAG CAG GAT GCC AGC AAG CAG TGG GAC ACC TTC TTG
ala tyr ser met tyr thr asn trp glu gln asp gly ser lys gln trp asp thr phe leu 361/121                            391/131
TCC GCT GAG CTG CCC GAC TGG CTG GCC GCT AAC CGG GGC TTG GCC CCC GGT GGC CAT GCG
ser ala glu leu pro asp trp leu ala ala asn arg gly leu ala pro gly gly his ala 421/141                            451/151
GCC GTT GGC GCC GCT CAG GGC GGT TAC GGG GCG ATG GCG CTG GCG GCC TTC CAC CCC GAC
ala val gly ala ala gln gly gly tyr gly ala met ala leu ala ala phe his pro asp
```

```
481/161                                     511/171
CGC TTC GGC TTC GCT GGC TCG ATG TCG GGC TTT TTG TAC CCG TCG AAC ACC ACC ACC AAC
arg phe gly phe ala gly ser met ser gly phe leu tyr pro ser asn thr thr thr asn 541/181                                     571/191
GGT GCG ATC GCG GCG GGC ATG CAG CAA TTC GGC GGT GTG GAC ACC AAC GGA ATG TGG GGA
gly ala ile ala ala gly met gln gln phe gly gly val asp thr asn gly met trp gly 601/201                                     631/211
GCA CCA CAG CTG GGT CGG TGG AAG TGG CAC GAC CCG TGG GTG CAT GCC AGC CTG CTG GCG
ala pro gln leu gly arg trp lys trp his asp pro trp val his ala ser leu leu ala 661/221                                     691/231
CAA AAC AAC ACC CGG GTG TGG GTG TGG AGC CCG ACC AAC CCG GGA GCC AGC GAT CCC GCC
gln asn asn thr arg val trp val trp ser pro thr asn pro gly ala ser asp pro ala 721/241                                     751/251
GCC ATG ATC GGC CAA GCC GCC GAG GCG ATG GGT AAC AGC CGC ATG TTC TAC AAC CAG TAT
ala mer ile gly gln ala ala glu ala met gly asn ser arg met phe tyr asn gln tyr 781/261                                     811/271
CGC AGC GTC GGC GGG CAC AAC GGA CAC TTC GAC TTC CCA GCC AGC GGT GAC AAC GGC TGG
arg ser val gly gly his asn gly his phe asp phe pro ala ser gly asp asn gly trp 841/281                                     871/291
GGC TCG TGG GCG CCC CAG CTG GGC GCT ATG TCG GGC GAT ATC GTC GGT GCG ATC CGC TAA
gly ser trp ala pro gln leu gly ala met ser gly asp ile val gly ala ile arg OCH
```

This sequence data, combined with the physical properties ascertained using SDS-PAGE, allow these representative majorly abundant extracellular products of the present invention to be characterized and distinguished. The analysis described indicates that these proteins constitute the majority of the extracellular products of *M. tuberculosis*, with the 71 KD, 30 KD, 32A KD, 23 KD and 16 KD products comprising approximately 60% by weight of the total available extracellular product. It is further estimated that the 30 KD protein may constitute up to 25% by weight of the total products released by *M. tuberculosis*. Thus, individual exemplary majorly abundant extracellular products of *M. tuberculosis* useful in the practice of the present invention may range anywhere from 15 approximately 0.5% up to approximately 25% of the total weight of the extracellular products.

As previously discussed, following the inability of traditional Western blot analysis to consistently identify the most immunogenically specific extracellular products, the present inventor decided to analyze the immunogenicity of the majorly abundant extracellular products based upon their abundance and consequent ease of identification and isolation. Surprisingly, it was found that these majorly abundant extracellular products induce unexpectedly effective immune responses leading this inventor to conclude that they may function as vaccines. This surprising discovery led to the development of the nonlimiting functional theory of this invention discussed above.

To demonstrate the efficacy of the present invention, additional experiments were conducted using individual majorly abundant extracellular products and combinations thereof at various exemplary dosages to induce protective immunity in art accepted laboratory models. More specifically, purified individual majorly abundant extracellular products were used to induce protective immunity in guinea pigs which were then challenged with *M. tuberculosis*. Upon showing that these proteins were capable of inducing protective immunity, combinations of five purified majorly abundant extracellular products was similarly tested using differing routes of administration. In particular the 30 KD abundant extracellular product was used to induce protective immunity in the accepted animal model as was the purified form of the 71 KD extracellular product. As with the individual exemplary majorly abundant extracellular products the combination vaccines of five majorly abundant extracellular products conferred protection against challenge with lethal doses of *M. tuberculosis* as well. Results of the various studies of these exemplary vaccines of the present invention follow.

Specific pathogen-free male Hartley strain guinea pigs (Charles River Breeding Laboratories, North Wilmington, Mass.) were used in all experiments involving immunogenic or aerosol challenges with *M. tuberculosis*. The animals were housed two or three to a stainless steel cage and allowed free access to standard guinea pig chow and water. After arrival at the animal facility, the guinea pigs were observed for at least one week prior to the start of each experiment to ensure that they were healthy.

Initial experiments were conducted using individual majorly abundant extracellular products believed to comprise between 3% to 25% of the total extracellular proteins normally present. These experiments demonstrate that majorly abundant extracellular products elicit an effective immune response. More particularly, isolated 30 KD and 71 KD extracellular products were shown to be individually capable of generating a cell-mediated immune response that protected guinea pigs upon exposure to lethal doses of *M. tuberculosis* as follows.

EXAMPLE 3

Purified 30 KD Protein Skin Testing for Cell-Mediated Immunity of 30 KD Immunized Guinea Pigs To illustrate that a measurable immune response can be induced by purified forms of abundant extracellular products, a cutaneous hypersensitivity assay was performed. Guinea pigs were immunized with the exemplary majorly abundant *M. tuberculosis* 30 KD secretory product purified according to Example 2 and believed to comprise approximately 25% of the total extracellular product of *M. tuberculosis*. In three independent experiments, guinea pigs were immunized three times three weeks apart with 100 µg of substantially purified 30 KD protein in SAF adjuvant. Control animals were similarly injected with. buffer in SAF. Three weeks after the last immunization the guinea pigs were challenged with the exemplary 30 KD protein in a cutaneous hypersensitivity assay.

Guinea pigs were shaved over the back and injections of 0.1, 1 and 10 µg of 30 KD protein were administered intradermally with resulting erythema (redness of the skin) and induration measured after 24 hours as shown in Table A below. Data are reported in terms of mean measurement values for the group ± standard error (SE) as determined using traditional methods. ND indicates that this particular aspect of the invention was not done.

TABLE A

| Guinea Pig Status | n | 0.1 µg | 1.0 µg | 10.0 µg |
|---|---|---|---|---|
| Erythema (mm) to 30 KD (Mean ± SE) | | | | |
| Expt. 1 | | | | |
| Immunized | 6 | 1.2 ± 0.5 | 3.9 ± 0.8 | 6.9 ± 1.0 |
| Controls | 5 | ND | ND | 3.0 ± 0.9 |
| Expt. 2 | | | | |
| Immunized | 6 | 0.5 ± 0.5 | 5.4 ± 0.7 | 8.1 ± 0.6 |
| Controls | 3 | 0 ± 0 | 2.5 ± 0 | 1.7 ± 0.8 |
| Expt. 3 | | | | |
| Immunized | 6 | ND | 1.7 ± 1.1 | 6.2 ± 0.3 |
| Controls | 3 | ND | ND | 2.0 ± 0.0 |
| Induration (mm) to 30 KD (Mean ± SE) | | | | |
| Expt. 1 | | | | |
| Immunized | 6 | 0 ± 0 | 3.3 ± 0.3 | 5.6 ± 0.9 |
| Controls | 5 | ND | ND | 1.6 ± 1.0 |
| Expt. 2 | | | | |
| Immunized | 6 | 0 ± 0 | 3.8 ± 0.7 | 4.9 ± 1.2 |
| Controls | 3 | 0 ± 0 | 0.8 ± 0.8 | 1.7 ± 0.8 |
| Expt. 3 | | | | |
| Immunized | 6 | ND | 1.1 ± 1.1 | 4.7 ± 0.4 |
| Controls | 3 | ND | 0 ± 0 | 0 ± 0 |

As shown in Table A, guinea pigs immunized with the exemplary 30 KD secretory product exhibited a strong cell-mediated immune response as evidenced by marked erythema and induration. In contrast, the control animals exhibited minimal response.

To confirm the immunoreactivity of the 30 KD secretory product and show its applicability to infectious tuberculosis, nonimmunized guinea pigs were infected with *M. tuberculosis* and challenged with this protein as follows:

EXAMPLE 4

Purified 30 KD Protein Testing for Cell-Mediated Immune Responses of Guinea Pigs Infected with *M. tuberculosis*

To obtain bacteria for use in experiments requiring the infection of guinea pigs, *M. tuberculosis* was first cultured on 7H11 agar and passaged once through a guinea pig lung to insure that they were virulent. For this purpose, guinea pigs were challenged by aerosol with a 10 ml suspension of bacteria in 7H9 broth containing approximately $5 \times 10^4$ bacteria/ml. After the guinea pigs became ill, the animals were sacrificed and the lungs, containing prominent *M. tuberculosis* lesions, were removed. Each lung was ground up and cultured on 7H11 agar for 7 days to 10 days. The bacteria were scraped from the plates, diluted in 7H9 broth containing 10% glycerol, sonicated in a water bath to obtain a single cell suspension, and frozen slowly at $-70°$ C. at a concentration of approximately $2 \times 10^7$ viable bacteria/ml. Viability of the frozen cells was measured by thawing the bacterial suspension and culturing serial dilutions of the suspension on 7H11 agar.

Just before a challenge, a vial of bacterial cells was thawed and diluted to the desired concentration in 7H9 broth.

The guinea pigs were exposed to aerosols of the viable *M. tuberculosis* in a specially designed lucite aerosol chamber. The aerosol chamber measured 14 by 13 by 24 in. and contained two 6 inch diameter portals on opposite sides for introducing or removing guinea pigs. The aerosol inlet was located at the center of the chamber ceiling. A vacuum pump (Gast Mfg. Co., Benton Harbor, Mich.) delivered air at 30 $lb/in^2$ to a nebulizer-venturi unit (Mes Inc., Burbank, Calif.), and an aerosol was generated from a 10-ml suspension of bacilli. A 0.2 µm breathing circuit filter unit (Pall Biomedical Inc., Fajardo, Puerto Rico) was located at one end of the chamber to equilibrate the pressure inside and outside of the assembly. Due to safety considerations, the aerosol challenges were conducted with the chamber placed completely within a laminar flow hood.

The animals were exposed to pathogenic aerosol for 30 minutes during which time the suspension of bacilli in the nebulizer was completely exhausted. Each aerosol was generated from the 10 ml suspension containing approximately $5.0 \times 10^4$ bacterial particles per ml. Previous studies have shown that guinea pig exposure to this concentration of bacteria consistently produces infections in nonprotected animals. Following aerosol infection, the guinea pigs were housed in stainless steel cages contained within a laminar flow biohazard safety enclosure (Airo Clean Engineering Inc., Edgemont, Pa.) and observed for signs of illness. The animals were allowed free access to standard guinea pig chow and water throughout the experiment.

In this experiment, the infected guinea pigs were sacrificed and splenic lymphocyte proliferation was measured in response to various concentrations of the 30 KD protein. More specifically, splenic lymphocytes were obtained and purified as described by Brieman and Horwitz (*J. Exp. Med.* 164:799-811) which is incorporated herein by reference. The lymphocytes were adjusted to a final concentration of $10^7$/ml in RPMI 1640 (GIBCO Laboratories, Grand Island, N.Y.) containing penicillin (100 U/ml), streptomycin (100 µg/ml), and 10% fetal calf serum (GIBCO) and incubated with various concentrations of purified 30 KD secretory product in a total volume of 100 µl in microtest wells (96-well round-bottom tissue culture plate; Falcon Labware, Oxnard, Calif.) for 2 days at 37° C. in 5% $CO_2$-95% air and 100% humidity. Noninfected animals were used as negative controls. At the end of the incubation period, 0.25 µci of [$^3$H]thymidine (New England Nuclear, Boston, Mass.) was added to each well and the cells were further incubated for 2 hours at 37° C. in 5% $CO_2$-95% air at 100% humidity. A multisample automated cell harvester (Skatron Inc., Sterling, Va.) was used to wash each well, and the effluent was passed through a filtermat (Skatron). Filtermat sections representing separate microtest wells were placed in scintillation vials, and 2 ml of Ecoscint H liquid scintillation cocktail (National Diagnostics, Manville, N.J.) was added.

Beta particle emission was measured in a beta scintillation counter (Beckman Instruments Inc., Fullerton, Calif.).

Tissue samples from the infected and noninfected guinea pigs were assayed against 1 and 10 µg/ml of isolated 30 KD secretory protein. Samples were then monitored for their ability to incorporate [$^3$H]thymidine. The results of these assays were tabulated and presented in Table B below.

Data are reported as a stimulation index which, for the purposes of this disclosure, is defined as: mean [$^3$H]thymidine incorporation of lymphocytes incubated with antigen/mean [$^3$H]thymidine incorporation of lymphocytes incubated without antigen.

TABLE B

| Guinea Pig Status | n | Stimulation Indices to 30 KD (Mean ± SE) | |
|---|---|---|---|
| | | 1.0 µg/ml | 10.0 µg/ml |
| Infected | 6 | 2.2 ± 0.2 | 9.7 ± 4.6 |
| Controls | 6 | 1.5 ± 0.3 | 2.0 ± 0.8 |

As shown in Table B, the cells of the infected animals exhibited a strong response to the exemplary 30 KD protein as manifested by dose dependant splenic lymphocyte proliferation in response to exposure to this majorly abundant secretory product. Conversely, the uninfected control animals showed little lymphocyte proliferation. Accordingly, the 30 KD secretory product clearly induces a cell-mediated immune response in mammals infected with *M. tuberculosis*.

To illustrate the protective aspects of the vaccines of the present invention, guinea pigs were immunized with purified 30 KD protein and exposed to *M. tuberculosis* as follows.

EXAMPLE 5

Challenge of 30 KD Immunized Guinea Pig with Aerosolized *M. tuberculosis*

As before, the animals were immunized three times at three week intervals with 100 μg of the exemplary 30 KD secretory protein in SAF. Control guinea pigs were immunized with 120 μg of bulk EP in SAF or sham-immunized with buffer in the same adjuvant. Three weeks after the last immunization, the animals were challenged with aerosolized *M. tuberculosis* as described in Example 4.The survival rates for the three groups of animals were monitored and are graphically presented in FIG. 4. Absolute mortality was determined 14 weeks after challenge as presented in Table C below.

TABLE C

| Status of Guinea Pigs | Survivors/ Challenged | Percent Survival |
|---|---|---|
| 30 KD Immunized | 4/6 | 67% |
| EP Immunized | 3/6 | 50% |
| Sham Immunized | 1/6 | 17% |

As shown in FIG. 4 guinea pigs immunized three times with the exemplary 30 KD protein were protected against death. Approximately 67% of the guinea pigs immunized with the 30 KD protein survived whereas only 17% of the control sham-immunized guinea pigs survived.

Weight retention of the immunized animals was also monitored (data not shown) and further illustrates the prophylactic capacity of vaccines incorporating majorly abundant extracellular products produced by pathogenic bacteria as taught by the present invention. While the immunized animals appeared to maintain their weight, the high mortality rate of the sham-immunized animals precluded the graphical comparison between the immunized animals and the control animals.

Following conclusion of the weight monitoring study, the surviving animals were sacrificed and the right lung and spleen of each animal was assayed for viable *M. tuberculosis*. The animals were soaked in 2% amphyl solution (National Laboratories, Montvale, N.J.), and the lungs and spleen were removed aseptically. The-number of macroscopic primary surface lesions in the lungs were enumerated by visual inspection. Colony forming units (CFU) of *M. tuberculosis* in the right lung and spleen were determined by homogenizing each organ in 10 ml of 7H9 with a mortar and pestle and 90-mesh Norton Alundum (Fisher), serially diluting the tissue homogenate in 7H9, and culturing the dilutions on duplicate plates of 7Hll agar by using drops of 0.1 ml/drop. All plates were kept in modular incubator chambers and incubated 12 to 14 days at 37° C. in 5% $CO_2$, 95% air at 100% humidity. The assay was conducted using this protocol and the results of the counts are presented in Table D below in terms of mean colony forming units (CFU) ± standard error (SE).

TABLE D

| Guinea Pig Status | n | Mean CFU ± SE Right Lung | Spleen |
|---|---|---|---|
| 30 KD Immunized | 4 | $3.4 \pm 1.7 \times 10^7$ | $7.7 \pm 3.9 \times 10^6$ |
| Sham-immunized | 1 | $1.8 \times 10^8$ | $8.5 \times 10^7$ |
| Log-Difference | | 0.73 | 1.04 |

As shown in Table D, immunization with the exemplary 30 KD secretory protein limited the growth of *M. tuberculosis* in the lung and the spleen. Although only data from the one surviving sham-immunized animal was available for comparative purposes, the four surviving 30 KD immunized animals had 0.7 log fewer CFU in their lungs and 1 log fewer CFU in their spleen than the surviving sham-immunized animal. Based on previous demonstrations of a high correlation between CFU counts and mortality, the surviving animal likely had fewer CFU in the lungs and spleen than the animals who died before a CFU analysis could be performed. Again this reduction of CFU in the lungs and spleens of the immunized animals conclusively demonstrates the scope and operability of the present invention.

The immunoprotective potential of another majorly abundant extracellular product from *M. tuberculosis*, the 71 KD extracellular product, was tested in its isolated form to demonstrate its immunoprotective capacity.

EXAMPLE 6

Purified 71 KD Protein Skin Test of Guinea Pigs Immunized with a Bulk Preparation of EP To demonstrate the potential of 71 KD protein to provoke an effective immune response in animals, this isolated majorly abundant extracellular product was used to skin test guinea pigs immunized with a bulk preparation of *M. tuberculosis* extracellular proteins (EP) in a cutaneous hypersensitivity assay. As discussed above, bulk EP will impart acquired immunity against infection by *M. tuberculosis* but to a lesser extent than the vaccines of the present invention.

Guinea pigs were immunized on two occasions spaced three weeks apart, with 120 µg of a bulk preparation of EP prepared as detailed in Example 1. The vaccination was prepared in incomplete Freunds adjuvant with sham-immunized animals receiving buffer in place of EP. Three weeks after the last vaccination the guinea pigs from each group were shaved over the back and skin tested with an intradermal injection of 0.1, 1.0 and 10 µg of 71 KD protein. 10.0 µg of buffer was used as a control and all injections were performed using a total volume of 0.1 ml. The diameters of erythema and induration were measured after 24 hours with the results as shown in Table E below. Data are reported in terms of mean measurement values for the group ± standard error (SE) as determined using traditional methods.

TABLE E

| Guinea Pig Status | n | 0.1 µg | 1.0 µg | 10.0 µg |
|---|---|---|---|---|
| | | Erythema (mm) to 71 KD (Mean ± SE) | | |
| Immunized | 4 | 6.5 ± 0.7 | 11.9 ± 1.4 | 18.9 ± 2.2 |
| Controls | 3 | 2.5 ± 1.4 | 5.0 ± 2.9 | 11.8 ± 2.1 |
| | | Induration (mm) to 71 KD (Mean ± SE) | | |
| Immunized | 4 | 3.6 ± 1.1 | 6.8 ± 1.1 | 11.6 ± 0.8 |
| Controls | 3 | 0.7 ± 0.7 | 3.7 ± 0.9 | 7.8 ± 1.0 |

The responses of the immunized animals were almost twice the response of the guinea pigs challenged with buffer alone and were comparable to those challenged with bulk EP identical to that used to immunize the animals (data not shown).

To further confirm that the purified exemplary 71 KD majorly abundant extracellular product elicits cell-mediated immune responses, the bulk EP immunized guinea pigs were sacrificed and splenic lymphocyte proliferation was measured in response to various concentrations of the 71 KD protein. Nonimmunized animals were used as controls. Following the protocol of Example 4, the lymphocytes were incubated with and without 71 KD protein for 2 days and then assayed for their capacity to incorporate [$^3$H]thymidine.

Data is reported in terms of stimulation indices calculated as in Example 4. The results of this 71 KD challenge are shown in Table F below.

TABLE F

| Guinea Pig Status | n | 0.01 µg/ml | 0.1 µg/ml | 1.0 µg/ml |
|---|---|---|---|---|
| | | Stimulation Indices to 71 KD (Mean ± SE) | | |
| Immunized | 4 | 1.5 ± 0.1 | 2.3 ± 0.5 | 8.1 ± 2.2 |
| Controls | 2 | 1.7 ± 0.6 | 1.6 ± 0.4 | 2.5 ± 0.6 |
| | | Stimulation Indices to EP (Mean ± SE) | | |
| Immunized | 4 | 1.5 ± 0.1 | 2.2 ± 0.3 | 5.3 ± 1.4 |
| Controls | 2 | 1.4 ± 0.2 | 1.5 ± 0.2 | 1.2 ± 0.1 |

As shown in Table F, stimulation indices for the lymphocyte proliferation assay were comparable to the results obtained in the cutaneous hypersensitivity assay. Both the 71 KD and bulk EP tested samples showed responses between two and three times higher than those obtained with the controls indicating that isolated exemplary 71 KD majorly abundant extracellular product is capable of provoking a cell-mediated immune response in animals immunized with *M. tuberculosis* extracts. However, it should again be emphasized that the purified majorly abundant or principal extracellular product is free of the problems associated with prior art or bulk compositions and is more readily adaptable to synthetic and commercial production making the vaccines of the present invention superior to the prior art.

More particularly the bulk preparation cannot be manufactured easily on a large scale through modern biomolecular techniques. Any commercial production of these unrefined bulk preparations containing all extracellular products would involve culturing vast amounts of the target pathogen or a closely related species and harvesting the resultant supernatant fluid. Such production methodology is highly susceptible to contamination by the target pathogen, toxic byproducts or other parasitic agents. Further, the large number of immunogenic determinants in such a preparation is far more likely to provoke a toxic immune reaction in a susceptible segment of the immunized population. Using these unrefined bulk preparations also negates the use of the most popular skin tests currently used for tuberculosis screening and control.

In direct contrast, the vaccines of the present invention can be mass-produced in relative safety using high yield transformed hosts. Similarly, the vaccines of the present invention can be produced in identical, easy to standardize batches as opposed to the wider variable production of bulk extracellular products. Moreover, as the number of immunogenic determinants presented to the host immune system is relatively small, toxic reactions and the chance of invalidating popular screening tests are greatly reduced.

EXAMPLE 7

Purified 71 KD Protein Skin Test of 71 KD Immunized Guinea Pigs

Following demonstration that the isolated exemplary 71 KD majorly abundant extracellular product generates a cell-mediated immune response in bulk EP immunized animals, it was shown that the purified form of this majorly abundant product was able to induce a cell-mediated immune response in animals immunized with 71 KD.

Guinea pigs were twice vaccinated with 100 µg of purified 71 KD protein in SAF three weeks apart. Control animals were sham-immunized with buffer in SAF on the same schedule. Three weeks after the last immunization both sets of animals were intradermally challenged with 1 and 10 µg of isolated 71 KD protein. The resulting erythema and indurations were measured after 24 hours with the results shown in Table G below.

TABLE G

| Guinea Pig Status | n | 0 µg | 1.0 µg | 10.0 µg |
|---|---|---|---|---|
| | | Erythema (mm) to 71 KD (Mean ± SE) | | |
| Immunized | 3 | 0 ± 0 | 6.5 ± 1.5 | 15.0 ± 1.5 |
| Controls | 3 | 0 ± 0 | 2.7 ± 1.3 | 6.7 ± 1.3 |
| | | Induration (mm) to 71 KD (Mean ± SE) | | |
| Immunized | 3 | 0 ± 0 | 3.0 ± 1.0 | 9.3 ± 0.3 |
| Controls | 3 | 0 ± 0 | 0 ± 0 | 1.3 ± 1.3 |

The extent of induration and erythema was much greater in the immunized animals than in the nonimmunized control animals demonstrating that a strong cell-mediated immune response to 71 KD protein had been initiated by the vaccination protocol of the present invention.

To further confirm the capacity of this abundant extracellular product to induce an effective immune response on its own in accordance with the teachings of the present invention, lymphocyte proliferation assays were performed. Animals immunized as in Table G were sacrificed and splenic lymphocyte proliferative assays were run using the protocol established in Example 4. The tissue samples from the 71 KD immunized guinea pigs and those from the control guinea pigs were challenged with 0.1, 1 and 10 μg/ml of isolated 71 KD protein and monitored for their ability to incorporate [$^3$H]thymidine. Stimulation indices were calculated as previously described. The results of these assays are presented in Table H below.

TABLE H

| Guinea Pig | | Stimulation Indices to 71 KD (Mean ± SE) | | |
|---|---|---|---|---|
| Status | n | 0.1 μg/ml | 1.0 μg/ml | 10.0 μg/ml |
| Immunized | 3 | 4.0 ± 1.3 | 5.6 ± 2.5 | 12.2 ± 5.1 |
| Controls | 3 | 1.3 ± 0.3 | 1.3 ± 0.3 | 3.2 ± 1.5 |

As with the cutaneous hypersensitivity assay, the 71 KD immunized animals showed a much higher response to purified 71 KD than did the sham-immunized controls. Though expected of a foreign protein, such results clearly show that a majorly abundant extracellular product has the capacity to induce an cell-mediated immune response.

After establishing that an isolated majorly abundant extracellular protein will induce an effective cell-mediated immune response, further experiments were conducted to confirm that any such response is cross-reactive against tubercle bacilli as follows.

EXAMPLE 8

Purified 71 KD Protein Challenge of Guinea Pigs Infected with *M. tuberculosis*

Nonimmunized guinea pigs were infected with aerosolized *M. tuberculosis* as reported in Example 4. Purified protein derivative (PPD-CT68; Connaught Laboratories Ltd.) was employed as the positive control to ensure that the infected animals were demonstrating a cell-mediated immune response indicative of *M. tuberculosis*. Widely used in the Mantoux test for tuberculosis exposure, PPD is generally prepared by ammonium sulfate fractionation and comprises a mixture of small proteins having an average molecular weight of approximately 10 KD. Immune responses to PPD are substantially analogous to those provoked by the bulk EP fractions isolated in Example 1.

Three weeks after infection the guinea pigs were challenged intradermally with 0.1, 1 and 10 μg of the exemplary purified majorly abundant 71 KD extracellular protein. Uninfected animals used as controls were similarly challenged with the isolated protein. The extent of erythema and induration were measured 24 hours later with the results reported in Table I below.

TABLE I

| Guinea Pig Status | n | 0.1 μg | 1.0 μg | 10.0 μg |
|---|---|---|---|---|
| | | Erythema (mm) to 71 KD (Mean ± SE) | | |
| Infected | 7 | 9.5 ± 1.7 | 13.4 ± 1.3 | 19.7 ± 1.3 |
| Controls | 6 | 2.3 ± 2.3 | 3.5 ± 2.2 | 7.8 ± 1.9 |
| | | Induration (mm) to 71 KD (Mean ± SE) | | |
| Infected | 7 | 5.3 ± 1.8 | 8.7 ± 1.6 | 13.4 ± 1.1 |
| Controls | 6 | 0 ± 0 | 0.8 ± 0.8 | 0 ± 0 |

As shown in Table I, strong immune responses are present in the infected animals challenged with the exemplary purified majorly abundant extracellular protein of the present invention. These responses are on the order of three to four times greater for erythema and more than 10 times greater for induration than those of the uninfected animals, confirming that the prominent 71 KD extracellular protein induces a strong cell-mediated immune response in *M. tuberculosis*-infected animals.

To further corroborate these results the infected animals and uninfected animals were sacrificed and subjected to a lymphocyte proliferative assay according to the protocol of Example 4. The tissue samples from both sets of guinea pigs were assayed against 0.1, 1 and 10 μg/ml of isolated 71 KD protein and PPD. The samples were then monitored for their ability to incorporate [$^3$H]thymidine as previously described with the results of these assays presented in Table J below.

TABLE J

| Guinea Pig Status | n | 0.1 μg/ml | 1.0 μg/ml | 10. μg/ml |
|---|---|---|---|---|
| | | Stimulation Indices to 71 KD (Mean ± SE) | | |
| Infected | 3 | 2.4 ± 0.5 | 6.2 ± 1.8 | 29.1 ± 16.2 |
| Controls | 3 | 1.1 ± 0.1 | 2.6 ± 0.8 | 18.2 ± 6.1 |
| | | Stimulation Indices to PPD (Mean ± SE) | | |
| Infected | 3 | 1.0 ± 0.1 | 4.0 ± 1.5 | 11.4 ± 3.4 |
| Controls | 3 | 0.9 ± 0.2 | 0.9 ± 0.03 | 1.5 ± 0.3 |

As with the results of the cutaneous sensitivity assay, Table J shows that the stimulation indices were much higher for the infected tissue than for the uninfected samples. More specifically, the mean peak stimulation index of infected animals was 2-fold higher to the exemplary 71 KD protein and 3-fold higher to PPD than it was to uninfected controls confirming that a strong cell-mediated immune response is induced in animals infected with *M. tuberculosis* by the exemplary majorly abundant extracellular protein vaccines of the present invention.

Following this demonstration of cross-reactivity between the exemplary purified 71 KD majorly abundant protein and *M. tuberculosis*, additional experiments were performed to demonstrate that an effective immune response could be stimulated by these exemplary purified samples of the majorly abundant extracellular products as disclosed by the present invention.

EXAMPLE 9

Challenge of 71 KD Immunized Guinea Pigs with Aerosolized *M. tuberculosis*

To demonstrate the immunoprotective capacity of exemplary majorly abundant or principal extracellular protein vaccines, guinea pigs were immunized twice, 3 weeks apart, with 100 μg of the exemplary majorly abundant 71 KD protein purified according to Example 2. Control animals were immunized with 120 μg bulk EP from Example 1 or buffer. All animals were immunized using the adjuvant SAF. Three weeks after the last immunization, guinea pigs immunized with the exemplary 71 KD protein were skin-tested with 10 μg of the material to evaluate whether a cell-mediated immune response had developed. The control animals and 71 KD immunized guinea pigs were then infected with aerosolized *M. tuberculosis* as detailed in Example 4. Following infection the animals were monitored and weighed for six months.

Figure 5:
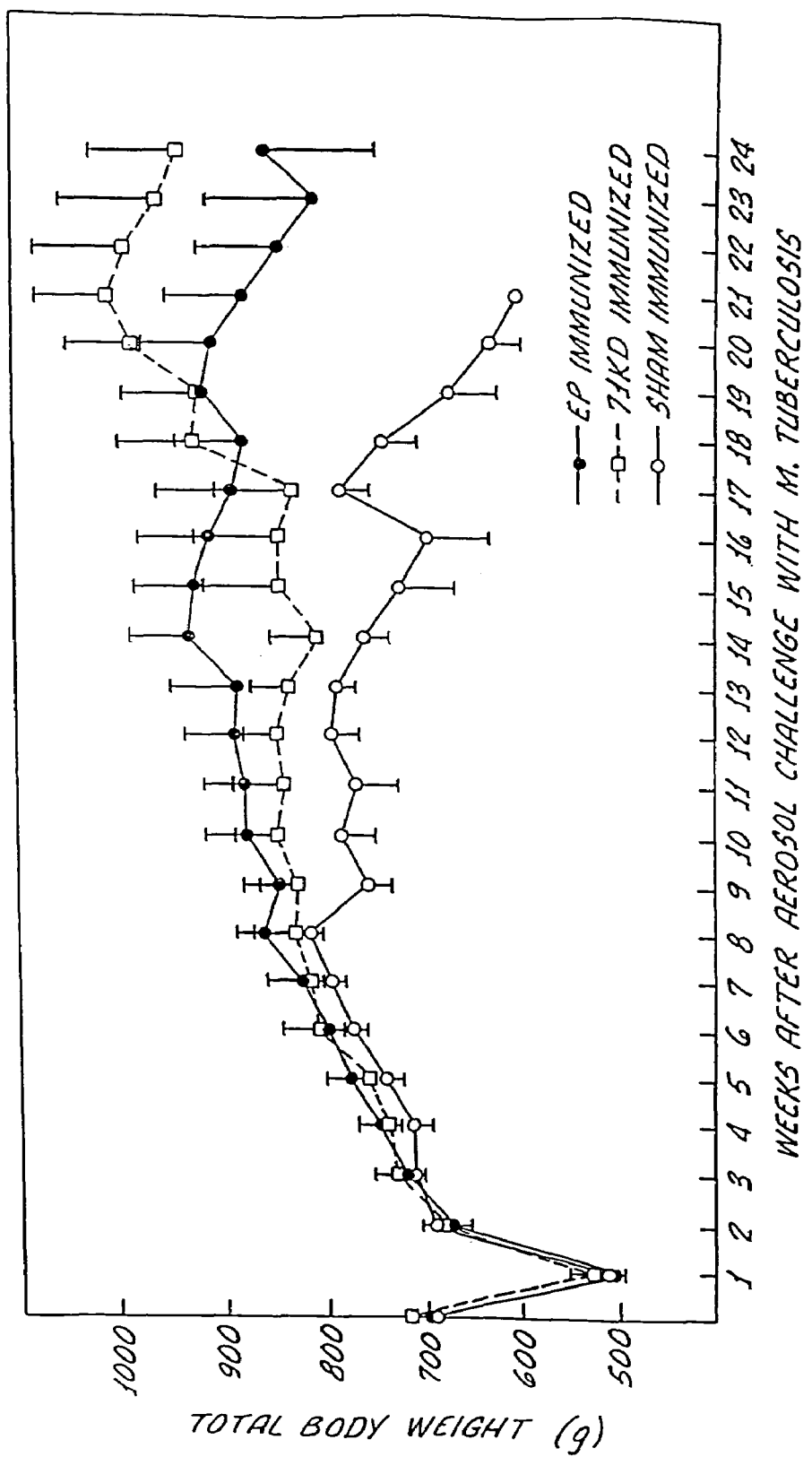
FIG. 5 is a graphical comparison of mean guinea pig body weight of animals immunized with purified majorly abundant 71 KD extracellular product versus positive controls immunized with a prior art bulk preparation of extracellular proteins from M. tuberculosis and nonimmunized negative controls following exposure to an aerosolized lethal dose of M. tuberculosis.
Figure 6:
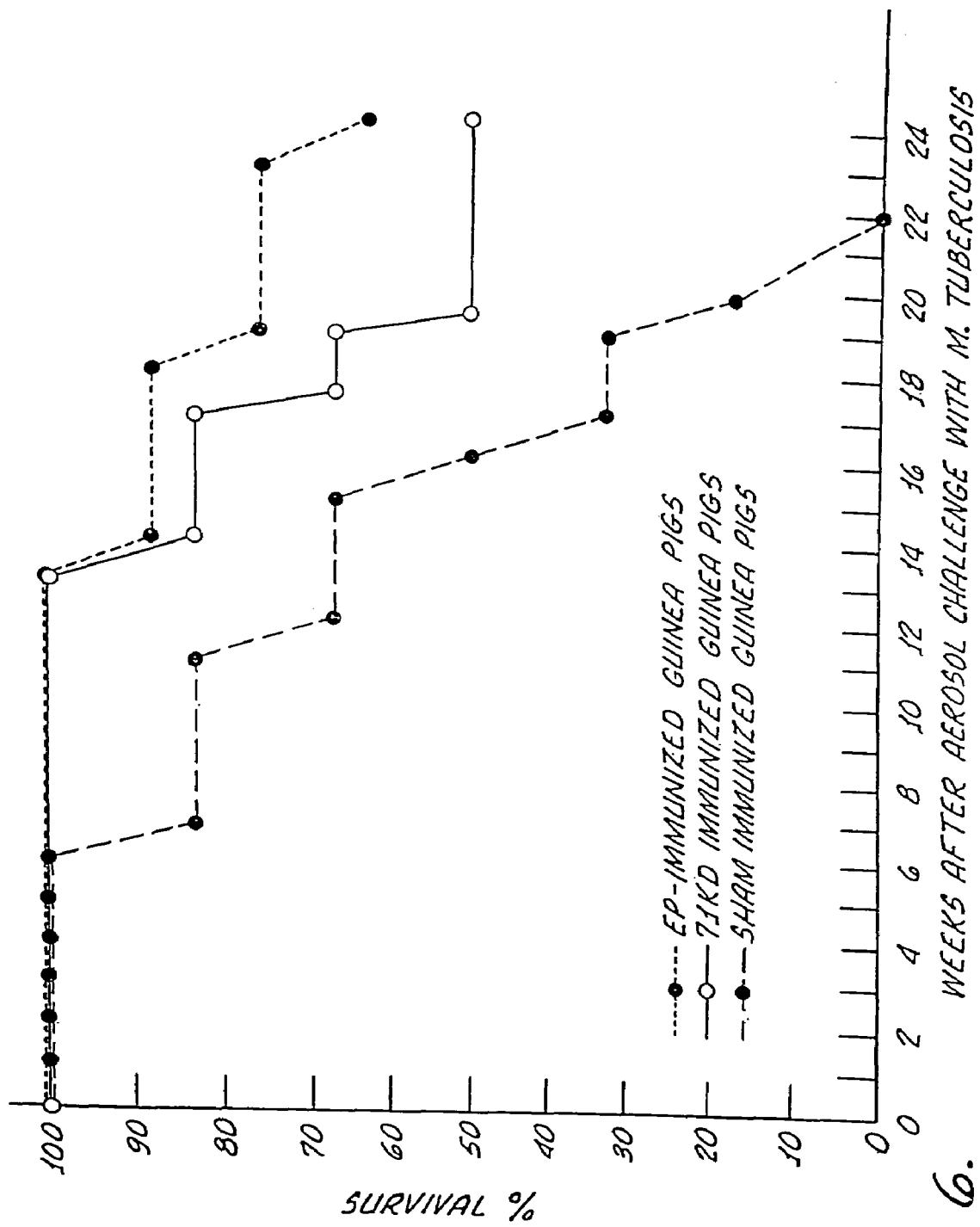
FIG. 6 is a graphical comparison of the survival rate of guinea pigs immunized in FIG. 5 with exemplary majorly abundant purified 71 KD extracellular product of M. tuberculosis versus positive controls immunized with a prior art bulk preparation of extracellular proteins from M. tuberculosis and nonimmunized negative controls following exposure to an aerosolized lethal dose of M. tuberculosis.

The graph of FIG. 5 contrasts the weight loss experienced by the sham-immunized group to the relatively normal weight gain shown by the 71 KD and bulk EP immunized animals. Data are the mean weights ± SE for each group. Mortality curves for the same animals are shown in the graph of FIG. 6. The absolute mortality rates for the study are reported in Table K below.

TABLE K

| Status of Guinea Pigs | Survivors/ Challenged | Percent Survival |
|---|---|---|
| 71 KD Immunized | 3/6 | 50% |
| EP Immunized | 5/8 | 62.5% |
| Sham Immunized | 0/6 | 0% |

Both the weight loss curves and the mortality rates clearly show that the majorly abundant extracellular proteins of the present invention confer a prophylactic immune response. This is emphasized by the fact that 100% of the nonimmunized animals died before the end of the monitoring period.

EXAMPLE 10

Challenge of 71 KD Immunized Guinea Pigs with Aerosolized *M. tuberculosis*

Figure 7:
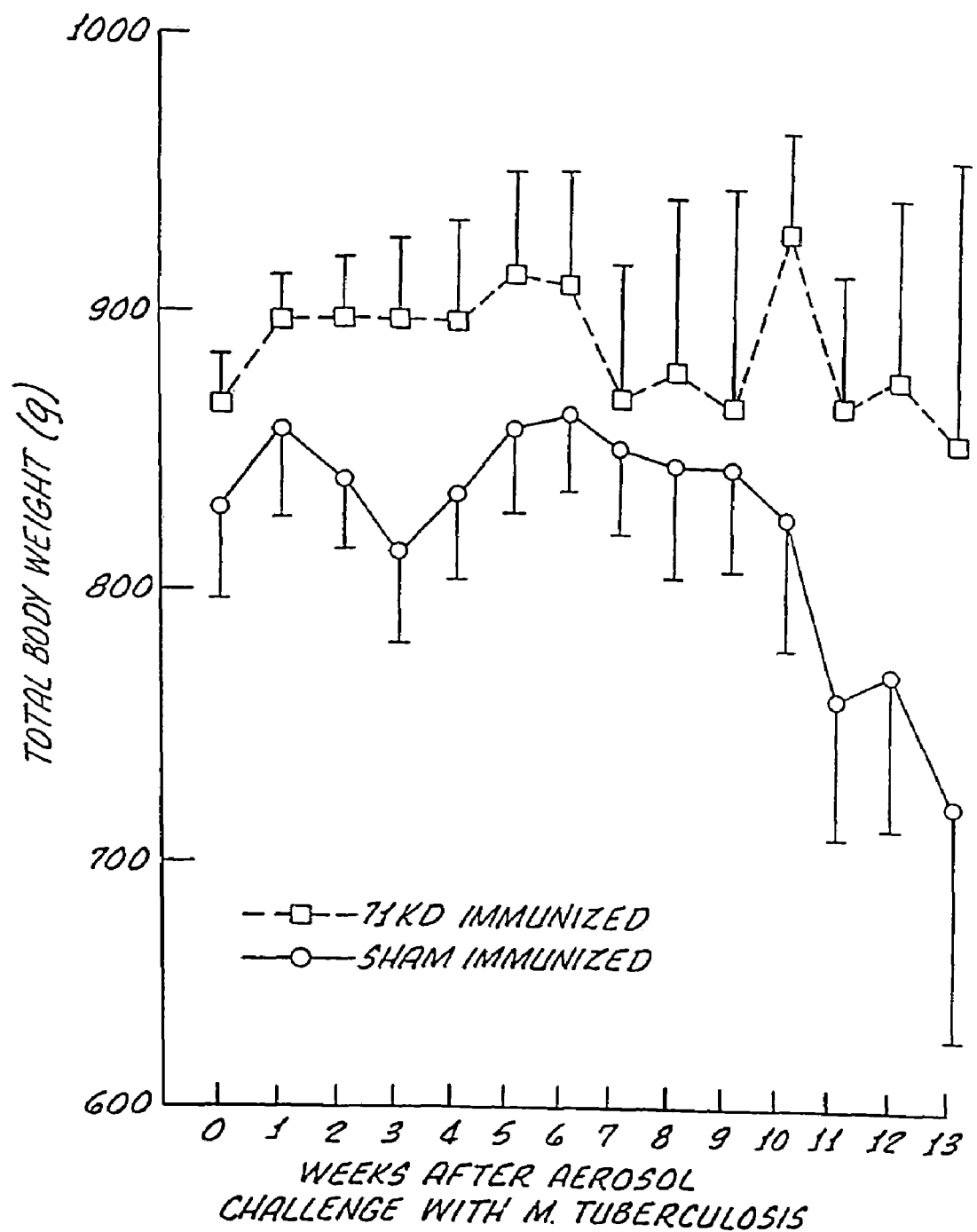
FIG. 7 is a graphical comparison of mean guinea pig body weight of animals immunized with exemplary purified majorly abundant 71 KD extracellular product and nonimmunized negative controls following exposure to an aerosolized lethal dose of M. tuberculosis in a second, separate experiment.

A similar experiment was conducted to verify the results of the previous Example and show that the administration of an exemplary principal extracellular protein can confer a protective immune response in animals. In this experiment, guinea pigs were again immunized three times, 3 weeks apart, with 100 μg of the 71 KD extracellular protein in SAF. Control guinea pigs were sham-immunized with buffer in SAF. Three weeks after the last immunization, the animals were challenged with aerosolized *M. tuberculosis* and weighed weekly for 13 weeks. Mean weights ± SE for each group of 6 guinea pigs were calculated and are graphically represented in FIG. 7. This curve shows that the sham-immunized animals lost a considerable amount of weight over the monitoring period while the immunized animals maintained a fairly consistent body weight. As loss of body mass or "consumption" is one of the classical side effects of tuberculosis, these results indicate that the growth and proliferation of tubercle bacilli in the immunized animals was inhibited by the exemplary vaccine of the present invention.

Protective immunity having been developed in guinea pigs through vaccination with an abundant extracellular product in an isolated form, experiments were run to demonstrate the inter-species immunoreactivity of the vaccines of the present invention and to further confirm the validity and applicability of the guinea pig model.

EXAMPLE 11

Figure 8:
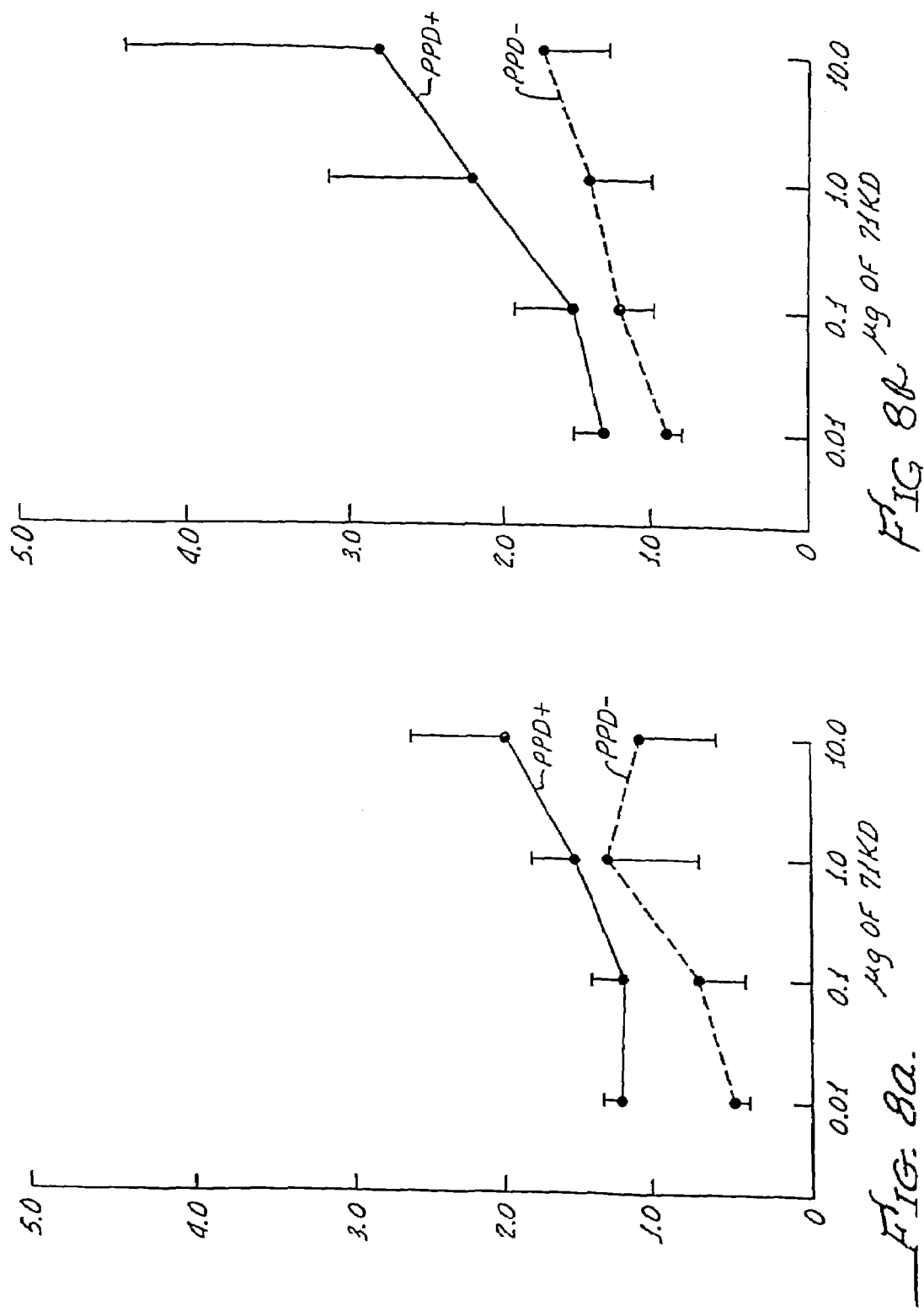
FIGS. 8a and b are graphical comparisons of lymphocyte proliferative responses to exemplary purified majorly abundant 71 KD extracellular product in PPD+(indicative of infection with M. tuberculosis) and PPD−human subjects.
FIG. 8b is a graph of the values measured at 4 days after incubation.

Testing Cell-Mediated Immunity of PPD Positive Humans with Purified 71 KD Protein To assess the cell-mediated component of a human immune response to the exemplary 71 KD majorly abundant protein, the proliferation of peripheral blood lymphocytes from PPD-positive and PPD-negative individuals to the protein were studied in the standard lymphocyte proliferation assay as reported in Example 4 above. A positive PPD, or tuberculin, response is well known in the art as being indicative of previous exposure to *M. tuberculosis*. The proliferative response and corresponding incorporation of [$^3$H]thymidine were measured at two and four days. Data for these studies is shown in FIGS. 8a and 8b. FIG. 8a shows the response to various revels of 71 KD after two days while FIG. 8b shows the same responses at four days.

As illustrated in FIGS. 8a and 8b, the mean peak stimulation index of PPD-positive individuals was twofold higher to the 71 KD protein and threefold higher to PPD than that of PPD negative individuals. Among PPD-positive individuals, there was a linear correlation between the peak stimulation indices to the exemplary 71 KD protein and to PPD demonstrating that a strong cell-mediated response is stimulated by the most prominent or majorly abundant extracellular products of *M. tuberculosis* in humans previously exposed to *M. tuberculosis*. This data corresponds to the reactivity profile seen in guinea pigs and confirms the applicability of the guinea pig model to other mammals subject to infection.

Thus, as with the previously discussed 30 KD exemplary protein, the development of a strong immune response to the majorly abundant 71 KD extracellular product demonstrates the broad scope of the present invention as evidenced by the fact that the 71 KD product is also effective at stimulating cell-mediated immunity in humans.

Again, it should be emphasized that the present invention is not limited to the extracellular products of *M. tuberculosis* or to the use of the exemplary 71 KD protein. Rather the teachings of the present invention are applicable to any majorly abundant extracellular product as demonstrated in the examples.

Additional studies were performed in order to ascertain whether combinations of majorly abundant extracellular products of *M. tuberculosis* would provide protective immunity as well. In general, these studies utilized guinea pigs which were immunized either intradermally or subcutaneously with various dosages of vaccines comprising combinations of 5 purified extracellular proteins of *M. tuberculosis* in SAF three times, 3 or 4 weeks apart.

The first protein combination used for the immunization procedure, labeled Combination I, was comprised of 71 KD, 32A KD, 30 KD, 23 KD, and 16 KD proteins purified according to the protocols described in Example 2. This combination is believed to comprise up to 60% of the total extracellular protein normally present in *M. tuberculosis* culture supernatants. These proteins selected for use in Combination I, are identified with an asterisk in FIG. 2. Combination I vaccine containing 100 μg, 20 μg, or 2 μg of each protein was administered intradermally with the adjuvant SAF. Combination I vaccine containing 20 μg of each protein was also administered subcutaneously in similar experiments. Negative control guinea pigs were shamimmunized with equivalent volumes of SAF and buffer on the same schedule while positive controls were immunized using 120 μg of the bulk extracellular protein preparation from Example 1 in SAF. All injection volumes were standardized using buffer.

EXAMPLE 12

Response of Combination I Immunized Guinea Pigs to a Challenge with Combination I Vaccine To determine if the animals had developed a measurable immune response following vaccination with the Combination I mixture of principal extracellular products, a cutaneous hypersensitivity assay was performed. Guinea pigs were shaved over the back and injected intradermally with 1.0 μg and 10.0 μg of the same combination of the five purified extracellular proteins. 10.0 μg of buffer was used as a control and all injections were performed using a total volume of 0.1 ml. The diameters of erythema and induration at skin tests sites were measured at 24 hours after injection.

The results of the measurements are presented in

TABLE L

| Guinea Pig Status | n | PD | 1.0 μg | 10.0 μg |
|---|---|---|---|---|
| | | | Erythema (mm) (Mean ± SE) | |
| Immunized | 6 | 0 | 11.4 ± 4.6 | 17.4 ± 2.6 |
| Controls | 6 | 0 | ND | 6.0 ± 0.5 |
| | | | Induration (mm) (Mean ± SE) | |
| Immunized | 6 | 0 | 7.3 ± 0.8 | 11.6 ± 1.2 |
| Controls | 6 | 0 | ND | 4.2 ± 0.3 |

The data clearly demonstrate that a strong cell-mediated immune response to the Combination I extracellular proteins was generated by the vaccinated animals. The immunized guinea pigs show erythema and induration measurements almost three times greater than the control animals.

EXAMPLE 13

Immunoprotective Analysis of Combination I Vaccine against Aerosolized *M. tuberculosis*

Three weeks after the last immunization, the guinea pigs used for the preceding hypersensitivity assay were challenged with aerosolized *M. tuberculosis*, Erdman strain and weighed weekly for 10 weeks. This aerosol challenge was performed using the protocol of Example 4. Six animals immunized with 100 μg of the principal extracellular products of Combination I, along with equal sized groups of positive and negative controls, were challenged simultaneously with aerosolized *M. tuberculosis*. Positive controls were immunized three times with 120 μg EP in SAF.

Guinea pigs that died before the end of the observation period were autopsied and examined for evidence of gross *tuberculosis* lesions. Such lesions were found in all animals which expired during the study.

Differences between immunized and control animals in mean weight profiles after aerosol challenge were analyzed by repeated measures analysis of variance (ANOVA). Differences between immunized and control guinea pigs in survival after challenge were analyzed by the two-tailed Fisher exact test. Data are the mean weights ± standard error (SE) for each group of six guinea pigs.

Figure 9:
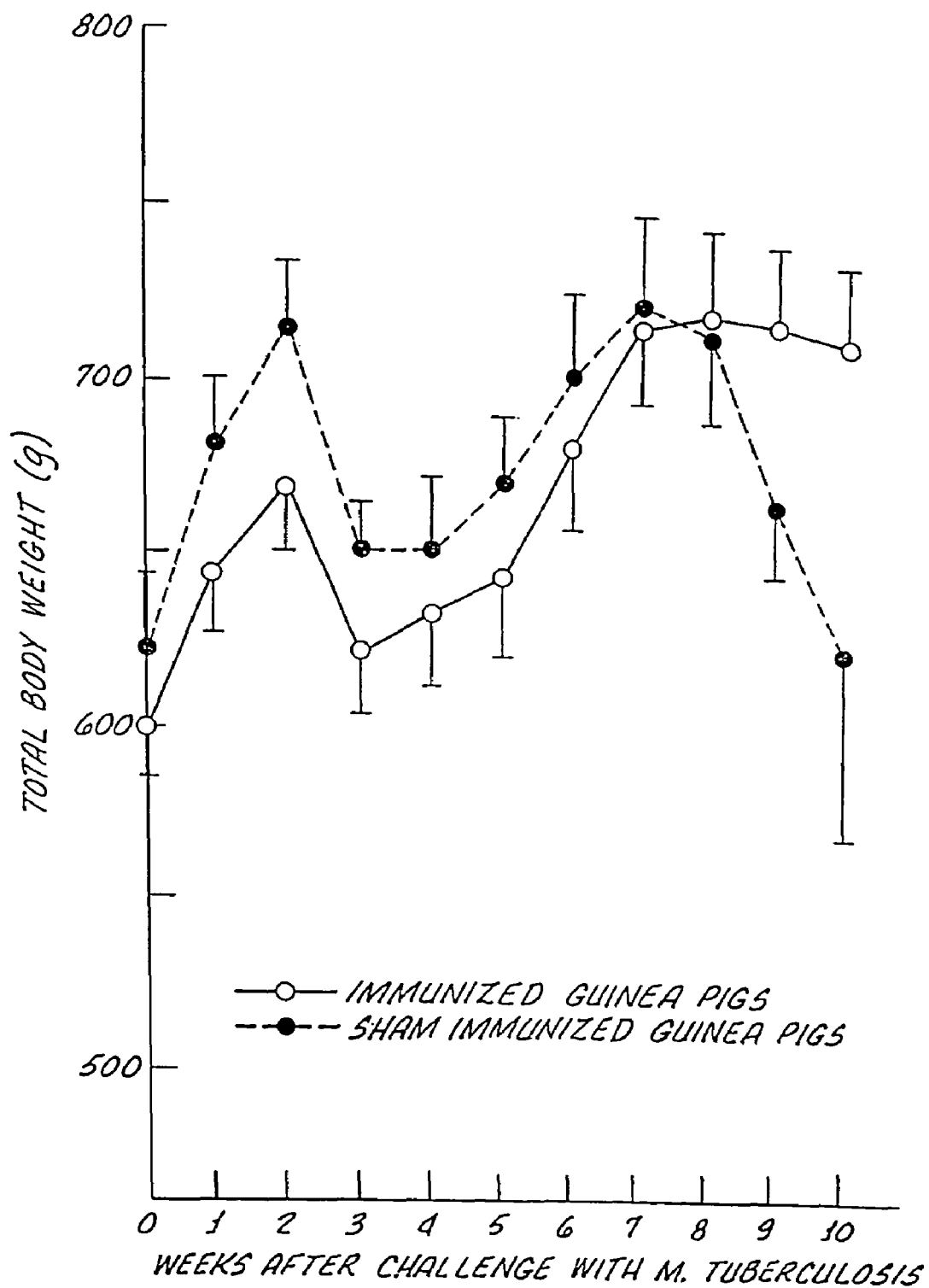
FIG. 9 is a graphical comparison of mean guinea pig body weight of animals immunized with vaccine comprising a combination of extracellular products produced according to the teachings of the present invention and nonimmunized controls following exposure to an aerosolized lethal dose of M. tuberculosis.

Results of the weekly weight determinations following challenge are shown in FIG. 9. Compared with guinea pigs immunized with the combination of extracellular products, sham-immunized animals lost 15.9% of their total body weight. Weights of the positive controls were similar to those of animals immunized with the combination of five purified extracellular proteins. Body weights were normalized immediately before challenge. The difference between animals immunized with Combination I and sham-immunized controls was highly significant with $p<0.0000001$ by repeated measures ANOVA.

Mortality was determined ten and one-half weeks after challenge. All three of the sham-immunized animals died within three days of each other between ten and ten and one-half weeks after challenge. The mortality results of the experiment are provided in Table M below.

TABLE M

| Status of Guinea Pigs | Survivors/Challenged | Percent Survival |
|---|---|---|
| Combination Immunized | 6/6 | 100% |
| EP-Immunized | 5/6 | 83% |
| Sham-Immunized | 3/6 | 50% |

Following the conclusion of the weight monitoring study, the surviving animals were sacrificed by hypercarbia and the right lung and spleen of each animal was assayed for viable *M. tuberculosis* using the protocol of Example 5. The results of the counts, including the 3 animals that died the last week of the experiment, are presented in Table N below in terms of mean colony forming units (CFU) ± standard error (SE).

TABLE N

| Guinea Pig | | Mean CFU ± SE | |
|---|---|---|---|
| Status | n | Right Lung | Spleen |
| Sham-immunized | 6 | $8.9 \pm 5.4 \times 10^7$ | $1.3 \pm 0.7 \times 10^7$ |
| Immunized | 6 | $3.4 \pm 1.7 \times 10^6$ | $1.8 \pm 0.6 \times 10^6$ |
| EP-immunized | 6 | $1.7 \pm 0.7 \times 10^7$ | $5.0 \pm 2.8 \times 10^6$ |

The log difference between the concentration of bacilli in the lung of the animals immunized with the combination of purified proteins and that of the sham-immunized animals was 1.4 while the log difference of bacilli in the spleen was 0.9. Parallelling this, on gross inspection at autopsy immunized animals had markedly decreased lung involvement with tuberculosis compared with sham-immunized controls. Positive control animals immunized with the bulk extracellular preparation (EP) of Example 1 showed 0.7 log more bacilli in the lung and 0.5 log more bacilli in the spleen than animals immunized with the Combination I mixture of purified extracellular proteins.

EXAMPLE 14

Immunoprotection Analysis of Combination I Vaccine at Low Doses through Intradermal and Subcutaneous Delivery While Example 13 confirmed that Combination I proteins demonstrated immunoprotection in animals immunized intradermally with 100 μg of each protein (30+32A+16+23+ 71) 3 times, 4 weeks apart, an alternative study was conducted to demonstrate the immunoprotective capacity of lower doses of Combination I proteins, specifically 20 μg or 2 μg of each protein. As in Example 13, guinea pigs (6 animals per group) were immunized with Combination I proteins (30+32A+16+23 +71) intradermally in SAF 4 times, 3 weeks apart. Animals received either 20 μg or each protein per immunization or 2 μg of each protein per immunization. Control animals were sham-immunized utilizing the previous protocol. Three weeks later, the animals were challenged with aerosolized M. tuberculosis and weights were measured weekly for 9 weeks. All immunized animals survived to the end of the experiment while one sham-immunized animal died before the end of the experiment. As the following results illustrate, doses 5 fold and even 50 fold lower than those of Example 13 protected immunized animals from aerosolized M. tuberculosis and that delivery by both the intradermal and subcutaneous route was effective.

Compared with guinea pigs immunized with 20 μg of each protein of Combination I, sham-immunized animals lost 12% of their total body weight during the 9 weeks of the experiment (weights were normalized to just before challenge). Compared with guinea pigs immunized with 2 μg of each protein of Combination I, sham-immunized animals lost 11% of their normalized total body weight. Thus, guinea pigs immunized intradermally with low doses of Combination I proteins were protected against weight loss after aerosol challenge with M. tuberculosis.

Similarly, guinea pigs immunized intradermally with low doses of Combination I proteins also were protected against splenomegaly associated with dissemination of M. tuberculosis to the spleen. As shown in Table O, whereas animals immunized with 20 μg or 2 μg of each protein of Combination I had spleens weighing an average of 4.6±1.2 g and 4.0±0.8 g (Mean±SE), respectively, sham-immunized animals had spleens weighing an average of 9.6±1.8 g (Table 1), or more than twice as much.

TABLE O

| Status of Guinea Pigs | n | Spleen Weight (g) Mean ± SE |
|---|---|---|
| Sham-Immunized | 5 | 9.6 ± 1.8 |
| Immunized (20 μg) | 6 | 4.6 ± 1.2 |
| Immunized (2 μg) | 6 | 4.0 ± 0.8 |

Guinea pigs immunized intradermally with low doses of Combination I proteins also had fewer CFU of M. tuberculosis in their spleens. As shown in Table P, when compared with sham-immunized animals, guinea pigs immunized with 20 μg or 2 μg of each protein of Combination I had an average of 0.6 and 0.4 log fewer CFU, respectively, in their spleens.

TABLE P

| Guinea Pig Status | n | CFU in Spleen Mean ± SE | Log Difference |
|---|---|---|---|
| Sham-Immunized | 5 | $3.1 ± 2.3 \times 10^6$ | |
| Immunized (20 μg) | 6 | $8.1 ± 2.4 \times 10^5$ | −0.6 |
| Immunized (2 μg) | 6 | $1.2 ± 0.6 \times 10^6$ | −0.4 |

Moreover, guinea pigs immunized subcutaneously with Combination I proteins were also protected against weight loss, splenomegaly, and growth of M. tuberculosis in the spleen. In the same experiment described in Example 14, guinea pigs were also immunized subcutaneously rather than intradermally with 20 μg of Combination I proteins, 4 times, 3 weeks apart. These animals were protected from challenge almost as much as the animals immunized intradermally with 20 μg of Combination I proteins.

EXAMPLE 15

Response of Combination I and Combination II Immunized Guinea Pigs to Challenge with Combination I and Combination II Additional studies were performed to ascertain whether other combinations of majorly abundant extracellular products of M. tuberculosis would provide protective immunity as well. One study utilized guinea pigs which were immunized with a vaccine comprising two combinations —Combination I (71, 32A, 30, 23, and 16) and Combination II (32A, 30, 24, 23, and 16). Combination II is believed to comprise up to 62% of the total extracellular protein normally present in M. tuberculosis supernatants. Animals (6 per group) were immunized four times with 100 μg of each protein in Combination I or II in SAF, 3 weeks apart. Negative control animals were sham-immunized with equivalent volumes of SAF and buffer on the same schedule.

As in Example 12, the animals were tested for cutaneous delayed-type hypersensitivity to determine if the animals developed a measurable immune response following vaccination. Animals immunized with Combination II had 16.8±1.3 mm (Mean±SE) erythema and 12.8±1.2 mm induration in response to skin-testing with Combination II whereas sham-immunized animals had only 1.3±0.8 mm erythema and 0.3±3 mm induration in response to Combination II. Thus, animals immunized with Combination II had greater than 12 fold more erythema and greater than 40 fold more induration than controls. By way of comparison, animals immunized with Combination I had 21.3±2.0 mm erythema and 15.8±0.1 mm induration in response to skin-testing with Combination I, whereas sham-immunized animals had only 6.4±0.8 mm erythema and 2.6±0.7 mm induration in response to Combination I. Thus, animals immunized with Combination I had greater than 3 fold more erythema and greater than 6 fold more induration than controls. The difference from controls for Combination II proteins was even greater than that for Combination I proteins.

In the same experiment, animals immunized with a lower dose of Combination II proteins (20 μg of each protein vs. 100 μg) also developed strong cutaneous hypersensitivity to Combination II. They had 21.0±2.0 mm erythema and 15.3±0.9 mm induration in response to Combination II, whereas the sham-immunized animals had only 1.3±0.8 mm erythema and 0.3±0.3 mm induration, as noted above. Thus, animals immunized with a lower dose of Combination II proteins had greater than 16 fold erythema and greater than 50 fold more induration than controls, a difference that was even greater than for animals immunized with the higher dose of Combination II proteins.

EXAMPLE 16

Immunoprotective Analysis of Combination I and II Vaccine against Aerosolized *M. tuberculosis*

Three weeks after the last immunization, the guinea pigs used for the preceding hypersensitivity assay were challenged with aerosolized *M. tuberculosis*, Erdman strain as in Example 13 and weighed weekly for 7 weeks. As in Example 13, 6 animals were in each group. During the first 7 weeks after challenge, sham-immunized animals lost an average of 19.5 g. In contrast, animals immunized with Combination II (100 μg of each protein) gained 52.4 g and animals immunized with Combination II at a lower dose (20 μg of each protein) gained an average of 67.2g. By way of contrast, animals immunized with Combination I gained 68 g. Thus, compared with guinea pigs immunized with Combination II (100 μg), sham-immunized animals lost 11% of their total body weight. Compared with guinea pigs immunized with Combination II at a lower dose (20 μg), sham-immunized animals lost 14% of their total body weight. Compared with animals immunized with Combination I, sham-immunized animals also lost 14% of their total body weight.

EXAMPLE 17

Response of Guinea Pigs Immunized with Combinations III through XII to a Challenge with the Same Vaccine or its Components Additional experiments were performed to demonstrate the effectiveness of various combinations of *M. tuberculosis* majorly abundant extracellular products. In these studies, Hartley type guinea pigs were immunized intradermally with vaccines comprising combinations of 2 or more majorly abundant extracellular products purified as in Example 2. The purified extracellular products are identified using their apparent molecular weight as determined by SDS-PAGE. The guinea pigs were immunized with the following combinations of majorly abundant extracellular products.

| Combination | Protein Constituents |
|---|---|
| III | 30 + 32A + 32B + 16 + 23 |
| IV | 30 + 32A |
| V | 30 + 32B |
| VI | 30 + 16 |
| VII | 30 + 23 |
| VIII | 30 + 71 |
| IX | 30 + 23.5 |
| X | 30 + 12 |
| XI | 30 + 24 |
| XII | 30 + 58 |

Each combination vaccine included 100 μg of each listed protein. The combination vaccines were volumetrically adjusted and injected intradermally in the adjuvant SAF. As before the guinea pigs were immunized four times, three weeks apart.

A cutaneous hypersensitivity assay was performed to determine if the animals had developed a measurable immune response following vaccination with the Combinations III to XII. Groups of six guinea pigs were shaved over the back and injected intradermally with the same combination of purified extracellular products to which they were immunized. For this challenge 10 μg of each of the proteins in the combination were injected. All injections were performed using a total volume of 0.1 ml. Sham-immunized controls, which had been immunized with SAF only were also skin-tested with Combinations III to XII, again using 10 μg of each protein in the respective combination. The diameters of erythema and induration at skin tests sites were measured 24 hours after injection as described in Example 3.

The results of these measurements are presented in Table Q below. Data are again reported in terms of mean measurement values for the group ± standard error (SE) as determined using traditional methods.

TABLE Q

| Vaccine Combination | Skin Test Combination | Diameter of Skin Reaction (mm) | |
|---|---|---|---|
| | | Erythema | Induration |
| III | III | 12.2 ± 2.0 | 6.8 ± 0.8 |
| IV | IV | 9.9 ± 0.5 | 6.3 ± 0.2 |
| V | V | 13.0 ± 1.1 | 8.1 ± 0.7 |
| VI | VI | 19.2 ± 1.2 | 12.4 ± 0.5 |
| VII | VII | 14.3 ± 1.0 | 8.7 ± 0.4 |
| VIII | VIII | 18.9 ± 1.1 | 12.6 ± 0.8 |
| IX | IX | 17.0 ± 0.9 | 12.1 ± 0.9 |
| X | X | 19.3 ± 1.4 | 13.6 ± 1.2 |
| XI | XI | 18.3 ± 1.2 | 12.4 ± 0.8 |
| XII | XII | 17.7 ± 0.9 | 14.0 ± 1.2 |
| Sham | III | 4.8 ± 0.9 | 2.0 ± 0.0 |
| Sham | IV | 4.3 ± 1.1 | 2.0 ± 0.0 |
| Sham | V | 5.0 ± 0.5 | 2.0 ± 0.0 |
| Sham | VI | 4.5 ± 0.3 | 2.0 ± 0.0 |
| Sham | VII | 4.5 ± 0.3 | 2.0 ± 0.0 |
| Sham | VIII | 3.3 ± 0.3 | 2.3 ± 0.3 |
| Sham | IX | 3.7 ± 0.3 | 2.0 ± 0.0 |
| Sham | X | 3.7 ± 0.4 | 2.0 ± 0.0 |
| Sham | XI | 3.7 ± 0.2 | 2.0 ± 0.0 |
| Sham | XII | 3.8 ± 0.2 | 2.0 ± 0.0 |

The results clearly demonstrate that a strong cell-mediated immune response was generated to each of the combinations of purified extracellular proteins. The immunized guinea pigs showed erythema at least twice and usually 3 fold or more that of controls for all combinations. Further, the immunized guinea pigs showed induration at least 3 fold that of controls for all combinations.

EXAMPLE 18

ImmunoProtective Analysis of Combinations III-XII against Aerosolized *M. tuberculosis*

To demonstrate the prophylactic efficacy of these exemplary combinations of purified extracellular products, guinea pigs immunized with Combinations III through XII were challenged with *M. tuberculosis* three weeks after the last immunization using the protocol of Example 4.

Consistent with earlier results guinea pigs immunized with Combinations III through XII were all protected against death after challenge. At 4 weeks after challenge, 2 of 6 sham-immunized animals (33%) died compared with 0 animals in groups immunized with Combinations IV-XII and 1 of 6 animals (17%) in the group immunized with Combination III. At 10 weeks after challenge, 50% of the sham-immunized animals had died compared with 0 deaths in the animals in groups immunized with Combinations IX and XII (0%), 1 of 6 deaths (17%) in the animals in the groups immunized with Combination III, IV, V, VI, X, and XI, 1 of 5 deaths (20%) in the animals immunized with Combination VIII, and 2 of 6 deaths (33%) in the animals immunized with Combination VII.

Guinea pigs that died before the end of the observation period were autopsied and examined for evidence of gross *tuberculosis* lesions. Lesions were found in all animals which expired during the study.

Following the conclusion of the mortality study, the surviving animals were sacrificed by hypercarbia and the spleen of each animal was assayed for viable *M. tuberculosis* using the protocol of Example 5. The results are presented in Table R below in terms of mean colony forming units (CFU) along with the log decrease from the sham immunized animals. An asterisk next to the CFU value indicates that spleen counts were zero on one animal in each group. For purposes of calculation, zero counts were treated as $10^3$ CFU per spleen or 3 logs.

TABLE R

| Vaccine Group | CFU in Spleen (Mean Log) | Log Decrease from Sham |
|---|---|---|
| III | 5.99 | .5 |
| IV | 5.41 | 1.1 |
| V | 6.27 | .3 |
| VI | <5.80* | >.7 |
| VII | <5.61* | >.9 |
| VIII | 6.47 | .1 |
| IX | <5.85* | >.7 |
| XXI | <5.74* | >.8 |
| XII | 5.93 | .6 |
|  | 6.03 | .5 |
| Sham | 6.53 | — |

Animals immunized with Combinations III, IV, VI, VII, IX, X, XI, and XII had at least 0.5 log fewer colony forming units of *M. tuberculosis* in their spleens on the average than the sham-immunized controls. In particular, combinations IV and VII proved to be especially effective, reducing the average number of colony forming units by roughly a factor of ten. Animals immunized with Combinations V and VIII had 0.3 and 0.1 log fewer colony forming units (CFU), respectively, in their spleens on average, than sham-immunized controls. This dramatic reduction in colony forming units in the animals immunized in accordance with the teachings of the present invention once again illustrates the immunoprotective operability of the present invention.

EXAMPLE 19

Response of Guinea Pigs Immunized with 3 Different Dosages of Combination XIII to a Challenge with Combination XIII To further define the operability and scope of the present invention as well as to demonstrate the efficacy of additional combinations of purified extracellular products, guinea pigs were immunized as before using alternative vaccination dosages. Specifically, 50 µg, 100 µg and 200 µg of an alternative combination of 3 majorly abundant extracellular products identified as Combination XIII and comprising the 30 KD, 32(A) KD, and 16 KD proteins. As with the preceding examples, groups of animals were immunized intradermally 4 times, 3 weeks apart with the alternative dosages of Combination XIII in SAF.

A cutaneous hypersensitivity assay was performed to determine if the animals had developed a measurable immune response following vaccination. The animals were shaved over the back and injected intradermally with Combination XIII containing 10.0 µg of each of the purified extracellular products. All injections were performed using a total volume of 0.1 ml. Sham-immunized controls were also skin-tested with the same dosage of Combination XIII. The diameters of erythema and induration at skin-test sites were measured 24 hours after injection.

The results are presented in Table S below in terms of mean measurement values for the group ± standard error (SE) as determined using traditional methods

TABLE S

| Vaccine Combination | Vaccine Dose (µg) | Diameter of Skin Reaction (mm) | |
|---|---|---|---|
|  |  | Erythema | Induration |
| XIII | 50 | 17.8 ± 1.3 | 13.2 ± 1.0 |
| XIII | 100 | 11.2 ± 0.9 | 7.3 ± 0.4 |
| XIII | 200 | 10.0 ± 0.7 | 7.0 ± 0.4 |
| Sham | 0 | 5.7 ± 0.5 | 0.2 ± 0.2 |

Once again, these results clearly demonstrate that a strong cell-mediated immune response to Combination XIII was generated in animals immunized with each of the three dosages of Combination XIII. The immunized animals exhibited erythema about two to three times that of controls. Even more strikingly, the immunized animals exhibited induration at least 35 fold that of control animals which exhibited a minimal response in all cases.

EXAMPLE 20

Immunoprotective Analysis of Combination XIII in Three Different Dosaqes against Aerosolized *M. tuberculosis*

To further demonstrate the protective immunity aspects of the vaccines of the present invention at various dosages, the immunized guinea pigs (6 per group) used for the preceding cutaneous hypersensitivity assay were challenged with aerosolized *M. tuberculosis* three weeks after the last immunization. The aerosol challenge was performed using the protocol detailed in Example 4. A control group of 12 sham-immunized animals was challenged simultaneously.

Figure 10:
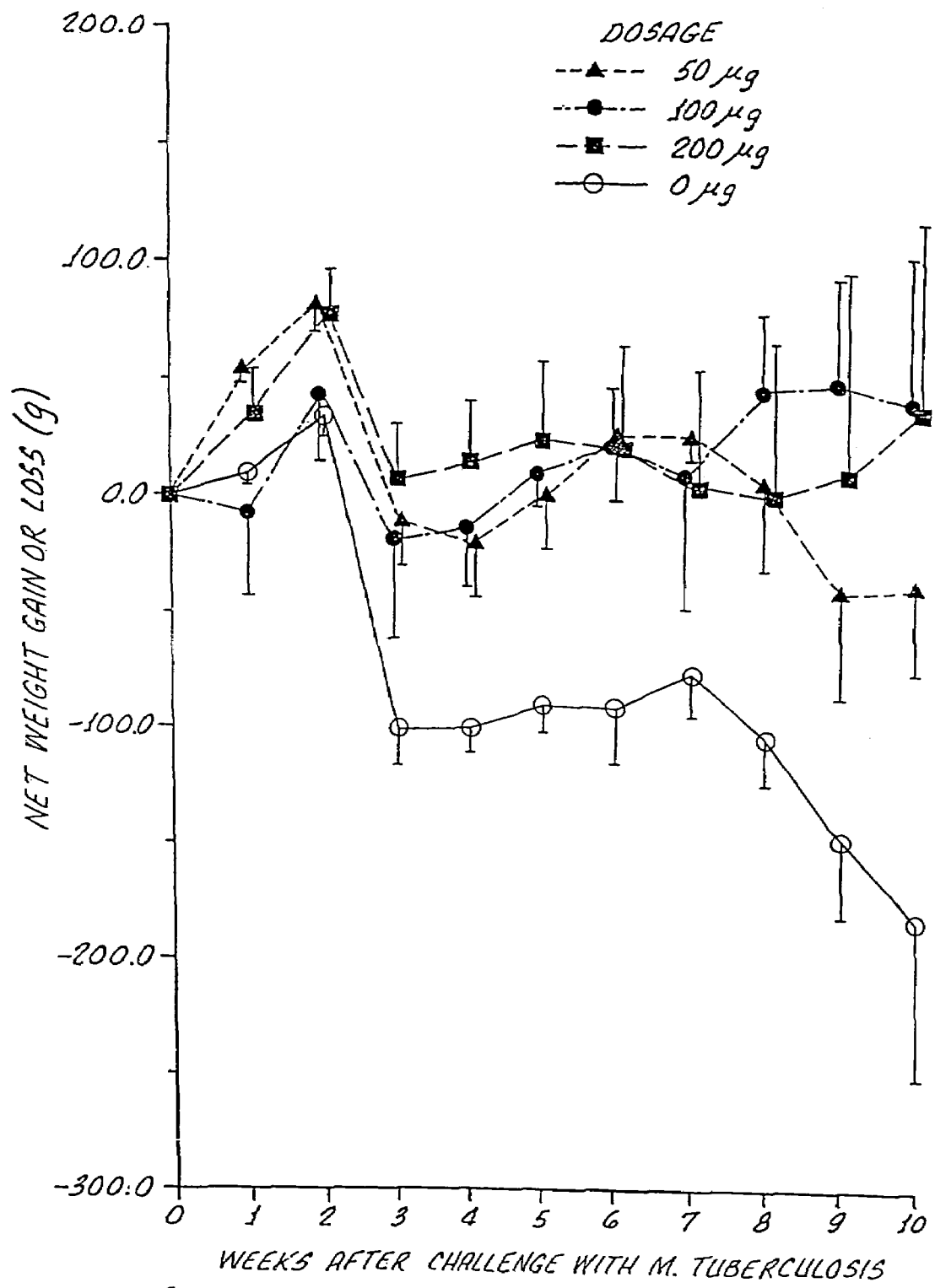
FIG. 10 is a graphical comparison of mean guinea pig body weight of animals immunized with three different dosages of a vaccine comprising a combination of extracellular products produced according to the teachings of the present invention and nonimmunized controls following exposure to an aerosolized lethal dose of M. tuberculosis.

Results of the weekly weight determinations following challenge are graphically represented in FIG. 10 and distinctly show guinea pigs immunized with each of the three dosages of Combination XIII were protected from weight loss. Animals immunized with the higher dosages of Combination XIII (100 and 200 µg) actually showed a net gain in weight and animals immunized with the lower dosage (50 µg) showed a relatively small loss in weight. In contrast, the sham immunized animals lost approximately 22% of their total body weight in the weeks immediately after challenge and averaged a loss of 182 g over the 10 week observation period.

Table U below illustrates the percent weight change for immunized and control animals as determined by taking the mean weight at the end of the challenge, subtracting the mean weight at the start of the challenge and dividing the result by the mean weight at the start of the challenge.

Similarly, the percent protection was determined by subtracting the mean percent weight loss of the controls from the mean percent weight gain or loss of the immunized animals.

TABLE U

| Immunogen | Dosage | % Weight Change | % Protection from Weight Loss |
|---|---|---|---|
| Combination XIII | 50 | −4% | 18% |
| Combination XIII | 100 | +7% | 29% |
| Combination XIII | 200 | +5% | 27% |
| Sham | Sham | −22% | — |

Table U shows that the sham-immunized animals lost a considerable amount of weight (18%-29%) over the monitoring period compared with the immunized animals. FIG. 10 provides a more graphic illustration of the net weight loss for each group of immunized animals versus sham-control animals plotted at weekly intervals over the ten week monitoring period. As loss of body mass or "consumption" is one of the classical side effects of tuberculosis, these results indicate that the growth and proliferation of tubercle bacilli in the immunized animals was inhibited by the three different dosages of the exemplary combination vaccine of the present invention.

EXAMPLE 21

Immunoprotective Analysis of Combinations XIV-XVIII against Challenge with Combinations XIV-XVIII To further demonstrate the scope of the present invention and the broad range of effective vaccines which may be formulated in accordance with the teachings thereof, five additional combination vaccines, Combinations XIV through XVIII, were tested in guinea pigs. Identified by the apparent molecular weight of the purified extracellular products determined using SDS-PAGE, the composition of each of the combination vaccines is given below.

| Combination | Protein Constituents |
|---|---|
| XIV | 30, 32A, 16, 32B, 24, 23, 45 |
| XV | 30, 32A, 16, 32B, 24, 23, 45, 23.5, 12 |
| XVI | 30, 32A, 16, 32B, 24, 23 |
| XVII | 30, 32A, 16, 32B, 24, 71 |
| XVIII | 30, 32A, 32B |
| I | 30, 32A, 16, 23, 71 |

In addition to the new combination vaccines and appropriate controls, Combination I was also used in this series of experiments. Guinea pigs were immunized intradermally with 50 μg of each protein of Combination XIV or XV and with 100 μg of each protein of Combinations I, XVI, XVII, and XVIII all in SAF adjuvant. The animals were immunized a total of four times, with each injection three weeks apart.

A cutaneous hypersensitivity assay was performed to determine if the animals had developed a measurable immune response following vaccination using the previously discussed protocol. Guinea pigs were shaved over the back and injected intradermally with the same combination of purified extracellular proteins to which they were immunized. For each challenge the appropriate combination vaccine containing 10 μg of each protein was injected. All injections were performed using a total volume of 0.1 ml. Sham-immunized controls were also skin-tested with the same dosage of each combination. The diameters of erythema and induration at skin test sites were measured at 24 hours after injection as described in Example 3.

The results of these measurements are presented in Table V below, reported in terms of mean measurement values for the group ± standard error (SE) as determined using traditional methods.

TABLE V

| Vaccine Combination | Skin Test Combination | Diameter of Skin Reaction (mm) | |
|---|---|---|---|
| | | Erythema | Induration |
| XIV | XIV | 13.3 ± 0.7 | 9.1 ± 0.4 |
| XV | XV | 10.4 ± 0.4 | 6.5 ± 0.4 |
| XVI | XVI | 8.0 ± 1.8 | 5.1 ± 1.0 |
| XVII | XVII | 9.4 ± 0.9 | 6.1 ± 1.1 |
| XVIII | XVIII | 13.6 ± 1.2 | 8.7 ± 0.7 |
| I | I | 10.0 ± 0.3 | 6.7 ± 0.2 |
| Sham | XIV | 5.5 ± 1.6 | 0.4 ± 0.2 |
| Sham | XV | 6.1 ± 0.5 | 0.4 ± 0.2 |
| Sham | XVI | 4.6 ± 1.4 | 0.4 ± 0.2 |
| Sham | XVII | 5.7 ± 1.2 | 0.2 ± 0.2 |
| Sham | XVIII | 2.1 ± 1.1 | 0 ± 0 |
| Sham | I | 6.0 ± 1.2 | 0.6 ± 0.2 |

These results clearly demonstrate that a strong cell-mediated immune response was generated to Combinations XIV through XVIII, and, as before, to Combination I. Immunized animals exhibited erythema about twice that of controls. Even more strikingly, the immunized animals exhibited induration at least 10 fold greater than the sham-immunized controls which exhibited a minimal response in all cases.

EXAMPLE 22

Immunoprotective Analysis of Combinations XIV-XVIII and Combination I against Aerosolized *M. tuberculosis*

To confirm the immunoreactivity of the combination vaccines of Example 21 and to demonstrate their applicability to infectious *tuberculosis*, the immunized guinea pigs used for the preceding cutaneous hypersensitivity assay were challenged with aerosolized *M. tuberculosis* three weeks after the last immunization and monitored using the protocol of Example 4. A control group of 12 sham-immunized animals, the same as used in Example 20, was similarly challenged. The results of these challenge are graphically represented in FIG. 11 and shown in Table W directly below.

Percent weight change was determined by taking the mean weight at the end of the challenge, subtracting the mean weight at the start of the challenge and dividing the result by the mean weight at the start of the challenge. Similarly, the percent protection was determined by subtracting the mean percent weight loss of the controls from the mean percent weight gain or loss of the immunized animals.

TABLE W

| Immunogen | % Weight Change | % Protection from Weight Loss |
| --- | --- | --- |
| Combination XIV | 3% | 25% |
| Combination XV | -4% | 18% |
| Combination XVI | -15% | 7% |
| Combination XVII | -11% | 11% |
| Combination XVIII | -12% | 10% |
| Combination I | -11% | 11% |
| Sham | -22% | |

As shown in Table W, guinea pigs immunized with each of the combination vaccines were protected from weight loss. Sham-immunized animals lost approximately 22% of their total combined body weight. In contrast the prophylactic effect of the combination vaccines resulted in actual weight gain for one of the test groups and a reduced amount of weight loss in the others. Specifically, animals immunized with Combination XIV. evidenced a 3% weight gain while those animals immunized with the other combinations lost only 4% to 15% of their total combined weight.

Figure 11:
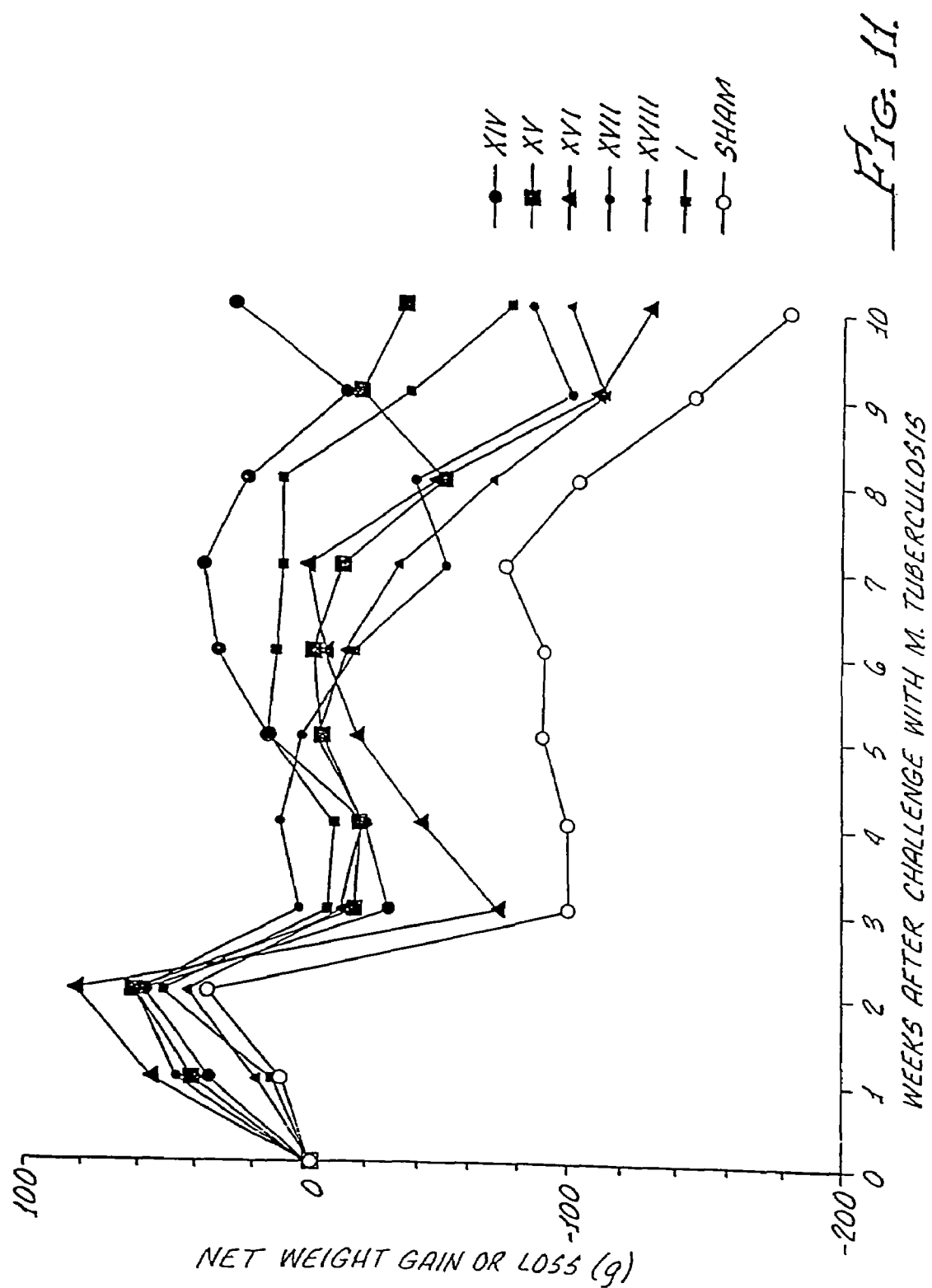
FIG. 11 is a graphical comparison of mean guinea pig body weight of animals immunized with vaccines comprising six different combinations of extracellular products produced according to the teachings of the present invention and nonimmunized controls following exposure to an aerosolized lethal dose of M. tuberculosis.

These results are shown graphically in FIG. 11 which plots weekly weight determinations in terms of net weight gain or loss for each group of animals following aerosolized challenge. This statistically significant difference between the net weight loss for the immunized animals and the sham-immunized controls shown in FIG. 11 provides further evidence for the immunoprophylactic response generated by the combination vaccines of the present invention.

EXAMPLE 23

Cell-Mediated Immunity in Guinea Pigs Immunized with Three Different Adjuvants

In order to further demonstrate the broad applicability and versatility of the vaccine formulations of the present invention, immunogenic studies were conducted using different adjuvants. Specifically three different immunogens, purified 30 KD protein, Combination I (30, 32A, 16, 23, 71) and Combination XIII (30, 32A, 16) were each formulated using three different adjuvants, Syntex Adjuvant Formulation I (SAF), incomplete Freunds adjuvant (IFA) and Monophosphoryl Lipid A containing adjuvant (MPL). Such adjuvants are generally known to enhance the immune response of an organism when administered with an immunogen.

Guinea pigs were immunized intradermally with 100 µg of each protein comprising Combinations I and XIII and approximately 100 µg of purified 30 KD protein in each of the three different adjuvant formulations. The guinea pigs were immunized with each formulation a total of three times with injections three weeks apart.

Following immunization, a cutaneous hypersensitivity assay was performed to determine if the guinea pigs had developed a measurable immune response. Guinea pigs were shaved over the back and injected intradermally with the same immunogen to which they had been immunized. For the challenge, 10 µg of each protein in Combinations I and XIII or 10 µg of purified 30 KD protein was injected in a total volume of 100 µl. Sham-immunized guinea pigs, vaccinated with one of the three adjuvants, were skin-tested with each of the immunogen formulations containing the same adjuvant. The diameters of erythema and induration at skin test sites were measured 24 hours after challenge as described in Example 3.

The results of these measurements are presented in Table X below. As previously discussed data are reported in terms of mean measurement values. for the group ± standard error as determined using accepted statistical techniques.

TABLE X

| Vaccine | Adjuvant | Skin Test Reagent | Diameter of Skin Reaction (mm) | |
| --- | --- | --- | --- | --- |
| | | | Erythema | Induration |
| 30 | SAF | 30 | 10.7 ± 1.6 | 5.8 ± 1.5 |
| 30 | IFA | 30 | 8.8 ± 0.7 | 4.6 ± 0.7 |
| 30 | MPL | 30 | 10.2 ± 1.7 | 5.3 ± 1.5 |
| XIII | SAF | XIII | 7.3 ± 0.5 | 4.1 ± 0.5 |
| XIII | IFA | XIII | 6.8 ± 0.9 | 3.5 ± 0.5 |
| XIII | MPL | XIII | 6.3 ± 0.4 | 3.4 ± 0.3 |
| I | SAF | I | 6.9 ± 0.6 | 4.0 ± 0.3 |
| I | IFA | I | 6.8 ± 0.2 | 3.6 ± 0.3 |
| I | MPL | I | 7.4 ± 0.4 | 3.9 ± 0.5 |
| Sham | SAF | 30 | 0.7 ± 0.7 | 1.0 ± 0 |
| Sham | IFA | 30 | 0 ± 0 | 0 ± 0 |
| Sham | MPL | 30 | 0 ± 0 | 0 ± 0 |
| Sham | SAF | XIII | 1.0 ± 1.0 | 1.0 ± 0 |
| Sham | IFA | XIII | 0 ± 0 | 0.3 ± 0.3 |
| Sham | MPL | XIII | 0 ± 0 | 0 ± 0 |
| Sham | SAF | I | 4.7 ± 0.3 | 1.0 ± 0 |
| Sham | IFA | I | 2.0 ± 1.0 | 0.7 ± 0.3 |
| Sham | MPL | I | 1.0 ± 1.0 | 0.7 ± 0.3 |

As shown in the data presented in Table X, the combination vaccines and purified extracellular products of the present invention provide a strong cell-mediated immunogenic response when formulated with different adjuvants. Moreover, each one of the three adjuvants provided about the same immunogenic response for each respective immunogen. In general, the immunized guinea pigs exhibited erythema diameters approximately seven to ten times that of the sham-immunized guinea pigs while indurations were approximately four to six times greater than measured in the control animals.

The ability of the present invention to provoke a strong immunogenic response in combination with different adjuvants facilitates vaccine optimization. That is, adjuvants used to produce effective vaccine formulations in accordance with the teachings herein may be selected based largely on consideration of secondary criteria such as stability, lack of side effects, cost and ease of storage. These and other criteria, not directly related to the stimulation of an immune response, are particularly important when developing vaccine formulations for widespread use under relatively primitive conditions.

EXAMPLE 24

Immunoprotective Analysis of Combinations XIX-XXVIII against Challenge with Combinations XIX-XXVIII The broad scope of the present invention was further demonstrated through the generation of an immune response using ten additional combination vaccines, Combinations XIX through XXVIII. In addition to the new combination vaccines and appropriate controls, Combinations IV and XIII were also used as positive controls to provoke an immune response in guinea pigs. Identified by the apparent molecular weight of the purified extracellular products determined using SDS-PAGE, the composition of each of the combination vaccines is given below.

| Combination | Protein Constituents |
|---|---|
| XIX | 30, 32A, 23 |
| XX | 30, 32A, 23.5 |
| XXI | 30, 32A, 24 |
| XXII | 30, 32A, 71 |
| XXIII | 30, 32A, 16, 23 |
| XXIV | 30, 32A, 16, 23.5 |
| XXV | 30, 32A, 16, 24 |
| XXVI | 30, 32A, 16, 71 |
| XXVII | 30, 32A, 16, 32B |
| XXVIII | 30, 32A, 16, 45 |
| IV | 30, 32A |
| XIII | 30, 32A, 16 |

The guinea pigs were immunized a total of four times, with each injection three weeks apart. Each combination vaccine used to immunize the animals consisted of 100 μg of each protein in SAF adjuvant to provide a total volume of 0.1 ml.

Using the protocol discussed in Example 3, a cutaneous hypersensitive assay was performed to determine if the animals had developed a measurable immune response following vaccination with the selected combination vaccine. The guinea pigs were shaved over the back and injected intradermally with the same combination of purified extracellular proteins with which they were immunized. The protein combinations used to challenge the animals consisted of 10 μg of each protein. Sham immunized controls were also skin-tested with the same dosage of each combination. As in Example 3, the diameters of erythema and induration at the skin test sites were measured at 24 hours after injection.

The results of these measurements are presented in Table Y below, reported in terms of mean measurement values for the group of animals ± standard error.

TABLE Y

| Vaccine Combination | Skin Test Combination | Diameter of Skin Reaction (mm) | |
|---|---|---|---|
| | | Erythema | Induration |
| XIX | XIX | 8.5 ± 0.6 | 3.9 ± 0.3 |
| XX | XX | 8.2 ± 0.3 | 3.7 ± 0.3 |
| XXI | XXI | 11.1 ± 1.1 | 4.5 ± 0.4 |
| XXII | XXII | 9.4 ± 0.8 | 4.3 ± 0.4 |
| XXIII | XXIII | 8.3 ± 1.1 | 3.0 ± 0.3 |
| XXIV | XXIV | 8.5 ± 0.9 | 3.4 ± 0.5 |
| XXV | XXV | 7.9 ± 0.5 | 3.2 ± 0.4 |
| XXVI | XXVI | 8.9 ± 0.7 | 3.3 ± 0.5 |
| XXVII | XXVII | 7.2 ± 1.0 | 2.8 ± 0.5 |
| XXVIII | XXVIII | 8.5 ± 0.5 | 2.8 ± 0.3 |
| IV | IV | 9.0 ± 0.9 | 4.1 ± 0.3 |
| XIII | XIII | 9.4 ± 0.9 | 4.3 ± 0.3 |
| Sham | XIX | 4.0 ± 2.6 | 1.0 ± 0 |
| Sham | XX | 1.3 ± 1.3 | 1.0 ± 0 |
| Sham | XXI | 3.5 ± 1.0 | 1.3 ± 1.3 |
| Sham | XXII | 1.3 ± 1.3 | 1.0 ± 1.0 |
| Sham | XXIII | 0 ± 0 | 1.0 ± 0 |
| Sham | XXIV | 0 ± 0 | 1.0 ± 0 |
| Sham | XXV | 0 ± 0 | 1.0 ± 0 |
| Sham | XXVI | 2.3 ± 2.3 | 2.0 ± 1.0 |
| Sham | XXVII | 0 ± 0 | 1.0 ± 0 |
| Sham | XXVIII | 2.0 ± 1.2 | 1.0 ± 0 |
| Sham | IV | 2.8 ± 1.6 | 1.0 ± 0 |
| Sham | XIII | 1.5 ± 1.5 | 1.0 ± 0 |

The results presented in Table Y explicitly show that a strong cell-mediated immune response was generated to Combinations XIX through XXVIII when challenged with the same immunogens. As before, a strong cell-mediated immune response was also provoked by Combinations IV and XIII. The erythema exhibited by the immunized guinea pigs was at least twice, and generally proved to be and more then four fold greater than, the reaction provoked in the corresponding sham immunized control animals. Similarly, the induration exhibited by the immunized animals was at least twice, and generally three to four times greater than, that of the nonimmunized controls. The substantially stronger immune response generated among the animals immunized in accordance with the teachings of the present invention once again illustrates the immunoprotective operability of the combination vaccines of the present invention.

Those skilled in the art will also appreciate additional benefits of the vaccines and methods of the present invention. For example, because individual compounds or selected combinations of highly purified molecular species are used for the subject vaccines rather than whole bacteria or components thereof, the vaccines of the present invention are considerably less likely to provoke a toxic response when compared with prior art attenuated or killed bacterial vaccines. Moreover, the molecular vaccines of the present invention are not life threatening to immunocompromised individuals. In fact, the compositions of the present invention may be used therapeutically to stimulate a directed immune response to a pathogenic agent in an infected individual.

Selective use of majorly abundant extracellular products or their immunogenic analogs also prevents the development of an opsonizing humoral response which can increase the pathogenesis of intracellular bacteria. As the protective immunity generated by this invention is directed against unbound-proteins, any opsonic response will simply result in the phagocytosis and destruction of the majorly abundant extracellular product rather than the expedited inclusion of the parasitic bacteria. Moreover, the selective use of purified extracellular products reduces the potential for generating a response which precludes the use of widely used screening and control techniques based on host recognition of immunogenic agents. Unlike prior art vaccines, the screening tests could still be performed using an immunoreactive molecule that is expressed by the pathogen but not included in the vaccines made according to the present invention. The use of such an immunogenic determinant would only provoke a response in those individuals which had been exposed to the target pathogen allowing appropriate measures to be taken.

Another advantage of the present invention is that purified extracellular products are easily obtained in large quantities and readily isolated using techniques well known in the art as opposed to the attenuated bacteria and bacterial components of prior art vaccines. Since the immunoreactive products of the present invention are naturally released extracellularly into the surrounding media for most organisms of interest, removal of intracellular contaminants and cellular debris is simplified. Further, as the most prominent or majorly abundant extracellular products or immunogenic analogs thereof are used to stimulate the desired immune response, expression levels and culture concentrations of harvestable product is generally elevated in most production systems. Accordingly, whatever form of production is employed, large scale isolation of the desired products is easily accomplished through routine biochemical procedures such as chromatography or ultrafiltration. These inherent attributes and molecular characteristics of the immunogenic determinants used in the present invention greatly facilitate the production of a consistent, standardized, high quality composition for use on a large scale.

Alternatively, the use of purified molecular compounds based on the immunogenic properties of the most prominent or majorly abundant extracellular products of target pathogens also makes the large scale synthetic generation of the immunoactive vaccine components of the present invention relatively easy. For instance, the extracellular products of interest or their immunogenic analogs may be cloned into a nonpathogenic host bacteria using recombinant DNA technology and harvested in safety. Molecular cloning techniques well known in the art may be used for isolating and expressing DNA corresponding to the extracellular products of interest, their homologs or any segments thereof in selected high expression vectors for insertion in host bacteria such as *Escherichia coli*. Exemplary techniques may be found in II R. Anon, Synthetic Vaccines 31-77 (1987), Tam et al., *Incorporation of T and B Epitopes of the Circumsporozoite Protein in a Chemically Defined Synthetic Vaccine Against Malaria*, 171 J. Exp. Med. 299-306 (1990), and Stover et al., *Protective Immunity Elicited by Recombinant Bacille Calmette-Guerin (BCG) Expressing Outer Surface Protein A (OspA) Lipoprotein: A Candidate Lyme Disease Vaccine*, 178 J. Exp. Med. 197-209 (1993).

The present invention involves a process for using a host cell to produce a majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein and respective analogs, homologs, and subunits thereof. Examples of practice demonstrating preferred methods for expressing the extracellular proteins of the present invention are as follows:

EXAMPLE 25

Expression of Recombinant 30 KD Protein

For the expression of the mature 30 KD protein, the gene encoding the 30 KD protein was engineered such that the initiator phenylalanine of the mature protein was fused to a glycine residue artificially inserted at the NcoI site or carboxyl terminus of the pelB leader sequence in pET22b (Novagen, Madison, Wis.) (see FIG. 14). This strategy provided a fusion molecule from which the mature 30 KD protein could be easily released and led to the expression of relatively large quantities of recombinant 30 KD protein over a period of 4 hours. Thereafter, expression of recombinant protein reached a plateau. Expression of the recombinant molecules continued for up to 8 hours without exerting serious detrimental effects on the bacterial culture. A typical yield from 1 liter of *E. coli* culture was approximately 50 mg, amounting to nearly 25% of the total cell protein.

To achieve expression of recombinant 30 KD protein in its full-length or truncated version, constructs in pET22b were expressed in *E. coli* BL21(DE3)pLysS upon induction with 1 mM isopropyl-β-D-thiogalactopyranoside (IPTG). Samples of induced cultures were taken at hourly intervals for up to 8 hours and aliquots of the culture supernatants and cell pellets were run on 12.5% denaturing polyacrylamide gels and stained with Coomassie brilliant blue R. Recombinant protein was purified as described by Horwitz, M. A., Lee, B.-W. E., Dillon, B. J., and Harth, G. (1995) Protective immunity against tuberculosis induced by vaccination with major extracellular proteins of *Mycobacterium tuberculosis*. Proc Natl Acad Sci USA 92:1530-1534, with the exception that all chromatography steps included the addition of 8 M urea to the buffers. The purified recombinant protein was dialyzed against phosphate buffered saline and remained soluble.

Figure 15:
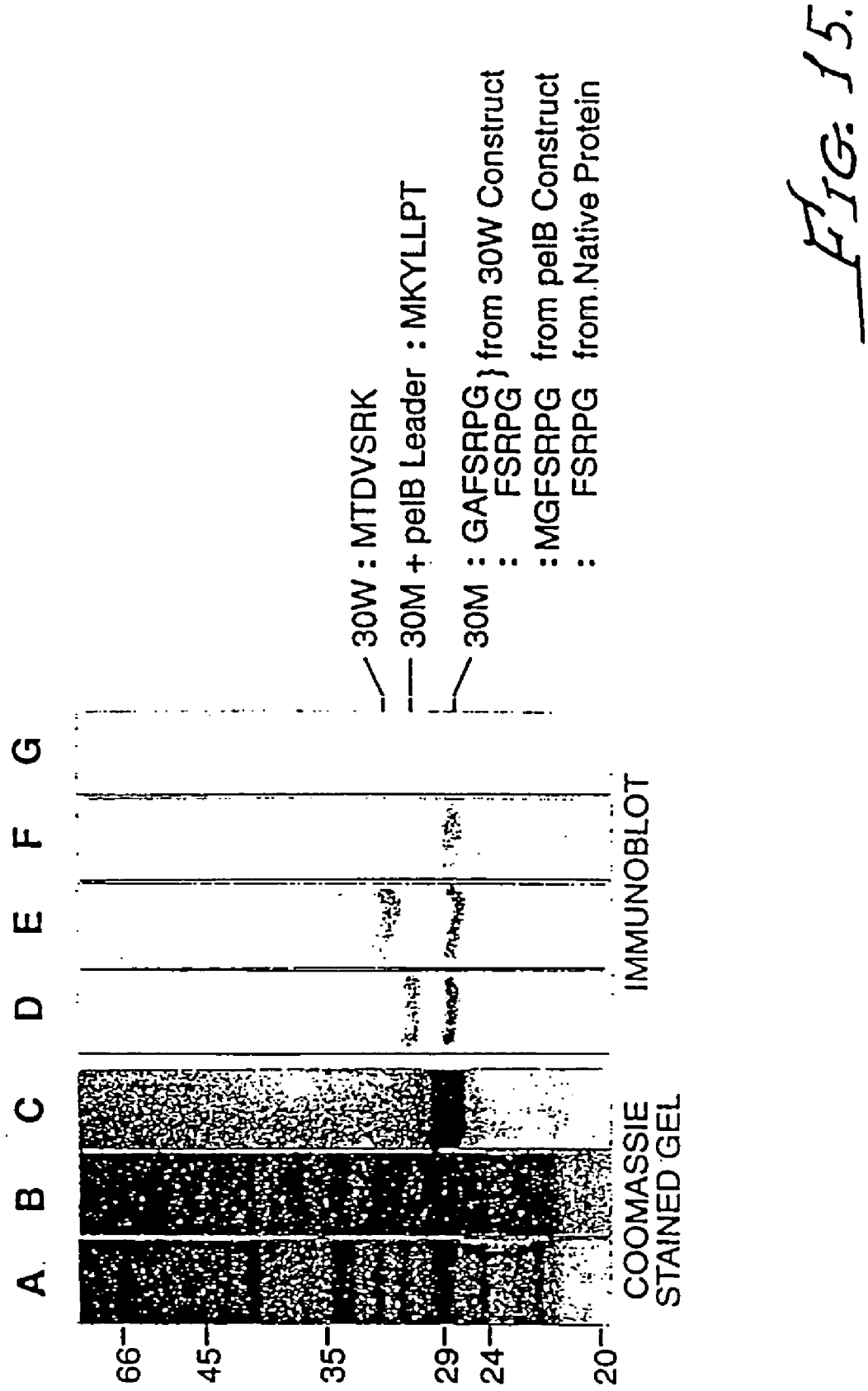
FIG. 15 shows electrophoresis test results and a Western blot analysis which confirm the expression of full-length and mature 30 KD protein in E. coli BL21(DE3)pLysS.

The mature 30 KD protein was expressed in the pET22b vector either with its own or the plasmid encoded pelB leader peptide. The results of the electrophoresis of the cell pellets are shown in FIG. 15. Lanes A and B show Coomassie stained protein extracts upon IPTG induction of bacteria carrying the pET22b vector with the mature 30 KD protein gene fused to the pelB leader DNA sequence (A) and the pET22b vector with the full-length 30 KD protein gene (B). Lane C shows mature 30 KD protein isolated from *M. tuberculosis* culture filtrates as a reference. Lanes D, E, and F show a Western blot analysis of the same proteins as in A, B, and C probed with anti-30/32A-B KD complex specific antibodies. Lane G, protein extract from *E. coil* cultures carrying the pET22b vector alone, probed with the same antibodies. Positions of full-length and mature 30 KD proteins are marked 30W and 30M, respectively, and these recombinant proteins are further identified by their first 5 or 7 N-terminal amino acids. Numbers on the left refer to molecular mass standards in KD.

EXAMPLE 26

Expression of Soluble, Processed, Extracellular, *M. tuberculosis* 30 KD Major Secretory Protein Using The Plasmid pSMT3 in *Mycobacterium smegmatis* and *Mycobacterium vaccae*

Figure 16:
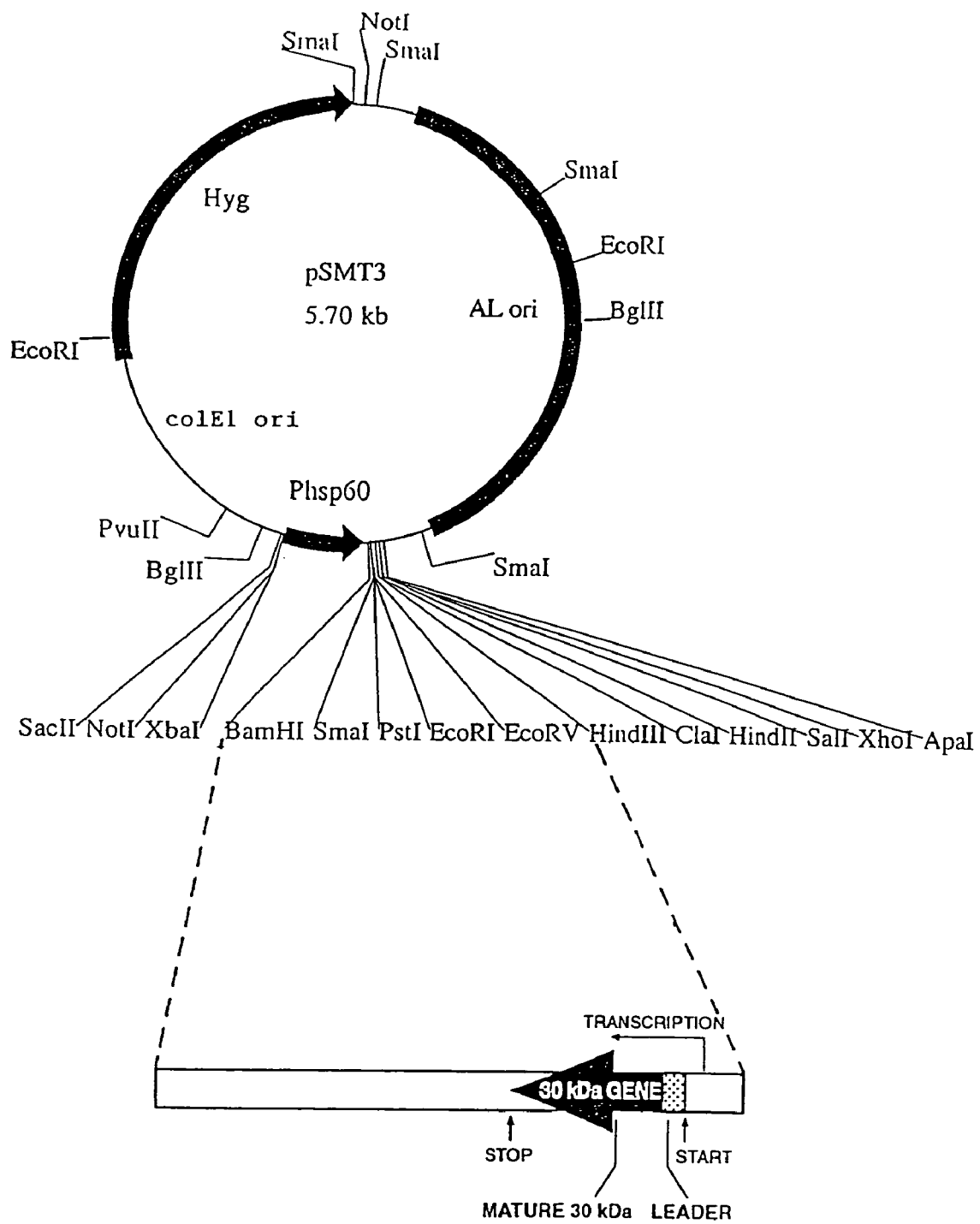
FIG. 16 is a diagrammatic representation of an alternate construct system used to express the 30 KD protein.

This example is directed to demonstrating the expression and secretion of the *M. tuberculosis* 30 KD major secretory protein in a *mycobacterium*. We used the pSMT3 plasmid (Dr. Douglas B. Young, Dept. Medical Microbiology, St. Mary's Hospital Medical School, Norfolk Place, London, W2 1PG, United Kingdom, a 5.7 kb (kilo basepairs) plasmid with both *E. coli* (col E1 ori) and *mycobacterium* (*Mycobacterium fortuitum* plasmid pAL5000 ori) origins of replication, a hygromycin resistance marker, a hsp60 promoter (*Mycobacterium bovis* BCG heat shock protein promoter sequence), and a multicloning site downstream of the hsp60 promoter. The expression system is shown diagrammatically in FIG. 16.

The insert consisted of a 4.7 kb HindIII-BamHI genomic DNA fragment from *M. tuberculosis* Erdman strain containing the sequence for the 30 KD protein. The insert was cloned into pSMT3 in *E. coil* DH5α and recombinant plasmid DNA was transformed into *M. smegmatis* 1-2c and *M. vaccae* R877R (National Collection of Type Cultures (NCTC) 11659) by electroporation at a setting of 6250 V/cm and 25 µFarad. *M. smegmatis* 1-2c is a cured isolate of strain *M. smegmatis* mc$^2$6, which is a single cell isolate of ATCC 607 (American Type Culture Collection) which was prepared from *M. smegmatis* mc$^2$6 by the procedure described in: Zhang, Y., Lathigra, R., Grabe, T., Catty, D., and Young, D., 1991, *Molecular Microbiology* 5(2):381-391. *M. smegmatis* mc$^2$6 was isolated from ATCC 607 by the procedure described in: Jacobs, W. R., Tuckman, M., and Bloom, B. R., 1987, *Nature*, 327:532-535. Using 1 µg of recombinant plasmid DNA and approximately 4×10$^9$ CFU of mycobacteria, this method yielded 100-200 hygromycin-resistant transformants. The transformants were stable in broth culture and constitutively expressed the *M. tuberculosis* 30 KD protein, yielding approximately 10 mg processed protein/L of culture. Most importantly, the protein was soluble and approximately 90% of the expressed protein was secreted in the culture supernatant (see FIG. 17).

Figure 17:
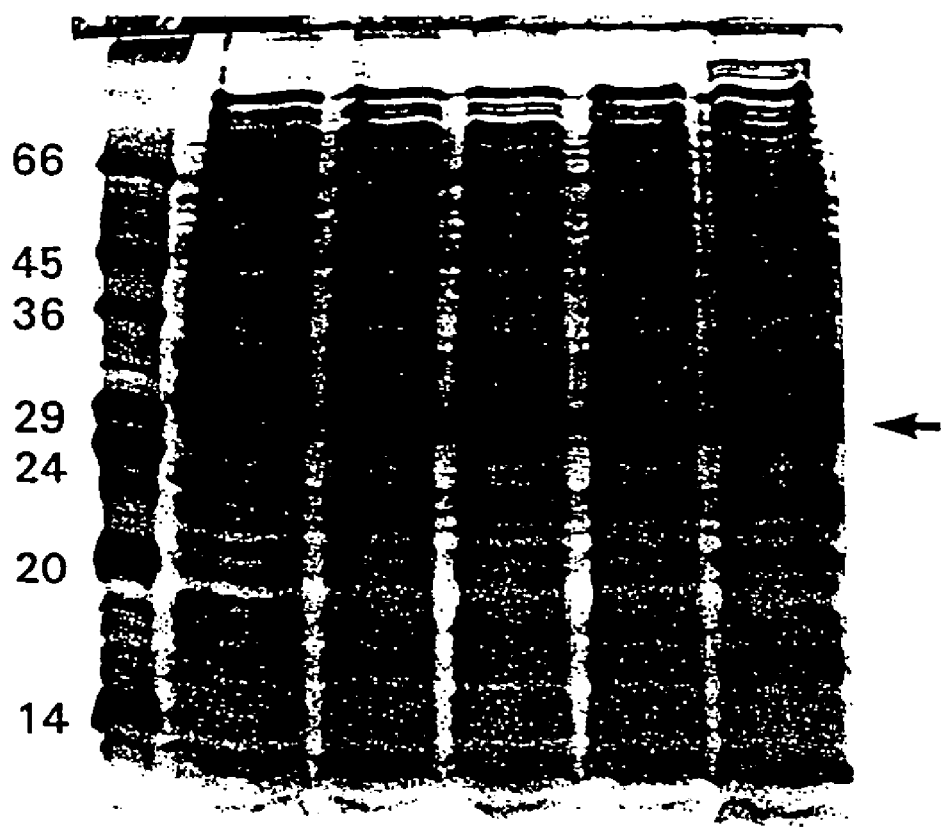
FIG. 17 shows electrophoresis test results which confirm the expression of the M. tuberculosis 30 KD protein in M. smegmatis.
Figure 18:
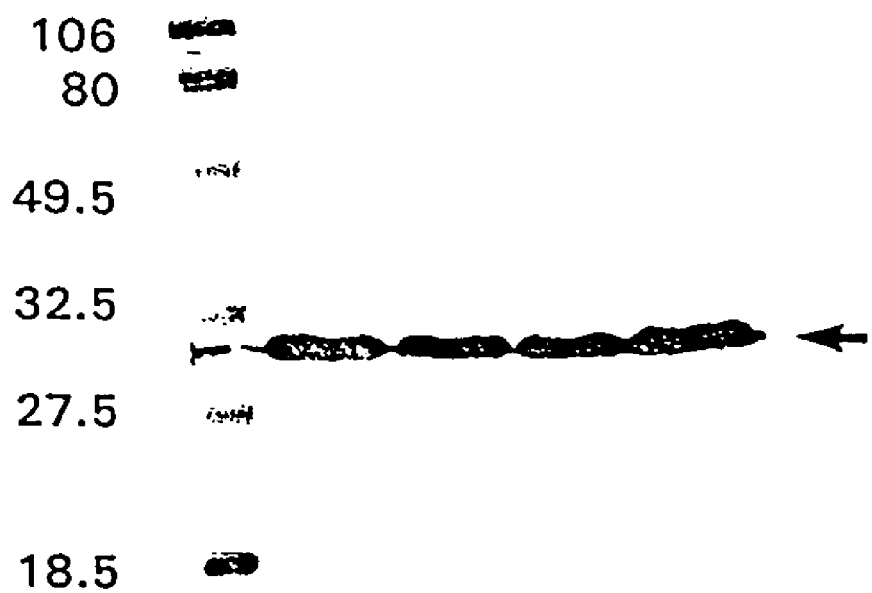
FIG. 18 depicts the results of a Western blot analysis, confirming the expression of the M. tuberculosis 30 KD protein in M. smegmatis.
Figure 20:
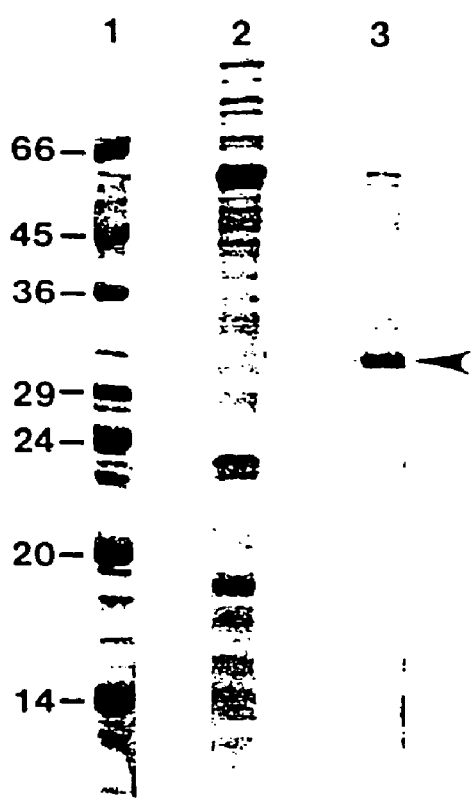
FIG. 20 shows electrophoresis test results comparing secretion of recombinant mature *M. tuberculosis* 32A KD major extracellular protein at 28° C. (Lane 3) and 37° C. (Lane 2).

The electrophoresis results shown in FIG. 17 were obtained as follows. Supernatant fluid from each of 5 recombinant *M. smegmatis* clones containing the pSMT3 construct with the *M. tuberculosis* 30 KD gene was subjected to SDS-PAGE (solium dodecyl sulfate-polyacrylamide gel electrophoresis) analysis (5 right most lanes). The major protein (arrow in FIG. 17) is the recombinant mature *M. tuberculosis* 30 KD major secretory protein. The left most lane depicts molecular mass standards (66, 45, 36, 29, 24, 20, 14 KD). The recombinant protein migrates just above the 29 KD marker.

Western blot analysis was used to confirm that the major extracellular protein in the culture supernatant was the recombinant mature *M. tuberculosis* 30 KD major secretory protein. The results are shown in FIG. 18. In FIG. 18, the proteins depicted in the four rightmost lanes of FIG. 17 were subjected to SDS-PAGE and blotted onto nitrocellulose (4 right most lanes). The blot was probed with rabbit polyclonal antibody specific to the *M. tuberculosis* 30/32 KD protein complex. Only the recombinant *M. tuberculosis* 30 KD protein is stained (arrow). The lane to the left contains prestained molecular mass markers (106, 80, 49.5, 32.5, 27.5, and 18.5 KD). The recombinant protein migrates between the 32.5 and 27.5 KD mass standards.

In addition, N-terminal sequence analysis of the first 6 N-terminal amino acids yielded FSRPGL, confirming that the N-terminal sequence was identical to that of the mature *M. tuberculosis* 30 KD protein.

Two constructs in pET20 (Novagen, Madison, Wis.), one for the mature 30 KD protein and the other for the 32A KD protein, failed to yield expression of either protein in *E. coli*. The isolation of pKK233 is described by Amann, E. and Brosius, J. (1985) *Gene*, 40:183-190. pTrc99A (Pharmacia Biotech, Sweden) may be used in place of the pKK233 vector. Three different constructs in pKK233—one for the full-length 30 KD protein, one for the full-length 32 KD protein, and one for the mature 30 KD protein—failed to yield expression of any of the proteins in *E. coli.*

One construct in pRSET-A for the mature 30 KD protein yielded a fusion protein in *E. coli*, but the 30 KD protein could not be cleaved free of this fusion protein with enterokinase. Similarly, two constructs in pTrx-Fus, one for the mature 30 KD protein and one for the mature 32 KD protein, yielded fusion proteins in *E. coli* from which the *M. tuberculosis* proteins could not be efficiently cleaved with enterokinase. A summary of the suitability of various expression systems is set forth in Table Z. All of the inserts are for the 32A KD protein.

TABLE Z

| PLASMID | INSERT | JUNCTIONS | HOST STRAIN | EXPRESSION | SOLUBILITY/YIELD | COMMENTS |
|---|---|---|---|---|---|---|
| pET22b | Full-length 30K | 5'-NdeI-ATG-30K(F-L)-TGA---N---EcoRI-Vector-3' | BL21(DE3)/pLyS unstable | Yes, no Fusion 100 mg/L | insoluble (pellet) 1 mg/L; purified | 40% Processing F-L/mature/mature + 2aa |
| pET22b | Full-length 32K | 5-NdeI-ATG-32K(F-L)-TAG---N---EcoRI-Vector-3' | BL2I(DE3)/pLysS unstable | Yes, no Fusion 100 mg/L | insoluble (pellet) 1 mg/L; purified | 90% Processing F-L/mature + 2aa |
| pET22b | Mature 30K | 5'-NdeI-pelB-NcoI-GGG-TTC-30K(M)-TGA-N-EcoRI-Vector-3' | BL21(DE3)/pLysS unstable | Yes, pelB-Fusion 120 mg/L | insoluble (pellet) 1 mg/L; purified | 50% Processing pelB + /mature /mature + 2aa |
| pET22b | Mature 32K | 5'-NdeI-pelB-NcoI-GGG-TTT-32K(M)-TAG-N-EcoRI-Vector-3' | BL21(DE3)/pLysS unstable | Yes, pelB-Fusion 150 mg/L | insoluble (pellet) 1 mg/L; purified | 60% Processing pelB + /mature /mature + 2aa |
| pET22b | Mature 30K | 5'-NdeI-TTC--30K(M)--TGA--N--EcoRI-Vector-3' | BL21(DE3)/pLysS | No | | |
| pET22b | Mature 32K | 5'-NdeI-TTT--32K(M)--TAG--N--EcoRI-Vector-3' | BL21(DE3)/pLysS | No | | |
| pET20 | Mature 30K | 5'-NdeI-TTC--30K(M)--TGA--N--EcoRI-Vecor-3' | BL21(DE3)/pLyS | No | | |
| pET20 | Mature 32K | 5'-NdeI-TTT--32K(M)--TAG--N--EcoRI-Vector-3' | BL21(DE3)/pLysS | No | | |
| pSMT3 | Full-length 30K | 5'-phsp60--MCS-BHI-4.7kbgen.30K-HdIII-MCS--Vector-3' | M. smegmatis 1-2c | Yes, no Fusion 10 mg/L | soluble (supernatant) | 90% Processing |
| pSMT3 | Full-length 30K | 5'phsp60--MCS-BHI-4.7kbgen.30K-HdIII--MCS--Vector-3' | M. vaccae R877R NCTC11659 | Yes, no Fusion 10 mg/L | soluble (supernatant) | 90% processing |
| pRSET-A | Mature 30K | 5'-MCS-(EK)-BamHI-TTC--30K(M)--TGA-N-EcoRI-Vector-3' | BL21(DE3)/pLysS stable | Yes, Fusion 100 mg/L | insoluble (pellet) not purified | No EK cleavage mature + 2aa |
| pTrxFus | Mature 30K | 5'-Trx-(EK)-KpnI-TTC--30K(M)-TGA--N--BamHI-Vector-3' | G1724 & G1698 stable in G1698 | Yes, Trx Fusion 50 mg/L | soluble (cytoplasm) not purified | 10% EK cleavage mature + 2aa |
| pTrxFus | Mature 32K | 5'-Trx-(EK)-KpnI-TTT-32K(M)-TAG--N--BamHI-Vector-3' | G1724 & G1698 stable in G1698 | Yes, Trx-Fusion 50 mg/L | soluble (cytoplasm) not purified | 10% EK cleavage mature + 2aa |
| pKK233 | Full-length 30K | 5'-NcoI-N-ATG-30K(F-L)-TGA-N-EcoRI(bI)HindIII(bI)-Vector-3' | JM109 | No | | |
| pKK233 | Full-length 32K | 5'-NcoI-N-ATG-32K(F-L)-TAG-N-EcoRI(bI)/HindIII(bI)-Vector-3' | JM109 | No | | |
| pKK233 | Mature 30K | 5'-NcoI(blunt)-TTC---30K(M)---TGA--N---HindIII-Vector-JM109 3' | | | | |
| pBK33 | Mature 30K | 5'-sacB-BamHI-TTC--30K(M)--TGA--N--BamHI-Vector-3' | B. subtilis BD168 & No 170 | | | |
| pBK33 | Mature 32K | 5'-sacB-BamHI-TTT--32K(M)--TAG--N-BamHI-Vector-3' | B. subtilis BD168 & No 170 | | | |
| pPL608 | Full-length 30K | 5'-SmaI-200N-ATG-30K(F-L)-TGA-200N-HincII-Vector-3' | B. subtilis Bd168 & No 170 | | | |

As can be seen from Table Z, not all constructs resulted in protein expression. A leader sequence in front of the structural gene was required for expression. Thus, one pET22b construct containing the mature 30 KD protein gene and one construct containing the mature 32A KD protein gene failed to express either protein. Successful expression in pET22b of the 30 and 32A KD *M. tuberculosis* proteins was obtained by adding the respective leader sequence of the protein in front of the structural gene. For both proteins, this resulted in expression of both the full-length and processed protein. These constructs were relatively stable in *E. coli*, i.e. they expressed the recombinant proteins after 2 or 3 subcultures but not after additional subculturing.

Successful expression in pET22b of the 30 and 32A KD *M. tuberculosis* proteins was also obtained by adding the *E. coli*-derived pelB leader sequence in front of the structural gene for each protein. Expression levels in these constructs were even higher than in those utilizing the respective leader sequences of the 30 or 32A KD proteins. However, a drawback of the pelB constructs was their instability. These constructs lost their ability to express any recombinant protein after one subculture Previously, expression and secretion of the *M. tuberculosis* 32A KD protein had been achieved in *Mycobacterium smegmatis* and *Mycobacterium vaccae* using pSMT3 based expression constructs containing a −4.5 kb DNA fragment which was flanked by EcoRV restriction sites and which encoded the full-length 32A protein gene. However, in contrast to the case with the *M. tuberculosis* 30 KD major extracellular protein and the *M. tuberculosis* 16 KD major extracellular protein, use of these constructs resulted in the intracellular accumulation of *M. tuberculosis* 32A KD protein and did not yield high-level secretion of the *M. tuberculosis* 32A KD protein.

The present invention functions by culturing the recombinant strains of *Mycobacterium smegmatis* containing DNA fragments encoding the full-length 32A KD major extracellular protein at 28° C. rather than 37° C., the usual temperature for culturing these bacteria. When cultured at 28° C., the recombinant mycobacterium expresses and secretes large quantities of the 32A KD protein. The secreted protein can then be purified from the culture supernatant fluid by conventional purification techniques.

Prior to the present invention, only small amounts of recombinant *M. tuberculosis* 32A KD protein could be obtained from recombinant mycobacteria expressing the protein. The invention allows large amounts of recombinant 32A protein to be obtained from the culture filtrate of recombinant mycobacteria, which secrete the 32A KD protein into the culture medium. Thus, the cost-effective production of recombinant 32A KD protein becomes possible.

EXAMPLE 27

The gene from the *M. tuberculosis* 32A KD major extracellular protein was cloned into *Mycobacterium smegmatis* using a pSMT3-based expression construct containing an ~4.5 kb DNA fragment, flanked by EcoRV restriction sites, that encoded the full-length 32A KD protein (Construct A in FIG. 19). The recombinant *M. smegmatis* was cultured in 7H9 medium containing 2% glucose at 37° C. and 28° C. The culture filtrate of each organism was then collected and subjected to SDS-PAGE analysis. When *M. smegmatis* containing the pSMT3 vector with the full-length 32A KD protein gene was cultured at 37° C., virtually no 32A KD protein was present in the culture filtrate, (Lane 2 of FIG. 20). However, when the same *M. smegmatis* strain was cultured at 28° C., a large amount of 32A KD protein was secreted and present in the culture filtrate (Lane 3, arrowhead). Lane 1 shows molecular weight standards, the molecular weight×$10^{-3}$ being noted to the left of the standards. Lane 2 shows filtrate from *M. smegmatis* containing the pSMT3 vector with the full-length *M. tuberculosis* 32A KD protein gene that was cultured at 37° C. Lane 3 shows filtrate from *M. smegmatis* containing pSMT3 vector with the full-length *M. tuberculosis* 32A KD protein gene that was cultured at 28° C.

*M. smegmatis* containing constructs B, D, E, and G also expressed and secreted large amounts of recombinant *M. tuberculosis* 32A KD protein when cultured at 28° C.

An N-terminal amino acid analysis of recombinant *Mycobacterium tuberculosis* 32A KD protein expressed and secreted by *Mycobacterium smegmatis* at 28° C. gives the following sequence:

```
                                    (SEQ ID NO: 167)
             1         6
             F S R P G L P
```

Two recombinant *M. smegmatis* strains (Constructs A and D) containing the full length *M. tuberculosis* 32A KD protein gene were cultured at 28° C. The culture filtrate of each organism was obtained and an aliquot subjected to denaturing SDS-PAGE analysis. The proteins were transferred to polyvinylidine fluoride (PVDF) membranes and the Coomassie blue R stained band migrating at 32 KD was cut out and subjected to automated amino acid sequence determination. The sequence shown above is in the conventional one-letter code.

The N-terminal sequence of the recombinant protein secreted by *M. smegmatis* containing either Construct A or D is identical to the native *M. tuberculosis* 32A KD protein, confirming that the recombinant *M. tuberculosis* 32A KD protein in *M. smegmatis* is processed the same way as the native *M. tuberculosis* 32A KD in *M. tuberculosis.*

Similarly, the extracellular proteins, their analogs, homologs or immunoreactive protein subunits may be chemically synthesized on a large scale in a relatively pure form using common laboratory techniques and automated sequencer technology. This mode of production is particularly attractive for constructing peptide subunits or lower molecular weight analogs corresponding to antigenic determinants of the extracellular products. Exemplary techniques for the production of smaller protein subunits are well known in the art and may be found in II R. Anon, *Synthetic Vaccines* 15-30 (1987), and in A. Streitwieser, Jr., *Introduction to Organic Chemistry* 953-55 (3rd ed. 1985). Alternative techniques may be found in Gross et al., "Nonenzymatic Cleavage of Peptide Bonds: The Methionine Residues in Bovine Pancreatic Ribonuclease," 237 *The Journal of Biological Chemistry* No. 6 (1962), Mahoney, "High-Yield Cleavage of Tryptophanyl Peptide Bonds by o-Iodosobenzoic Acid," 18 *Biochemistry* No. 17 (1979), and Shoolnik et al., "Gonococcal Pili," 159 *Journal of Experimental Medicine* (1984). Other immunogenic techniques such as anti-idiotyping or directed molecular evolution using peptides, nucleotides or other molecules such as mimetics can also be employed to generate effective, immunoreactive compounds capable of producing the desired prophylactic response.

Nucleic acid molecules useful for the practice of the present invention may be expressed from a variety of vectors, including, for example, viral vectors such as herpes viral vectors (e.g., U.S. Pat. No. 5,288,641), retroviruses (e.g., EP 0,415,731; WO 90/07936, WO 91/0285, WO 94/03622; WO 93/25698; WO 93/25234; U.S. Pat. No.

5,219,740; WO 89/09271; WO 86/00922; WO 90/02797; WO 90/02806; U.S. Pat. No. 4,650,764; U.S. Pat. No. 5,124,263; U.S. Pat. No. 4,861,719; WO 93/11230; WO 93/10218; Vile and Hart, *Cancer Res*. 53:3860-3864, 1993; Vile and Hart, *Cancer Res*. 53:962-967, 1993; Ram et al., *Cancer Res*. 53:83-88, 1993; Takamiya et al., *J. Neurosci. Res*. 33:493-503, 1992; Baba et al., *J. Neurosurg*. 79:729-735, 1993), pseudotyped viruses, adenoviral vectors (e.g., WO 94/26914, WO 93/9191; Kolls et al., *PNAS* 91(1):215-219, 1994; Kass-Eisler et al., *PNAS* 90(24):11498-502, 1993; Guzman et al., *Circulation* 88(6):2838-48, 1993; Guzman et al., *Cir. Res*. 73(6):1202-1207, 1993; Zabner et al., *Cell* 75(2):207-216, '993; Li et al., *Hum. Gene Ther*. 4(4):403-409, 1993; Caillaud et al., *Eur. J. Neurosci*. 5(10: 1287-1291, 1993; Vincent et al., *Nat. Genet*. 5(2):130=134, 1993; Jaffe et al., *Nat. Genet*. 1(5):372-378, 1992; and Levrero et al., *Gene* 101(2):195-202, 1991), adenovirus-associated viral vectors (Flotte et al., *PNAS* 90(22):10613-10617, 1993), parvovirus vectors (Koering et al., *Hum. Gene Therap*. 5:457-463, 1994), and pox virus vectors (Panicali and Paoletti, *PNAS* 79:4927-4931, 1982). Typical expression vectors are disclosed in copending application Ser. No. 08/545,926, filed Oct. 20, 1995, the disclosure of which is incorporated herein by reference.

The nucleic acid molecules (or vectors, i.e., an assembly capable of directing the expression of a sequence of interest) may be introduced into host cells by a wide variety of mechanisms, including, for example, transfection, including, for example, DNA linked to killed adenovirus (Michael et al., *J. Biol. Chem*. 268(10:6866-6869, 1993; and Curiel et al., *Hum. Gene Ther*. 3(2):147-154, 1992), cytofectin=mediated introduction (DMRIE-DOPE, Vical, Calif.), direct DNA injection (Acsadi et al., *Nature* 352:815-818, 1991); DNA ligand (Wu et al., *J. of Biol. Chem*. 264:16985-16987, 1989); lipofection (Felgner et al., *Proc. Natl. Acad. Sci, USA* 84:7413-7417, 1989); liposomes (Pickering et al., *Circ*. 89(1):13-21, 1994; and Wang et al., *PNAS* 84:7851-7855, 1987); microprojectile bombardment (Williams et al., *PNAS* 88:2726-2730, 1991); and direct delivery of nucleic acids which encode the enzyme itself, either alone (Vile and hart, *Cancer Res*. 53:3860-3864, 1993); or utilizing PEG-nucleic acid complexes (see also WO 93/18759; WO 93/04701; WO 93/07283 and WO 93/07282).

As an additional alternative, DNA or other genetic material encoding one or more genes capable of inducing the expression of one or more of the extracellular products, homologs, analogs, or subunits of the present invention can be directly injected into a mammalian host utilizing so called "naked DNA" techniques. Following the in vivo introduction and the resultant uptake of the genetic construct by the host's cells the host will begin the endogenous production of the one or more encoded immunoreactive products engendering an effective immune response to subsequent challenge. As those skilled in the art will appreciate, coupling the genetic construct to eucaryotic promoter sequences and/or secretion signals may facilitate the endogenous expression and subsequent secretion of the encoded immunoreactive product or products. Exemplary techniques for the utilization of naked DNA as a vaccine can be found in International Patent No. WO 9421797 A (Merck & Co. Inc. and ViCal Inc.), International Patent Application No. WO 9011092 (ViCal Inc.), and, Robinson, *Protection Against a Lethal Influenza Virus Challenge by Immunization with a Hemagglutinin-Expressing Plasmid DNA*, 11 Vaccine 9 (1993), and in Ulmer et al., *Heterologous Protection Against Influenza by Injection of DNA Encoding a Viral Protein*, 259 Science (1993), incorporated by reference herein.

Alternatively, techniques for the fusion of a strongly immunogenic protein tail have been disclosed in Tao et al., *Idiotype/Granulocyte-Macrophage Colony-Stimulating Factor Fusion Protein as a Vaccine for B-Ceo Lymphoma*, 362 Nature (1993), and for T-cell epitope mapping in Good et al., *Human T-Cell Recognition of the Circumsporozoite Protein of Plasmodium falciparum: Immunodominant T-Cell Domains Map to the Polymorphic Regions of the Molecule*, 85 Proc. Natl. Acad. Sci. USA (1988), and Gao et al., *Identification and Characterization of T Helper Epitopes in the Nucleoprotein of Influenza A Virus*, 143 The Journal of Immunology No. 9 (1989).

As many bacterial genera exhibit homology, the foregoing examples are provided for the purposes of illustration and are not intended to limit the scope and content of the present invention or to restrict the invention to the genus *Mycobacterium* or to particular species or serogroups therein or to vaccines against *tuberculosis* alone. It should also be reemphasized that the prevalence of interspecies homology in the DNA and corresponding proteins of microorganisms enables the vaccines of the present invention to induce cross-reactive immunity. Because the immunodominant epitopes of the majorly abundant extracellular products may provide cross-protective immunity against challenge with other serogroups and species of the selected genera, those skilled in the art will appreciate that vaccines directed against one species may be developed using the extracellular products or immunogenic analogs of another species.

For example, *M. bovis* is between 90% and 100% homologous with *M. tuberculosis* and is highly cross-reactive in terms of provoking an immune response. Accordingly, vaccines based on abundant extracellular products of *M. bovis* or other *Mycobacterium* can offer various degrees of protection against infection by *M. tuberculosis* and vice versa. Thus, it is contemplated as being within the scope of the present invention to provide an immunoprophylactic response against several bacterial species of the same genera using an highly homologous immunogenic determinant of an appropriate majorly abundant extracellular product.

It should also be emphasized that the immunogenic determinant selected to practice the present invention may be used in many different forms to elicit an effective protective or immunodiagnostic immune response. Thus the mode of presentation of the one or more immunogenic determinants of selected majorly abundant extracellular products to the host immune system is not critical and may be altered to facilitate production or administration. For example, the vaccines of the present invention may be formulated using whole extracellular products or any immunostimulating fraction thereof including peptides, protein subunits, immunogenic analogs and homologs as noted above.

In accordance with the teachings of the present invention, effective protein subunits of the majorly abundant extracellular products of *M. tuberculosis* can be identified in a genetically diverse population of a species of mammal. The resultant immunodominant T-cell epitopes identified should be recognized by other mammals including humans and cattle. These immunodominant T-cell epitopes are therefore useful for vaccines as well as for immunodiagnostic reagents. An exemplary study identifying the immunodominant T-cell epitopes of the 30 KD major secretory protein of *M. tuberculosis* was conducted as follows.

EXAMPLE 28

Immunodominant Epitope Mapping of the 30 KD Protein

Figure 12A:
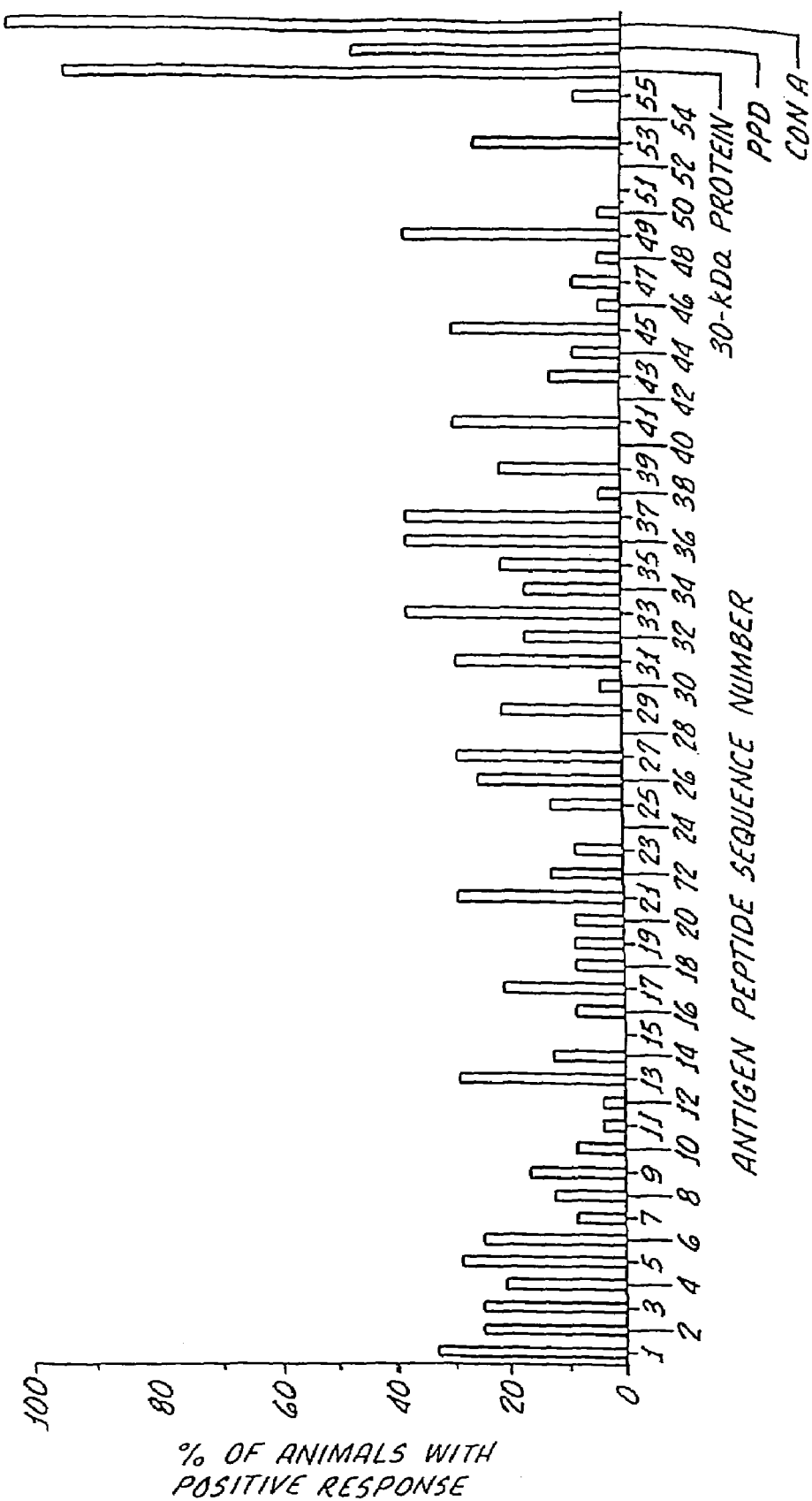
FIGS. 12a and b are graphical illustrations of the mapping of the immunodominant epitopes of the 30 KD protein of M. tuberculosis.
Figure 12B:
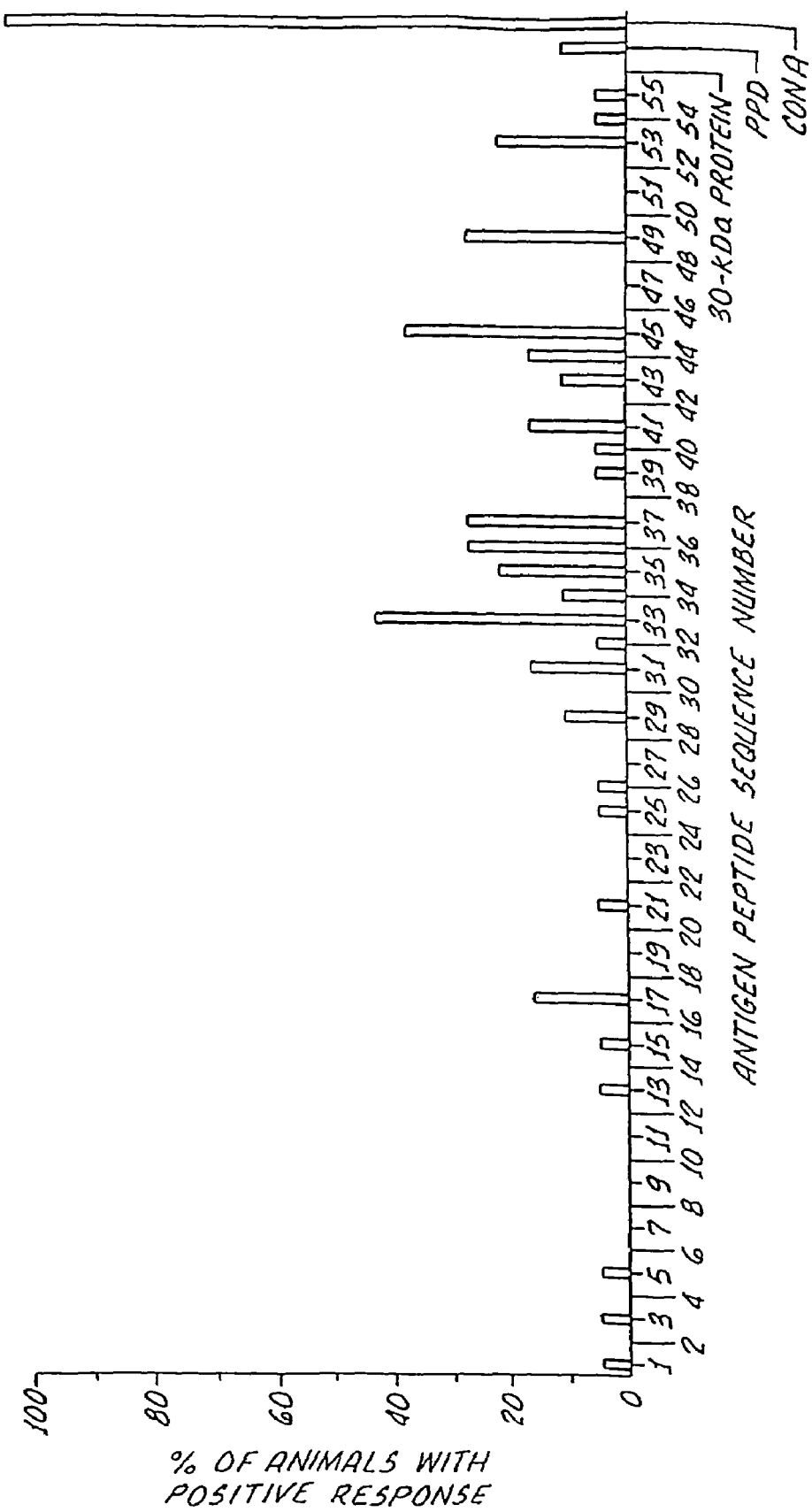
FIG. 12b illustrates a corresponding set of data for a group of 19 sham immunized guinea pigs. The response of each group of animals to native 30 KD protein, purified protein derivative (PPD) and concanavalin A (con A) appears at the right of each graph.
Figure 13:
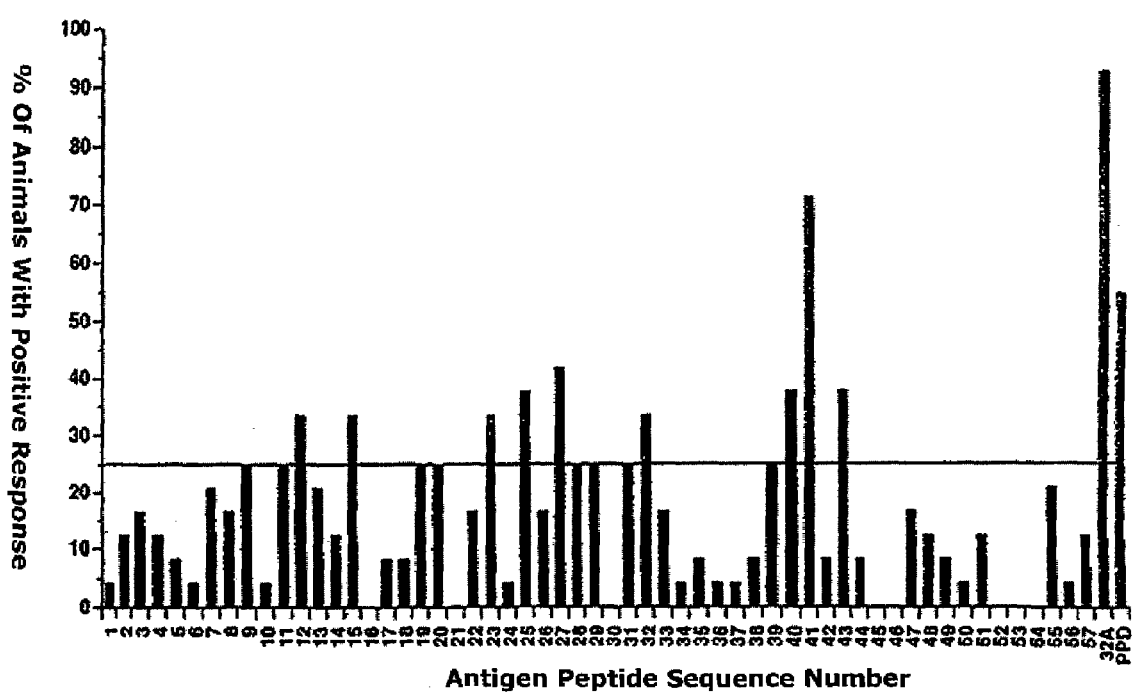
FIG. 13 is a graphical illustration of the mapping of the immunodominant epitopes of the 32A KD protein of M. tuberculosis.

Fifty-five synthetic peptides (15-mers) covering the entire native 30 KD protein and overlapping by 10 amino acids were used for splenic lymphocyte proliferation assays to identify the immunodominant T-cell epitopes of the 30 KD major secretory protein of *M. tuberculosis* 55. The sequence of each 15-mer synthetic peptide utilized is given below in conjunction with an identification number (1-55) corresponding to the antigen peptide sequence numbers in FIGS. 12*a* and *b* as well as an identification of the amino acid residues and relative position of each sequence.

| No. | Residues | Peptide Sequence | Seq ID No. |
|---|---|---|---|
| 1 | 1-15 | F S R P G L P V E Y L Q V P S | 37 |
| 2 | 6-20 | L P V E Y L Q V P S P S M G R | 38 |
| 3 | 11-25 | L Q V P S P S M G R D I K V Q | 39 |
| 4 | 16-30 | P S M G R D I K V Q F Q S G G | 40 |
| 5 | 21-35 | D I K V Q F Q S G G N N S P A | 41 |
| 6 | 26-40 | F Q S G G N N S P A V Y L L D | 42 |
| 7 | 31-45 | N N S P A V Y L L D G L R A Q | 43 |
| 8 | 36-50 | V Y L L D G L R A Q D D Y N G | 44 |
| 9 | 41-55 | G L R A Q D D Y N G W D I N T | 45 |
| 10 | 46-60 | D D Y N G W D I N T P A F E W | 46 |
| 11 | 51-65 | W D I N T P A F E W Y Y Q S G | 47 |
| 12 | 56-70 | P A F E W Y Y Q S G L S I V M | 48 |
| 13 | 61-75 | Y Y Q S G L S I V M P V G G Q | 49 |
| 14 | 66-80 | L S I V M P V G G Q S S F Y S | 50 |
| 15 | 71-85 | P V G G Q S S F Y S D W Y S P | 51 |
| 16 | 76-90 | S S F Y S D W Y S P A C G K A | 52 |
| 17 | 81-95 | D W Y S P A C G K A G C Q T Y | 53 |
| 18 | 86-100 | A C G K A G C Q T Y K W E T F | 54 |
| 19 | 91-105 | G C Q T Y K W E T F L T S E L | 55 |
| 20 | 96-110 | K W E T F L T S E L P Q W L S | 56 |
| 21 | 101-115 | L T S E L P Q W L S A N R A V | 57 |
| 22 | 106-120 | P Q W L S A N R A V K P T G S | 58 |
| 23 | 111-125 | A N R A V K P T G S A A I G L | 59 |
| 24 | 116-130 | K P T G S A A I G L S M A G S | 60 |
| 25 | 121-135 | A A I G L S M A G S S A M I L | 61 |
| 26 | 126-140 | S M A G S S A M I L A A Y H P | 62 |
| 27 | 131-145 | S A M I L A A Y H P Q Q F I Y | 63 |
| 28 | 136-150 | A A Y H P Q Q F I Y A G S L S | 64 |
| 29 | 141-155 | Q Q F I Y A G S L S A L L D P | 65 |
| 30 | 146-160 | A G S L S A L L D P S Q G M G | 66 |
| 31 | 151-165 | A L L D P S Q G M G P S L I G | 67 |
| 32 | 156-170 | S Q G M G P S L I G L A M G D | 68 |
| 33 | 161-175 | P S L I G L A M G D A G G Y K | 69 |
| 34 | 166-180 | L A M G D A G G Y K A A D M W | 70 |
| 35 | 171-185 | A G G Y K A A D M W G P S S D | 71 |
| 36 | 176-190 | A A D M W G P S S D P A W E R | 72 |
| 37 | 181-195 | G P S S D P A W E R N D P T Q | 73 |
| 38 | 186-200 | P A W E R N D P T Q Q I P K L | 74 |
| 39 | 191-205 | N D P T Q Q I P K L V A N N T | 75 |
| 40 | 196-210 | Q I P K L V A N N T R L W V Y | 76 |
| 41 | 201-215 | V A N N T R L W V Y C G N G T | 77 |
| 42 | 206-220 | R L W V Y C G N G T P N E L G | 78 |
| 43 | 211-225 | C G N G T P N E L G G A N I P | 79 |
| 44 | 216-230 | P N E L G G A N I P A E F L E | 80 |
| 45 | 221-235 | G A N I P A E F L E N F V R S | 81 |
| 46 | 226-240 | A E F L E N F V R S S N L K F | 82 |
| 47 | 231-245 | N F V R S S N L K F Q D A Y N | 83 |
| 48 | 236-250 | S N L K F Q D A Y N A A G G H | 84 |
| 49 | 241-255 | Q D A Y N A A G G H N A V F N | 85 |
| 50 | 246-260 | A A G G H N A V F N F P P N G | 86 |
| 51 | 251-265 | N A V F N F P P N G T H S W E | 87 |
| 52 | 256-270 | F P P N G T H S W E Y W G A Q | 88 |
| 53 | 261-275 | T H S W E Y W G A Q L N A M K | 89 |
| 54 | 266-280 | Y W G A Q L N A M K G D L Q S | 90 |
| 55 | 271-285 | L N A M K G D L Q S S L G A G | 91 |

Splenic lymphocytes were obtained from outbred male Hartley strain guinea pigs (Charles River Breeding Laboratories) that had been immunized intradermally 3-4 times with 100 μg of purified 30 KD protein emulsified in SAF (Allison and Byars, 1986). Control animals received phosphate buffered saline in SAF. Cell mediated immune responses were evaluated by skin testing as described above. Lymphocytes were seeded in 96-well tissue culture plates (Falcon Labware) and incubated in triplicate with the synthetic 15-mer peptides at 20 μg $ml^{-1}$, purified 30 KD protein at 20 μg $ml^{-1}$, purified protein derivative [(PPD); Connaught Laboratories LTD] at 20 μg $ml^{-1}$, or concanavalin A at 10 μg $ml^{-1}$ for 2 days in the presence of 10 U polymyxin B. Subsequently, cells were labeled for 16 h with 1 μCi [$^3$H]thymidine (New England Nuclear) and then harvested (Breiman and Horwitz, 1987). A positive proliferative response was defined as follows: (dpm of antigen)−(dpm of medium)≧1500 and (dpm of antigen)/(dpm of medium)

≧1.2. Immunodominant epitopes recognized by greater than 25% of the guinea pigs immunized with purified *M. tuberculosis* 30 KD protein are presented in Table AA below and graphically illustrated in FIGS. 12*a* and 12*b*.

TABLE AA

| Peptide No. | Inclusive Amino Acids for Mature Protein | Seq. ID No. |
|---|---|---|
| 1 | 1-15 | 37 |
| 2 | 6-20 | 38 |
| 3 | 11-25 | 39 |
| 5 | 21-35 | 41 |
| 6 | 26-40 | 42 |
| 13 | 61-75 | 49 |
| 21 | 101-115 | 57 |
| 26 | 126-140 | 62 |
| 27 | 131-145 | 63 |
| 31 | 151-165 | 67 |
| 33 | 161-175 | 69 |
| 36 | 176-190 | 72 |
| 37 | 181-195 | 73 |
| 41 | 201-215 | 77 |
| 45 | 221-235 | 81 |
| 49 | 241-255 | 85 |
| 53 | 261-275 | 89 |

The results presented in Table AA identify the immunodominant T-cell epitopes of the 30 KD major secretory protein of *M. tuberculosis*. Those skilled in the art will appreciate that earlier investigators have studied the 30 KD protein of *M. bovis* which is highly related to *M. tuberculosis* protein. However, these earlier studies of the *M. bovis* protein differ markedly from the foregoing study in that the prior art studied actual patients, BCG vaccinees, patients with tuberculosis, or PPD-positive individuals. Because the response to this protein in such individuals is often weak, the prior art epitope mapping studies were difficult and of questionable accuracy. In contrast, the study of Example 25 utilized outbred guinea pigs immunized with purified protein, thereby focusing the immune system on this single protein and producing a very strong cell-mediated immune response. Moreover, these guinea pigs were studied within a few weeks of immunization, at the peak of T-cell responsiveness.

Previously, two types of studies aimed at identifying epitopes of the *M. tuberculosis* 32A KD protein have been conducted. The first type examined the T-cell responses to peptides (overlapping the entire sequence of the protein) of humans who were a) tuberculin (PPD) positive; in part as a result of vaccination with BCG; b) lepromin positive; c) had TB; or d) had leprosy. (P. Launois, R. Deleys, M. N. Niang, A. Drowart, M. Adrien, P. Deirckx, J.-L. Cartel, J.-L. Sarthou, J.-P. van Vooren, and K. Huygen, 1994, "T-Cell epitope mapping of the major secreted mycobacterial antigen AG85A in *tuberculosis* and leprosy", *Infect. and Immun*. 62:3679-3687.) The response to this protein in these people is often weak, making it difficult to map epitopes accurately. In order to overcome these difficulties, outbred guinea pigs were immunized with purified protein, focusing the immune system on this single protein and producing a very strong cell-mediated immune response. The response was studied at the peak of T-cell responsiveness, i.e., within a few weeks of immunization.

The second type of previous study examined T-cell responses to peptides of inbred mice infected with BCG. (K. Huygen, E. Lozes, B. Gilles, A. Drowart, K. Palfliet, F. Jurion, I. Roland, M. Art, M. DuFaux, J. Nyabenda, J. De Bruyn, J.-P. van Vooren, and R. Deleys, 1994, "Mapping of TH1 helper T-cell epitopes on major secreted mycobacterial antigen 85A in mice infected with live *Mycobacterium bovis* BCG", *Infect. and Immun*., 62:363-370.) Such a study is unlikely to yield results predictive of the diverse responses of multiple MHC types found in humans.

To obtain predictive results, in accordance with the present invention, a large number of outbred guinea pigs with a wide diversity of HLA types were studied. The epitopes of the 32A KD protein recognized by 25% or more of the guinea pigs therefore are strongly immunodominant and recognized by multiple HLA types. Hence, they are likely to be generally recognized by HLA molecules of other species including humans, cattle, and other mammals. Such study should be highly predictive of immunodominant epitopes recognized by humans and other mammals. In addition, the mouse study referred to above relied on responses of BCG-infected animals. Such animals may a) not reflect *M. tuberculosis*-infected animals and b) not develop as strong a response to a specific protein—in this case, the 32A KD protein—as animals without active disease.

EXAMPLE 29

Immunodominant Epitope Mapping of the 32A KD Protein

The procedure of Example 28 was repeated except that the fifty-seven synthetic peptides (15-mers) covering the entire native 32A KD proteins were used. The sequence of each 15-mer targeted is shown in Table AB:

TABLE AB

| No. | Residues | Peptide Sequence | Seq. ID No. |
|---|---|---|---|
| 1 | 1-15 | F S R P G L P V E Y L Q V P S | 96 |
| 2 | 6-20 | L P V E Y L Q V P S P S M G R | 97 |
| 3 | 11-25 | L Q V P S P S M G R D I K V Q | 98 |
| 4 | 16-30 | P S M G R D I K V Q F Q S G G | 99 |
| 5 | 21-35 | D I K V Q F Q S G G A N S P A | 100 |
| 6 | 26-40 | F Q S G G A N S P A L Y L L D | 101 |
| 7 | 31-45 | A N S P A L Y L L D G L R A Q | 102 |
| 8 | 36-50 | L Y L L D G L R A Q D D F S G | 103 |
| 9 | 41-55 | G L R A Q D D F S G W D I N T | 104 |
| 10 | 46-60 | D D F S G W D I N T P A F E W | 105 |
| 11 | 51-65 | W D I N T P A F E W Y D Q S G | 106 |
| 12 | 56-70 | P A F E W Y D Q S G L S V V M | 107 |
| 13 | 61-75 | Y D Q S G L S V V M P V G G Q | 108 |
| 14 | 66-80 | L S V V M P V G G Q S S F Y S | 109 |
| 15 | 71-85 | P V G G Q S S F Y S D W Y Q P | 110 |
| 16 | 76-90 | S S F Y S D W Y Q P A C G K A | 111 |
| 17 | 81-95 | D W Y Q P A C G K A G C Q T Y | 112 |
| 18 | 86-100 | A C G K A G C Q T Y K W E T F | 113 |
| 19 | 91-105 | G C Q T Y K W E T F L T S E L | 114 |

TABLE AB-continued

| No. | Residues | Peptide Sequence | Seq. ID No. |
|---|---|---|---|
| 20 | 96-110 | K W E T F L T S E L P G W L Q | 115 |
| 21 | 101-115 | L T S E L P G W L Q A N R H V | 116 |
| 22 | 106-120 | P G W L Q A N R H V K P T G S | 117 |
| 23 | 111-125 | A N R H V K P T G S A V V G L | 118 |
| 24 | 116-130 | K P T G S A V V G L S M A A S | 119 |
| 25 | 121-135 | A V V G L S M A A S S A L T L | 120 |
| 26 | 126-140 | S M A A S S A L T L A I Y H P | 121 |
| 27 | 131-145 | S A L T L A I Y H P Q Q F V Y | 122 |
| 28 | 136-150 | A I Y H P Q Q F V Y A G A M S | 123 |
| 29 | 141-155 | Q Q F V Y A G A M S G L L D P | 124 |
| 30 | 146-160 | A G A M S G L L D P S Q A M G | 125 |
| 31 | 151-165 | G L L D P S Q A M G P T L I G | 126 |
| 32 | 156-170 | S Q A M G P T L I G L A M G D | 127 |
| 33 | 161-175 | P T L I G L A M G D A G G Y K | 128 |
| 34 | 166-180 | L A M G D A G G Y K A S D M W | 129 |
| 35 | 171-185 | A G G Y K A S D M W G P K E D | 130 |
| 36 | 176-190 | A S D M W G P K E D P A W Q R | 131 |
| 37 | 181-195 | G P K E D P A W Q R N D P L L | 132 |
| 38 | 186-200 | P A W Q R N D P L L N V G K L | 133 |
| 39 | 191-205 | N D P L L N V G K L I A N N T | 134 |
| 40 | 196-210 | N V G K L I A N N T R V W V Y | 135 |
| 41 | 201-215 | I A N N T R V W V Y C G N G K | 136 |
| 42 | 206-220 | R V W V Y C G N G K P S D L G | 137 |
| 43 | 211-225 | C G N G K P S D L G G N N L P | 138 |
| 44 | 216-230 | P S D L G G N N L P A K F L E | 139 |
| 45 | 221-235 | G N N L P A K F L E G F V R T | 140 |
| 46 | 226-240 | A K F L E G F V R T S N I K F | 141 |
| 47 | 231-245 | G F V R T S N I K F Q D A Y N | 142 |
| 48 | 236-250 | S N I K F Q D A Y N A G G G H | 143 |
| 49 | 241-255 | Q D A Y N A G G G H N G V F D | 144 |
| 50 | 246-260 | A G G G H N G V F D F P D S G | 145 |
| 51 | 251-265 | N G V F D F P D S G T H S W E | 146 |
| 52 | 256-270 | F P D S G T H S W E Y W G A Q | 147 |
| 53 | 261-275 | T H S W E Y W G A Q L N A M K | 148 |
| 54 | 266-280 | Y W G A Q L N A M K P D L Q R | 149 |
| 55 | 271-285 | L N A M K P D L Q R A L G A T | 150 |
| 56 | 276-290 | P D L Q R A L G A T P N T G P | 151 |
| 57 | 281-295 | A L G A T P N T G P A P Q G A | 152 |

As shown in the following table, for technical reasons, synthetic peptide numbers 1A, 5A, 15A, 26A, 29A, 43A, and 56A differed slightly from the corresponding 15-mers targeted.

TABLE AC

| No. | Residues | Peptide Sequence | Seq. ID No. |
|---|---|---|---|
| 1A | 1-18 | F S R P G L P V E Y L Q V P S P S M | 153 |
| 5A | 21-36 | D I K V Q F Q S G G A N S P A L | 154 |
| 15A | 71-87 | P V G G Q S S F Y S D W Y Q P A C | 155 |
| 26A | 126-142 | S M A A S S A L T L A I Y H P Q Q | 156 |
| 29A | 140-157 | P Q Q F V Y A G A M S G L L D P S Q | 157 |
| 43A | 211-227 | C G N G K P S D L G G N N L P A K | 158 |
| 49A | 240-255 | F Q D A Y N A G G G H N G V F D | 159 |
| 56A | 276-289 | P D L Q R A L G A T P N T G | 160 |

Immunodominant T-cell epitopes of the 32A KD major secretory protein of *M. tuberculosis* recognized by greater than 25% of the guinea pigs immunized with purified *M. tuberculosis* 32A KD protein are presented in Table AD below and graphically illustrated in FIG. 13.

TABLE AD

| Peptide* | Inclusive Amino Acids for Mature Protein | Sequence ID No. |
|---|---|---|
| 9 | 41-55 | 104 |
| 11 | 51-65 | 106 |
| 12 | 56-70 | 107 |
| 15 | 71-85 | 110 |
| 19 | 91-105 | 114 |
| 20 | 96-110 | 115 |
| 23 | 111-125 | 118 |
| 25 | 121-135 | 120 |
| 27 | 131-145 | 122 |
| 28 | 136-150 | 123 |
| 29 | 141-155 | 124 |
| 31 | 151-165 | 126 |
| 32 | 156-170 | 127 |
| 39 | 191-205 | 134 |
| 40 | 196-210 | 135 |
| 41 | 201-215 | 136 |
| 43 | 211-225 | 138 |

In accordance with the teachings of the present invention one or more of the immunodominant epitopes identified above can be incorporated into a vaccine against tuberculosis. For example, individual immunodominant epitopes can be synthesized and used individually or in combination in a multiple antigen peptide system. Alternatively, two or more immunodominant epitopes can be linked together chemically. The peptides, either linked together or separately, can be combined with an appropriate adjuvant and used in subunit vaccines for humans or other mammals. In addition, the immunodominant epitopes can be used in new immunodiagnostic reagents such as new skin tests.

Specific exemplary adjuvants used in the instant invention to enhance the activity of the selected immunogenic determinants are SAF, adjuvants containing Monophosphoryl Lipid A (MPL), Freund's incomplete adjuvant, Freund's complete adjuvant containing killed bacteria, gamma interferons (Radford et al., *American Society of Hepatology* 2008-2015, 1991; Watanabe et al., *PNAS* 86:9456-9460, 1989; Gansbacher et al., *Cancer Research* 50:7820-7825, 1990; Maio et al., *Can. Immunol. Immunother.* 30:34-42, 1989; U.S. Pat. Nos. 4,762,791 and 4,727,138), IL-12, IL-15 (Grabstein et al., *Science* 264:965-968, 1994), MF 59, MF 59 plus MTP, MF 59 plus IL-12, MPL plus TDM (trehalose dimycolate), QS-21, QS-21 plus IL-12, IL-2 (American Type Culture Collection Nos. 39405, 39452 and 39516; see also U.S. Pat. No. 4,518,584), dimethyldioctadecyl ammonium (ddA), ddA plus dextran, alum, Quil A, ISCOMS, (Immunostimulatory Complexes), Liposomes, Lipid Carriers, Protein Carriers, and Microencapsulation techniques. Additional adjuvants that may be useful in the present invention are water-in-oil emulsions, mineral salts (for example, alum), nucleic acids, block polymer surfactants, and microbial cell walls (peptido glycolipids). While not limiting the scope of the invention it is believed that adjuvants may magnify immune responses by allowing the slow release of antigens from the site of injection and/or modulation of the milieu at the site of injection including the cellular and cytokine constituents.

Particularly preferred is IL-12 either alone or in conjunction with another adjuvant. It has been found that immunization of guinea pigs with purified major *M. tuberculosis* extracellular proteins in the presence of IL-12 alone, or in the presence of IL-12 plus another adjuvant, for example, MF 59, enhances protective immunity over that obtained without IL-12. By increasing the capacity of the vaccine to induce protective immunity, IL-12 renders the vaccine more efficacious.

It was known that murine IL-12 stimulates both murine lymphoblasts and human lymphoblasts, and that human IL-12 stimulates human lymphoblasts, but it was not known if either mouse or human IL-12 stimulates guinea pig lymphoblasts. To determine if murine or human IL-12 stimulates guinea pig lymphoblasts, IL-12 activity was assayed using the protocol described in Current Protocols in Immunology, 1993, Cytokines and their Receptors entitled "Lymphoblasts Proliferation Assay for IL-12 Activity" Alternate Protocol), pages 6.16.3 through 6.16.5.

EXAMPLE 30

Spleen cells were isolated from a male Hartley strain guinea pig, incubated at a concentration of $10^7$ cells/75cm$^2$ culture flask containing 20 ml supplemented medium for 3 days with PHA at a concentration of 8 µg/ml, diluted 1:1 with supplemental medium, and incubated for 1 day with IL-2 at a concentration of 50 IU/ml. The lymphoblasts were washed, counted, dispensed into 96 well flat-bottom, microtiter plates at a cell density of $2 \times 10^4$ lymphoblasts/well, and incubated for 24 h with 0 to 5 µg/ml IL-12 (R&D Systems, Minneapolis, Minn.). $^3$H-thymidine (0.25 µCi) was added to each well for an additional 18 h, and the cells then were harvested and assayed for incorporated $^3$H-thymidine.

Figure 21:
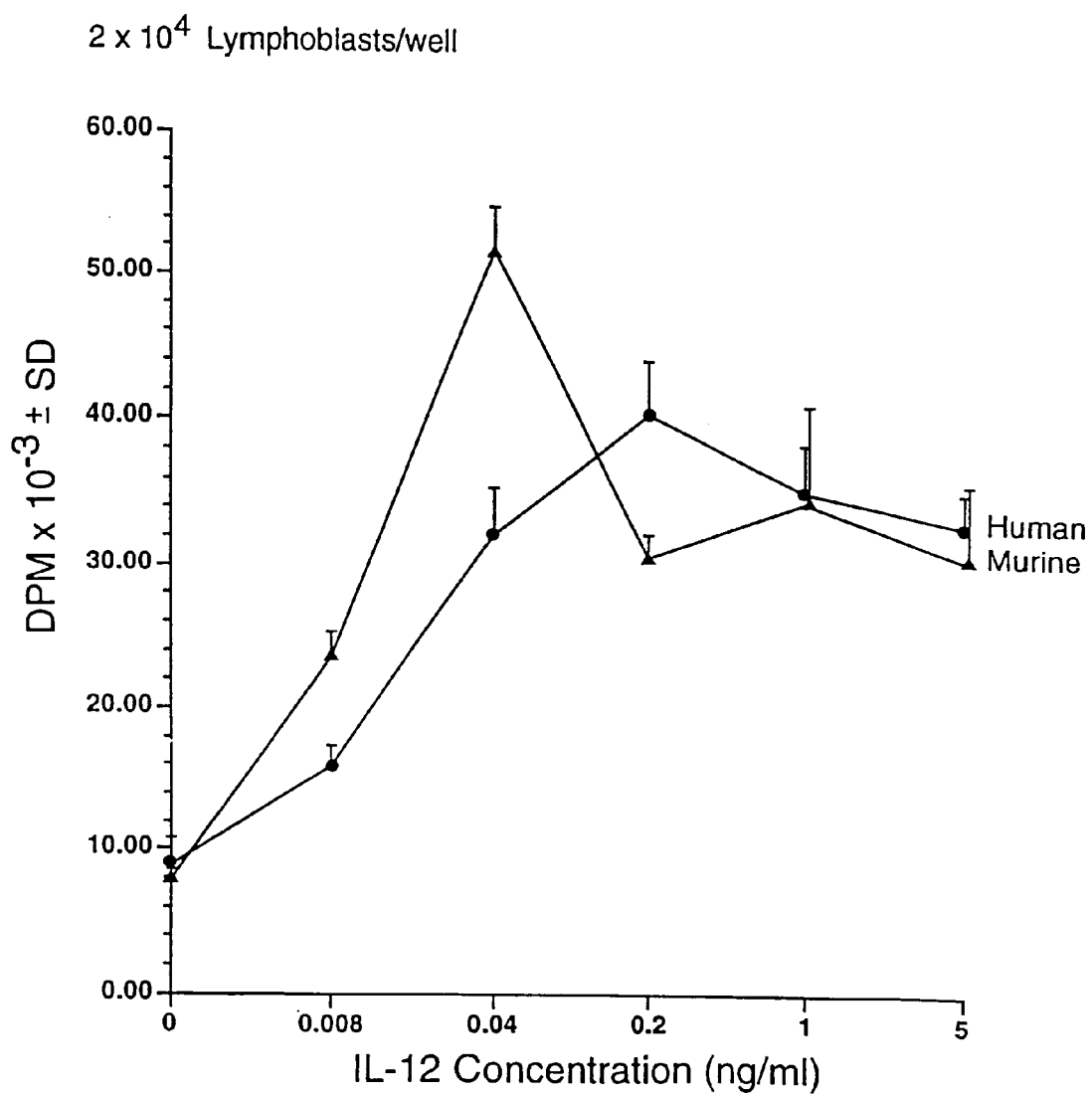
FIG. 21 is a graphical comparison of the growth of guinea pig lymphoblasts in the presence of various concentrations of recombinant human and murine IL-12.
Figure 22:
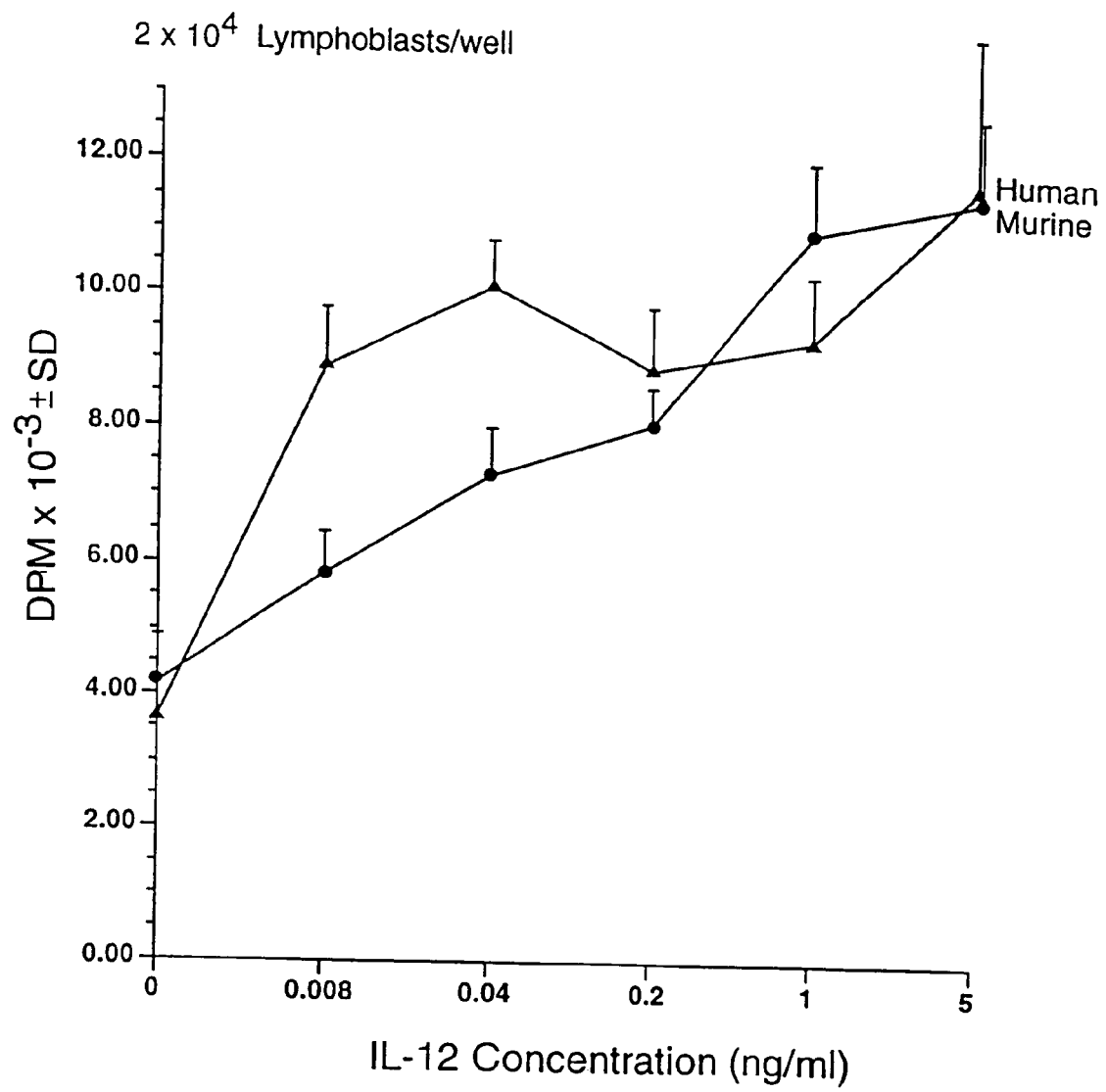
FIG. 22 is a graphical comparison of the growth of guinea pig lymphoblasts in the presence of various concentrations of recombinant human and murine IL-12 from a guinea pig different from that of FIG. 21.

The results of two independent experiments using spleen cells from different outbred guinea pigs are shown in FIG. 21 and FIG. 22. Data are the mean DPM±S.D. for sextuplicate wells.

In each experiment, both murine and human IL-12 strongly stimulated proliferation of guinea pig lymphoblasts in a dose-dependent fashion.

To determine if IL-12 would enhance the efficacy of a vaccine consisting of purified *M. tuberculosis* 30, 32A, and 16KD major extracellular proteins, guinea pigs were immunized with the vaccine in the presence or absence of IL-12 and challenged with virulent *M. tuberculosis* by aerosol. IL-12 was found to enhance the capacity of the vaccine to protect the animals against weight loss and growth of *M. tuberculosis* in the lungs of challenged animals.

EXAMPLE 31

Figure 23:
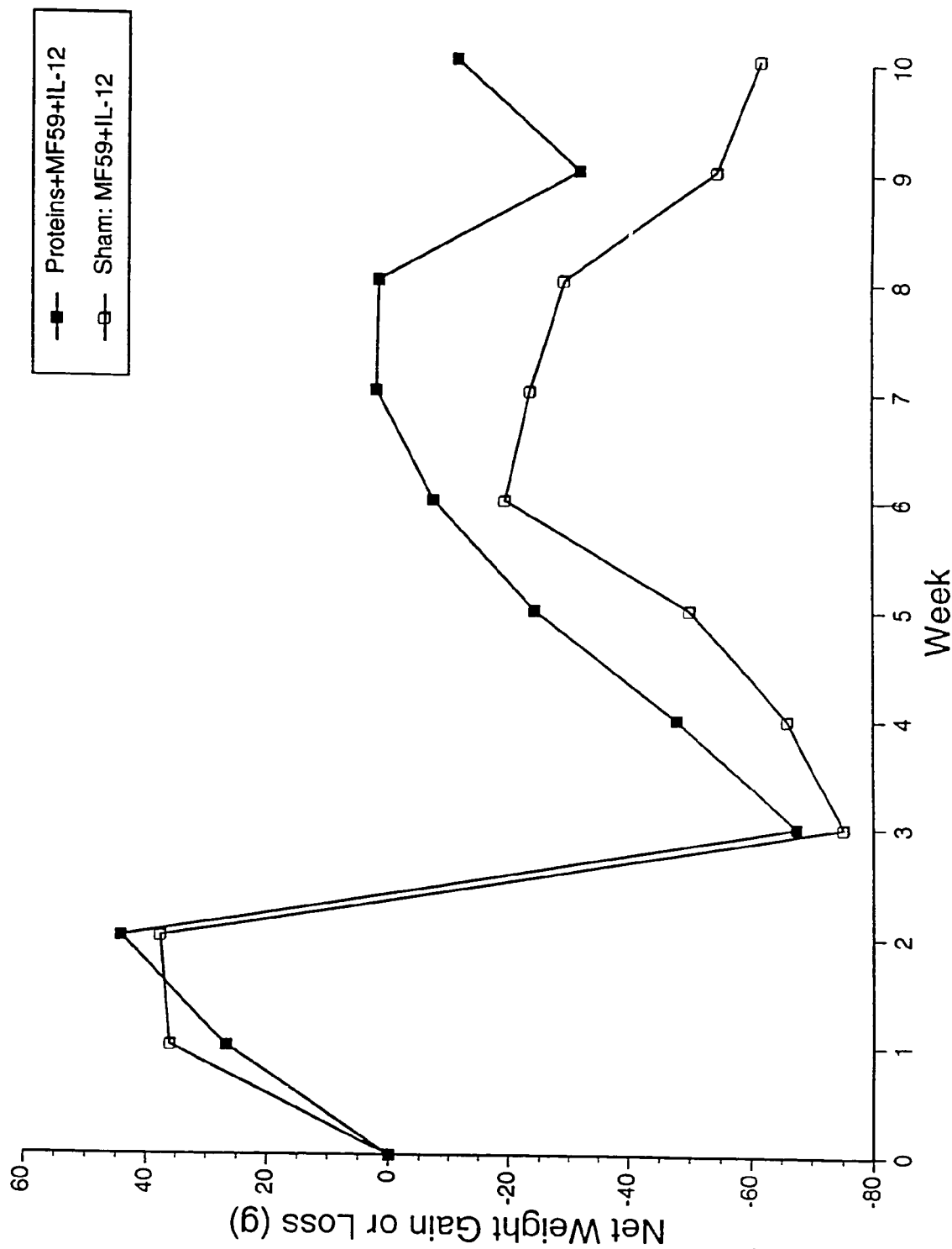
FIG. 23 is a graphical comparison of mean guinea pig body weight gain or loss of animals immunized with a vaccine comprising a combination of purified 32A KD, 30 KD, and 16 KD extracellular proteins, MF 59 adjuvant, and IL-12 versus nonimmunized controls following exposure to an aerosolized lethal dose of *M. tuberculosis*.

Guinea pigs (6 per group) were immunized intradermally three times with 100 µg of purified *M. tuberculosis* 30, 32A and 16 KD major extracellular proteins in the presence of adjuvant (MF 59) and recombinant mouse IL-12 purchased from R&D Systems (Minneapolis, Minn.). Control animals (6 per group) were sham-immunized with adjuvant and IL-12 only. The animals were then challenged with an aerosol of virulent *M. tuberculosis* Erdman strain and weighed weekly thereafter until killed at 10 weeks. Sham-immunized animals exhibited greater weight loss than animals immunized with the proteins in the presence of adjuvant plus IL-12.The results are shown in FIG. 23.

EXAMPLE 32

Figure 24:
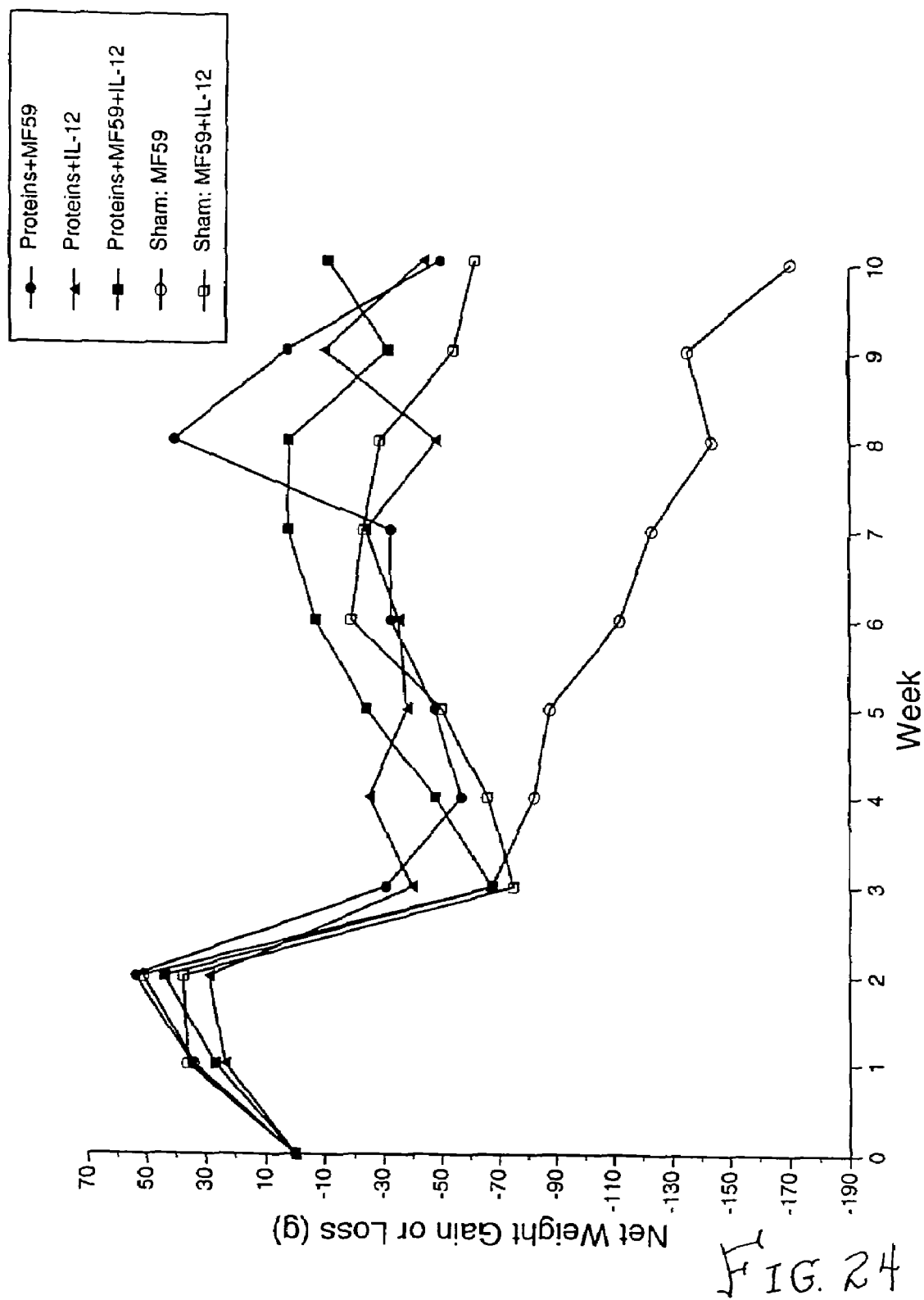
FIG. 24 is a graphical comparison of mean guinea pig body weight gain or loss of animals immunized with a vaccine comprising a combination of purified 32A KD, 30 KD, and 16 KD extracellular proteins with MF 59 adjuvant, with IL-12, and with a mixture of MF 59 and IL-12 versus nonimmunized controls following exposure to an aerosolized lethal dose of *M. tuberculosis*.
Figure 26:
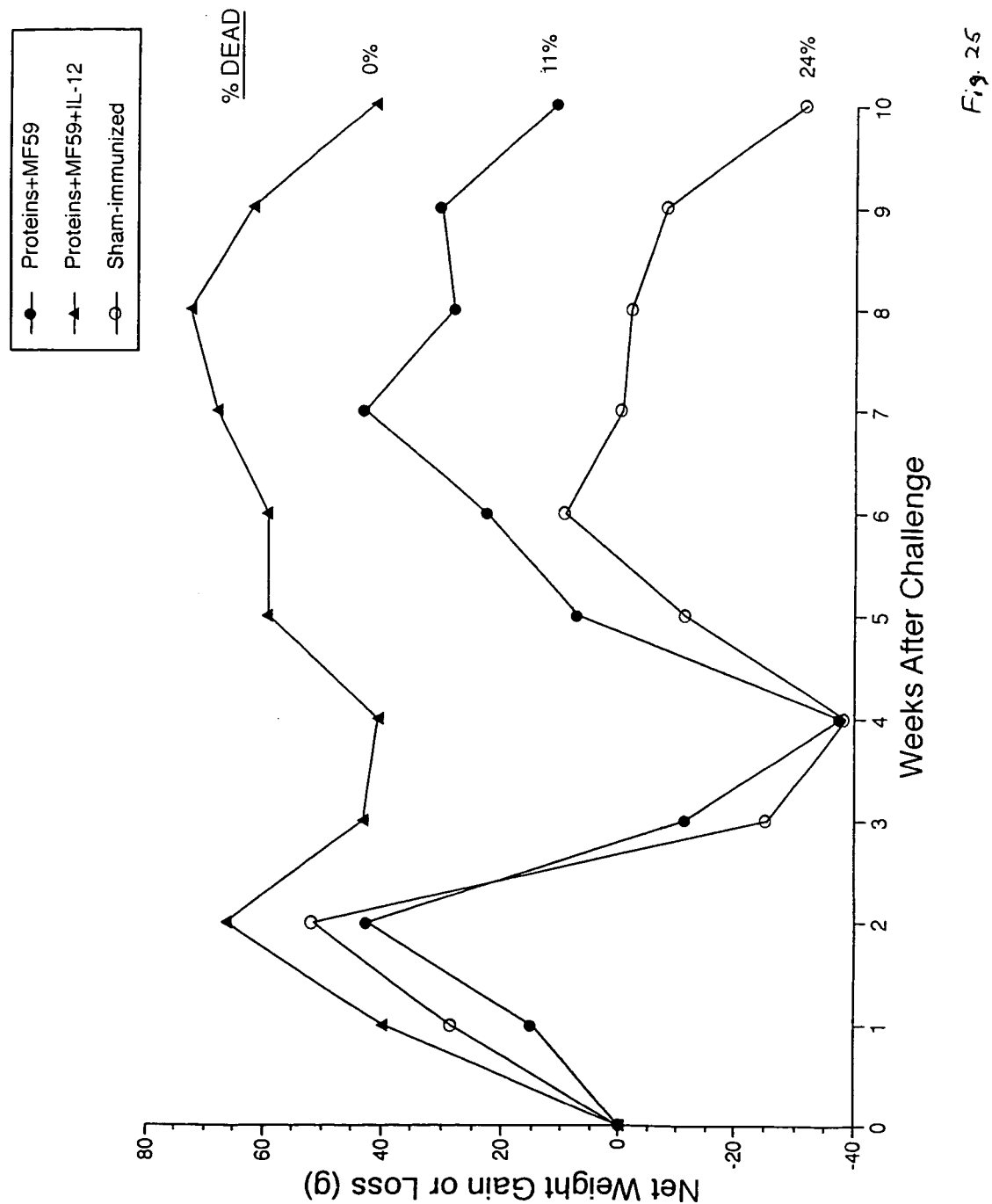

Guinea pigs (6 per group) were immunized three times intradermally with 100 µg of purified *M. tuberculosis* 30, 32A, and 16 KD major extracellular proteins in the presence of adjuvant (MF 59) alone, IL-12 alone, or adjuvant +IL-12 or sham-immunized with adjuvant alone, or adjuvant +IL-12. IL-12 was purchased from R&D Systems. The animals were then challenged with virulent *M. tuberculosis* Erdman strain and weighed weekly thereafter until killed at 10 weeks. FIG. 24 shows the mean net weight gain or loss of each group from the weight on the day of the challenge. Animals immunized with the proteins exhibited less weight loss than both groups of sham-immunized controls. Of the sham-immunized animals, animals immunized with adjuvant in the presence of IL-12 lost less weight than animals immunized with adjuvant only. Of the protein-immunized animals, animals immunized with proteins in the presence of adjuvant plus IL-12 exhibited less weight loss over the course of the experiment than animals immunized with the proteins in the presence of either IL-12 only or adjuvant only. Thus, during the critical period of disease from 4 to 10 weeks after challenge, animals immunized with proteins in the presence of both adjuvant and IL-12 exhibited the least amount of weight loss at weeks 5, 6, 7, and 10 and the second least amount of weight loss at weeks 4 and 8.

EXAMPLE 33

Animals were immunized three times intradermally with 100 µg of *M. tuberculosis* 30, 32A, and 16 KD major extracellular proteins in the presence of MF 59 or MF 59 +IL-12, or sham-immunized with MF 59 only, IL-12 only or MF 59 +IL-12. The animals were challenged with virulent *M. tuberculosis* by aerosol, observed for 10 weeks, and killed. The right lung was removed and cultured for *M. tuberculosis* on 7H11 agar plates. Data shown in Table AE are the mean CFU per right lung.

TABLE AE

CFU in Lungs of Animals Immunized with 3 purified Major Extracellular *M. tuberculosis* Proteins (30, 32A, 16 KD) in the Presence of Various Adjuvants

| | | Mean $\log_{10}$ CFU |
|---|---|---|
| A. | Sham - Immunized (MF 59 only) | 7.7 |
| B. | Sham - Immunized (MF 59 + IL-12) | 7.0 |
| C. | Protein - Immunized (MF 59 only) | 7.0 |
| D. | Protein - Immunized (IL-12 only) | 6.9 |
| E. | Protein - Immunized (MF 59 + IL-12) | 6.6 |

Animals immunized with proteins had fewer CFU than animals sham-immunized without proteins but with the same adjuvant preparation. Thus, animals immunized with proteins plus MF 59 (C) had 0.7 log fewer CFU in the lungs than animals immunized with MF 59 only (A); and animals immunized with proteins with MF 59 +IL-12 (E) had 0.4 log fewer CFU in the lungs than animals immunized with MF 59 +IL-12 only (B), and 1.1 log fewer CFU in the lungs than animals immunized with MF 59 only.

Animals immunized with proteins in the presence of IL-12 had fewer CFU than animals immunized with proteins in the absence of IL-12. Thus, animals immunized with proteins in MF 59+IL-12 (E) had 0.4 log fewer CFU in the lungs than animals immunized with proteins in the presence of MF 59 only.

EXAMPLE 34

Guinea pigs were immunized intradermally three times with 100 μg of purified *M. tuberculosis* 30, 32A, and 16KD major extracellular proteins in the presence of adjuvant (MF59) only (9 animals), or in the presence of adjuvant (MF59) plus recombinant mouse IL-12 (9 animals) purchased from R&D Systems (Minneapolis, Minn.). Control animals were sham-immunized with various adjuvants only (17 animals). The animals were then challenged with an aerosol of virulent *M. tuberculosis* Erdman strain and weighed weekly thereafter until killed at 10 weeks. Sham-immunized animals exhibited greater weight loss than animals immunized with the proteins in the presence of either adjuvant only or adjuvant plus IL-12. Of the animals immunized with proteins, animals immunized with proteins in the presence of adjuvant only lost more weight than animals immunized with proteins in the presence of adjuvant plus IL-12. Furthermore, sham-immunized animals had a higher mortality during the course of the experiment −24% of the sham-immunized animals died vs. only 6% of animals immunized with proteins. Of the animals immunized with proteins, animals immunized with proteins in the presence of adjuvant only had a higher mortality (11%) than animals immunized with proteins in the presence of adjuvant plus IL-12 (0%). The results are shown in FIG. 25.

Those skilled in the art will also appreciate that DNA encoding the peptides can be synthesized and used to express the peptides, individually or collectively, or can be combined in a DNA vaccine injected directly into humans or other mammals. A construct consisting of only the immunogenic epitopes (or the DNA coding therefor) would focus the immune response on the protective portions of the molecule. By avoiding irrelevant or even immunosuppressive epitopes such a construct may induce a stronger and more protective immune response.

Smaller protein subunits of the majorly abundant extracellular products, molecular analogs thereof, genes encoding therefore, and respective combinations thereof are within the scope of the present invention as long as they provoke effective immunoprophylaxis or function as an immunodiagnostic reagent. Moreover, recombinant protein products such as fusion proteins or extracellular products modified through known molecular recombinant techniques are entirely compatible with the teachings of the present invention. In addition, immunogenically generated analogs of the selected immunoactive determinants or peptides and nucleotides derived using directed evolution are also within the scope of the invention. Moreover, the selected immunoactive determinants can be modified so as to bind more tightly to specific MHC molecules of humans or other species or be presented more efficiently by antigen presenting cells. Further, the selected immunoactive determinants can be modified so as to resist degradation in the vaccinated host.

Similarly, the formulation and presentation of the immunogenic agent to the host immune system is not limited to solutions of proteins or their analogs in adjuvant. For example, the immunogenic determinant derived from the appropriate extracellular proteins may be expressed by *M. tuberculosis*, different species of *Mycobacteria*, different species of bacteria, phage, mycoplasma or virus that is nonpathogenic and modified using recombinant technology. In such cases the whole live organism may be formulated and used to stimulate the desired response. Conversely, large scale vaccination programs in hostile environments may require very stable formulations without complicating adjuvants or additives. Further, the vaccine formulation could be directed to facilitate the stability or immunoreactivity of the active component when subjected to harsh conditions such as lyophilization or oral administration or encapsulation. Accordingly, the present invention encompasses vastly different formulations of the immunogenic determinants comprising the subject vaccines depending upon the intended use of the product.

Those skilled in the art will appreciate that vaccine dosages should be determined for each pathogen and host utilizing routine experimentation. At present, it is believed that the lowest practical dosage will be on the order of 0.1 μg though dosages of 2.0 μg, 20.0 μg, 100 μg and even 1 mg may be optimum for the appropriate system. The proper dosage can be administered using any conventional immunization technique and sequence known in the art.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A vaccinating agent for use in promoting an effective immune response, in a mammalian host, against an infectious pathogen from the genus *Mycobacterium*, said vaccinating agent comprising:
   at least a portion of at least one majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein and respective analogs, homologs, and subunits thereof; and
   an adjuvant selected from the group consisting of IL-12 and MF 59.

2. The vaccinating agent of claim 1 wherein said at least one majorly abundant extracellular product is *M. tuberculosis* 32A KD protein.

3. The vaccinating agent of claim 1 wherein said at least one majorly abundant extracellular product is a mixture of *M. tuberculosis* 32A KD protein, 30 KD protein, and 16 KD protein.

4. The vaccinating agent of claim 1 wherein said adjuvant is IL-12.

5. The vaccinating agent of claim 1 wherein said adjuvant is a mixture of IL-12 and MF 59.

6. A method for immunizing a mammalian host against an infectious pathogen of the genus *Mycobacterium*, said method comprising the steps of:
   providing a vaccinating agent comprising at least a portion of at least one majorly abundant extracellular product selected from the group consisting of *M. tuberculosis* 110 KD protein, 80 KD protein, 71 KD protein, 58 KD protein, 45 KD protein, 32A KD protein, 328 KD protein, 30 KD protein, 24 KD protein, 23.5 KD protein, 23 KD protein, 16 KD protein, 14 KD protein, 12 KD protein and respective analogs, homologs, and subunits thereof, and an adjuvant selected from the group consisting of IL-12 and MF 59; and
   introducing said vaccinating agent into said mammalian host to induce an effective immune response to subsequent infection by said infectious pathogen.

7. The method of claim 6 wherein said at least one majorly abundant extracellular product is *M. tuberculosis* 32A KD protein.

8. The method of claim 6 wherein said at least one majorly abundant extracellular product is a mixture of *M. tuberculosis* 32A KD protein, 30 KD protein, and 16 KD protein.

9. The method of claim 6 wherein said adjuvant is IL-12.

10. The method of claim 6 wherein said adjuvant is a mixture of IL-12 and MF 59.

11. A vaccinating agent for use in promoting an effective immune response, in a mammalian host, against an infectious pathogen from the genus *Mycobacterium*, said vaccinating agent comprising:
   at least one immunodominant epitope of at least one majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein, and respective analogs, homologs, and subunits thereof.

12. The vaccinating agent of claim 11 wherein said at least one majorly abundant extracellular product is *M. tuberculosis* 32A KD protein.

13. The vaccinating agent of claim 12 wherein said at least one immunodominant epitope is selected from the group consisting of *M. tuberculosis* 32A KD protein subunits having the amino acid sequences

| Peptide Sequence | Seq. ID No. |
|---|---|
| G L R A Q D D F S G W D I N T | 104 |
| W D I N T P A F E W Y D Q S G | 106 |
| P A F E W Y D Q S G L S V V M | 107 |
| P V G G Q S S F Y S D W Y Q P | 110 |
| G C Q T Y K W E T F L T S E L | 114 |
| K W E T F L T S E L P G W L Q | 115 |
| A N R H V K P T G S A V V G L | 118 |
| A V V G L S M A A S S A L T L | 120 |
| S A L T L A I Y H P Q Q F V Y | 122 |
| A I Y H P Q Q F V Y A G A M S | 123 |
| Q Q F V Y A G A M S G L L D P | 124 |
| G L L D P S Q A M G P T L I G | 126 |
| S Q A M G P T L I G L A M G D | 127 |
| N D P L L N V G K L I A N N T | 134 |
| N V G K L I A N N T R V W V Y | 135 |
| I A N N T R V W V Y C G N G K | 136 |
| C G N G K P S D L G G N N L P | 138 | and respective analogs, homologs, and subunits thereof including single or multiple amino acid substitutions, deletions, insertions, and inversions.

14. An immunodiagnostic agent for use in promoting a detectable immune response in a mammalian host identifying an infectious pathogen from the genus *Mycobacterium*, said immunodiagnostic agent comprising:

at least one immunodominant epitope of at least one majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 1KD protein and respective analogs, homologs, and subunits thereof.

15. The immunodiagnostic agent of claim 14 wherein said at least one majorly abundant extracellular product is *M. tuberculosis* 32A KD protein.

16. The immunodiagnostic agent of claim 15 wherein said at least one immunodominant epitope is selected from the group consisting of *M. tuberculosis* 32A KD protein subunits having the amino acid sequences

| Peptide Sequence | Seq. ID No. |
| --- | --- |
| G L R A Q D D F S G W D I N T | 104 |
| W D I N T P A F E W Y D Q S G | 106 |
| P A F E W Y D Q S G L S V V M | 107 |
| P V G G Q S S F Y S D W Y Q P | 110 |
| G C Q T Y K W E T F L T S E L | 114 |
| K W E T F L T S E L P G W L Q | 115 |
| A N R H V K P T G S A V V G L | 118 |
| A V V G L S M A A S S A L T L | 120 |
| S A L T L A I Y H P Q Q F V Y | 122 |
| A I Y H P Q Q F V Y A G A M S | 123 |
| Q Q F V Y A G A M S G L L D P | 124 |
| G L L D P S Q A M G P T L I G | 126 |
| S Q A M G P T L I G L A M G D | 127 |
| N D P L L N V G K L I A N N T | 134 |
| N V G K L I A N N T R V W V Y | 135 |
| I A N N T R V W V Y C G N G K | 136 |
| C G N G K P S D L G G N N L P | 138 | and respective analogs, homologs, and subunits thereof including single or multiple amino acid substitutions, deletions, insertions, and inversions.

17. A method of immunizing a mammalian host against an infectious pathogen of the genus *Mycobacterium*, said method comprising the steps of:

providing at least one immunodominant epitope of at least one majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein and respective analogs, homologs, and subunits thereof; and introducing said at least one immunodominant epitope to said mammalian host to induce an effective immune response to subsequent infection by said infectious pathogen.

18. The method of claim 17 wherein said at least one majorly abundant extracellular product is *M. tuberculosis* 32A KD protein.

19. The method of claim 18 wherein said at least one immunodominant epitope is selected from the group consisting of *M. tuberculosis* 32A KD protein subunits having the amino acid sequences

| Peptide Sequence | Seq. ID No. |
| --- | --- |
| G L R A Q D D F S G W D I N T | 104 |
| W D I N T P A F E W Y D Q S G | 106 |
| P A F E W Y D Q S G L S V V M | 107 |
| P V G G Q S S F Y S D W Y Q P | 110 |
| G C Q T Y K W E T F L T S E L | 114 |
| K W E T F L T S E L P G W L Q | 115 |
| A N R H V K P T G S A V V G L | 118 |
| A V V G L S M A A S S A L T L | 120 |
| S A L T L A I Y H P Q Q F V Y | 122 |
| A I Y H P Q Q F V Y A G A M S | 123 |
| Q Q F V Y A G A M S G L L D P | 124 |
| G L L D P S Q A M G P T L I G | 126 |
| S Q A M G P T L I G L A M G D | 127 |
| N D P L L N V G K L I A N N T | 134 |
| N V G K L I A N N T R V W V Y | 135 |
| I A N N T R V W V Y C G N G K | 136 |
| C G N G K P S D L G G N N L P | 138 | and respective analogs, homologs, and subunits thereof including single or multiple amino acid substitutions, deletions, insertions, and inversions.

20. A method for detecting the presence of an immune response in a mammal against a pathogen of the genus *Mycobacterium*, said method comprising the steps of:

providing at least one immunodominant epitope of at least one majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein and respective analogs, homologs, and subunits thereof;

administering said at least one immunodominant epitope to said mammal; and measuring the resultant immune response.

21. The method of claim 20 wherein said at least one majorly abundant extracellular product is *M. tuberculosis* 32A KD protein.

22. The method of claim 21 wherein said at least one immunodominant epitope is selected from the group consisting of *M. tuberculosis* 32A KD protein subunits having the amino acid sequences

| Peptide Sequence | Seq. ID No. |
|---|---|
| G L R A Q D D F S G W D I N T | 104 |
| W D I N T P A F E W Y D Q S G | 106 |
| P A F E W Y D Q S G L S V V M | 107 |
| P V G G Q S S F Y S D W Y Q P | 110 |
| G C Q T Y K W E T F L T S E L | 114 |
| K W E T F L T S E L P G W L Q | 115 |
| A N R H V K P T G S A V V G L | 118 |
| A V V G L S M A A S S A L T L | 120 |
| S A L T L A I Y H P Q Q F V Y | 122 |
| A I Y H P Q Q F V Y A G A M S | 123 |
| Q Q F V Y A G A M S G L L D P | 124 |
| G L L D P S Q A M G P T L I G | 126 |
| S Q A M G P T L I G L A M G D | 127 |
| N D P L L N V G K L I A N N T | 134 |
| N V G K L I A N N T R V W V Y | 135 |

-continued

| Peptide Sequence | Seq. ID No. |
|---|---|
| I A N N T R V W V Y C G N G K | 136 |
| C G N C K P S D L G G N N L P | 138 | and respective analogs, homologs, and subunits thereof including single or multiple maino acid substitutions, deletions, insertions, and inversions.

23. A process for producing a majorly abundant extracellular product selected from the group consisting of *M. tuberculosis* 110 KD protein, 80 KD protein, 71 KD protein, 58 KD protein, 45 KD protein, 32A KD protein, 32B KD protein, 30 KD protein, 24 KD protein, 23.5 KD protein, 23 KD protein, 16 KD protein, 14 KD protein, 12 KD protein and respective analogs, homologs, and subunits thereof, said process comprising the steps of:

transforming a host cell with a vector to form a transformed cell, said vector comprising a nucleic acid molecule encoding one of said majorly abundant extracellular products; and culturing said transformed cell to thereby produce said majorly abundant extracellular product.

24. The process of claim 23 wherein said nucleic acid molecule encodes for the 32A KD *M. tuberculosis* protein.

25. The process of claim 24 which includes the additional step of recovering said majorly abundant extracellular product that is produced by culturing of said transformed cell.

26. The process of claim 24 wherein said vector comprises pSMT3.

27. The process of claim 24 wherein said host cell is *M. smegmatis* or *M. vaccae*.

28. The process of claim 24 wherein said transformed cell is cultured at a temperature of 28° C.

\* \* \* \* \*

UNITED STATES PATENT AND TRADEMARK OFFICE
CERTIFICATE OF CORRECTION

PATENT NO. : 7,300,660 B2
APPLICATION NO. : 10/695155
DATED : November 27, 2007
INVENTOR(S) : Marcus A. Horwitz, Gunter Harth and Bai-Yu Lee It is certified that error appears in the above-identified patent and that said Letters Patent is hereby corrected as shown below:

Col. 153 line 45 "328" should read --32B--.

Col. 155 line 7 "12 1KD" should read --12 KD--.

Signed and Sealed this

Twenty Second Day of April, 2008

JON W. DUDAS
*Director of the United States Patent and Trademark Office*

SEQUENCE LISTING

<160> NUMBER OF SEQ ID NOS: 167

<210> SEQ ID NO 1
<211> LENGTH: 5
<212> TYPE: PRT
<213> ORGANISM: Mycobacterium tuberculosis

<400> SEQUENCE: 1

Asn Ser Lys Ser Val
1               5

<210> SEQ ID NO 2
<211> LENGTH: 5
<212> TYPE: PRT
<213> ORGANISM: Mycobacterium tuberculosis

<400> SEQUENCE: 2

Thr Asp Arg Val Ser
1               5

<210> SEQ ID NO 3
<211> LENGTH: 5
<212> TYPE: PRT
<213> ORGANISM: Mycobacterium tuberculosis

<400> SEQUENCE: 3

Ala Arg Ala Val Gly
1               5

<210> SEQ ID NO 4
<211> LENGTH: 5
<212> TYPE: PRT
<213> ORGANISM: Mycobacterium tuberculosis

<400> SEQUENCE: 4

Thr Glu Lys Thr Pro
1               5

<210> SEQ ID NO 5
<211> LENGTH: 5
<212> TYPE: PRT
<213> ORGANISM: Mycobacterium tuberculosis

<400> SEQUENCE: 5

Asp Pro Glu Pro Ala
1               5

<210> SEQ ID NO 6
<211> LENGTH: 5
<212> TYPE: PRT
<213> ORGANISM: Mycobacterium tuberculosis

<400> SEQUENCE: 6

Phe Ser Arg Pro Gly
1               5

<210> SEQ ID NO 7
<211> LENGTH: 5
<212> TYPE: PRT
<213> ORGANISM: Mycobacterium tuberculosis

<400> SEQUENCE: 7

Phe Ser Arg Pro Gly

-continued

```
1               5

<210> SEQ ID NO 8
<211> LENGTH: 5
<212> TYPE: PRT
<213> ORGANISM: Mycobacterium tuberculosis

<400> SEQUENCE: 8

Phe Ser Arg Pro Gly
1               5

<210> SEQ ID NO 9
<211> LENGTH: 5
<212> TYPE: PRT
<213> ORGANISM: Mycobacterium tuberculosis

<400> SEQUENCE: 9

Ala Pro Tyr Glu Asn
1               5

<210> SEQ ID NO 10
<211> LENGTH: 5
<212> TYPE: PRT
<213> ORGANISM: Mycobacterium tuberculosis

<400> SEQUENCE: 10

Ala Pro Lys Thr Tyr
1               5

<210> SEQ ID NO 11
<211> LENGTH: 5
<212> TYPE: PRT
<213> ORGANISM: Mycobacterium tuberculosis

<400> SEQUENCE: 11

Ala Glu Thr Tyr Leu
1               5

<210> SEQ ID NO 12
<211> LENGTH: 5
<212> TYPE: PRT
<213> ORGANISM: Mycobacterium tuberculosis

<400> SEQUENCE: 12

Ala Tyr Pro Ile Thr
1               5

<210> SEQ ID NO 13
<211> LENGTH: 5
<212> TYPE: PRT
<213> ORGANISM: Mycobacterium tuberculosis

<400> SEQUENCE: 13

Ala Asp Pro Arg Leu
1               5

<210> SEQ ID NO 14
<211> LENGTH: 5
<212> TYPE: PRT
<213> ORGANISM: Mycobacterium tuberculosis

<400> SEQUENCE: 14

Phe Asp Thr Arg Leu
1               5
```

```
<210> SEQ ID NO 15
<211> LENGTH: 40
<212> TYPE: PRT
<213> ORGANISM: Mycobacterium tuberculosis

<400> SEQUENCE: 15

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu Asp
        35                  40

<210> SEQ ID NO 16
<211> LENGTH: 40
<212> TYPE: PRT
<213> ORGANISM: Mycobacterium tuberculosis

<400> SEQUENCE: 16

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu Asp
        35                  40

<210> SEQ ID NO 17
<211> LENGTH: 22
<212> TYPE: PRT
<213> ORGANISM: Mycobacterium tuberculosis

<400> SEQUENCE: 17

Phe Ser Arg Pro Gly Leu Pro Val Glu Tyr Leu Gln Val Pro Ser Ala
1               5                   10                  15

Ser Met Gly Arg Asp Ile
            20

<210> SEQ ID NO 18
<211> LENGTH: 48
<212> TYPE: PRT
<213> ORGANISM: Mycobacterium tuberculosis

<400> SEQUENCE: 18

Phe Asp Thr Arg Leu Met Arg Leu Glu Asp Glu Met Lys Glu Gly Arg
1               5                   10                  15

Tyr Glu Val Arg Ala Glu Leu Pro Gly Val Asp Pro Asp Lys Asp Val
            20                  25                  30

Asp Ile Met Val Arg Asp Gly Gln Leu Thr Ile Lys Ala Glu Arg Thr
        35                  40                  45

<210> SEQ ID NO 19
<211> LENGTH: 30
<212> TYPE: PRT
<213> ORGANISM: Mycobacterium tuberculosis

<400> SEQUENCE: 19

Ala Asp Pro Arg Leu Gln Phe Thr Ala Thr Thr Leu Ser Gly Ala Pro
1               5                   10                  15

Phe Asp Gly Ala Ser Leu Gln Gly Lys Pro Ala Val Leu Trp
            20                  25                  30
```

```
<210> SEQ ID NO 20
<211> LENGTH: 30
<212> TYPE: PRT
<213> ORGANISM: Mycobacterium tuberculosis

<400> SEQUENCE: 20

Ala Asp Pro Arg Leu Gln Phe Thr Ala Thr Thr Leu Ser Gly Ala Pro
 1               5                  10                  15

Phe Asp Gly Ala Asn Leu Gln Gly Lys Pro Ala Val Leu Trp
            20                  25                  30

<210> SEQ ID NO 21
<211> LENGTH: 47
<212> TYPE: PRT
<213> ORGANISM: Mycobacterium tuberculosis
<220> FEATURE:
<221> NAME/KEY: MOD_RES
<222> LOCATION: (43)..(43)
<223> OTHER INFORMATION: Variable amino acid

<400> SEQUENCE: 21

Ala Tyr Pro Ile Thr Gly Lys Leu Gly Ser Glu Leu Thr Met Thr Asp
 1               5                  10                  15

Thr Val Gly Gln Val Val Leu Gly Trp Lys Val Ser Asp Leu Phe Lys
            20                  25                  30

Ser Thr Ala Val Ile Pro Gly Tyr Thr Val Xaa Glu Gln Gln Ile
        35                  40                  45

<210> SEQ ID NO 22
<211> LENGTH: 47
<212> TYPE: PRT
<213> ORGANISM: Mycobacterium tuberculosis
<220> FEATURE:
<221> NAME/KEY: MOD_RES
<222> LOCATION: (43)..(43)
<223> OTHER INFORMATION: Variable amino acid

<400> SEQUENCE: 22

Ala Tyr Pro Ile Thr Gly Lys Leu Gly Ser Glu Leu Thr Met Thr Asp
 1               5                  10                  15

Thr Val Gly Gln Val Val Leu Gly Trp Lys Val Ser Asp Leu Tyr Lys
            20                  25                  30

Ser Thr Ala Val Ile Pro Gly Tyr Thr Val Xaa Glu Gln Gln Ile
        35                  40                  45

<210> SEQ ID NO 23
<211> LENGTH: 22
<212> TYPE: PRT
<213> ORGANISM: Mycobacterium tuberculosis

<400> SEQUENCE: 23

Ala Glu Thr Tyr Leu Pro Asp Leu Asp Trp Asp Tyr Gly Ala Leu Glu
 1               5                  10                  15

Pro His Ile Ser Gly Gln
            20

<210> SEQ ID NO 24
<211> LENGTH: 13
<212> TYPE: PRT
<213> ORGANISM: Mycobacterium tuberculosis
<220> FEATURE:
<221> NAME/KEY: MOD_RES
<222> LOCATION: (6)..(6)
<223> OTHER INFORMATION: Variable amino acid
```

```
<400> SEQUENCE: 24

Ala Pro Lys Thr Tyr Xaa Glu Glu Leu Lys Gly Thr Asp
1               5                  10

<210> SEQ ID NO 25
<211> LENGTH: 60
<212> TYPE: PRT
<213> ORGANISM: Mycobacterium tuberculosis
<220> FEATURE:
<221> NAME/KEY: MOD_RES
<222> LOCATION: (56)..(56)
<223> OTHER INFORMATION: Variable amino acid

<400> SEQUENCE: 25

Ala Pro Tyr Glu Asn Leu Met Val Pro Ser Pro Ser Met Gly Arg Asp
1               5                  10                  15

Ile Pro Val Ala Phe Leu Ala Gly Gly Pro His Ala Val Tyr Leu Leu
            20                  25                  30

Asp Ala Phe Asn Ala Gly Pro Asp Val Ser Asn Trp Val Thr Ala Gly
        35                  40                  45

Asn Ala Met Met Thr Leu Ala Xaa Lys Gly Ile Cys
    50                  55                  60

<210> SEQ ID NO 26
<211> LENGTH: 60
<212> TYPE: PRT
<213> ORGANISM: Mycobacterium tuberculosis
<220> FEATURE:
<221> NAME/KEY: MOD_RES
<222> LOCATION: (56)..(56)
<223> OTHER INFORMATION: Variable amino acid

<400> SEQUENCE: 26

Ala Pro Tyr Glu Asn Leu Met Val Pro Ser Pro Ser Met Gly Arg Asp
1               5                  10                  15

Ile Pro Val Ala Phe Leu Ala Gly Gly Pro His Ala Val Tyr Leu Leu
            20                  25                  30

Asp Ala Phe Asn Ala Gly Pro Asp Val Ser Asn Trp Val Thr Ala Gly
        35                  40                  45

Asn Ala Met Met Thr Leu Ala Xaa Lys Gly Ile Ser
    50                  55                  60

<210> SEQ ID NO 27
<211> LENGTH: 40
<212> TYPE: PRT
<213> ORGANISM: Mycobacterium tuberculosis

<400> SEQUENCE: 27

Phe Ser Arg Pro Gly Leu Pro Val Glu Tyr Leu Gln Val Pro Ser Pro
1               5                  10                  15

Ser Met Gly Arg Asp Ile Lys Val Gln Phe Gln Ser Gly Gly Asn Asn
            20                  25                  30

Ser Pro Ala Val Tyr Leu Leu Asp
        35                  40

<210> SEQ ID NO 28
<211> LENGTH: 40
<212> TYPE: PRT
<213> ORGANISM: Mycobacterium tuberculosis

<400> SEQUENCE: 28
```

```
Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
                20                  25                  30

Ser Pro Ala Leu Tyr Leu Leu Asp
        35                  40

<210> SEQ ID NO 29
<211> LENGTH: 22
<212> TYPE: PRT
<213> ORGANISM: Mycobacterium tuberculosis
<220> FEATURE:
<221> NAME/KEY: MOD_RES
<222> LOCATION: (17)..(17)
<223> OTHER INFORMATION: Variable amino acid

<400> SEQUENCE: 29

Phe Ser Arg Pro Gly Leu Pro Val Glu Tyr Leu Gln Val Pro Ser Ala
1               5                   10                  15

Xaa Met Gly Arg Asp Ile
                20

<210> SEQ ID NO 30
<211> LENGTH: 30
<212> TYPE: PRT
<213> ORGANISM: Mycobacterium tuberculosis
<220> FEATURE:
<221> NAME/KEY: MOD_RES
<222> LOCATION: (30)..(30)
<223> OTHER INFORMATION: Variable amino acid

<400> SEQUENCE: 30

Asp Pro Glu Pro Ala Pro Pro Val Pro Asp Asp Ala Ala Ser Pro Pro
1               5                   10                  15

Asp Asp Ala Ala Ala Pro Pro Ala Pro Ala Asp Pro Pro Xaa
                20                  25                  30

<210> SEQ ID NO 31
<211> LENGTH: 20
<212> TYPE: PRT
<213> ORGANISM: Mycobacterium tuberculosis

<400> SEQUENCE: 31

Thr Glu Lys Thr Pro Asp Asp Val Phe Lys Leu Ala Lys Asp Glu Lys
1               5                   10                  15

Val Leu Tyr Leu
                20

<210> SEQ ID NO 32
<211> LENGTH: 6
<212> TYPE: PRT
<213> ORGANISM: Mycobacterium tuberculosis

<400> SEQUENCE: 32

Ala Arg Ala Val Gly Ile
1               5

<210> SEQ ID NO 33
<211> LENGTH: 8
<212> TYPE: PRT
<213> ORGANISM: Mycobacterium tuberculosis

<400> SEQUENCE: 33

Thr Asp Arg Val Ser Val Gly Asn
```

<210> SEQ ID NO 34
<211> LENGTH: 22
<212> TYPE: PRT
<213> ORGANISM: Mycobacterium tuberculosis
<220> FEATURE:
<221> NAME/KEY: MOD_RES
<222> LOCATION: (17)..(17)
<223> OTHER INFORMATION: Variable amino acid

<400> SEQUENCE: 34

Asn Ser Lys Ser Val Asn Ser Phe Gly Ala His Asp Thr Leu Lys Val
1               5                   10                  15

Xaa Glu Arg Lys Arg Gln
            20

<210> SEQ ID NO 35
<211> LENGTH: 978
<212> TYPE: DNA
<213> ORGANISM: Mycobacterium tuberculosis
<220> FEATURE:
<221> NAME/KEY: CDS
<222> LOCATION: (1)..(978)

<400> SEQUENCE: 35

```
atg aca gac gtg agc cga aag att cga gct tgg gga cgc cga ttg atg    48
Met Thr Asp Val Ser Arg Lys Ile Arg Ala Trp Gly Arg Arg Leu Met
 1               5                   10                  15 atc ggc acg gca gcg gct gta gtc ctt ccg ggc ctg gtg ggg ctt gcc    96
Ile Gly Thr Ala Ala Ala Val Val Leu Pro Gly Leu Val Gly Leu Ala
                20                  25                  30 ggc gga gcg gca acc gcg ggc gcg ttc tcc cgg ccg ggg ctg ccg gtc   144
Gly Gly Ala Ala Thr Ala Gly Ala Phe Ser Arg Pro Gly Leu Pro Val
            35                  40                  45 gag tac ctg cag gtg ccg tcg ccg tcg atg ggc cgc gac atc aag gtt   192
Glu Tyr Leu Gln Val Pro Ser Pro Ser Met Gly Arg Asp Ile Lys Val
        50                  55                  60 cag ttc cag agc ggt ggg aac aac tca cct gcg gtt tat ctg ctc gac   240
Gln Phe Gln Ser Gly Gly Asn Asn Ser Pro Ala Val Tyr Leu Leu Asp
 65                  70                  75                  80 ggc ctg cgc gcc caa gac gac tac aac ggc tgg gat atc aac acc ccg   288
Gly Leu Arg Ala Gln Asp Asp Tyr Asn Gly Trp Asp Ile Asn Thr Pro
                 85                  90                  95 gcg ttc gag tgg tac tac cag tcg gga ctg tcg ata gtc atg ccg gtc   336
Ala Phe Glu Trp Tyr Tyr Gln Ser Gly Leu Ser Ile Val Met Pro Val
            100                 105                 110 ggc ggg cag tcc agc ttc tac agc gac tgg tac agc ccg gcc tgc ggt   384
Gly Gly Gln Ser Ser Phe Tyr Ser Asp Trp Tyr Ser Pro Ala Cys Gly
        115                 120                 125 aag gct ggc tgc cag act tac aag tgg gaa acc ttc ctg acc agc gag   432
Lys Ala Gly Cys Gln Thr Tyr Lys Trp Glu Thr Phe Leu Thr Ser Glu
    130                 135                 140 ctg ccg caa tgg ttg tcc gcc aac agg gcc gtg aag ccc acc ggc agc   480
Leu Pro Gln Trp Leu Ser Ala Asn Arg Ala Val Lys Pro Thr Gly Ser
145                 150                 155                 160 gct gca atc ggc ttg tcg atg gcc ggc tcg tcg gca atg atc ttg gcc   528
Ala Ala Ile Gly Leu Ser Met Ala Gly Ser Ser Ala Met Ile Leu Ala
                165                 170                 175 gcc tac cac ccc cag cag ttc atc tac gcc ggc tcg ctg tcg gcc ctg   576
Ala Tyr His Pro Gln Gln Phe Ile Tyr Ala Gly Ser Leu Ser Ala Leu
            180                 185                 190
```

```
ctg gac ccc tct cag ggg atg ggg cct agc ctg atc ggc ctc gcg atg      624
Leu Asp Pro Ser Gln Gly Met Gly Pro Ser Leu Ile Gly Leu Ala Met
        195                 200                 205 ggt gac gcc ggc ggt tac aag gcc gca gac atg tgg ggt ccc tcg agt      672
Gly Asp Ala Gly Gly Tyr Lys Ala Ala Asp Met Trp Gly Pro Ser Ser
210                 215                 220 gac ccg gca tgg gag cgc aac gac cct acg cag cag atc ccc aag ctg      720
Asp Pro Ala Trp Glu Arg Asn Asp Pro Thr Gln Gln Ile Pro Lys Leu
225                 230                 235                 240 gtc gca aac aac acc cgg cta tgg gtt tat tgc ggg aac ggc acc ccg      768
Val Ala Asn Asn Thr Arg Leu Trp Val Tyr Cys Gly Asn Gly Thr Pro
                245                 250                 255 aac gag ttg ggc ggt gcc aac ata ccc gcc gag ttc ttg gag aac ttc      816
Asn Glu Leu Gly Gly Ala Asn Ile Pro Ala Glu Phe Leu Glu Asn Phe
            260                 265                 270 gtt cgt agc agc aac ctg aag ttc cag gat gcg tac aac gcc gcg ggc      864
Val Arg Ser Ser Asn Leu Lys Phe Gln Asp Ala Tyr Asn Ala Ala Gly
        275                 280                 285 ggg cac aac gcc gtg ttc aac ttc ccg ccc aac ggc acg cac agc tgg      912
Gly His Asn Ala Val Phe Asn Phe Pro Pro Asn Gly Thr His Ser Trp
    290                 295                 300 gag tac tgg ggc gct cag ctc aac gcc atg aag ggt gac ctg cag agt      960
Glu Tyr Trp Gly Ala Gln Leu Asn Ala Met Lys Gly Asp Leu Gln Ser
305                 310                 315                 320 tcg tta ggc gcc ggc tga                                              978
Ser Leu Gly Ala Gly
                325

<210> SEQ ID NO 36
<211> LENGTH: 1017
<212> TYPE: DNA
<213> ORGANISM: Mycobacterium tuberculosis
<220> FEATURE:
<221> NAME/KEY: CDS
<222> LOCATION: (1)..(1017)

<400> SEQUENCE: 36 atg cag ctt gtt gac agg gtt cgt ggc gcc gtc acg ggt atg tcg cgt       48
Met Gln Leu Val Asp Arg Val Arg Gly Ala Val Thr Gly Met Ser Arg
1               5                   10                  15 cga ctc gtg gtc ggg gcc gtc ggc gcg gcc cta gtg tcg ggt ctg gtc       96
Arg Leu Val Val Gly Ala Val Gly Ala Ala Leu Val Ser Gly Leu Val
            20                  25                  30 ggc gcc gtc ggt ggc acg gcg acc gcg ggg gca ttt tcc cgg ccg ggc      144
Gly Ala Val Gly Gly Thr Ala Thr Ala Gly Ala Phe Ser Arg Pro Gly
        35                  40                  45 ttg ccg gtg gag tac ctg cag gtg ccg tcg ccg tcg atg ggc cgt gac      192
Leu Pro Val Glu Tyr Leu Gln Val Pro Ser Pro Ser Met Gly Arg Asp
    50                  55                  60 atc aag gtc caa ttc caa agt ggt ggt gcc aac tcg ccc gcc ctg tac      240
Ile Lys Val Gln Phe Gln Ser Gly Gly Ala Asn Ser Pro Ala Leu Tyr
65                  70                  75                  80 ctg ctc gac ggc ctg cgc gcg cag gac gac ttc agc ggc tgg gac atc      288
Leu Leu Asp Gly Leu Arg Ala Gln Asp Asp Phe Ser Gly Trp Asp Ile
                85                  90                  95 aac acc ccg gcg ttc gag tgg tac gac cag tcg ggc ctg tcg gtg gtc      336
Asn Thr Pro Ala Phe Glu Trp Tyr Asp Gln Ser Gly Leu Ser Val Val
            100                 105                 110 atg ccg gtg ggt ggc cag tca agc ttc tac tcc gac tgg tac cag ccc      384
Met Pro Val Gly Gly Gln Ser Ser Phe Tyr Ser Asp Trp Tyr Gln Pro
        115                 120                 125
```

| | | |
|---|---|---|
| gcc tgc ggc aag gcc ggt tgc cag act tac aag tgg gag acc ttc ctg<br>Ala Cys Gly Lys Ala Gly Cys Gln Thr Tyr Lys Trp Glu Thr Phe Leu<br>130                        135                       140 | 432 |

```
gcc tgc ggc aag gcc ggt tgc cag act tac aag tgg gag acc ttc ctg      432
Ala Cys Gly Lys Ala Gly Cys Gln Thr Tyr Lys Trp Glu Thr Phe Leu
        130             135                 140 acc agc gag ctg ccg ggg tgg ctg cag gcc aac agg cac gtc aag ccc      480
Thr Ser Glu Leu Pro Gly Trp Leu Gln Ala Asn Arg His Val Lys Pro
145                 150                 155                 160 acc gga agc gcc gtc gtc ggt ctt tcg atg gct gct tct tcg gcg ctg      528
Thr Gly Ser Ala Val Val Gly Leu Ser Met Ala Ala Ser Ser Ala Leu
                165                 170                 175 acg ctg gcg atc tat cac ccc cag cag ttc gtc tac gcg gga gcg atg      576
Thr Leu Ala Ile Tyr His Pro Gln Gln Phe Val Tyr Ala Gly Ala Met
            180                 185                 190 tcg ggc ctg ttg gac ccc tcc cag gcg atg ggt ccc acc ctg atc ggc      624
Ser Gly Leu Leu Asp Pro Ser Gln Ala Met Gly Pro Thr Leu Ile Gly
        195                 200                 205 ctg gcg atg ggt gac gct ggc ggc tac aag gcc tcc gac atg tgg ggc      672
Leu Ala Met Gly Asp Ala Gly Gly Tyr Lys Ala Ser Asp Met Trp Gly
    210                 215                 220 ccg aag gag gac ccg gcg tgg cag cgc aac gac ccg ctg ttg aac gtc      720
Pro Lys Glu Asp Pro Ala Trp Gln Arg Asn Asp Pro Leu Leu Asn Val
225                 230                 235                 240 ggg aag ctg atc gcc aac aac acc cgc gtc tgg gtg tac tgc ggc aac      768
Gly Lys Leu Ile Ala Asn Asn Thr Arg Val Trp Val Tyr Cys Gly Asn
                245                 250                 255 ggc aag ccg tcg gat ctg ggt ggc aac aac ctg ccg gcc aag ttc ctc      816
Gly Lys Pro Ser Asp Leu Gly Gly Asn Asn Leu Pro Ala Lys Phe Leu
            260                 265                 270 gag ggc ttc gtg cgg acc agc aac atc aag ttc caa gac gcc tac aac      864
Glu Gly Phe Val Arg Thr Ser Asn Ile Lys Phe Gln Asp Ala Tyr Asn
        275                 280                 285 gcc ggt ggc ggc cac aac ggc gtg ttc gac ttc ccg gac agc ggt acg      912
Ala Gly Gly Gly His Asn Gly Val Phe Asp Phe Pro Asp Ser Gly Thr
    290                 295                 300 cac agc tgg gag tac tgg ggc gcg cag ctc aac gct atg aag ccc gac      960
His Ser Trp Glu Tyr Trp Gly Ala Gln Leu Asn Ala Met Lys Pro Asp
305                 310                 315                 320 ctg caa cgg gca ctg ggt gcc acg ccc aac acc ggg ccc gcg ccc cag     1008
Leu Gln Arg Ala Leu Gly Ala Thr Pro Asn Thr Gly Pro Ala Pro Gln
                325                 330                 335 ggc gcc tag                                                         1017
Gly Ala <210> SEQ ID NO 37
<211> LENGTH: 15
<212> TYPE: PRT
<213> ORGANISM: Mycobacterium tuberculosis

<400> SEQUENCE: 37

Phe Ser Arg Pro Gly Leu Pro Val Glu Tyr Leu Gln Val Pro Ser
1               5                   10                  15

<210> SEQ ID NO 38
<211> LENGTH: 15
<212> TYPE: PRT
<213> ORGANISM: Mycobacterium tuberculosis

<400> SEQUENCE: 38

Leu Pro Val Glu Tyr Leu Gln Val Pro Ser Pro Ser Met Gly Arg
1               5                   10                  15

<210> SEQ ID NO 39
```

```
<211> LENGTH: 15
<212> TYPE: PRT
<213> ORGANISM: Mycobacterium tuberculosis

<400> SEQUENCE: 39

Leu Gln Val Pro Ser Pro Ser Met Gly Arg Asp Ile Lys Val Gln
1               5                   10                  15

<210> SEQ ID NO 40
<211> LENGTH: 15
<212> TYPE: PRT
<213> ORGANISM: Mycobacterium tuberculosis

<400> SEQUENCE: 40

Pro Ser Met Gly Arg Asp Ile Lys Val Gln Phe Gln Ser Gly Gly
1               5                   10                  15

<210> SEQ ID NO 41
<211> LENGTH: 15
<212> TYPE: PRT
<213> ORGANISM: Mycobacterium tuberculosis

<400> SEQUENCE: 41

Asp Ile Lys Val Gln Phe Gln Ser Gly Gly Asn Asn Ser Pro Ala
1               5                   10                  15

<210> SEQ ID NO 42
<211> LENGTH: 15
<212> TYPE: PRT
<213> ORGANISM: Mycobacterium tuberculosis

<400> SEQUENCE: 42

Phe Gln Ser Gly Gly Asn Asn Ser Pro Ala Val Tyr Leu Leu Asp
1               5                   10                  15

<210> SEQ ID NO 43
<211> LENGTH: 15
<212> TYPE: PRT
<213> ORGANISM: Mycobacterium tuberculosis

<400> SEQUENCE: 43

Asn Asn Ser Pro Ala Val Tyr Leu Leu Asp Gly Leu Arg Ala Gln
1               5                   10                  15

<210> SEQ ID NO 44
<211> LENGTH: 15
<212> TYPE: PRT
<213> ORGANISM: Mycobacterium tuberculosis

<400> SEQUENCE: 44

Val Tyr Leu Leu Asp Gly Leu Arg Ala Gln Asp Asp Tyr Asn Gly
1               5                   10                  15

<210> SEQ ID NO 45
<211> LENGTH: 15
<212> TYPE: PRT
<213> ORGANISM: Mycobacterium tuberculosis

<400> SEQUENCE: 45

Gly Leu Arg Ala Gln Asp Asp Tyr Asn Gly Trp Asp Ile Asn Thr
1               5                   10                  15

<210> SEQ ID NO 46
<211> LENGTH: 15
<212> TYPE: PRT
```

-continued

<213> ORGANISM: Mycobacterium tuberculosis

<400> SEQUENCE: 46

Asp Asp Tyr Asn Gly Trp Asp Ile Asn Thr Pro Ala Phe Glu Trp
1               5                   10                  15

<210> SEQ ID NO 47
<211> LENGTH: 15
<212> TYPE: PRT
<213> ORGANISM: Mycobacterium tuberculosis

<400> SEQUENCE: 47

Trp Asp Ile Asn Thr Pro Ala Phe Glu Trp Tyr Tyr Gln Ser Gly
1               5                   10                  15

<210> SEQ ID NO 48
<211> LENGTH: 15
<212> TYPE: PRT
<213> ORGANISM: Mycobacterium tuberculosis

<400> SEQUENCE: 48

Pro Ala Phe Glu Trp Tyr Tyr Gln Ser Gly Leu Ser Ile Val Met
1               5                   10                  15

<210> SEQ ID NO 49
<211> LENGTH: 15
<212> TYPE: PRT
<213> ORGANISM: Mycobacterium tuberculosis

<400> SEQUENCE: 49

Tyr Tyr Gln Ser Gly Leu Ser Ile Val Met Pro Val Gly Gly Gln
1               5                   10                  15

<210> SEQ ID NO 50
<211> LENGTH: 15
<212> TYPE: PRT
<213> ORGANISM: Mycobacterium tuberculosis

<400> SEQUENCE: 50

Leu Ser Ile Val Met Pro Val Gly Gly Gln Ser Ser Phe Tyr Ser
1               5                   10                  15

<210> SEQ ID NO 51
<211> LENGTH: 15
<212> TYPE: PRT
<213> ORGANISM: Mycobacterium tuberculosis

<400> SEQUENCE: 51

Pro Val Gly Gly Gln Ser Ser Phe Tyr Ser Asp Trp Tyr Ser Pro
1               5                   10                  15

<210> SEQ ID NO 52
<211> LENGTH: 15
<212> TYPE: PRT
<213> ORGANISM: Mycobacterium tuberculosis

<400> SEQUENCE: 52

Ser Ser Phe Tyr Ser Asp Trp Tyr Ser Pro Ala Cys Gly Lys Ala
1               5                   10                  15

<210> SEQ ID NO 53
<211> LENGTH: 15
<212> TYPE: PRT
<213> ORGANISM: Mycobacterium tuberculosis -continued

<400> SEQUENCE: 53

Asp Trp Tyr Ser Pro Ala Cys Gly Lys Ala Gly Cys Gln Thr Tyr
1               5                   10                  15

<210> SEQ ID NO 54
<211> LENGTH: 15
<212> TYPE: PRT
<213> ORGANISM: Mycobacterium tuberculosis

<400> SEQUENCE: 54

Ala Cys Gly Lys Ala Gly Cys Gln Thr Tyr Lys Trp Glu Thr Phe
1               5                   10                  15

<210> SEQ ID NO 55
<211> LENGTH: 15
<212> TYPE: PRT
<213> ORGANISM: Mycobacterium tuberculosis

<400> SEQUENCE: 55

Gly Cys Gln Thr Tyr Lys Trp Glu Thr Phe Leu Thr Ser Glu Leu
1               5                   10                  15

<210> SEQ ID NO 56
<211> LENGTH: 15
<212> TYPE: PRT
<213> ORGANISM: Mycobacterium tuberculosis

<400> SEQUENCE: 56

Lys Trp Glu Thr Phe Leu Thr Ser Glu Leu Pro Gln Trp Leu Ser
1               5                   10                  15

<210> SEQ ID NO 57
<211> LENGTH: 15
<212> TYPE: PRT
<213> ORGANISM: Mycobacterium tuberculosis

<400> SEQUENCE: 57

Leu Thr Ser Glu Leu Pro Gln Trp Leu Ser Ala Asn Arg Ala Val
1               5                   10                  15

<210> SEQ ID NO 58
<211> LENGTH: 15
<212> TYPE: PRT
<213> ORGANISM: Mycobacterium tuberculosis

<400> SEQUENCE: 58

Pro Gln Trp Leu Ser Ala Asn Arg Ala Val Lys Pro Thr Gly Ser
1               5                   10                  15

<210> SEQ ID NO 59
<211> LENGTH: 15
<212> TYPE: PRT
<213> ORGANISM: Mycobacterium tuberculosis

<400> SEQUENCE: 59

Ala Asn Arg Ala Val Lys Pro Thr Gly Ser Ala Ala Ile Gly Leu
1               5                   10                  15

<210> SEQ ID NO 60
<211> LENGTH: 15
<212> TYPE: PRT
<213> ORGANISM: Mycobacterium tuberculosis

<400> SEQUENCE: 60

```
Lys Pro Thr Gly Ser Ala Ala Ile Gly Leu Ser Met Ala Gly Ser
1               5                   10                  15
```

<210> SEQ ID NO 61
<211> LENGTH: 15
<212> TYPE: PRT
<213> ORGANISM: Mycobacterium tuberculosis

<400> SEQUENCE: 61

```
Ala Ala Ile Gly Leu Ser Met Ala Gly Ser Ser Ala Met Ile Leu
1               5                   10                  15
```

<210> SEQ ID NO 62
<211> LENGTH: 15
<212> TYPE: PRT
<213> ORGANISM: Mycobacterium tuberculosis

<400> SEQUENCE: 62

```
Ser Met Ala Gly Ser Ser Ala Met Ile Leu Ala Ala Tyr His Pro
1               5                   10                  15
```

<210> SEQ ID NO 63
<211> LENGTH: 15
<212> TYPE: PRT
<213> ORGANISM: Mycobacterium tuberculosis

<400> SEQUENCE: 63

```
Ser Ala Met Ile Leu Ala Ala Tyr His Pro Gln Gln Phe Ile Tyr
1               5                   10                  15
```

<210> SEQ ID NO 64
<211> LENGTH: 15
<212> TYPE: PRT
<213> ORGANISM: Mycobacterium tuberculosis

<400> SEQUENCE: 64

```
Ala Ala Tyr His Pro Gln Gln Phe Ile Tyr Ala Gly Ser Leu Ser
1               5                   10                  15
```

<210> SEQ ID NO 65
<211> LENGTH: 15
<212> TYPE: PRT
<213> ORGANISM: Mycobacterium tuberculosis

<400> SEQUENCE: 65

```
Gln Gln Phe Ile Tyr Ala Gly Ser Leu Ser Ala Leu Leu Asp Pro
1               5                   10                  15
```

<210> SEQ ID NO 66
<211> LENGTH: 15
<212> TYPE: PRT
<213> ORGANISM: Mycobacterium tuberculosis

<400> SEQUENCE: 66

```
Ala Gly Ser Leu Ser Ala Leu Leu Asp Pro Ser Gln Gly Met Gly
1               5                   10                  15
```

<210> SEQ ID NO 67
<211> LENGTH: 15
<212> TYPE: PRT
<213> ORGANISM: Mycobacterium tuberculosis

<400> SEQUENCE: 67

```
Ala Leu Leu Asp Pro Ser Gln Gly Met Gly Pro Ser Leu Ile Gly
1               5                   10                  15
```

<210> SEQ ID NO 68
<211> LENGTH: 15
<212> TYPE: PRT
<213> ORGANISM: Mycobacterium tuberculosis

<400> SEQUENCE: 68

Ser Gln Gly Met Gly Pro Ser Leu Ile Gly Leu Ala Met Gly Asp
1               5                   10                  15

<210> SEQ ID NO 69
<211> LENGTH: 15
<212> TYPE: PRT
<213> ORGANISM: Mycobacterium tuberculosis

<400> SEQUENCE: 69

Pro Ser Leu Ile Gly Leu Ala Met Gly Asp Ala Gly Gly Tyr Lys
1               5                   10                  15

<210> SEQ ID NO 70
<211> LENGTH: 15
<212> TYPE: PRT
<213> ORGANISM: Mycobacterium tuberculosis

<400> SEQUENCE: 70

Leu Ala Met Gly Asp Ala Gly Gly Tyr Lys Ala Ala Asp Met Trp
1               5                   10                  15

<210> SEQ ID NO 71
<211> LENGTH: 15
<212> TYPE: PRT
<213> ORGANISM: Mycobacterium tuberculosis

<400> SEQUENCE: 71

Ala Gly Gly Tyr Lys Ala Ala Asp Met Trp Gly Pro Ser Ser Asp
1               5                   10                  15

<210> SEQ ID NO 72
<211> LENGTH: 15
<212> TYPE: PRT
<213> ORGANISM: Mycobacterium tuberculosis

<400> SEQUENCE: 72

Ala Ala Asp Met Trp Gly Pro Ser Ser Asp Pro Ala Trp Glu Arg
1               5                   10                  15

<210> SEQ ID NO 73
<211> LENGTH: 15
<212> TYPE: PRT
<213> ORGANISM: Mycobacterium tuberculosis

<400> SEQUENCE: 73

Gly Pro Ser Ser Asp Pro Ala Trp Glu Arg Asn Asp Pro Thr Gln
1               5                   10                  15

<210> SEQ ID NO 74
<211> LENGTH: 15
<212> TYPE: PRT
<213> ORGANISM: Mycobacterium tuberculosis

<400> SEQUENCE: 74

Pro Ala Trp Glu Arg Asn Asp Pro Thr Gln Gln Ile Pro Lys Leu
1               5                   10                  15

```
<210> SEQ ID NO 75
<211> LENGTH: 15
<212> TYPE: PRT
<213> ORGANISM: Mycobacterium tuberculosis

<400> SEQUENCE: 75

Asn Asp Pro Thr Gln Gln Ile Pro Lys Leu Val Ala Asn Asn Thr
1               5                   10                  15

<210> SEQ ID NO 76
<211> LENGTH: 15
<212> TYPE: PRT
<213> ORGANISM: Mycobacterium tuberculosis

<400> SEQUENCE: 76

Gln Ile Pro Lys Leu Val Ala Asn Asn Thr Arg Leu Trp Val Tyr
1               5                   10                  15

<210> SEQ ID NO 77
<211> LENGTH: 15
<212> TYPE: PRT
<213> ORGANISM: Mycobacterium tuberculosis

<400> SEQUENCE: 77

Val Ala Asn Asn Thr Arg Leu Trp Val Tyr Cys Gly Asn Gly Thr
1               5                   10                  15

<210> SEQ ID NO 78
<211> LENGTH: 15
<212> TYPE: PRT
<213> ORGANISM: Mycobacterium tuberculosis

<400> SEQUENCE: 78

Arg Leu Trp Val Tyr Cys Gly Asn Gly Thr Pro Asn Glu Leu Gly
1               5                   10                  15

<210> SEQ ID NO 79
<211> LENGTH: 15
<212> TYPE: PRT
<213> ORGANISM: Mycobacterium tuberculosis

<400> SEQUENCE: 79

Cys Gly Asn Gly Thr Pro Asn Glu Leu Gly Gly Ala Asn Ile Pro
1               5                   10                  15

<210> SEQ ID NO 80
<211> LENGTH: 15
<212> TYPE: PRT
<213> ORGANISM: Mycobacterium tuberculosis

<400> SEQUENCE: 80

Pro Asn Glu Leu Gly Gly Ala Asn Ile Pro Ala Glu Phe Leu Glu
1               5                   10                  15

<210> SEQ ID NO 81
<211> LENGTH: 15
<212> TYPE: PRT
<213> ORGANISM: Mycobacterium tuberculosis

<400> SEQUENCE: 81

Gly Ala Asn Ile Pro Ala Glu Phe Leu Glu Asn Phe Val Arg Ser
1               5                   10                  15

<210> SEQ ID NO 82
<211> LENGTH: 15
```

```
<212> TYPE: PRT
<213> ORGANISM: Mycobacterium tuberculosis

<400> SEQUENCE: 82

Ala Glu Phe Leu Glu Asn Phe Val Arg Ser Ser Asn Leu Lys Phe
1               5                   10                  15

<210> SEQ ID NO 83
<211> LENGTH: 15
<212> TYPE: PRT
<213> ORGANISM: Mycobacterium tuberculosis

<400> SEQUENCE: 83

Asn Phe Val Arg Ser Ser Asn Leu Lys Phe Gln Asp Ala Tyr Asn
1               5                   10                  15

<210> SEQ ID NO 84
<211> LENGTH: 15
<212> TYPE: PRT
<213> ORGANISM: Mycobacterium tuberculosis

<400> SEQUENCE: 84

Ser Asn Leu Lys Phe Gln Asp Ala Tyr Asn Ala Ala Gly Gly His
1               5                   10                  15

<210> SEQ ID NO 85
<211> LENGTH: 15
<212> TYPE: PRT
<213> ORGANISM: Mycobacterium tuberculosis

<400> SEQUENCE: 85

Gln Asp Ala Tyr Asn Ala Ala Gly Gly His Asn Ala Val Phe Asn
1               5                   10                  15

<210> SEQ ID NO 86
<211> LENGTH: 15
<212> TYPE: PRT
<213> ORGANISM: Mycobacterium tuberculosis

<400> SEQUENCE: 86

Ala Ala Gly Gly His Asn Ala Val Phe Asn Phe Pro Pro Asn Gly
1               5                   10                  15

<210> SEQ ID NO 87
<211> LENGTH: 15
<212> TYPE: PRT
<213> ORGANISM: Mycobacterium tuberculosis

<400> SEQUENCE: 87

Asn Ala Val Phe Asn Phe Pro Pro Asn Gly Thr His Ser Trp Glu
1               5                   10                  15

<210> SEQ ID NO 88
<211> LENGTH: 15
<212> TYPE: PRT
<213> ORGANISM: Mycobacterium tuberculosis

<400> SEQUENCE: 88

Phe Pro Pro Asn Gly Thr His Ser Trp Glu Tyr Trp Gly Ala Gln
1               5                   10                  15

<210> SEQ ID NO 89
<211> LENGTH: 15
<212> TYPE: PRT
<213> ORGANISM: Mycobacterium tuberculosis
```

<400> SEQUENCE: 89

Thr His Ser Trp Glu Tyr Trp Gly Ala Gln Leu Asn Ala Met Lys
1               5                   10                  15

<210> SEQ ID NO 90
<211> LENGTH: 15
<212> TYPE: PRT
<213> ORGANISM: Mycobacterium tuberculosis

<400> SEQUENCE: 90

Tyr Trp Gly Ala Gln Leu Asn Ala Met Lys Gly Asp Leu Gln Ser
1               5                   10                  15

<210> SEQ ID NO 91
<211> LENGTH: 15
<212> TYPE: PRT
<213> ORGANISM: Mycobacterium tuberculosis

<400> SEQUENCE: 91

Leu Asn Ala Met Lys Gly Asp Leu Gln Ser Ser Leu Gly Ala Gly
1               5                   10                  15

<210> SEQ ID NO 92
<211> LENGTH: 480
<212> TYPE: DNA
<213> ORGANISM: Mycobacterium tuberculosis
<220> FEATURE:
<221> NAME/KEY: CDS
<222> LOCATION: (1)..(480)

<400> SEQUENCE: 92

| | |
|---|---|
| atg aag ctc acc aca atg atc aag acg gca gta gcg gtc gtg gcc atg<br>Met Lys Leu Thr Thr Met Ile Lys Thr Ala Val Ala Val Val Ala Met<br>1              5                  10               15 | 48 |
| gcg gcc atc gcg acc ttt gcg gca ccg gtc gcg ttg gct gcc tat ccc<br>Ala Ala Ile Ala Thr Phe Ala Ala Pro Val Ala Leu Ala Ala Tyr Pro<br>                 20                 25               30 | 96 |
| atc acc gaa aaa ctt ggc agt gag cta acg atg acc gac acc gtt ggc<br>Ile Thr Glu Lys Leu Gly Ser Glu Leu Thr Met Thr Asp Thr Val Gly<br>         35                 40                 45 | 144 |
| caa gtc gtg ctc ggc tgg aag gtc agt gat ctc aaa tcc agc acg gca<br>Gln Val Val Leu Gly Trp Lys Val Ser Asp Leu Lys Ser Ser Thr Ala<br>50                55                 60 | 192 |
| gtc atc ccc ggc tat ccg gtg gcc ggc cag gtc tgg gag gcc act gcc<br>Val Ile Pro Gly Tyr Pro Val Ala Gly Gln Val Trp Glu Ala Thr Ala<br>65                70                75               80 | 240 |
| acg gtc aat gcg att cgc ggc agc gtc acg ccc gcg gtc tcg cag ttc<br>Thr Val Asn Ala Ile Arg Gly Ser Val Thr Pro Ala Val Ser Gln Phe<br>                85                 90               95 | 288 |
| aat gcc cgc acc gcc gac ggc atc aac tac cgg gtg ctg tgg caa gcc<br>Asn Ala Arg Thr Ala Asp Gly Ile Asn Tyr Arg Val Leu Trp Gln Ala<br>            100              105             110 | 336 |
| gcg ggc ccc gac acc att agc gga gcc act atc ccc caa ggc gaa caa<br>Ala Gly Pro Asp Thr Ile Ser Gly Ala Thr Ile Pro Gln Gly Glu Gln<br>         115               120              125 | 384 |
| tcg acc ggc aaa atc tac ttc gat gtc acc ggc cca tcg cca acc atc<br>Ser Thr Gly Lys Ile Tyr Phe Asp Val Thr Gly Pro Ser Pro Thr Ile<br>130               135              140 | 432 |
| gtc gcg atg aac aac ggc atg gag gat ctg ctg att tgg gag ccg tag<br>Val Ala Met Asn Asn Gly Met Glu Asp Leu Leu Ile Trp Glu Pro<br>145               150              155             160 | 480 |

-continued

```
<210> SEQ ID NO 93
<211> LENGTH: 1437
<212> TYPE: DNA
<213> ORGANISM: Mycobacterium tuberculosis
<220> FEATURE:
<221> NAME/KEY: CDS
<222> LOCATION: (1)..(1434)

<400> SEQUENCE: 93 gtg acg gaa aag acg ccc gac gac gtc ttc aaa ctt gcc aag gac gag      48
Val Thr Glu Lys Thr Pro Asp Asp Val Phe Lys Leu Ala Lys Asp Glu
 1               5                  10                  15 aag gtc gaa tat gtc gac gtc cgg ttc tgt gac ctg cct ggc atc atg      96
Lys Val Glu Tyr Val Asp Val Arg Phe Cys Asp Leu Pro Gly Ile Met
             20                  25                  30 cag cac ttc acg att ccg gct tcg gcc ttt gac aag agc gtg ttt gac     144
Gln His Phe Thr Ile Pro Ala Ser Ala Phe Asp Lys Ser Val Phe Asp
         35                  40                  45 gac ggc ttg gcc ttt gac ggc tcg tcg att cgc ggg ttc cag tcg atc     192
Asp Gly Leu Ala Phe Asp Gly Ser Ser Ile Arg Gly Phe Gln Ser Ile
     50                  55                  60 cac gaa tcc gac atg ttg ctt ctt ccc gat ccc gag acg gcg cgc atc     240
His Glu Ser Asp Met Leu Leu Leu Pro Asp Pro Glu Thr Ala Arg Ile
 65                  70                  75                  80 gac ccg ttc cgc gcg gcc aag acg ctg aat atc aac ttc ttt gtg cac     288
Asp Pro Phe Arg Ala Ala Lys Thr Leu Asn Ile Asn Phe Phe Val His
                 85                  90                  95 gac ccg ttc acc ctg gag ccg tac tcc cgc gac ccg cgc aac atc gcc     336
Asp Pro Phe Thr Leu Glu Pro Tyr Ser Arg Asp Pro Arg Asn Ile Ala
            100                 105                 110 cgc aag gcc gag aac tac ctg atc agc act ggc atc gcc gac acc gca     384
Arg Lys Ala Glu Asn Tyr Leu Ile Ser Thr Gly Ile Ala Asp Thr Ala
        115                 120                 125 tac ttc ggc gcc gag gcc gag ttc tac att ttc gat tcg gtg agc ttc     432
Tyr Phe Gly Ala Glu Ala Glu Phe Tyr Ile Phe Asp Ser Val Ser Phe
    130                 135                 140 gac tcg cgc gcc aac ggc tcc ttc tac gag gtg gac gcc atc tcg ggg     480
Asp Ser Arg Ala Asn Gly Ser Phe Tyr Glu Val Asp Ala Ile Ser Gly
145                 150                 155                 160 tgg tgg aac acc ggc gcg gcg acc gag gcc gac ggc agt ccc aac cgg     528
Trp Trp Asn Thr Gly Ala Ala Thr Glu Ala Asp Gly Ser Pro Asn Arg
                165                 170                 175 ggc tac aag gtc cgc cac aag ggc ggg tat ttc cca gtg gcc ccc aac     576
Gly Tyr Lys Val Arg His Lys Gly Gly Tyr Phe Pro Val Ala Pro Asn
            180                 185                 190 gac caa tac gtc gac ctg cgc gac aag atg ctg acc aac ctg atc aac     624
Asp Gln Tyr Val Asp Leu Arg Asp Lys Met Leu Thr Asn Leu Ile Asn
        195                 200                 205 tcc ggc ttc atc ctg gag aag ggc cac cac gag gtg ggc agc ggc gga     672
Ser Gly Phe Ile Leu Glu Lys Gly His His Glu Val Gly Ser Gly Gly
    210                 215                 220 cag gcc gag atc aac tac cag ttc aat tcg ctg ctg cac gcc gcc gac     720
Gln Ala Glu Ile Asn Tyr Gln Phe Asn Ser Leu Leu His Ala Ala Asp
225                 230                 235                 240 gac atg cag ttg tac aag tac atc atc aag aac acc gcc tgg cag aac     768
Asp Met Gln Leu Tyr Lys Tyr Ile Ile Lys Asn Thr Ala Trp Gln Asn
                245                 250                 255 ggc aaa acg gtc acg ttc atg ccc aag ccg ctg ttc ggc gac aac ggg     816
Gly Lys Thr Val Thr Phe Met Pro Lys Pro Leu Phe Gly Asp Asn Gly
            260                 265                 270
```

```
tcc ggc atg cac tgt cat cag tcg ctg tgg aag gac ggg gcc ccg ctg      864
Ser Gly Met His Cys His Gln Ser Leu Trp Lys Asp Gly Ala Pro Leu
            275                 280                 285 atg tac gac gag acg ggt tat gcc ggt ctg tcg gac acg gcc cgt cat      912
Met Tyr Asp Glu Thr Gly Tyr Ala Gly Leu Ser Asp Thr Ala Arg His
        290                 295                 300 tac atc ggc ggc ctg tta cac cac gcg ccg tcg ctg ctg gcc ttc acc      960
Tyr Ile Gly Gly Leu Leu His His Ala Pro Ser Leu Leu Ala Phe Thr
305                 310                 315                 320 aac ccg acg gtg aac tcc tac aag cgg ctg gtt ccc ggt tac gag gcc     1008
Asn Pro Thr Val Asn Ser Tyr Lys Arg Leu Val Pro Gly Tyr Glu Ala
                325                 330                 335 ccg atc aac ctg gtc tat agc cag cgc aac cgg tcg gca tgc gtg cgc     1056
Pro Ile Asn Leu Val Tyr Ser Gln Arg Asn Arg Ser Ala Cys Val Arg
            340                 345                 350 atc ccg atc acc ggc agc aac ccg aag gcc aag cgg ctg gag ttc cga     1104
Ile Pro Ile Thr Gly Ser Asn Pro Lys Ala Lys Arg Leu Glu Phe Arg
        355                 360                 365 agc ccc gac tcg tcg ggc aac ccg tat ctg gcg ttc tcg gcc atg ctg     1152
Ser Pro Asp Ser Ser Gly Asn Pro Tyr Leu Ala Phe Ser Ala Met Leu
370                 375                 380 atg gca ggc ctg gac ggt atc aag aac aag atc gag ccg cag gcg ccc     1200
Met Ala Gly Leu Asp Gly Ile Lys Asn Lys Ile Glu Pro Gln Ala Pro
385                 390                 395                 400 gtc gac aag gat ctc tac gag ctg ccg ccg gaa gag gcc gcg agt atc     1248
Val Asp Lys Asp Leu Tyr Glu Leu Pro Pro Glu Glu Ala Ala Ser Ile
                405                 410                 415 ccg cag act ccg acc cag ctg tca gat gtg atc gac cgt ctc gag gcc     1296
Pro Gln Thr Pro Thr Gln Leu Ser Asp Val Ile Asp Arg Leu Glu Ala
            420                 425                 430 gac cac gaa tac ctc acc gaa gga ggg gtg ttc aca aac gac ctg atc     1344
Asp His Glu Tyr Leu Thr Glu Gly Gly Val Phe Thr Asn Asp Leu Ile
        435                 440                 445 gag acg tgg atc agt ttc aag cgc gaa aac gag atc gag ccg gtc aac     1392
Glu Thr Trp Ile Ser Phe Lys Arg Glu Asn Glu Ile Glu Pro Val Asn
450                 455                 460 atc cgg ccg cat ccc tac gaa ttc gcg ctg tac tac gac gtt taa         1437
Ile Arg Pro His Pro Tyr Glu Phe Ala Leu Tyr Tyr Asp Val
465                 470                 475

<210> SEQ ID NO 94
<211> LENGTH: 687
<212> TYPE: DNA
<213> ORGANISM: Mycobacterium tuberculosis
<220> FEATURE:
<221> NAME/KEY: CDS
<222> LOCATION: (1)..(687)

<400> SEQUENCE: 94 gtg cgc atc aag atc ttc atg ctg gtc acg gct gtc gtt ttg ctc tgt       48
Val Arg Ile Lys Ile Phe Met Leu Val Thr Ala Val Val Leu Leu Cys
1               5                   10                  15 tgt tcg ggt gtg gcc acg gcc gcg ccc aag acc tac tgc gag gag ttg       96
Cys Ser Gly Val Ala Thr Ala Ala Pro Lys Thr Tyr Cys Glu Glu Leu
                20                  25                  30 aaa ggc acc gat acc ggc cag gcg tgc cag att caa atg tcc gac ccg      144
Lys Gly Thr Asp Thr Gly Gln Ala Cys Gln Ile Gln Met Ser Asp Pro
            35                  40                  45 gcc tac aac atc aac atc agc ctg ccc agt tac tac ccc gac cag aag      192
Ala Tyr Asn Ile Asn Ile Ser Leu Pro Ser Tyr Tyr Pro Asp Gln Lys
        50                  55                  60
```

| | |
|---|---|
| tcg ctg gaa aat tac atc gcc cag acg cgc gac aag ttc ctc agc gcg<br>Ser Leu Glu Asn Tyr Ile Ala Gln Thr Arg Asp Lys Phe Leu Ser Ala<br>65                     70                    75                  80 | 240 |
| gcc aca tcg tcc act cca cgc gaa gcc ccc tac gaa ttg aat atc acc<br>Ala Thr Ser Ser Thr Pro Arg Glu Ala Pro Tyr Glu Leu Asn Ile Thr<br>                 85                    90                  95 | 288 |
| tcg gcc aca tac cag tcc gcg ata ccg ccg cgt ggt acg cag gcc gtg<br>Ser Ala Thr Tyr Gln Ser Ala Ile Pro Pro Arg Gly Thr Gln Ala Val<br>                100                  105                 110 | 336 |
| gtg ctc aag gtc tac cag aac gcc ggc ggc acg cac cca acg acc acg<br>Val Leu Lys Val Tyr Gln Asn Ala Gly Gly Thr His Pro Thr Thr Thr<br>115                    120                  125 | 384 |
| tac aag gcc ttc gat tgg gac cag gcc tat cgc aag cca atc acc tat<br>Tyr Lys Ala Phe Asp Trp Asp Gln Ala Tyr Arg Lys Pro Ile Thr Tyr<br>                130                  135                 140 | 432 |
| gac acg ctg tgg cag gct gac acc gat ccg ctg cca gtc gtc ttc ccc<br>Asp Thr Leu Trp Gln Ala Asp Thr Asp Pro Leu Pro Val Val Phe Pro<br>145                   150                  155                160 | 480 |
| att gtg caa ggt gaa ctg agc aag cag acc gga caa cag gta tcg ata<br>Ile Val Gln Gly Glu Leu Ser Lys Gln Thr Gly Gln Gln Val Ser Ile<br>                  165                  170                175 | 528 |
| gcg ccg aat gcc ggc ttg gac ccg gtg aat tat cag aac ttc gca gtc<br>Ala Pro Asn Ala Gly Leu Asp Pro Val Asn Tyr Gln Asn Phe Ala Val<br>                180                  185                 190 | 576 |
| acg aac gac ggg gtg att ttc ttc aac ccg ggg gag ttg ctg ccc<br>Thr Asn Asp Gly Val Ile Phe Phe Phe Asn Pro Gly Glu Leu Leu Pro<br>                195                  200                205 | 624 |
| gaa gca gcc ggc cca acc cag gta ttg gtc cca cgt tcc gcg atc gac<br>Glu Ala Ala Gly Pro Thr Gln Val Leu Val Pro Arg Ser Ala Ile Asp<br>210                    215                  220 | 672 |
| tcg atg ctg gcc tag<br>Ser Met Leu Ala<br>225 | 687 |

```
<210> SEQ ID NO 95
<211> LENGTH: 900
<212> TYPE: DNA
<213> ORGANISM: Mycobacterium tuberculosis
<220> FEATURE:
<221> NAME/KEY: CDS
<222> LOCATION: (1)..(900)

<400> SEQUENCE: 95
```

| | |
|---|---|
| atg aag ggt cgg tcg gcg ctg ctg cgg gcg ctc tgg att gcc gca ctg<br>Met Lys Gly Arg Ser Ala Leu Leu Arg Ala Leu Trp Ile Ala Ala Leu<br>1                   5                    10                  15 | 48 |
| tca ttc ggg ttg ggc ggt gtc gcg gta gcc gcg gaa ccc acc gcc aag<br>Ser Phe Gly Leu Gly Gly Val Ala Val Ala Ala Glu Pro Thr Ala Lys<br>                 20                   25                  30 | 96 |
| gcc gcc cca tac gag aac ctg atg gtg ccg tcg ccc tcg atg ggc cgg<br>Ala Ala Pro Tyr Glu Asn Leu Met Val Pro Ser Pro Ser Met Gly Arg<br>                35                   40                 45 | 144 |
| gac atc ccg gtg gcc ttc cta gcc ggt ggg ccg cac gcg gtg tat ctg<br>Asp Ile Pro Val Ala Phe Leu Ala Gly Gly Pro His Ala Val Tyr Leu<br>          50                  55                  60 | 192 |
| ctg gac gcc ttc aac gcc ggc ccg gat gtc agt aac tgg gtc acc gcg<br>Leu Asp Ala Phe Asn Ala Gly Pro Asp Val Ser Asn Trp Val Thr Ala<br>65                       70                    75                  80 | 240 |
| ggt aac gcg atg aac acg ttg gcg ggc aag ggg att tcg gtg gtg gca<br>Gly Asn Ala Met Asn Thr Leu Ala Gly Lys Gly Ile Ser Val Val Ala<br>                 85                   90                  95 | 288 |

```
ccg gcc ggt ggt gcg tac agc atg tac acc aac tgg gag cag gat ggc        336
Pro Ala Gly Gly Ala Tyr Ser Met Tyr Thr Asn Trp Glu Gln Asp Gly
            100                 105                 110 agc aag cag tgg gac acc ttc ttg tcc gct gag ctg ccc gac tgg ctg        384
Ser Lys Gln Trp Asp Thr Phe Leu Ser Ala Glu Leu Pro Asp Trp Leu
        115                 120                 125 gcc gct aac cgg ggc ttg gcc ccc ggt ggc cat gcg gcc gtt ggc gcc        432
Ala Ala Asn Arg Gly Leu Ala Pro Gly Gly His Ala Ala Val Gly Ala
    130                 135                 140 gct cag ggc ggt tac ggg gcg atg gcg ctg gcg gcc ttc cac ccc gac        480
Ala Gln Gly Gly Tyr Gly Ala Met Ala Leu Ala Ala Phe His Pro Asp
145                 150                 155                 160 cgc ttc ggc ttc gct ggc tcg atg tcg ggc ttt ttg tac ccg tcg aac        528
Arg Phe Gly Phe Ala Gly Ser Met Ser Gly Phe Leu Tyr Pro Ser Asn
                165                 170                 175 acc acc acc aac ggt gcg atc gcg gcg ggc atg cag caa ttc ggc ggt        576
Thr Thr Thr Asn Gly Ala Ile Ala Ala Gly Met Gln Gln Phe Gly Gly
            180                 185                 190 gtg gac acc aac gga atg tgg gga gca cca cag ctg ggt cgg tgg aag        624
Val Asp Thr Asn Gly Met Trp Gly Ala Pro Gln Leu Gly Arg Trp Lys
        195                 200                 205 tgg cac gac ccg tgg gtg cat gcc agc ctg ctg gcg caa aac aac acc        672
Trp His Asp Pro Trp Val His Ala Ser Leu Leu Ala Gln Asn Asn Thr
    210                 215                 220 cgg gtg tgg gtg tgg agc ccg acc aac ccg gga gcc agc gat ccc gcc        720
Arg Val Trp Val Trp Ser Pro Thr Asn Pro Gly Ala Ser Asp Pro Ala
225                 230                 235                 240 gcc atg atc ggc caa gcc gcc gag gcg atg ggt aac agc cgc atg ttc        768
Ala Met Ile Gly Gln Ala Ala Glu Ala Met Gly Asn Ser Arg Met Phe
                245                 250                 255 tac aac cag tat cgc agc gtc ggc ggg cac aac gga cac ttc gac ttc        816
Tyr Asn Gln Tyr Arg Ser Val Gly Gly His Asn Gly His Phe Asp Phe
            260                 265                 270 cca gcc agc ggt gac aac ggc tgg ggc tcg tgg gcg ccc cag ctg ggc        864
Pro Ala Ser Gly Asp Asn Gly Trp Gly Ser Trp Ala Pro Gln Leu Gly
        275                 280                 285 gct atg tcg ggc gat atc gtc ggt gcg atc cgc taa                        900
Ala Met Ser Gly Asp Ile Val Gly Ala Ile Arg
    290                 295                 300

<210> SEQ ID NO 96
<211> LENGTH: 15
<212> TYPE: PRT
<213> ORGANISM: Mycobacterium tuberculosis

<400> SEQUENCE: 96

Phe Ser Arg Pro Gly Leu Pro Val Glu Tyr Leu Gln Val Pro Ser
1               5                   10                  15

<210> SEQ ID NO 97
<211> LENGTH: 15
<212> TYPE: PRT
<213> ORGANISM: Mycobacterium tuberculosis

<400> SEQUENCE: 97

Leu Pro Val Glu Tyr Leu Gln Val Pro Ser Pro Ser Met Gly Arg
1               5                   10                  15

<210> SEQ ID NO 98
<211> LENGTH: 15
<212> TYPE: PRT
<213> ORGANISM: Mycobacterium tuberculosis
```

-continued

```
<400> SEQUENCE: 98

Leu Gln Val Pro Ser Pro Ser Met Gly Arg Asp Ile Lys Val Gln
1               5                   10                  15

<210> SEQ ID NO 99
<211> LENGTH: 15
<212> TYPE: PRT
<213> ORGANISM: Mycobacterium tuberculosis

<400> SEQUENCE: 99

Pro Ser Met Gly Arg Asp Ile Lys Val Gln Phe Gln Ser Gly Gly
1               5                   10                  15

<210> SEQ ID NO 100
<211> LENGTH: 15
<212> TYPE: PRT
<213> ORGANISM: Mycobacterium tuberculosis

<400> SEQUENCE: 100

Asp Ile Lys Val Gln Phe Gln Ser Gly Gly Ala Asn Ser Pro Ala
1               5                   10                  15

<210> SEQ ID NO 101
<211> LENGTH: 15
<212> TYPE: PRT
<213> ORGANISM: Mycobacterium tuberculosis

<400> SEQUENCE: 101

Phe Gln Ser Gly Gly Ala Asn Ser Pro Ala Leu Tyr Leu Leu Asp
1               5                   10                  15

<210> SEQ ID NO 102
<211> LENGTH: 15
<212> TYPE: PRT
<213> ORGANISM: Mycobacterium tuberculosis

<400> SEQUENCE: 102

Ala Asn Ser Pro Ala Leu Tyr Leu Leu Asp Gly Leu Arg Ala Gln
1               5                   10                  15

<210> SEQ ID NO 103
<211> LENGTH: 15
<212> TYPE: PRT
<213> ORGANISM: Mycobacterium tuberculosis

<400> SEQUENCE: 103

Leu Tyr Leu Leu Asp Gly Leu Arg Ala Gln Asp Asp Phe Ser Gly
1               5                   10                  15

<210> SEQ ID NO 104
<211> LENGTH: 15
<212> TYPE: PRT
<213> ORGANISM: Mycobacterium tuberculosis

<400> SEQUENCE: 104

Gly Leu Arg Ala Gln Asp Asp Phe Ser Gly Trp Asp Ile Asn Thr
1               5                   10                  15

<210> SEQ ID NO 105
<211> LENGTH: 15
<212> TYPE: PRT
<213> ORGANISM: Mycobacterium tuberculosis

<400> SEQUENCE: 105
```

Asp Asp Phe Ser Gly Trp Asp Ile Asn Thr Pro Ala Phe Glu Trp
1               5                   10                  15

<210> SEQ ID NO 106
<211> LENGTH: 15
<212> TYPE: PRT
<213> ORGANISM: Mycobacterium tuberculosis

<400> SEQUENCE: 106

Trp Asp Ile Asn Thr Pro Ala Phe Glu Trp Tyr Asp Gln Ser Gly
1               5                   10                  15

<210> SEQ ID NO 107
<211> LENGTH: 15
<212> TYPE: PRT
<213> ORGANISM: Mycobacterium tuberculosis

<400> SEQUENCE: 107

Pro Ala Phe Glu Trp Tyr Asp Gln Ser Gly Leu Ser Val Val Met
1               5                   10                  15

<210> SEQ ID NO 108
<211> LENGTH: 16
<212> TYPE: PRT
<213> ORGANISM: Mycobacterium tuberculosis

<400> SEQUENCE: 108

Tyr Asp Gln Ser Gly Leu Ser Val Val Met Pro Val Val Gly Gly Gln
1               5                   10                  15

<210> SEQ ID NO 109
<211> LENGTH: 15
<212> TYPE: PRT
<213> ORGANISM: Mycobacterium tuberculosis

<400> SEQUENCE: 109

Leu Ser Val Val Met Pro Val Gly Gly Gln Ser Ser Phe Tyr Ser
1               5                   10                  15

<210> SEQ ID NO 110
<211> LENGTH: 15
<212> TYPE: PRT
<213> ORGANISM: Mycobacterium tuberculosis

<400> SEQUENCE: 110

Pro Val Gly Gly Gln Ser Ser Phe Tyr Ser Asp Trp Tyr Gln Pro
1               5                   10                  15

<210> SEQ ID NO 111
<211> LENGTH: 15
<212> TYPE: PRT
<213> ORGANISM: Mycobacterium tuberculosis

<400> SEQUENCE: 111

Ser Ser Phe Tyr Ser Asp Trp Tyr Gln Pro Ala Cys Gly Lys Ala
1               5                   10                  15

<210> SEQ ID NO 112
<211> LENGTH: 15
<212> TYPE: PRT
<213> ORGANISM: Mycobacterium tuberculosis

<400> SEQUENCE: 112

Asp Trp Tyr Gln Pro Ala Cys Gly Lys Ala Gly Cys Gln Thr Tyr

```
                1               5              10              15
```

<210> SEQ ID NO 113
<211> LENGTH: 15
<212> TYPE: PRT
<213> ORGANISM: Mycobacterium tuberculosis

<400> SEQUENCE: 113

```
Ala Cys Gly Lys Ala Gly Cys Gln Thr Tyr Lys Trp Glu Thr Phe
1               5                  10                  15
```

<210> SEQ ID NO 114
<211> LENGTH: 15
<212> TYPE: PRT
<213> ORGANISM: Mycobacterium tuberculosis

<400> SEQUENCE: 114

```
Gly Cys Gln Thr Tyr Lys Trp Glu Thr Phe Leu Thr Ser Glu Leu
1               5                  10                  15
```

<210> SEQ ID NO 115
<211> LENGTH: 15
<212> TYPE: PRT
<213> ORGANISM: Mycobacterium tuberculosis

<400> SEQUENCE: 115

```
Lys Trp Glu Thr Phe Leu Thr Ser Glu Leu Pro Gly Trp Leu Gln
1               5                  10                  15
```

<210> SEQ ID NO 116
<211> LENGTH: 15
<212> TYPE: PRT
<213> ORGANISM: Mycobacterium tuberculosis

<400> SEQUENCE: 116

```
Leu Thr Ser Glu Leu Pro Gly Trp Leu Gln Ala Asn Arg His Val
1               5                  10                  15
```

<210> SEQ ID NO 117
<211> LENGTH: 15
<212> TYPE: PRT
<213> ORGANISM: Mycobacterium tuberculosis

<400> SEQUENCE: 117

```
Pro Gly Trp Leu Gln Ala Asn Arg His Val Lys Pro Thr Gly Ser
1               5                  10                  15
```

<210> SEQ ID NO 118
<211> LENGTH: 15
<212> TYPE: PRT
<213> ORGANISM: Mycobacterium tuberculosis

<400> SEQUENCE: 118

```
Ala Asn Arg His Val Lys Pro Thr Gly Ser Ala Val Val Gly Leu
1               5                  10                  15
```

<210> SEQ ID NO 119
<211> LENGTH: 15
<212> TYPE: PRT
<213> ORGANISM: Mycobacterium tuberculosis

<400> SEQUENCE: 119

```
Lys Pro Thr Gly Ser Ala Val Val Gly Leu Ser Met Ala Ala Ser
1               5                  10                  15
```

<210> SEQ ID NO 120
<211> LENGTH: 15
<212> TYPE: PRT
<213> ORGANISM: Mycobacterium tuberculosis

<400> SEQUENCE: 120

Ala Val Val Gly Leu Ser Met Ala Ala Ser Ser Ala Leu Thr Leu
1               5                   10                  15

<210> SEQ ID NO 121
<211> LENGTH: 15
<212> TYPE: PRT
<213> ORGANISM: Mycobacterium tuberculosis

<400> SEQUENCE: 121

Ser Met Ala Ala Ser Ser Ala Leu Thr Leu Ala Ile Tyr His Pro
1               5                   10                  15

<210> SEQ ID NO 122
<211> LENGTH: 15
<212> TYPE: PRT
<213> ORGANISM: Mycobacterium tuberculosis

<400> SEQUENCE: 122

Ser Ala Leu Thr Leu Ala Ile Tyr His Pro Gln Gln Phe Val Tyr
1               5                   10                  15

<210> SEQ ID NO 123
<211> LENGTH: 15
<212> TYPE: PRT
<213> ORGANISM: Mycobacterium tuberculosis

<400> SEQUENCE: 123

Ala Ile Tyr His Pro Gln Gln Phe Val Tyr Ala Gly Ala Met Ser
1               5                   10                  15

<210> SEQ ID NO 124
<211> LENGTH: 15
<212> TYPE: PRT
<213> ORGANISM: Mycobacterium tuberculosis

<400> SEQUENCE: 124

Gln Gln Phe Val Tyr Ala Gly Ala Met Ser Gly Leu Leu Asp Pro
1               5                   10                  15

<210> SEQ ID NO 125
<211> LENGTH: 15
<212> TYPE: PRT
<213> ORGANISM: Mycobacterium tuberculosis

<400> SEQUENCE: 125

Ala Gly Ala Met Ser Gly Leu Leu Asp Pro Ser Gln Ala Met Gly
1               5                   10                  15

<210> SEQ ID NO 126
<211> LENGTH: 15
<212> TYPE: PRT
<213> ORGANISM: Mycobacterium tuberculosis

<400> SEQUENCE: 126

Gly Leu Leu Asp Pro Ser Gln Ala Met Gly Pro Thr Leu Ile Gly
1               5                   10                  15

<210> SEQ ID NO 127

```
<211> LENGTH: 15
<212> TYPE: PRT
<213> ORGANISM: Mycobacterium tuberculosis

<400> SEQUENCE: 127

Ser Gln Ala Met Gly Pro Thr Leu Ile Gly Leu Ala Met Gly Asp
1               5                   10                  15

<210> SEQ ID NO 128
<211> LENGTH: 15
<212> TYPE: PRT
<213> ORGANISM: Mycobacterium tuberculosis

<400> SEQUENCE: 128

Pro Thr Leu Ile Gly Leu Ala Met Gly Asp Ala Gly Gly Tyr Lys
1               5                   10                  15

<210> SEQ ID NO 129
<211> LENGTH: 15
<212> TYPE: PRT
<213> ORGANISM: Mycobacterium tuberculosis

<400> SEQUENCE: 129

Leu Ala Met Gly Asp Ala Gly Gly Tyr Lys Ala Ser Asp Met Trp
1               5                   10                  15

<210> SEQ ID NO 130
<211> LENGTH: 15
<212> TYPE: PRT
<213> ORGANISM: Mycobacterium tuberculosis

<400> SEQUENCE: 130

Ala Gly Gly Tyr Lys Ala Ser Asp Met Trp Gly Pro Lys Glu Asp
1               5                   10                  15

<210> SEQ ID NO 131
<211> LENGTH: 15
<212> TYPE: PRT
<213> ORGANISM: Mycobacterium tuberculosis

<400> SEQUENCE: 131

Ala Ser Asp Met Trp Gly Pro Lys Glu Asp Pro Ala Trp Gln Arg
1               5                   10                  15

<210> SEQ ID NO 132
<211> LENGTH: 15
<212> TYPE: PRT
<213> ORGANISM: Mycobacterium tuberculosis

<400> SEQUENCE: 132

Gly Pro Lys Glu Asp Pro Ala Trp Gln Arg Asn Asp Pro Leu Leu
1               5                   10                  15

<210> SEQ ID NO 133
<211> LENGTH: 15
<212> TYPE: PRT
<213> ORGANISM: Mycobacterium tuberculosis

<400> SEQUENCE: 133

Pro Ala Trp Gln Arg Asn Asp Pro Leu Leu Asn Val Gly Lys Leu
1               5                   10                  15

<210> SEQ ID NO 134
<211> LENGTH: 15
<212> TYPE: PRT
```

-continued

<213> ORGANISM: Mycobacterium tuberculosis

<400> SEQUENCE: 134

Asn Asp Pro Leu Leu Asn Val Gly Lys Leu Ile Ala Asn Asn Thr
1               5                   10                  15

<210> SEQ ID NO 135
<211> LENGTH: 15
<212> TYPE: PRT
<213> ORGANISM: Mycobacterium tuberculosis

<400> SEQUENCE: 135

Asn Val Gly Lys Leu Ile Ala Asn Asn Thr Arg Val Trp Val Tyr
1               5                   10                  15

<210> SEQ ID NO 136
<211> LENGTH: 15
<212> TYPE: PRT
<213> ORGANISM: Mycobacterium tuberculosis

<400> SEQUENCE: 136

Ile Ala Asn Asn Thr Arg Val Trp Val Tyr Cys Gly Asn Gly Lys
1               5                   10                  15

<210> SEQ ID NO 137
<211> LENGTH: 15
<212> TYPE: PRT
<213> ORGANISM: Mycobacterium tuberculosis

<400> SEQUENCE: 137

Arg Val Trp Val Tyr Cys Gly Asn Gly Lys Pro Ser Asp Leu Gly
1               5                   10                  15

<210> SEQ ID NO 138
<211> LENGTH: 15
<212> TYPE: PRT
<213> ORGANISM: Mycobacterium tuberculosis

<400> SEQUENCE: 138

Cys Gly Asn Gly Lys Pro Ser Asp Leu Gly Gly Asn Asn Leu Pro
1               5                   10                  15

<210> SEQ ID NO 139
<211> LENGTH: 15
<212> TYPE: PRT
<213> ORGANISM: Mycobacterium tuberculosis

<400> SEQUENCE: 139

Pro Ser Asp Leu Gly Gly Asn Asn Leu Pro Ala Lys Phe Leu Glu
1               5                   10                  15

<210> SEQ ID NO 140
<211> LENGTH: 15
<212> TYPE: PRT
<213> ORGANISM: Mycobacterium tuberculosis

<400> SEQUENCE: 140

Gly Asn Asn Leu Pro Ala Lys Phe Leu Glu Gly Phe Val Arg Thr
1               5                   10                  15

<210> SEQ ID NO 141
<211> LENGTH: 15
<212> TYPE: PRT
<213> ORGANISM: Mycobacterium tuberculosis

```
<400> SEQUENCE: 141

Ala Lys Phe Leu Glu Gly Phe Val Arg Thr Ser Asn Ile Lys Phe
1               5                   10                  15

<210> SEQ ID NO 142
<211> LENGTH: 15
<212> TYPE: PRT
<213> ORGANISM: Mycobacterium tuberculosis

<400> SEQUENCE: 142

Gly Phe Val Arg Thr Ser Asn Ile Lys Phe Gln Asp Ala Tyr Asn
1               5                   10                  15

<210> SEQ ID NO 143
<211> LENGTH: 15
<212> TYPE: PRT
<213> ORGANISM: Mycobacterium tuberculosis

<400> SEQUENCE: 143

Ser Asn Ile Lys Phe Gln Asp Ala Tyr Asn Ala Gly Gly Gly His
1               5                   10                  15

<210> SEQ ID NO 144
<211> LENGTH: 15
<212> TYPE: PRT
<213> ORGANISM: Mycobacterium tuberculosis

<400> SEQUENCE: 144

Gln Asp Ala Tyr Asn Ala Gly Gly Gly His Asn Gly Val Phe Asp
1               5                   10                  15

<210> SEQ ID NO 145
<211> LENGTH: 15
<212> TYPE: PRT
<213> ORGANISM: Mycobacterium tuberculosis

<400> SEQUENCE: 145

Ala Gly Gly Gly His Asn Gly Val Phe Asp Phe Pro Asp Ser Gly
1               5                   10                  15

<210> SEQ ID NO 146
<211> LENGTH: 15
<212> TYPE: PRT
<213> ORGANISM: Mycobacterium tuberculosis

<400> SEQUENCE: 146

Asn Gly Val Phe Asp Phe Pro Asp Ser Gly Thr His Ser Trp Glu
1               5                   10                  15

<210> SEQ ID NO 147
<211> LENGTH: 15
<212> TYPE: PRT
<213> ORGANISM: Mycobacterium tuberculosis

<400> SEQUENCE: 147

Phe Pro Asp Ser Gly Thr His Ser Trp Glu Tyr Trp Gly Ala Gln
1               5                   10                  15

<210> SEQ ID NO 148
<211> LENGTH: 15
<212> TYPE: PRT
<213> ORGANISM: Mycobacterium tuberculosis

<400> SEQUENCE: 148
```

```
Thr His Ser Trp Glu Tyr Trp Gly Ala Gln Leu Asn Ala Met Lys
1               5                   10                  15

<210> SEQ ID NO 149
<211> LENGTH: 15
<212> TYPE: PRT
<213> ORGANISM: Mycobacterium tuberculosis

<400> SEQUENCE: 149

Tyr Trp Gly Ala Gln Leu Asn Ala Met Lys Pro Asp Leu Gln Arg
1               5                   10                  15

<210> SEQ ID NO 150
<211> LENGTH: 15
<212> TYPE: PRT
<213> ORGANISM: Mycobacterium tuberculosis

<400> SEQUENCE: 150

Leu Asn Ala Met Lys Pro Asp Leu Gln Arg Ala Leu Gly Ala Thr
1               5                   10                  15

<210> SEQ ID NO 151
<211> LENGTH: 15
<212> TYPE: PRT
<213> ORGANISM: Mycobacterium tuberculosis

<400> SEQUENCE: 151

Pro Asp Leu Gln Arg Ala Leu Gly Ala Thr Pro Asn Thr Gly Pro
1               5                   10                  15

<210> SEQ ID NO 152
<211> LENGTH: 15
<212> TYPE: PRT
<213> ORGANISM: Mycobacterium tuberculosis

<400> SEQUENCE: 152

Ala Leu Gly Ala Thr Pro Asn Thr Gly Pro Ala Pro Gln Gly Ala
1               5                   10                  15

<210> SEQ ID NO 153
<211> LENGTH: 18
<212> TYPE: PRT
<213> ORGANISM: Mycobacterium tuberculosis

<400> SEQUENCE: 153

Phe Ser Arg Pro Gly Leu Pro Val Glu Tyr Leu Gln Val Pro Ser Pro
1               5                   10                  15

Ser Met

<210> SEQ ID NO 154
<211> LENGTH: 16
<212> TYPE: PRT
<213> ORGANISM: Mycobacterium tuberculosis

<400> SEQUENCE: 154

Asp Ile Lys Val Gln Phe Gln Ser Gly Gly Ala Asn Ser Pro Ala Leu
1               5                   10                  15

<210> SEQ ID NO 155
<211> LENGTH: 17
<212> TYPE: PRT
<213> ORGANISM: Mycobacterium tuberculosis

<400> SEQUENCE: 155
```

-continued

Pro Val Gly Gly Gln Ser Ser Phe Tyr Ser Asp Trp Tyr Gln Pro Ala
1               5                   10                  15

Cys

<210> SEQ ID NO 156
<211> LENGTH: 17
<212> TYPE: PRT
<213> ORGANISM: Mycobacterium tuberculosis

<400> SEQUENCE: 156

Ser Met Ala Ala Ser Ser Ala Leu Thr Leu Ala Ile Tyr His Pro Gln
1               5                   10                  15

Gln

<210> SEQ ID NO 157
<211> LENGTH: 18
<212> TYPE: PRT
<213> ORGANISM: Mycobacterium tuberculosis

<400> SEQUENCE: 157

Pro Gln Gln Phe Val Tyr Ala Gly Ala Met Ser Gly Leu Leu Asp Pro
1               5                   10                  15

Ser Gln

<210> SEQ ID NO 158
<211> LENGTH: 17
<212> TYPE: PRT
<213> ORGANISM: Mycobacterium tuberculosis

<400> SEQUENCE: 158

Cys Gly Asn Gly Lys Pro Ser Asp Leu Gly Gly Asn Asn Leu Pro Ala
1               5                   10                  15

Lys

<210> SEQ ID NO 159
<211> LENGTH: 16
<212> TYPE: PRT
<213> ORGANISM: Mycobacterium tuberculosis

<400> SEQUENCE: 159

Phe Gln Asp Ala Tyr Asn Ala Gly Gly Gly His Asn Gly Val Phe Asp
1               5                   10                  15

<210> SEQ ID NO 160
<211> LENGTH: 14
<212> TYPE: PRT
<213> ORGANISM: Mycobacterium tuberculosis

<400> SEQUENCE: 160

Pro Asp Leu Gln Arg Ala Leu Gly Ala Thr Pro Asn Thr Gly
1               5                   10

<210> SEQ ID NO 161
<211> LENGTH: 325
<212> TYPE: PRT
<213> ORGANISM: Mycobacterium tuberculosis

<400> SEQUENCE: 161

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
                20                  25                  30

-continued

```
Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
 50                  55                  60

Gln Phe Gln Ser Gly Gly Asn Asn Ser Pro Ala Val Tyr Leu Leu Asp
 65                  70                  75                  80

Gly Leu Arg Ala Gln Asp Asp Tyr Asn Gly Trp Asp Ile Asn Thr Pro
                 85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
            115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
            210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
            275                 280                 285

Gly His Asn Ala Val Phe Asn Phe Pro Pro Asn Gly Thr His Ser Trp
            290                 295                 300

Glu Tyr Trp Gly Ala Gln Leu Asn Ala Met Lys Gly Asp Leu Gln Ser
305                 310                 315                 320

Ser Leu Gly Ala Gly
            325

<210> SEQ ID NO 162
<211> LENGTH: 338
<212> TYPE: PRT
<213> ORGANISM: Mycobacterium tuberculosis

<400> SEQUENCE: 162

Met Gln Leu Val Asp Arg Val Arg Gly Ala Val Thr Gly Met Ser Arg
  1               5                  10                  15

Arg Leu Val Val Gly Ala Val Gly Ala Ala Leu Val Ser Gly Leu Val
             20                  25                  30

Gly Ala Val Gly Gly Thr Ala Thr Ala Gly Ala Phe Ser Arg Pro Gly
             35                  40                  45

Leu Pro Val Glu Tyr Leu Gln Val Pro Ser Pro Ser Met Gly Arg Asp
 50                  55                  60

Ile Lys Val Gln Phe Gln Ser Gly Gly Ala Asn Ser Pro Ala Leu Tyr
```

```
              65                  70                  75                  80
Leu Leu Asp Gly Leu Arg Ala Gln Asp Asp Phe Ser Gly Trp Asp Ile
                    85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
            130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ser Ser Ala Leu
                    165                 170                 175

Thr Leu Ala Ile Tyr His Pro Gln Gln Phe Val Tyr Ala Gly Ala Met
                    180                 185                 190

Ser Gly Leu Leu Asp Pro Ser Gln Ala Met Gly Pro Thr Leu Ile Gly
                    195                 200                 205

Leu Ala Met Gly Asp Ala Gly Gly Tyr Lys Ala Ser Asp Met Trp Gly
210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                    245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
            275                 280                 285

Ala Gly Gly His Asn Gly Val Phe Asp Phe Pro Asp Ser Gly Thr
            290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                    325                 330                 335

Gly Ala

<210> SEQ ID NO 163
<211> LENGTH: 159
<212> TYPE: PRT
<213> ORGANISM: Mycobacterium tuberculosis

<400> SEQUENCE: 163

Met Lys Leu Thr Thr Met Ile Lys Thr Ala Val Ala Val Val Ala Met
1               5                   10                  15

Ala Ala Ile Ala Thr Phe Ala Ala Pro Val Ala Leu Ala Ala Tyr Pro
                20                  25                  30

Ile Thr Glu Lys Leu Gly Ser Glu Leu Thr Met Thr Asp Thr Val Gly
            35                  40                  45

Gln Val Val Leu Gly Trp Lys Val Ser Asp Leu Lys Ser Ser Thr Ala
        50                  55                  60

Val Ile Pro Gly Tyr Pro Val Ala Gly Gln Val Trp Glu Ala Thr Ala
65                  70                  75                  80

Thr Val Asn Ala Ile Arg Gly Ser Val Thr Pro Ala Val Ser Gln Phe
                85                  90                  95

Asn Ala Arg Thr Ala Asp Gly Ile Asn Tyr Arg Val Leu Trp Gln Ala
```

```
                    100                 105                 110
Ala Gly Pro Asp Thr Ile Ser Gly Ala Thr Ile Pro Gln Gly Glu Gln
        115                 120                 125

Ser Thr Gly Lys Ile Tyr Phe Asp Val Thr Gly Pro Ser Pro Thr Ile
130                 135                 140

Val Ala Met Asn Asn Gly Met Glu Asp Leu Leu Ile Trp Glu Pro
145                 150                 155

<210> SEQ ID NO 164
<211> LENGTH: 478
<212> TYPE: PRT
<213> ORGANISM: Mycobacterium tuberculosis

<400> SEQUENCE: 164

Val Thr Glu Lys Thr Pro Asp Asp Val Phe Lys Leu Ala Lys Asp Glu
 1               5                  10                  15

Lys Val Glu Tyr Val Asp Val Arg Phe Cys Asp Leu Pro Gly Ile Met
            20                  25                  30

Gln His Phe Thr Ile Pro Ala Ser Ala Phe Asp Lys Ser Val Phe Asp
        35                  40                  45

Asp Gly Leu Ala Phe Asp Gly Ser Ser Ile Arg Gly Phe Gln Ser Ile
    50                  55                  60

His Glu Ser Asp Met Leu Leu Pro Asp Pro Glu Thr Ala Arg Ile
65                  70                  75                  80

Asp Pro Phe Arg Ala Ala Lys Thr Leu Asn Ile Asn Phe Phe Val His
                85                  90                  95

Asp Pro Phe Thr Leu Glu Pro Tyr Ser Arg Asp Pro Arg Asn Ile Ala
            100                 105                 110

Arg Lys Ala Glu Asn Tyr Leu Ile Ser Thr Gly Ile Ala Asp Thr Ala
        115                 120                 125

Tyr Phe Gly Ala Glu Ala Glu Phe Tyr Ile Phe Asp Ser Val Ser Phe
    130                 135                 140

Asp Ser Arg Ala Asn Gly Ser Phe Tyr Glu Val Asp Ala Ile Ser Gly
145                 150                 155                 160

Trp Trp Asn Thr Gly Ala Ala Thr Glu Ala Asp Gly Ser Pro Asn Arg
                165                 170                 175

Gly Tyr Lys Val Arg His Lys Gly Gly Tyr Phe Pro Val Ala Pro Asn
            180                 185                 190

Asp Gln Tyr Val Asp Leu Arg Asp Lys Met Leu Thr Asn Leu Ile Asn
        195                 200                 205

Ser Gly Phe Ile Leu Glu Lys Gly His His Glu Val Gly Ser Gly Gly
    210                 215                 220

Gln Ala Glu Ile Asn Tyr Gln Phe Asn Ser Leu Leu His Ala Ala Asp
225                 230                 235                 240

Asp Met Gln Leu Tyr Lys Tyr Ile Ile Lys Asn Thr Ala Trp Gln Asn
                245                 250                 255

Gly Lys Thr Val Thr Phe Met Pro Lys Pro Leu Phe Gly Asp Asn Gly
            260                 265                 270

Ser Gly Met His Cys His Gln Ser Leu Trp Lys Asp Gly Ala Pro Leu
        275                 280                 285

Met Tyr Asp Glu Thr Gly Tyr Ala Gly Leu Ser Asp Thr Ala Arg His
    290                 295                 300

Tyr Ile Gly Gly Leu Leu His His Ala Pro Ser Leu Leu Ala Phe Thr
305                 310                 315                 320
```

```
Asn Pro Thr Val Asn Ser Tyr Lys Arg Leu Val Pro Gly Tyr Glu Ala
            325                 330                 335

Pro Ile Asn Leu Val Tyr Ser Gln Arg Asn Arg Ser Ala Cys Val Arg
            340                 345                 350

Ile Pro Ile Thr Gly Ser Asn Pro Lys Ala Lys Arg Leu Glu Phe Arg
            355                 360                 365

Ser Pro Asp Ser Ser Gly Asn Pro Tyr Leu Ala Phe Ser Ala Met Leu
    370                 375                 380

Met Ala Gly Leu Asp Gly Ile Lys Asn Lys Ile Glu Pro Gln Ala Pro
385                 390                 395                 400

Val Asp Lys Asp Leu Tyr Glu Leu Pro Pro Glu Glu Ala Ala Ser Ile
            405                 410                 415

Pro Gln Thr Pro Thr Gln Leu Ser Asp Val Ile Asp Arg Leu Glu Ala
            420                 425                 430

Asp His Glu Tyr Leu Thr Glu Gly Gly Val Phe Thr Asn Asp Leu Ile
            435                 440                 445

Glu Thr Trp Ile Ser Phe Lys Arg Glu Asn Glu Ile Glu Pro Val Asn
            450                 455                 460

Ile Arg Pro His Pro Tyr Glu Phe Ala Leu Tyr Tyr Asp Val
465                 470                 475

<210> SEQ ID NO 165
<211> LENGTH: 228
<212> TYPE: PRT
<213> ORGANISM: Mycobacterium tuberculosis

<400> SEQUENCE: 165

Val Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
            20                  25                  30

Lys Gly Thr Asp Thr Gly Gln Ala Cys Gln Ile Gln Met Ser Asp Pro
        35                  40                  45

Ala Tyr Asn Ile Asn Ile Ser Leu Pro Ser Tyr Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
            85                  90                  95

Ser Ala Thr Tyr Gln Ser Ala Ile Pro Pro Arg Gly Thr Gln Ala Val
        100                 105                 110

Val Leu Lys Val Tyr Gln Asn Ala Gly Gly Thr His Pro Thr Thr Thr
    115                 120                 125

Tyr Lys Ala Phe Asp Trp Asp Gln Ala Tyr Arg Lys Pro Ile Thr Tyr
130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
            165                 170                 175

Ala Pro Asn Ala Gly Leu Asp Pro Val Asn Tyr Gln Asn Phe Ala Val
        180                 185                 190

Thr Asn Asp Gly Val Ile Phe Phe Phe Asn Pro Gly Glu Leu Leu Pro
    195                 200                 205

Glu Ala Ala Gly Pro Thr Gln Val Leu Val Pro Arg Ser Ala Ile Asp
    210                 215                 220
```

Ser Met Leu Ala
225

<210> SEQ ID NO 166
<211> LENGTH: 299
<212> TYPE: PRT
<213> ORGANISM: Mycobacterium tuberculosis

<400> SEQUENCE: 166

Met Lys Gly Arg Ser Ala Leu Leu Arg Ala Leu Trp Ile Ala Ala Leu
 1               5                  10                  15

Ser Phe Gly Leu Gly Gly Val Ala Val Ala Ala Glu Pro Thr Ala Lys
                20                  25                  30

Ala Ala Pro Tyr Glu Asn Leu Met Val Pro Ser Pro Ser Met Gly Arg
            35                  40                  45

Asp Ile Pro Val Ala Phe Leu Ala Gly Gly Pro His Ala Val Tyr Leu
        50                  55                  60

Leu Asp Ala Phe Asn Ala Gly Pro Asp Val Ser Asn Trp Val Thr Ala
 65                  70                  75                  80

Gly Asn Ala Met Asn Thr Leu Ala Gly Lys Gly Ile Ser Val Val Ala
                85                  90                  95

Pro Ala Gly Gly Ala Tyr Ser Met Tyr Thr Asn Trp Glu Gln Asp Gly
            100                 105                 110

Ser Lys Gln Trp Asp Thr Phe Leu Ser Ala Glu Leu Pro Asp Trp Leu
        115                 120                 125

Ala Ala Asn Arg Gly Leu Ala Pro Gly Gly His Ala Ala Val Gly Ala
    130                 135                 140

Ala Gln Gly Gly Tyr Gly Ala Met Ala Leu Ala Ala Phe His Pro Asp
145                 150                 155                 160

Arg Phe Gly Phe Ala Gly Ser Met Ser Gly Phe Leu Tyr Pro Ser Asn
                165                 170                 175

Thr Thr Thr Asn Gly Ala Ile Ala Ala Gly Met Gln Gln Phe Gly Gly
            180                 185                 190

Val Asp Thr Asn Gly Met Trp Gly Ala Pro Gln Leu Gly Arg Trp Lys
        195                 200                 205

Trp His Asp Pro Trp Val His Ala Ser Leu Leu Ala Gln Asn Asn Thr
    210                 215                 220

Arg Val Trp Val Trp Ser Pro Thr Asn Pro Gly Ala Ser Asp Pro Ala
225                 230                 235                 240

Ala Met Ile Gly Gln Ala Ala Glu Ala Met Gly Asn Ser Arg Met Phe
                245                 250                 255

Tyr Asn Gln Tyr Arg Ser Val Gly Gly His Asn Gly His Phe Asp Phe
            260                 265                 270

Pro Ala Ser Gly Asp Asn Gly Trp Gly Ser Trp Ala Pro Gln Leu Gly
        275                 280                 285

Ala Met Ser Gly Asp Ile Val Gly Ala Ile Arg
    290                 295

<210> SEQ ID NO 167
<211> LENGTH: 7

```
<212> TYPE: PRT
<213> ORGANISM: Mycobacterium tuberculosis

<400> SEQUENCE: 167

Phe Ser Arg Pro Gly Leu Pro
 1               5
```